US007723498B2

(12) United States Patent
Wood et al.

(10) Patent No.: US 7,723,498 B2
(45) Date of Patent: May 25, 2010

(54) DIRECTED EVOLUTION OF RECOMBINANT MONOOXYGENASE NUCLEIC ACIDS AND RELATED POLYPEPTIDES AND METHODS OF USE

(75) Inventors: Thomas K. Wood, Tolland, CT (US); Gonul Vardar, Honolulu, HI (US)

(73) Assignee: University of Connecticut, Farmington, CT (US)

( * ) Notice: Subject to any disclaimer, the term of this patent is extended or adjusted under 35 U.S.C. 154(b) by 1024 days.

(21) Appl. No.: 11/145,405

(22) Filed: Jun. 3, 2005

(65) Prior Publication Data
US 2006/0051782 A1   Mar. 9, 2006

Related U.S. Application Data

(60) Provisional application No. 60/577,254, filed on Jun. 4, 2004.

(51) Int. Cl.
*C07H 21/02* (2006.01)
*C07K 14/00* (2006.01)
*C40B 40/06* (2006.01)
*C12Q 1/00* (2006.01)
*C12N 1/12* (2006.01)
*C12N 15/00* (2006.01)

(52) U.S. Cl. .................. 536/23.1; 530/350; 506/16; 435/4; 435/252.3; 435/325

(58) Field of Classification Search ............... 536/23.1; 530/350; 506/16; 435/4, 252.3, 325
See application file for complete search history.

(56) References Cited

U.S. PATENT DOCUMENTS 7,169,591 B1 *   1/2007   Steffan et al. ............... 435/189

FOREIGN PATENT DOCUMENTS

WO    WO 00/73425    * 12/2000

OTHER PUBLICATIONS

Bertoni et al., 1998, Analysis of the Gene Cluster Encoding Toluene/o-Xylene Monooxygenase from Pseudomonas stutzeri OX1, Applied Environmental Microbiology, 64(10): 3626-3632.*
Smith et al., 2002, Improved System for Protein Engineering of the Hydroxylase Compenent of Soluble Methane Monooxygenase, Applied Environmental Microbiology, 68(11): 5265-5273.*
Azerad, Robert, "Better enzymes for green chemistry", Chemical Biotechnology, p. 533-534.
Berry, A., et al., "Application of metabolic engineering to improve both the production and use of biotech indigo", Journal of Industrial Microbiology & Biotechnology, p. 127-133.
Bertoni, G. et al., "Cloning of the genes for and characterization of the early stages of toluene and o-xylene catabolism in pseudomonas stutzeri OX1", Applied and Environmental Microbiology, Vo. 62, No. 10., Oct 1996, p. 3704-3711.
Bertoni, G. et al., "Analysis of the gene cluster encoding toluene/o-xylene monooxygenase from pseudomonas stutzeri OX1", Applied and Environmental Microbiology, vol. 64, No. 10, Oct. 1998, p. 3626-3632.
Burton, S. et al, Biotransformation of phenols using immobilised polyphenol oxidase, Journal of Molecular Catalysis B: Enzymatic 5, 1998, p. 411-416.
Byrne, A. et al., "Sequence analysis of the gene cluster encoding toluene-3 monooxygenase from pseudomonas pickettii PK01", Elsevier Science B.V., 1995, p. 65-70.
Cafaro, V. et al., "Expression and purification of the recombinant subunits of toluene/o-xylene monooxygenase and reconstitution of the active complex", Eur. J. Biochem. 269, p. 5689-5699.
Canada, K. et al., "Directed evolution of toluene ortho-monooxygenase for enhanced 1-naphthol synthesis and chlorinated ethane degradation", Journal of Bacteriology, Jan. 2002. p. 344-349.
Cardy, D. et al., The methane monooxygenase gene cluster of methylosinus trichosporium: cloning and sequencing of the mmoC gene. Arch Microbiol, 1991, 156: p. 477-483.
Chauhan, S. et al., "Oxidation of trichloroethylene, 1,1-dichloroethylene, and chloroform by toluene/o-xylene monooxygenase from pseudomonas stutzeri OX1", Applied and Environmental Microbiology, Aug. 1998, p. 3023-3024.
Draths, K. et al., "Conversion of d-glucose into catechol: The not-so-common pathway of aromatic biosynthesis", American Chemical Society, 1991, 113, p. 9361-9363.
Draths, K. et al., "Environmentally compatible synthesis of catechol from d-glucose", American Chemical Society, 1995, 117, p. 2395-2400.
Eaton, R. et al., "Formation of indigo and related compounds from indolecarboxylic acids by aromatic acid-degrading bacteria: Chromogenic reactions for cloning genes encoding dioxygenases that act on aromatic acids", Journal of Bacteriology, Dec. 1995, p. 6983-6988.
Elango, N. et al., "Crystal structure of the hydroxylase component of methane monooxygenase from methylosinus trichosporium OB3b", Protein Science, 1997, 6:, p. 556-568.
Ensley, B. et al., "Expression of naphthalene oxidation genes in Escherichia coli results in the biosynthesis of indigo", Science, Vol. 222, p. 167-169.
Fishman, A. et al., "Protein engineering of toluene 4-monooxygenase of pseudomonas mendocina KR1 for synthesizing 4-nitrocatechol from nitrobenzene", Wiley Periodicals, Inc. 2004, p. 779-790.

(Continued)

*Primary Examiner*—Amber D. Steele
(74) *Attorney, Agent, or Firm*—McCarter & English, LLP

(57) ABSTRACT

The present invention relates to novel monooxygenase nucleic acids and polypeptides created using mutagenesis, DNA shuffling, or both, in a single iteration or multiple iterations, and methods for their creation and use. The monooxygenase enzymes of the present disclosure have particular utility as biocatalysts in industrial chemical redox reactions, such as the oxidation of aromatic hydrocarbons, for example, toluene, benzene, or nitrobenzene, into industrially desirable products. The systems and processes of the present invention are especially useful for the coupled synthesis and recovery of catechols, methylcatechols, resorcinols, methylresorcinols, hydroquinones, methylhydroquinones, hydroxybenzenes, cresols, nitrobenzenes, and nitrohydroxyquinones.

20 Claims, 60 Drawing Sheets

OTHER PUBLICATIONS

Fujita, Y. et al., "A color reaction of 1,2-diphenols based on colored complex formation with phenylfluorone and iron(III) and its application to the assay of catecholamines in pharmaceutical preparations", Chem. Pharm. Bull. (1985) vol. 33, p. 5385-5392.

Haigler, B. et al., "Biotransformation of nitrobenzene by bacteria containing toluene degradative pathways", Applied and Environmental Microbiology, Nov. 1991, p. 3156-3162.

Jain, R. et al., "Biodegradation of p-nitrophenol via 1,2,4-benzenetriol by an arthrobacter sp.", Applied and Environmental Microbiology, Aug. 1994, p. 3030-3032.

Johnson, G. et al., "Multiple pathways for toluene degradation in burkholderia sp. Strain JS150", Applied and Environmental Microbiology, Oct. 1997, p. 4047-4052.

Kadiyala, V. et al., "A two-component monooxygenase catalyzes both the hydroxylation of p-nitrophenol and the oxidative release of nitrite from 4-nitrocatechol in bacillus spaericus JS905", Applied and Environmental Microbiology, Jul. 1998, p. 2479-2484.

Kopp, D. et al., "Soluble methane monooxygenase:activation of dioxygen and methane", Mechanisms, p. 568-576.

Leahy, J. et al., "Evolution of the soluble diiron monooxygenases", FEMS Microbiology Reviews, 27, 2003, p. 449-479.

Luu, P. et al., "Monitoring trichloroethylene mineralization by pseudomonas cepacia G4 PR1", Applied Microbiol. Biotechnol., (1995) 44: p. 259-264.

Masunaga, S. et al., "Microbial transformation of o-cresol to dihydroxytoluenes by phenol acclimated activated sludge", Chemosphere, (1983), vol. 12, No. 7/8, p. 1075-1082.

Mermod, N. et al., "New route to bacterial production of indigo", Research Note, Bio/technology, vol. 4, Apr. 1986, p. 321-324.

Meyer, A. et al., "Changing the substrate reactivity of 2-hydroxybiphenyl 3-monooxygenase from pseudomonas azelaica HBP1 by directed evolution", Journal of Biological Chemistry, vol. 277, No. 7, Feb. 2002, p. 5575-5582.

Mitchell, K. et al., "Combined participation of hydroxylase active site residues and effector protein binding in a para to ortho modulation of toluene 4-monooxygenase regiospecificity", Biochemistry, 2002, 41, p. 3176-3188.

Miyazaki, K. et al., "Exploring nonnatural evolutionary pathways by saturation mutagenesis: Rapid improvement of protein function", Journal of Molecular Evolution, p. 716-720.

Moore, J. et al., "Directed evolution of a para-nitrobenzyl esterase for aqueous-organic solvents", Nature Biotechnology, vol. 14, Apr. 1996, p. 449-467.

Murdock, D. et al., "Construction of metabolic operons catalyzing the de novo biosynthesis of indigo in *Escherichia coli*", Bio/Technology, vol. 11, Mar. 1993, p. 381-386.

Newman, L. et al., "Purification and characterization of toluene 2-monooxygenase from burkholderia cepacia G4", Biochemistry, 1995, 34, p. 14066-14076.

Nordlund, I. et al., "Compete nucleotide sequence and polypeptide analysis of multicomponent phenol hydroxylase from pseudomonas sp. Strain CF600", Journal of Bacteriology, Dec. 1990, p. 6826-6833.

Oppenheim, S. et al., "Aromatic hydroxylation catalyzed by toluene 4-monooxygenase in organic solvent/aqueous buffer mixtures", Applied Biochemistry and Biotechnology, vol. 90, 2001, p. 187-197.

Pikus, J. et al., "Changes in the regiospecificity of aromatic hydroxylation produced by active site engineering in the diiron enzyme toluene 4-monooxygenase", Biochemistry, Aug. 1997, vol. 36, No. 31, p. 9283-9289.

Pikus, J. et al., "Threonine 201 in the diiron enzyme toluene 4-monooxygenase is not required for catalysis", Biochemistry, 2000, 39, p. 791-799.

Rui, L. et al., 'Saturation mutagenesis of toluene ortho-monooxygenase of burkholderia cepacia G4 for enhanced 1-naphthol synthesis and chloroform degradation, Applied and Environmental Microbiology, Jun. 2004, p. 3246-3252.

Rui, L. et al., "Protein engineering of toluene ortho-monooxygenase of burkholderia cepacia G4 for regiospecific hydroxylation of indole to form various indigoid compounds", Applied Genetics and Molecular Biotechnology, 2005, 66, p. 422-429.

Ryoo, D. et al., "Aerobic degradation of tetrachloroethylene by toluene-o-xylene monooxygenase of pseudomonas stutzeri OX1", Nature Biotechnology, vol. 18, Jul. 2000, p. 775-778.

Sakamoto, T. et al., "Laboratory evolution of toluene dioxygenase to accept 4-picoline a s a substrate", Applied and Environmental Microbiology, Sep. 2001, p. 3882-3887.

Stemmer, W., "DNA shuffling by random fragmentation and reassembly: In vitro recombination for molecular evolution", Proc. Natl. Acad. Sci., vol. 91, Oct. 1994, p. 10747-10751.

Shields, M. et al., "Novel pathway of toluene catabolism in the trichloroethylene-degrading bacterium G4", Applied Environmental Microbiology, Jun. 1989, p. 1624-1629.

Shim H. et al., "Aerobic degradation of mixtures of chlorinated aliphatics by cloned toluene-oxylene monooxygenase and toluene o-monooxygenase in resting cells", Biotechnology and Bioengineering, vol. 70. No. 6, Dec. 2000, p. 693-698.

Tao, Y. et al., "Oxidation of benzene to phenol, catechol, and 1,2,3-trihydroxybenzene by toluene 4-monooxygenase of pseudomonas mendocina KR1 and toluene 3-monooxygenase of ralstonia pickettii PKO1", Applied and Environmental Microbiology, Jul. 2004, p. 3814-3820.

Tao, Y. et al., "altering toluene 4-monooxygenase by active-site engineering for the synthesis of 3-methoxycatechol, methoxyhydroquinone, and methylhydroquinone", Journal of Bacteriology, Jul. 2004, p. 4705-4713.

Vardar, G. et al., "Protein engineering of toluene-o-xylene monooxygenase from pseudomonas stutzeri OX1 for oxidizing nitrobenzene to 3-nitrocatechol, 4-nitrocatechol, and nitrohydroquinone", Journal of Biotechnology, 115, (2005), p. 145-156.

Vardar G. et al., "Protein engineering of toluene-o-xylene monooxygenase from pseudomonas stutzeri OX1 for synthesizing 4-methylrosorcinol, methylhydroquinone, and pyrogallol", Applied and Environmental Microbiology, Jun. 2004, p. 3253-3262.

Zhao, H. et al., "Optimization of DNA shuffling for high fidelity recombination", Nucleic Acids Research, 1997, vol. 25, No. 6, p. 1307-1308.

* cited by examiner

FIGURE 1A

```
ToMO-wild_type              ATGTCAATGCTAAAAACGTGAAGATTGGTACGATCTTACGCGTACCACCAA
ToMO_E214G/D312N/M399V      ATGTCAATGCTAAAAACGTGAAGATTGGTACGATCTTACGCGTACCACCAA
ToMO_F205G                  ATGTCAATGCTAAAAACGTGAAGATTGGTACGATCTTACGCGTACCACCAA
ToMO_I100Q                  ATGTCAATGCTAAAAACGTGAAGATTGGTACGATCTTACGCGTACCACCAA
ToMO_M180T/E284G            ATGTCAATGCTAAAAACGTGAAGATTGGTACGATCTTACGCGTACCACCAA
                            *************************************************

ToMO-wild_type              CTGGACGCGCCTAAATATGTCACTGAAAACGAACTGTTTCCGGAGGAAATGA
ToMO_E214G/D312N/M399V      CTGGACGCGCCTAAATATGTCACTGAAAACGAACTGTTTCCGGAGGAAATGA
ToMO_F205G                  CTGGACGCGCCTAAATATGTCACTGAAAACGAACTGTTTCCGGAGGAAATGA
ToMO_I100Q                  CTGGACGCGCCTAAATATGTCACTGAAAACGAACTGTTTCCGGAGGAAATGA
ToMO_M180T/E284G            CTGGACGCGCCTAAATATGTCACTGAAAACGAACTGTTTCCGGAGGAAATGA
                            *************************************************

ToMO-wild_type              GCGGAGCACGTGGCATTCTATGGAAGCTTGGGAAAAATACGATGAACCG
ToMO_E214G/D312N/M399V      GCGGAGCACGTGGCATTCTATGGAAGCTTGGGAAAAATACGATGAACCG
ToMO_F205G                  GCGGAGCACGTGGCATTCTATGGAAGCTTGGGAAAAATACGATGAACCG
ToMO_I100Q                  GCGGAGCACGTGGCATTCTATGGAAGCTTGGGAAAAATACGATGAACCG
ToMO_M180T/E284G            GCGGAGCACGTGGCATTCTATGGAAGCTTGGGAAAAATACGATGAACCG
                            *************************************************

ToMO-wild_type              TACAAGATAACTTATCCGGAATACGTCAGTATTCAGCGAGAAAGGACTC
ToMO_E214G/D312N/M399V      TACAAGATAACTTATCCGGAATACGTCAGTATTCAGCGAGAAAGGACTC
ToMO_F205G                  TACAAGATAACTTATCCGGAATACGTCAGTATTCAGCGAGAAAGGACTC
ToMO_I100Q                  TACAAGATAACTTATCCGGAATACGTCAGTATTCAGCGAGAAAGGACTC
ToMO_M180T/E284G            TACAAGATAACTTATCCGGAATACGTCAGTATTCAGCGAGAAAGGACTC
                            *************************************************

ToMO-wild_type              CGGCGCATATTCAATCAAAGCGGCACTGGAGCGTGATGGTTTCGTTGATC
ToMO_E214G/D312N/M399V      CGGCGCATATTCAATCAAAGCGGCACTGGAGCGTGATGGTTTCGTTGATC
ToMO_F205G                  CGGCGCATATTCAATCAAAGCGGCACTGGAGCGTGATGGTTTCGTTGATC
ToMO_I100Q                  CGGCGCATATTCAATCAAAGCGGCACTGGAGCGTGATGGTTTCGTTGATC
ToMO_M180T/E284G            CGGCGCATATTCAATCAAAGCGGCACTGGAGCGTGATGGTTTCGTTGATC
                            *************************************************

ToMO-wild_type              GAGCCGATCCAGGCTGGGTTAGCACTATGCAACTTCACTTCGGAGCCGATC
ToMO_E214G/D312N/M399V      GAGCCGATCCAGGCTGGGTTAGCACTATGCAACTTCACTTCGGAGCCGATC
ToMO_F205G                  GAGCCGATCCAGGCTGGGTTAGCACTATGCAACTTCACTTCGGAGCCGATC
ToMO_I100Q                  GAGCCGATCCAGGCTGGGTTAGCACTATGCAACTTCACTTCGGAGCGCAA
ToMO_M180T/E284G            GAGCCGATCCAGGCTGGGTTAGCACTATGCAACTTCACTTCGGAGCCGATC
                            ********************************************
```

```
(FIG. 1B)
ToMO-wild_type              GCACTTGAAGAATACGCCGCAAGCACTGCTGAAGCCCGTATGGCGCGATT
ToMO_E214G/D312N/M399V      GCACTTGAAGAATACGCCGCAAGCACTGCTGAAGCCCGTATGGCGCGATT
ToMO_F205G                  GCACTTGAAGAATACGCCGCAAGCACTGCTGAAGCCCGTATGGCGCGATT
ToMO_I100Q                  GCACTTGAAGAATACGCCGCAAGCACTGCTGAAGCCCGTATGGCGCGATT
ToMO_M180T/E284G            GCACTTGAAGAATACGCCGCAAGCACTGCTGAAGCCCGTATGGCGCGATT
                            **************************************************

ToMO-wild_type              CGCCAAGGCACCGGGAAACCGGAATATGGCGACTTTCGGAATGATGGATG
ToMO_E214G/D312N/M399V      CGCCAAGGCACCGGGAAACCGGAATATGGCGACTTTCGGAATGATGGATG
ToMO_F205G                  CGCCAAGGCACCGGGAAACCGGAATATGGCGACTTTCGGAATGATGGATG
ToMO_I100Q                  CGCCAAGGCACCGGGAAACCGGAATATGGCGACTTTCGGAATGATGGATG
ToMO_M180T/E284G            CGCCAAGGCACCGGGAAACCGGAATATGGCGACTTTCGGAATGATGGATG
                            **************************************************

ToMO-wild_type              AAAACCGCCATGGGCAAATCCAACTTTACTTTCCGTATGCCAATGTCAAG
ToMO_E214G/D312N/M399V      AAAACCGCCATGGGCAAATCCAACTTTACTTTCCGTATGCCAATGTCAAG
ToMO_F205G                  AAAACCGCCATGGGCAAATCCAACTTTACTTTCCGTATGCCAATGTCAAG
ToMO_I100Q                  AAAACCGCCATGGGCAAATCCAACTTTACTTTCCGTATGCCAATGTCAAG
ToMO_M180T/E284G            AAAACCGCCATGGGCAAATCCAACTTTACTTTCCGTATGCCAATGTCAAG
                            **************************************************

ToMO-wild_type              CGGAGCAGGAAATGGGATTGGGCGCACAAAGCCATTCATACTAACGAATG
ToMO_E214G/D312N/M399V      CGGAGCAGGAAATGGGATTGGGCGCACAAAGCCATTCATACTAACGAATG
ToMO_F205G                  CGGAGCAGGAAATGGGATTGGGCGCACAAAGCCATTCATACTAACGAATG
ToMO_I100Q                  CGGAGCAGGAAATGGGATTGGGCGCACAAAGCCATTCATACTAACGAATG
ToMO_M180T/E284G            CGGAGCAGGAAATGGGATTGGGCGCACAAAGCCATTCATACTAACGAATG
                            **************************************************

ToMO-wild_type              GGCCGCAATCGCGGCACGGTCTTTCTTTGACGACATGATGATGACCCGCG
ToMO_E214G/D312N/M399V      GGCCGCAATCGCGGCACGGTCTTTCTTTGACGACATGATGATGACCCGCG
ToMO_F205G                  GGCCGCAATCGCGGCACGGTCTTTCTTTGACGACATGATGATGACCCGCG
ToMO_I100Q                  GGCCGCAATCGCGGCACGGTCTTTCTTTGACGACATGATGATGACCCGCG
ToMO_M180T/E284G            GGCCGCAATCGCGGCACGGTCTTTCTTTGACGACATGACGATGACCCGCG
                            ************************************* ************

ToMO-wild_type              ATTCCGTGGCCGTCTCTATCATGCTGACCTTCGCATTCGAAACAGGCTTC
ToMO_E214G/D312N/M399V      ATTCCGTGGCCGTCTCTATCATGCTGACCTTCGCATTCGAAACAGGCTTC
ToMO_F205G                  ATTCCGTGGCCGTCTCTATCATGCTGACCTTCGCATTCGAAACAGGCTTC
ToMO_I100Q                  ATTCCGTGGCCGTCTCTATCATGCTGACCTTCGCATTCGAAACAGGCTTC
ToMO_M180T/E284G            ATTCCGTGGCCGTCTCTATCATGCTGACCTTCGCATTCGAAACAGGCTTC
                            **************************************************
```

(FIG. 1C)

```
ToMO-wild_type         ACCAATATGCAGTTTCTCGGTTTGGCCGCTGCCGCTGACGCTGCTGAGGCCGGTGA
ToMO_E214G/D312N/M399V ACCAATATGCAGTTTCTCGGTTTGGCCGCTGCCGCTGACGCTGCTGAGGCCGGTGA
ToMO_F205G             ACCAATATGCAGTTTCTCGGGCTCGGTTTGGCCGCTGACGCTGCTGAGGCCGGTGA
ToMO_I100Q             ACCAATATGCAGTTTCTCGGTTTGGCCGCTGACGCTGCTGAGGCCGGTGA
ToMO_M180T/E284G       ACCAATATGCAGTTTCTCGGTTTGGCCGCTGACGCTGCTGAGGCCGGTGA
                       ***************            *********************

ToMO-wild_type         CCATACCTTTGCCAGCCTGATTTCAAGCATACAGACGACGAATCACGTC
ToMO_E214G/D312N/M399V CCATACCTTTGCCAGCCTGATTTCAAGCATACAGACGACGAATCACGTC
ToMO_F205G             CCATACCTTTGCCAGCCTGATTTCAAGCATACAGACGACGAATCACGTC
ToMO_I100Q             CCATACCTTTGCCAGCCTGATTTCAAGCATACAGACGACGAATCACGTC
ToMO_M180T/E284G       CCATACCTTTGCCAGCCTGATTTCAAGCATACAGACGACGAATCACGTC
                       *************************************************

(FIG. 1D)

| | |
|---|---|
| ToMO-wild_type | CAATTTGAACGTCAGTGCTTGATCTAGGGCTCGACAAACCCTGGTATTG |
| ToMO_E214G/D312N/M399V | CAATTTGAACGTCAGTGCTTGATCTAGGGCTCAACAAACCCTGGTATTG |
| ToMO_F205G | CAATTTGAACGTCAGTGCTTGATCTAGGGCTCGACAAACCCTGGTATTG |
| ToMO_I100Q | CAATTTGAACGTCAGTGCTTGATCTAGGGCTCGACAAACCCTGGTATTG |
| ToMO_M180T/E284G | CAATTTGAACGTCAGTGCTTGATCTAGGGCTCGACAAACCCTGGTATTG |
| | ************************** ***************** |

| | |
|---|---|
| ToMO-wild_type | GGATCAATTCATGCAAGACCTCGATGAAACACACCATGGCATGCACCTGG |
| ToMO_E214G/D312N/M399V | GGATCAATTCATGCAAGACCTCGATGAAACACACCATGGCATGCACCTGG |
| ToMO_F205G | GGATCAATTCATGCAAGACCTCGATGAAACACACCATGGCATGCACCTGG |
| ToMO_I100Q | GGATCAATTCATGCAAGACCTCGATGAAACACACCATGGCATGCACCTGG |
| ToMO_M180T/E284G | GGATCAATTCATGCAAGACCTCGATGAAACACACCATGGCATGCACCTGG |
| | ************************************************** |

| | |
|---|---|
| ToMO-wild_type | GCGTGTGGTATTGGCGCCCCACAGTCTGGTGGGATCCGGCAGCTGGTGTG |
| ToMO_E214G/D312N/M399V | GCGTGTGGTATTGGCGCCCCACAGTCTGGTGGGATCCGGCAGCTGGTGTG |
| ToMO_F205G | GCGTGTGGTATTGGCGCCCCACAGTCTGGTGGGATCCGGCAGCTGGTGTG |
| ToMO_I100Q | GCGTGTGGTATTGGCGCCCCACAGTCTGGTGGGATCCGGCAGCTGGTGTG |
| ToMO_M180T/E284G | GCGTGTGGTATTGGCGCCCCACAGTCTGGTGGGATCCGGCAGCTGGTGTG |
| | ************************************************** |

| | |
|---|---|
| ToMO-wild_type | TCTCCTGAAGAGCGGGAATGGCTGGAAGAGAAATATCCCGGTTGGAATGA |
| ToMO_E214G/D312N/M399V | TCTCCTGAAGAGCGGGAATGGCTGGAAGAGAAATATCCCGGTTGGAATGA |
| ToMO_F205G | TCTCCTGAAGAGCGGGAATGGCTGGAAGAGAAATATCCCGGTTGGAATGA |
| ToMO_I100Q | TCTCCTGAAGAGCGGGAATGGCTGGAAGAGAAATATCCCGGTTGGAATGA |
| ToMO_M180T/E284G | TCTCCTGAAGAGCGGGAATGGCTGGAAGAGAAATATCCCGGTTGGAATGA |
| | ************************************************** |

| | |
|---|---|
| ToMO-wild_type | TACCTGGGGCCAGTGTTGGATGTCATTACCGATAACCTAGTGAATGGTA |
| ToMO_E214G/D312N/M399V | TACCTGGGGCCAGTGTTGGATGTCATTACCGATAACCTAGTGAATGGTA |
| ToMO_F205G | TACCTGGGGCCAGTGTTGGATGTCATTACCGATAACCTAGTGAATGGTA |
| ToMO_I100Q | TACCTGGGGCCAGTGTTGGATGTCATTACCGATAACCTAGTGAATGGTA |
| ToMO_M180T/E284G | TACCTGGGGCCAGTGTTGGATGTCATTACCGATAACCTAGTGAATGGTA |
| | ************************************************** |

| | |
|---|---|
| ToMO-wild_type | AACCAGAGTTGACTGTTCCGAAACCCTACCCACGATCTGTAACATGTGC |
| ToMO_E214G/D312N/M399V | AACCAGAGTTGACTGTTCCGAAACCCTACCCACGATCTGTAACATGTGC |
| ToMO_F205G | AACCAGAGTTGACTGTTCCGAAACCCTACCCACGATCTGTAACATGTGC |
| ToMO_I100Q | AACCAGAGTTGACTGTTCCGAAACCCTACCCACGATCTGTAACATGTGC |
| ToMO_M180T/E284G | AACCAGAGTTGACTGTTCCGAAACCCTACCCACGATCTGTAACATGTGC |
| | ************************************************* |

(FIG. 1E)

```
ToMO-wild_type         AATCTCCCGATTGCCCATACTCCAGGTAATAAATGGAATGTAAAGGACTA
ToMO_E214G/D312N/M399V AATCTCCCGATTGCCCATACTCCAGGTAATAAATGGAATGTAAAGGACTA
ToMO_F205G             AATCTCCCGATTGCCCATACTCCAGGTAATAAATGGAATGTAAAGGACTA
ToMO_I100Q             AATCTCCCGATTGCCCATACTCCAGGTAATAAATGGAATGTAAAGGACTA
ToMO_M180T/E284G       AATCTCCCGATTGCCCATACTCCAGGTAATAAATGGAATGTAAAGGACTA
                       **************************************************

ToMO-wild_type         CCAGCTCGAATATGAGGGACGCCTTTACCACTTCGGCTCTGAGGCCGACC
ToMO_E214G/D312N/M399V CCAGCTCGAATATGAGGGACGCCTTTACCACTTCGGCTCTGAGGCCGACC
ToMO_F205G             CCAGCTCGAATATGAGGGACGCCTTTACCACTTCGGCTCTGAGGCCGACC
ToMO_I100Q             CCAGCTCGAATATGAGGGACGCCTTTACCACTTCGGCTCTGAGGCCGACC
ToMO_M180T/E284G       CCAGCTCGAATATGAGGGACGCCTTTACCACTTCGGCTCTGAGGCCGACC
                       **************************************************

ToMO-wild_type         GCTGGTGTTTCCAGATCGACCCGGAACGTTACGAAAACCATACGAACCTT
ToMO_E214G/D312N/M399V GCTGGTGTTTCCAGATCGACCCGGAACGTTACGAAAACCATACGAACCTT
ToMO_F205G             GCTGGTGTTTCCAGATCGACCCGGAACGTTACGAAAACCATACGAACCTT
ToMO_I100Q             GCTGGTGTTTCCAGATCGACCCGGAACGTTACGAAAACCATACGAACCTT
ToMO_M180T/E284G       GCTGGTGTTTCCAGATCGACCCGGAACGTTACGAAAACCATACGAACCTT
                       **************************************************

ToMO-wild_type         GTCGACCGATTCCTGAAAGTGAAATTCAGCCTGCGGATTTAGCGGGTGC
ToMO_E214G/D312N/M399V GTCGACCGATTCCTGAAAGTGAAATTCAGCCTGCGGATTTAGCGGGTGC
ToMO_F205G             GTCGACCGATTCCTGAAAGTGAAATTCAGCCTGCGGATTTAGCGGGTGC
ToMO_I100Q             GTCGACCGATTCCTGAAAGTGAAATTCAGCCTGCGGATTTAGCGGGTGC
ToMO_M180T/E284G       GTCGACCGATTCCTGAAAGTGAAATTCAGCCTGCGGATTTAGCGGGTGC
                       *************

FIGURE 2A

```
ToMO-wild_type            MSMLKREDWYDLTRTTNWTPKYVTENELFPEEMSGARGISMEAWEKYDEP
ToMO_E214G/D312N/M399V    MSMLKREDWYDLTRTTNWTPKYVTENELFPEEMSGARGISMEAWEKYDEP
ToMO_F205G                MSMLKREDWYDLTRTTNWTPKYVTENELFPEEMSGARGISMEAWEKYDEP
ToMO_I100Q                MSMLKREDWYDLTRTTNWTPKYVTENELFPEEMSGARGISMEAWEKYDEP
ToMO_I180T/E284G          MSMLKREDWYDLTRTTNWTPKYVTENELFPEEMSGARGISMEAWEKYDEP
                          **************************************************

ToMO-wild_type            YKITYPEYVSIQREKDSGAYSIKAALERDGFVDRADPGWVSTMQLHFGAI
ToMO_E214G/D312N/M399V    YKITYPEYVSIQREKDSGAYSIKAALERDGFVDRADPGWVSTMQLHFGAI
ToMO_F205G                YKITYPEYVSIQREKDSGAYSIKAALERDGFVDRADPGWVSTMQLHFGAI
ToMO_I100Q                YKITYPEYVSIQREKDSGAYSIKAALERDGFVDRADPGWVSTMQLHFGAI
ToMO_I180T/E284G          YKITYPEYVSIQREKDSGAYSIKAALERDGFVDRADPGWVSTMQLHFGAQ
                          ************************************************

ToMO-wild_type            ALEEYAASTAEARMARFAKAPGNRRNMATFGMMDENRHGQIQLYFPYANVK
ToMO_E214G/D312N/M399V    ALEEYAASTAEARMARFAKAPGNRRNMATFGMMDENRHGQIQLYFPYANVK
ToMO_F205G                ALEEYAASTAEARMARFAKAPGNRRNMATFGMMDENRHGQIQLYFPYANVK
ToMO_I100Q                ALEEYAASTAEARMARFAKAPGNRRNMATFGMMDENRHGQIQLYFPYANVK
ToMO_I180T/E284G          ALEEYAASTAEARMARFAKAPGNRRNMATFGMMDENRHGQIQLYFPYANVK
                          **************************************************

ToMO-wild_type            RSRKWDWAHKAIHTNEWAAIAARSFFDDMMTRDSVAVSIMLTFAFETGF
ToMO_E214G/D312N/M399V    RSRKWDWAHKAIHTNEWAAIAARSFFDDMMTRDSVAVSIMLTFAFETGF
ToMO_F205G                RSRKWDWAHKAIHTNEWAAIAARSFFDDMMTRDSVAVSIMLTFAFETGF
ToMO_I100Q                RSRKWDWAHKAIHTNEWAAIAARSFFDDMMTRDSVAVSIMLTFAFETGF
ToMO_I180T/E284G          RSRKWDWAHKAIHTNEWAAIAARSFFDDMTMTRDSVAVSIMLTFAFETGF
                          *****************************  *****************

ToMO-wild_type            TNMQFLGLAADAAEAGDHTFASLISSIQTDESRHAQQGGPSLKILVENGK
ToMO_E214G/D312N/M399V    TNMQFLGLAADAAEAGDHTFASLISSIQTDESRHAQQGGPSLKILVENGK
ToMO_F205G                TNMQGLGLAADAAEAGDHTFASLISSIQTDESRHAQQGGPSLKILVENGK
ToMO_I100Q                TNMQFLGLAADAAEAGDHTFASLISSIQTDESRHAQQGGPSLKILVENGK
ToMO_I180T/E284G          TNMQFLGLAADAAEAGDHTFASLISSIQTDESRHAQQGGPSLKILVENGK
                          ****  ********************************************

ToMO-wild_type            KDEAQQMVDVAIWRSWKLFSVLTGPIMDYYTPLESRNQSFKEFMLEWIVA
ToMO_E214G/D312N/M399V    KDEAQQMVDVAIWRSWKLFSVLTGPIMDYYTPLESRNQSFKEFMLEWIVA
ToMO_F205G                KDEAQQMVDVAIWRSWKLFSVLTGPIMDYYTPLESRNQSFKEFMLEWIVA
ToMO_I100Q                KDEAQQMVDVAIWRSWKLFSVLTGPIMDYYTPLESRNQSFKEFMLEWIVA
ToMO_I180T/E284G          KDEAQQMVDVAIWRSWKLFSVLTGPIMDYYTPLGSRNQSFKEFMLEWIVA
                          *********************************  **************
```

```
(FIG. 2B)
ToMO-wild_type             QFERQLLDLGLDKPWYWDQFMQDLDETHHGMHLGVWYWRPTVWWDPAAGV
ToMO_E214G/D312N/M399V     QFERQLLDLGLNKPWYWDQFMQDLDETHHGMHLGVWYWRPTVWWDPAAGV
ToMO_F205G                 QFERQLLDLGLDKPWYWDQFMQDLDETHHGMHLGVWYWRPTVWWDPAAGV
ToMO_I100Q                 QFERQLLDLGLDKPWYWDQFMQDLDETHHGMHLGVWYWRPTVWWDPAAGV
ToMO_I180T/E284G           QFERQLLDLGLDKPWYWDQFMQDLDETHHGMHLGVWYWRPTVWWDPAAGV
                           *********** **************************************

ToMO-wild_type             SPEEREWLEEKYPGWNDTWGQCWDVITDNLVNGKPELTVPETLPTICNMC
ToMO_E214G/D312N/M399V     SPEEREWLEEKYPGWNDTWGQCWDVITDNLVNGKPELTVPETLPTICNVC
ToMO_F205G                 SPEEREWLEEKYPGWNDTWGQCWDVITDNLVNGKPELTVPETLPTICNMC
ToMO_I100Q                 SPEEREWLEEKYPGWNDTWGQCWDVITDNLVNGKPELTVPETLPTICNMC
ToMO_I180T/E284G           SPEEREWLEEKYPGWNDTWGQCWDVITDNLVNGKPELTVPETLPTICNMC
                           ************************************************ *

ToMO-wild_type             NLPIAHTPGNKWNVKDYQLEYEGRLYHFGSEADRWCFQIDPERYENHTNL
ToMO_E214G/D312N/M399V     NLPIAHTPGNKWNVKDYQLEYEGRLYHFGSEADRWCFQIDPERYENHTNL
ToMO_F205G                 NLPIAHTPGNKWNVKDYQLEYEGRLYHFGSEADRWCFQIDPERYENHTNL
ToMO_I100Q                 NLPIAHTPGNKWNVKDYQLEYEGRLYHFGSEADRWCFQIDPERYENHTNL
ToMO_I180T/E284G           NLPIAHTPGNKWNVKDYQLEYEGRLYHFGSEADRWCFQIDPERYENHTNL
                           **************************************************

ToMO-wild_type             VDRFLKGEIQPADLAGALMYMSLEPGVMGDDAHDYEWVKAYQKKTNAA
ToMO_E214G/D312N/M399V     VDRFLKGEIQPADLAGALMYMSLEPGVMGDDAHDYEWVKAYQKKTNAA
ToMO_F205G                 VDRFLKGEIQPADLAGALMYMSLEPGVMGDDAHDYEWVKAYQKKTNAA
ToMO_I100Q                 VDRFLKGEIQPADLAGALMYMSLEPGVMGDDAHDYEWVKAYQKKTNAA
ToMO_I180T/E284G           VDRFLKGEIQPADLAGALMYMSLEPGVMGDDAHDYEWVKAYQKKTNAA
                           ************************************************
```

FIGURE 3A

```
ToMA3_A113I           MDTSVQKKKLGLKNRYAAMTRGLGWQTSYQPMEKVFPYDKYEGIKIHDWKWEDPFRLTM
ToMA3_A113G           MDTSVQKKKLGLKNRYAAMTRGLGWQTSYQPMEKVFPYDKYEGIKIHDWKWEDPFRLTM
ToMA3_A113S           MDTSVQKKKLGLKNRYAAMTRGLGWQTSYQPMEKVFPYDKYEGIKIHDWKWEDPFRLTM
ToMA3_A113F           MDTSVQKKKLGLKNRYAAMTRGLGWQTSYQPMEKVFPYDKYEGIKIHDWKWEDPFRLTM
ToMA3_A113H           MDTSVQKKKLGLKNRYAAMTRGLGWQTSYQPMEKVFPYDKYEGIKIHDWKWEDPFRLTM
ToMA3-wild-type       MDTSVQKKKLGLKNRYAAMTRGLGWQTSYQPMEKVFPYDKYEGIKIHDWKWEDPFRLTM
ToMA3_A113V           MDTSVQKKKLGLKNRYAAMTRGLGWQTSYQPMEKVFPYDKYEGIKIHDWKWEDPFRLTM
ToMA3_V106S/A113V     MDTSVQKKKLGLKNRYAAMTRGLGWQTSYQPMEKVFPYDKYEGIKIHDWKWEDPFRLTM
                      ************************************************************

ToMA3_A113I           DAYWKYQGEKEKKLYAVIDAFAQNNGQLSISDARYVNALKVFIQGVTPLEYMIHRGFAHI
ToMA3_A113G           DAYWKYQGEKEKKLYAVIDAFAQNNGQLSISDARYVNALKVFIQGVTPLEYMGHRGFAHI
ToMA3_A113S           DAYWKYQGEKEKKLYAVIDAFAQNNGQLSISDARYVNALKVFIQGVTPLEYMSHRGFAHI
ToMA3_A113F           DAYWKYQGEKEKKLYAVIDAFAQNNGQLSISDARYVNALKVFIQGVTPLEYMFHRGFAHI
ToMA3_A113H           DAYWKYQGEKEKKLYAVIDAFAQNNGQLSISDARYVNALKVFIQGVTPLEYMHHRGFAHI
ToMA3-wild-type       DAYWKYQGEKEKKLYAVIDAFAQNNGQLSISDARYVNALKVFIQGVTPLEYMAHRGFAHI
ToMA3_A113V           DAYWKYQGEKEKKLYAVIDAFAQNNGQLSISDARYVNALKVFIQGVTPLEYMVHRGFAHI
ToMA3_V106S/A113V     DAYWKYQGEKEKKLYAVIDAFAQNNGQLSISDARYVNALKVFIQGSTPLEYMVHRGFAHI
                      ******************************************** ********* ******

ToMA3_A113I           GRHFTGEGARVACQMQSIDELRHFQTEMHALSHYNKYFNGLHNSIHWYDRVWYLSVPKSF
ToMA3_A113G           GRHFTGEGARVACQMQSIDELRHFQTEMHALSHYNKYFNGLHNSIHWYDRVWYLSVPKSF
ToMA3_A113S           GRHFTGEGARVACQMQSIDELRHFQTEMHALSHYNKYFNGLHNSIHWYDRVWYLSVPKSF
ToMA3_A113F           GRHFTGEGARVACQMQSIDELRHFQTEMHALSHYNKYFNGLHNSIHWYDRVWYLSVPKSF
ToMA3_A113H           GRHFTGEGARVACQMQSIDELRHFQTEMHALSHYNKYFNGLHNSIHWYDRVWYLSVPKSF
ToMA3-wild-type       GRHFTGEGARVACQMQSIDELRHFQTEMHALSHYNKYFNGLHNSIHWYDRVWYLSVPKSF
ToMA3_A113V           GRHFTGEGARVACQMQSIDELRHFQTEMHALSHYNKYFNGLHNSIHWYDRVWYLSVPKSF
ToMA3_V106S/A113V     GRHFTGEGARVACQMQSIDELRHFQTEMHALSHYNKYFNGLHNSIHWYDRVWYLSVPKSF
                      ************************************************************

ToMA3_A113I           FEDAATGGPFEFLTAVSFSFEYVLTNLLFVPFMSGAAYNGDMSTVTFGFSAQSDESRHMT
ToMA3_A113G           FEDAATGGPFEFLTAVSFSFEYVLTNLLFVPFMSGAAYNGDMSTVTFGFSAQSDESRHMT
ToMA3_A113S           FEDAATGGPFEFLTAVSFSFEYVLTNLLFVPFMSGAAYNGDMSTVTFGFSAQSDESRHMT
ToMA3_A113F           FEDAATGGPFEFLTAVSFSFEYVLTNLLFVPFMSGAAYNGDMSTVTFGFSAQSDESRHMT
ToMA3_A113H           FEDAATGGPFEFLTAVSFSFEYVLTNLLFVPFMSGAAYNGDMSTVTFGFSAQSDESRHMT
ToMA3-wild-type       FEDAATGGPFEFLTAVSFSFEYVLTNLLFVPFMSGAAYNGDMSTVTFGFSAQSDESRHMT
ToMA3_A113V           FEDAATGGPFEFLTAVSFSFEYVLTNLLFVPFMSGAAYNGDMSTVTFGFSAQSDESRHMT
ToMA3_V106S/A113V     FEDAATGGPFEFLTAVSFSFEYVLTNLLFVPFMSGAAYNGDMSTVTFGFSAQSDESRHMT
                      ************************************************************
```

(FIG. 3B)

```
ToMA3_A113I         LGIECIKFMLEQDPDNVPIVQRWIDKWFWRGYRLLSIVAMMQDYMLPNRVMSWRESWEMY
ToMA3_A113G         LGIECIKFMLEQDPDNVPIVQRWIDKWFWRGYRLLSIVAMMQDYMLPNRVMSWRESWEMY
ToMA3_A113S         LGIECIKFMLEQDPDNVPIVQRWIDKWFWRGYRLLSIVAMMQDYMLPNRVMSWRESWEMY
ToMA3_A113F         LGIECIKFMLEQDPDNVPIVQRWIDKWFWRGYRLLSIVAMMQDYMLPNRVMSWRESWEMY
ToMA3_A113H         LGIECIKFMLEQDPDNVPIVQRWIDKWFWRGYRLLSIVAMMQDYMLPNRVMSWRESWEMY
ToMA3-wild-type     LGIECIKFMLEQDPDNVPIVQRWIDKWFWRGYRLLSIVAMMQDYMLPNRVMSWRESWEMY
ToMA3_A113V         LGIECIKFMLEQDPDNVPIVQRWIDKWFWRGYRLLSIVAMMQDYMLPNRVMSWRESWEMY
ToMA3_V106S/A113V   LGIECIKFMLEQDPDNVPIVQRWIDKWFWRGYRLLSIVAMMQDYMLPNRVMSWRESWEMY
                    ************************************************************

ToMA3_A113I         VEQNGGALFKDLARYGIRKPKGWDQACEGKDHISHQTFAVFYNYNAAAPIHTWVPTKEEM
ToMA3_A113G         VEQNGGALFKDLARYGIRKPKGWDQACEGKDHISHQTFAVFYNYNAAAPIHTWVPTKEEM
ToMA3_A113S         VEQNGGALFKDLARYGIRKPKGWDQACEGKDHISHQTFAVFYNYNAAAPIHTWVPTKEEM
ToMA3_A113F         VEQNGGALFKDLARYGIRKPKGWDQACEGKDHISHQTFAVFYNYNAAAPIHTWVPTKEEM
ToMA3_A113H         VEQNGGALFKDLARYGIRKPKGWDQACEGKDHISHQTFAVFYNYNAAAPIHTWVPTKEEM
ToMA3-wild-type     VEQNGGALFKDLARYGIRKPKGWDQACEGKDHISHQTFAVFYNYNAAAPIHTWVPTKEEM
ToMA3_A113V         VEQNGGALFKDLARYGIRKPKGWDQACEGKDHISHQTFAVFYNYNAAAPIHTWVPTKEEM
ToMA3_V106S/A113V   VEQNGGALFKDLARYGIRKPKGWDQACEGKDHISHQTFAVFYNYNAAAPIHTWVPTKEEM
                    ************************************************************

ToMA3_A113I         GWLSEKYPETFDKYRPRWDYWREQAAKGNRFYNKTLPMLCTTCQIPMIFTEPGDATKIC
ToMA3_A113G         GWLSEKYPETFDKYRPRWDYWREQAAKGNRFYNKTLPMLCTTCQIPMIFTEPGDATKIC
ToMA3_A113S         GWLSEKYPETFDKYRPRWDYWREQAAKGNRFYNKTLPMLCTTCQIPMIFTEPGDATKIC
ToMA3_A113F         GWLSEKYPETFDKYRPRWDYWREQAAKGNRFYNKTLPMLCTTCQIPMIFTEPGDATKIC
ToMA3_A113H         GWLSEKYPETFDKYRPRWDYWREQAAKGNRFYNKTLPMLCTTCQIPMIFTEPGDATKIC
ToMA3-wild-type     GWLSEKYPETFDKYRPRWDYWREQAAKGNRFYNKTLPMLCTTCQIPMIFTEPGDATKIC
ToMA3_A113V         GWLSEKYPETFDKYRPRWDYWREQAAKGNRFYNKTLPMLCTTCQIPMIFTEPGDATKIC
ToMA3_V106S/A113V   GWLSEKYPETFDKYRPRWDYWREQAAKGNRFYNKTLPMLCTTCQIPMIFTEPGDATKIC
                    ***********************************************************

ToMA3_A113I         YRESAYLGDKYHFCSDHCKEIFDNEPEKFVQSWLPPQQVYQGNCFKPDADPTKEGFDPLM
ToMA3_A113G         YRESAYLGDKYHFCSDHCKEIFDNEPEKFVQSWLPPQQVYQGNCFKPDADPTKEGFDPLM
ToMA3_A113S         YRESAYLGDKYHFCSDHCKEIFDNEPEKFVQSWLPPQQVYQGNCFKPDADPTKEGFDPLM
ToMA3_A113F         YRESAYLGDKYHFCSDHCKEIFDNEPEKFVQSWLPPQQVYQGNCFKPDADPTKEGFDPLM
ToMA3_A113H         YRESAYLGDKYHFCSDHCKEIFDNEPEKFVQSWLPPQQVYQGNCFKPDADPTKEGFDPLM
ToMA3-wild-type     YRESAYLGDKYHFCSDHCKEIFDNEPEKFVQSWLPPQQVYQGNCFKPDADPTKEGFDPLM
ToMA3_A113V         YRESAYLGDKYHFCSDHCKEIFDNEPEKFVQSWLPPQQVYQGNCFKPDADPTKEGFDPLM
ToMA3_V106S/A113V   YRESAYLGDKYHFCSDHCKEIFDNEPEKFVQSWLPPQQVYQGNCFKPDADPTKEGFDPLM
                    ************************************************************
```

(FIG. 3C)
```
ToMA3_A113I          ALLDYYNLNVGRDNFDFEGSEDQKNFAAWRGEVLQGEAK
ToMA3_A113G          ALLDYYNLNVGRDNFDFEGSEDQKNFAAWRGEVLQGEAK
ToMA3_A113S          ALLDYYNLNVGRDNFDFEGSEDQKNFAAWRGEVLQGEAK
ToMA3_A113F          ALLDYYNLNVGRDNFDFEGSEDQKNFAAWRGEVLQGEAK
ToMA3_A113H          ALLDYYNLNVGRDNFDFEGSEDQKNFAAWRGEVLQGEAK
ToMA3-wild-type      ALLDYYNLNVGRDNFDFEGSEDQKNFAAWRGEVLQGEAK
ToMA3_A113V          ALLDYYNLNVGRDNFDFEGSEDQKNFAAWRGEVLQGEAK
ToMA3_V106S/A113V    ALLDYYNLNVGRDNFDFEGSEDQKNFAAWRGEVLQGEAK
                     **************************************
```

FIGURE 4A

| | |
|---|---|
| ToMA3-wild-type | ATGGACACTTCTGTGCAGAAGAAGAAGAAACTCGGTTTAAAGAATCGTACGCAGCGATGACC |
| ToMA3_A113V | ATGGACACTTCTGTGCAGAAGAAGAAGAAACTCGGTTTAAAGAATCGTACGCAGCGATGACC |
| ToMA3_V106S/A113V | ATGGACACTTCTGTGCAGAAGAAGAAGAAACTCGGTTTAAAGAATCGTACGCAGCGATGACC |
| ToMA3_A113H | ATGGACACTTCTGTGCAGAAGAAGAAGAAACTCGGTTTAAAGAATCGTACGCAGCGATGACC |
| ToMA3_A113S | ATGGACACTTCTGTGCAGAAGAAGAAGAAACTCGGTTTAAAGAATCGTACGCAGCGATGACC |
| ToMA3_A113F | ATGGACACTTCTGTGCAGAAGAAGAAGAAACTCGGTTTAAAGAATCGTACGCAGCGATGACC |
| ToMA3_A113G | ATGGACACTTCTGTGCAGAAGAAGAAGAAACTCGGTTTAAAGAATCGTACGCAGCGATGACC |
| ToMA3_A113I | ATGGACACTTCTGTGCAGAAGAAGAAGAAACTCGGTTTAAAGAATCGTACGCAGCGATGACC |
| | ************************************************************ |
| ToMA3-wild-type | CGCGGTCTTGGCTGGCAGACCAGCTACCAGCCGATGGAGAAAGTGTTTCCGTACGACAAG |
| ToMA3_A113V | CGCGGTCTTGGCTGGCAGACCAGCTACCAGCCGATGGAGAAAGTGTTTCCGTACGACAAG |
| ToMA3_V106S/A113V | CGCGGTCTTGGCTGGCAGACCAGCTACCAGCCGATGGAGAAAGTGTTTCCGTACGACAAG |
| ToMA3_A113H | CGCGGTCTTGGCTGGCAGACCAGCTACCAGCCGATGGAGAAAGTGTTTCCGTACGACAAG |
| ToMA3_A113S | CGCGGTCTTGGCTGGCAGACCAGCTACCAGCCGATGGAGAAAGTGTTTCCGTACGACAAG |
| ToMA3_A113F | CGCGGTCTTGGCTGGCAGACCAGCTACCAGCCGATGGAGAAAGTGTTTCCGTACGACAAG |
| ToMA3_A113G | CGCGGTCTTGGCTGGCAGACCAGCTACCAGCCGATGGAGAAAGTGTTTCCGTACGACAAG |
| ToMA3_A113I | CGCGGTCTTGGCTGGCAGACCAGCTACCAGCCGATGGAGAAAGTGTTTCCGTACGACAAG |
| | ************************************************************ |
| ToMA3-wild-type | TACGAAGGCATCAAGATCCACGATTGGGATAAATGGGAAGACCCCTTCCGCCTGACCATG |
| ToMA3_A113V | TACGAAGGCATCAAGATCCACGATTGGGATAAATGGGAAGACCCCTTCCGCCTGACCATG |
| ToMA3_V106S/A113V | TACGAAGGCATCAAGATCCACGATTGGGATAAATGGGAAGACCCCTTCCGCCTGACCATG |
| ToMA3_A113H | TACGAAGGCATCAAGATCCACGATTGGGATAAATGGGAAGACCCCTTCCGCCTGACCATG |
| ToMA3_A113S | TACGAAGGCATCAAGATCCACGATTGGGATAAATGGGAAGACCCCTTCCGCCTGACCATG |
| ToMA3_A113F | TACGAAGGCATCAAGATCCACGATTGGGATAAATGGGAAGACCCCTTCCGCCTGACCATG |
| ToMA3_A113G | TACGAAGGCATCAAGATCCACGATTGGGATAAATGGGAAGACCCCTTCCGCCTGACCATG |
| ToMA3_A113I | TACGAAGGCATCAAGATCCACGATTGGGATAAATGGGAAGACCCCTTCCGCCTGACCATG |
| | ************************************************************ |
| ToMA3-wild-type | GACGCCTACTGGAAATATCAGGGCGAGAAGGAGAAGAAAAAAGCTTTACGCCGTCATCGACGCT |
| ToMA3_A113V | GACGCCTACTGGAAATATCAGGGCGAGAAGGAGAAGAAAAAAGCTTTACGCCGTCATCGACGCT |
| ToMA3_V106S/A113V | GACGCCTACTGGAAATATCAGGGCGAGAAGGAGAAGAAAAAAGCTTTACGCCGTCATCGACGCT |
| ToMA3_A113H | GACGCCTACTGGAAATATCAGGGCGAGAAGGAGAAGAAAAAAGCTTTACGCCGTCATCGACGCT |
| ToMA3_A113S | GACGCCTACTGGAAATATCAGGGCGAGAAGGAGAAGAAAAAAGCTTTACGCCGTCATCGACGCT |
| ToMA3_A113F | GACGCCTACTGGAAATATCAGGGCGAGAAGGAGAAGAAAAAAGCTTTACGCCGTCATCGACGCT |
| ToMA3_A113G | GACGCCTACTGGAAATATCAGGGCGAGAAGGAGAAGAAAAAAGCTTTACGCCGTCATCGACGCT |
| ToMA3_A113I | GACGCCTACTGGAAATATCAGGGCGAGAAGGAGAAGAAAAAAGCTTTACGCCGTCATCGACGCT |
| | ************************************************************ |

(FIG. 4B)

```
ToMA3-wild-type      TTCGCGCAGAACAACGGGCAGTTGAGCATTTCCGACGCGCGATATGTCAACGCACTCAAG
ToMA3_A113V          TTCGCGCAGAACAACGGGCAGTTGAGCATTTCCGACGCGCGATATGTCAACGCACTCAAG
ToMA3_V106S/A113V    TTCGCGCAGAACAACGGGCAGTTGAGCATTTCCGACGCGCGATATGTCAACGCACTCAAG
ToMA3_A113H          TTCGCGCAGAACAACGGGCAGTTGAGCATTTCCGACGCGCGATATGTCAACGCACTCAAG
ToMA3_A113S          TTCGCGCAGAACAACGGGCAGTTGAGCATTTCCGACGCGCGATATGTCAACGCACTCAAG
ToMA3_A113F          TTCGCGCAGAACAACGGGCAGTTGAGCATTTCCGACGCGCGATATGTCAACGCACTCAAG
ToMA3_A113G          TTCGCGCAGAACAACGGGCAGTTGAGCATTTCCGACGCGCGATATGTCAACGCACTCAAG
ToMA3_A113I          TTCGCGCAGAACAACGGGCAGTTGAGCATTTCCGACGCGCGATATGTCAACGCACTCAAG
                     ************************************************************

ToMA3-wild-type      GTGTTTATCCAGGGTGTGACACCGTTGGAGTATATGGCACACCGAGGTTTTGCCCACATT
ToMA3_A113V          GTGTTTATCCAGGGTGTGACACCGTTGGAGTATATGGTTCACCGAGGTTTTGCCCACATT
ToMA3_V106S/A113V    GTGTTTATCCAGGGTTCCACACCGTTGGAGTATATGGTTCACCGAGGTTTTGCCCACATT
ToMA3_A113H          GTGTTTATCCAGGGTGTGACACCGTTGGAGTATATGCATCACCGAGGTTTTGCCCACATT
ToMA3_A113S          GTGTTTATCCAGGGTGTGACACCGTTGGAGTATATGAGTCACCGAGGTTTTGCCCACATT
ToMA3_A113F          GTGTTTATCCAGGGTGTGACACCGTTGGAGTATATGTTTCACCGAGGTTTTGCCCACATT
ToMA3_A113G          GTGTTTATCCAGGGTGTGACACCGTTGGAGTATATGGGCACCGAGGTTTTGCCCACATT
ToMA3_A113I          GTGTTTATCCAGGGTGTGACACCGTTGGAGTATATGATCCACCGAGGTTTTGCCCACATT
                     ***********************************    *********************

ToMA3-wild-type      GGTCGGCATTTTACGGGTGAAGGGCACGTGTTGCTTGCCAGATGCAGTCCATCGACGAG
ToMA3_A113V          GGTCGGCATTTTACGGGTGAAGGGGCACGTGTTGCTTGCCAGATGCAGTCCATCGACGAG
ToMA3_V106S/A113V    GGTCGGCATTTTACGGGTGAAGGGGCACGTGTTGCTTGCCAGATGCAGTCCATCGACGAG
ToMA3_A113H          GGTCGGCATTTTACGGGTGAAGGGGCACGTGTTGCTTGCCAGATGCAGTCCATCGACGAG
ToMA3_A113S          GGTCGGCATTTTACGGGTGAAGGGGCACGTGTTGCTTGCCAGATGCAGTCCATCGACGAG
ToMA3_A113F          GGTCGGCATTTTACGGGTGAAGGGGCACGTGTTGCTTGCCAGATGCAGTCCATCGACGAG
ToMA3_A113G          GGTCGGCATTTTACGGGTGAAGGGGCACGTGTTGCTTGCCAGATGCAGTCCATCGACGAG
ToMA3_A113I          GGTCGGCATTTTACGGGTGAAGGGGCACGTGTTGCTTGCCAGATGCAGTCCATCGACGAG
                     ************************************************************

ToMA3-wild-type      CTGCGTCACTTCCAGACCGAAATGCATGCTCTCTCGCACTACAACAAGTATTTTAACGGT
ToMA3_A113V          CTGCGTCACTTCCAGACCGAAATGCATGCTCTCTCGCACTACAACAAGTATTTTAACGGT
ToMA3_V106S/A113V    CTGCGTCACTTCCAGACCGAAATGCATGCTCTCTCGCACTACAACAAGTATTTTAACGGT
ToMA3_A113H          CTGCGTCACTTCCAGACCGAAATGCATGCTCTCTCGCACTACAACAAGTATTTTAACGGT
ToMA3_A113S          CTGCGTCACTTCCAGACCGAAATGCATGCTCTCTCGCACTACAACAAGTATTTTAACGGT
ToMA3_A113F          CTGCGTCACTTCCAGACCGAAATGCATGCTCTCTCGCACTACAACAAGTATTTTAACGGT
ToMA3_A113G          CTGCGTCACTTCCAGACCGAAATGCATGCTCTCTCGCACTACAACAAGTATTTTAACGGT
ToMA3_A113I          CTGCGTCACTTCCAGACCGAAATGCATGCTCTCTCGCACTACAACAAGTATTTTAACGGT
                     ************************************************************
```

(FIG. 4C)

| | |
|---|---|
| ToMA3-wild-type | CTGCACAACTCCATTCATTGGTACGACCGGGTTTGGTATTTGTCGGTGCCCAAGTCATTT |
| ToMA3_A113V | CTGCACAACTCCATTCATTGGTACGACCGGGTTTGGTATTTGTCGGTGCCCAAGTCATTT |
| ToMA3_V106S/A113V | CTGCACAACTCCATTCATTGGTACGACCGGGTTTGGTATTTGTCGGTGCCCAAGTCATTT |
| ToMA3_A113H | CTGCACAACTCCATTCATTGGTACGACCGGGTTTGGTATTTGTCGGTGCCCAAGTCATTT |
| ToMA3_A113S | CTGCACAACTCCATTCATTGGTACGACCGGGTTTGGTATTTGTCGGTGCCCAAGTCATTT |
| ToMA3_A113F | CTGCACAACTCCATTCATTGGTACGACCGGGTTTGGTATTTGTCGGTGCCCAAGTCATTT |
| ToMA3_A113G | CTGCACAACTCCATTCATTGGTACGACCGGGTTTGGTATTTGTCGGTGCCCAAGTCATTT |
| ToMA3_A113I | CTGCACAACTCCATTCATTGGTACGACCGGGTTTGGTATTTGTCGGTGCCCAAGTCATTT |
| | ************************************************************ |
| ToMA3-wild-type | TTTGAAGACGGCGCACCGTGGACCGTTCGAGTTTCTTACCGCGGTGAGCTTTTCGTTC |
| ToMA3_A113V | TTTGAAGACGGCGCACCGTGGACCGTTCGAGTTTCTTACCGCGGTGAGCTTTTCGTTC |
| ToMA3_V106S/A113V | TTTGAAGACGGCGCACCGTGGACCGTTCGAGTTTCTTACCGCGGTGAGCTTTTCGTTC |
| ToMA3_A113H | TTTGAAGACGGCGCACCGTGGACCGTTCGAGTTTCTTACCGCGGTGAGCTTTTCGTTC |
| ToMA3_A113S | TTTGAAGACGGCGCACCGTGGACCGTTCGAGTTTCTTACCGCGGTGAGCTTTTCGTTC |
| ToMA3_A113F | TTTGAAGACGGCGCACCGTGGACCGTTCGAGTTTCTTACCGCGGTGAGCTTTTCGTTC |
| ToMA3_A113G | TTTGAAGACGGCGCACCGTGGACCGTTCGAGTTTCTTACCGCGGTGAGCTTTTCGTTC |
| ToMA3_A113I | TTTGAAGACGGCGCACCGTGGACCGTTCGAGTTTCTTACCGCGGTGAGCTTTTCGTTC |
| | ************************************************************ |
| ToMA3-wild-type | GAATATGTGTTGACCAACCTGCTGTTGTCCCCTTCATGTCGGTGCTGCTTACAACGGG |
| ToMA3_A113V | GAATATGTGTTGACCAACCTGCTGTTGTCCCCTTCATGTCGGTGCTGCTTACAACGGG |
| ToMA3_V106S/A113V | GAATATGTGTTGACCAACCTGCTGTTGTCCCCTTCATGTCGGTGCTGCTTACAACGGG |
| ToMA3_A113H | GAATATGTGTTGACCAACCTGCTGTTGTCCCCTTCATGTCGGTGCTGCTTACAACGGG |
| ToMA3_A113S | GAATATGTGTTGACCAACCTGCTGTTGTCCCCTTCATGTCGGTGCTGCTTACAACGGG |
| ToMA3_A113F | GAATATGTGTTGACCAACCTGCTGTTGTCCCCTTCATGTCGGTGCTGCTTACAACGGG |
| ToMA3_A113G | GAATATGTGTTGACCAACCTGCTGTTGTCCCCTTCATGTCGGTGCTGCTTACAACGGG |
| ToMA3_A113I | GAATATGTGTTGACCAACCTGCTGTTGTCCCCTTCATGTCGGTGCTGCTTACAACGGG |
| | ************************************************************ |
| ToMA3-wild-type | GACATGTCTACGGTCACTTTCGGTTTTTCGGCGCAAAGTGACGAATCGCGCCACATGACA |
| ToMA3_A113V | GACATGTCTACGGTCACTTTCGGTTTTTCGGCGCAAAGTGACGAATCGCGCCACATGACA |
| ToMA3_V106S/A113V | GACATGTCTACGGTCACTTTCGGTTTTTCGGCGCAAAGTGACGAATCGCGCCACATGACA |
| ToMA3_A113H | GACATGTCTACGGTCACTTTCGGTTTTTCGGCGCAAAGTGACGAATCGCGCCACATGACA |
| ToMA3_A113S | GACATGTCTACGGTCACTTTCGGTTTTTCGGCGCAAAGTGACGAATCGCGCCACATGACA |
| ToMA3_A113F | GACATGTCTACGGTCACTTTCGGTTTTTCGGCGCAAAGTGACGAATCGCGCCACATGACA |
| ToMA3_A113G | GACATGTCTACGGTCACTTTCGGTTTTTCGGCGCAAAGTGACGAATCGCGCCACATGACA |
| ToMA3_A113I | GACATGTCTACGGTCACTTTCGGTTTTTCGGCGCAAAGTGACGAATCGCGCCACATGACA |
| | ************************

(FIG. 4D)

```
ToMA3-wild-type      CTCGGCATCGAATGCATCAAGTTCATGCTAGAACAGGATCCGACAACGTGCCCATCGTG
ToMA3_A113V          CTCGGCATCGAATGCATCAAGTTCATGCTAGAACAGGATCCGACAACGTGCCCATCGTG
ToMA3_V106S/A113V    CTCGGCATCGAATGCATCAAGTTCATGCTAGAACAGGATCCGACAACGTGCCCATCGTG
ToMA3_A113H          CTCGGCATCGAATGCATCAAGTTCATGCTAGAACAGGATCCGACAACGTGCCCATCGTG
ToMA3_A113S          CTCGGCATCGAATGCATCAAGTTCATGCTAGAACAGGATCCGACAACGTGCCCATCGTG
ToMA3_A113F          CTCGGCATCGAATGCATCAAGTTCATGCTAGAACAGGATCCGACAACGTGCCCATCGTG
ToMA3_A113G          CTCGGCATCGAATGCATCAAGTTCATGCTAGAACAGGATCCGACAACGTGCCCATCGTG
ToMA3_A113I          CTCGGCATCGAATGCATCAAGTTCATGCTAGAACAGGATCCGACAACGTGCCCATCGTG
                     ************************************************************

ToMA3-wild-type      CAGCGCTGGATCGACAAGTGGTTCTGCGCGGCTATCGCTGTTGAGCATCGTGGCCATG
ToMA3_A113V          CAGCGCTGGATCGACAAGTGGTTCTGCGCGGCTATCGCTGTTGAGCATCGTGGCCATG
ToMA3_V106S/A113V    CAGCGCTGGATCGACAAGTGGTTCTGCGCGGCTATCGCTGTTGAGCATCGTGGCCATG
ToMA3_A113H          CAGCGCTGGATCGACAAGTGGTTCTGCGCGGCTATCGCTGTTGAGCATCGTGGCCATG
ToMA3_A113S          CAGCGCTGGATCGACAAGTGGTTCTGCGCGGCTATCGCTGTTGAGCATCGTGGCCATG
ToMA3_A113F          CAGCGCTGGATCGACAAGTGGTTCTGCGCGGCTATCGCTGTTGAGCATCGTGGCCATG
ToMA3_A113G          CAGCGCTGGATCGACAAGTGGTTCTGCGCGGCTATCGCTGTTGAGCATCGTGGCCATG
ToMA3_A113I          CAGCGCTGGATCGACAAGTGGTTCTGCGCGGCTATCGCTGTTGAGCATCGTGGCCATG
                     ************************************************************

ToMA3-wild-type      ATGCAGGACTACATGCTGCCCAACCGGTGATGAGCTGGCGCGAGAGCTGGGAGATGTAC
ToMA3_A113V          ATGCAGGACTACATGCTGCCCAACCGGTGATGAGCTGGCGCGAGAGCTGGGAGATGTAC
ToMA3_V106S/A113V    ATGCAGGACTACATGCTGCCCAACCGGTGATGAGCTGGCGCGAGAGCTGGGAGATGTAC
ToMA3_A113H          ATGCAGGACTACATGCTGCCCAACCGGTGATGAGCTGGCGCGAGAGCTGGGAGATGTAC
ToMA3_A113S          ATGCAGGACTACATGCTGCCCAACCGGTGATGAGCTGGCGCGAGAGCTGGGAGATGTAC
ToMA3_A113F          ATGCAGGACTACATGCTGCCCAACCGGTGATGAGCTGGCGCGAGAGCTGGGAGATGTAC
ToMA3_A113G          ATGCAGGACTACATGCTGCCCAACCGGTGATGAGCTGGCGCGAGAGCTGGGAGATGTAC
ToMA3_A113I          ATGCAGGACTACATGCTGCCCAACCGGTGATGAGCTGGCGCGAGAGCTGGGAGATGTAC
                     ************************************************************

ToMA3-wild-type      GTCGAGCAGAACGGCGGCGCGCGCTGTTCAAGGATCTTGCGCGTTATGGCATCCGCAAGCCC
ToMA3_A113V          GTCGAGCAGAACGGCGGCGCGCGCTGTTCAAGGATCTTGCGCGTTATGGCATCCGCAAGCCC
ToMA3_V106S/A113V    GTCGAGCAGAACGGCGGCGCGCGCTGTTCAAGGATCTTGCGCGTTATGGCATCCGCAAGCCC
ToMA3_A113H          GTCGAGCAGAACGGCGGCGCGCGCTGTTCAAGGATCTTGCGCGTTATGGCATCCGCAAGCCC
ToMA3_A113S          GTCGAGCAGAACGGCGGCGCGCGCTGTTCAAGGATCTTGCGCGTTATGGCATCCGCAAGCCC
ToMA3_A113F          GTCGAGCAGAACGGCGGCGCGCGCTGTTCAAGGATCTTGCGCGTTATGGCATCCGCAAGCCC
ToMA3_A113G          GTCGAGCAGAACGGCGGCGCGCGCTGTTCAAGGATCTTGCGCGTTATGGCATCCGCAAGCCC
ToMA3_A113I          GTCGAGCAGAACGGCGGCGCGCGCTGTTCAAGGATCTTGCGCGTTATGGCATCCGCAAGCCC
                     ************************************************************
```

(FIG. 4E)

```
ToMA3-wild-type      AAGGGCTGGGACCAGGCTTGCGAAGGCAAGGACCACATCAGCCATCAGACCTTCGCCGTA
ToMA3_A113V          AAGGGCTGGGACCAGGCTTGCGAAGGCAAGGACCACATCAGCCATCAGACCTTCGCCGTA
ToMA3_V106S/A113V    AAGGGCTGGGACCAGGCTTGCGAAGGCAAGGACCACATCAGCCATCAGACCTTCGCCGTA
ToMA3_A113H          AAGGGCTGGGACCAGGCTTGCGAAGGCAAGGACCACATCAGCCATCAGACCTTCGCCGTA
ToMA3_A113S          AAGGGCTGGGACCAGGCTTGCGAAGGCAAGGACCACATCAGCCATCAGACCTTCGCCGTA
ToMA3_A113F          AAGGGCTGGGACCAGGCTTGCGAAGGCAAGGACCACATCAGCCATCAGACCTTCGCCGTA
ToMA3_A113G          AAGGGCTGGGACCAGGCTTGCGAAGGCAAGGACCACATCAGCCATCAGACCTTCGCCGTA
ToMA3_A113I          AAGGGCTGGGACCAGGCTTGCGAAGGCAAGGACCACATCAGCCATCAGACCTTCGCCGTA
                     ************************************************************

ToMA3-wild-type      TTCTATAACTATAACGCCGGCCCCCATCCACACCTGGGTTCCCACAAAGAAGAAATG
ToMA3_A113V          TTCTATAACTATAACGCCGGCCCCCATCCACACCTGGGTTCCCACAAAGAAGAAATG
ToMA3_V106S/A113V    TTCTATAACTATAACGCCGGCCCCCATCCACACCTGGGTTCCCACAAAGAAGAAATG
ToMA3_A113H          TTCTATAACTATAACGCCGGCCCCCATCCACACCTGGGTTCCCACAAAGAAGAAATG
ToMA3_A113S          TTCTATAACTATAACGCCGGCCCCCATCCACACCTGGGTTCCCACAAAGAAGAAATG
ToMA3_A113F          TTCTATAACTATAACGCCGGCCCCCATCCACACCTGGGTTCCCACAAAGAAGAAATG
ToMA3_A113G          TTCTATAACTATAACGCCGGCCCCCATCCACACCTGGGTTCCCACAAAGAAGAAATG
ToMA3_A113I          TTCTATAACTATAACGCCGGCCCCCATCCACACCTGGGTTCCCACAAAGAAGAAATG
                     ************************************************************

ToMA3-wild-type      GGATGGCGTGTCGGAGAAGTACCCCGAGACGTTCGACAAGTATTACCGTCCGCGTTGGGAC
ToMA3_A113V          GGATGGCGTGTCGGAGAAGTACCCCGAGACGTTCGACAAGTATTACCGTCCGCGTTGGGAC
ToMA3_V106S/A113V    GGATGGCGTGTCGGAGAAGTACCCCGAGACGTTCGACAAGTATTACCGTCCGCGTTGGGAC
ToMA3_A113H          GGATGGCGTGTCGGAGAAGTACCCCGAGACGTTCGACAAGTATTACCGTCCGCGTTGGGAC
ToMA3_A113S          GGATGGCGTGTCGGAGAAGTACCCCGAGACGTTCGACAAGTATTACCGTCCGCGTTGGGAC
ToMA3_A113F          GGATGGCGTGTCGGAGAAGTACCCCGAGACGTTCGACAAGTATTACCGTCCGCGTTGGGAC
ToMA3_A113G          GGATGGCGTGTCGGAGAAGTACCCCGAGACGTTCGACAAGTATTACCGTCCGCGTTGGGAC
ToMA3_A113I          GGATGGCGTGTCGGAGAAGTACCCCGAGACGTTCGACAAGTATTACCGTCCGCGTTGGGAC
                     ************************************************************

ToMA3-wild-type      TACTGGCGCGAGCAGGCCGCCAAGGGCAACCGTTTCTACAACAAGACGCTGCCGATGCTC
ToMA3_A113V          TACTGGCGCGAGCAGGCCGCCAAGGGCAACCGTTTCTACAACAAGACGCTGCCGATGCTC
ToMA3_V106S/A113V    TACTGGCGCGAGCAGGCCGCCAAGGGCAACCGTTTCTACAACAAGACGCTGCCGATGCTC
ToMA3_A113H          TACTGGCGCGAGCAGGCCGCCAAGGGCAACCGTTTCTACAACAAGACGCTGCCGATGCTC
ToMA3_A113S          TACTGGCGCGAGCAGGCCGCCAAGGGCAACCGTTTCTACAACAAGACGCTGCCGATGCTC
ToMA3_A113F          TACTGGCGCGAGCAGGCCGCCAAGGGCAACCGTTTCTACAACAAGACGCTGCCGATGCTC
ToMA3_A113G          TACTGGCGCGAGCAGGCCGCCAAGGGCAACCGTTTCTACAACAAGACGCTGCCGATGCTC
ToMA3_A113I          TACTGGCGCGAGCAGGCCGCCAAGGGCAACCGTTTCTACAACAAGACGCTGCCGATGCTC
                     ************************************************************
```

(FIG. 4F)

```
ToMA3-wild-type    TGCACTACCTGCCAGATTCCGATGATATTCACCGAGCCTGGCGACGCAACCAAGATCTGC
ToMA3_A113V        TGCACTACCTGCCAGATTCCGATGATATTCACCGAGCCTGGCGACGCAACCAAGATCTGC
ToMA3_V106S/A113V  TGCACTACCTGCCAGATTCCGATGATATTCACCGAGCCTGGCGACGCAACCAAGATCTGC
ToMA3_A113H        TGCACTACCTGCCAGATTCCGATGATATTCACCGAGCCTGGCGACGCAACCAAGATCTGC
ToMA3_A113S        TGCACTACCTGCCAGATTCCGATGATATTCACCGAGCCTGGCGACGCAACCAAGATCTGC
ToMA3_A113F        TGCACTACCTGCCAGATTCCGATGATATTCACCGAGCCTGGCGACGCAACCAAGATCTGC
ToMA3_A113G        TGCACTACCTGCCAGATTCCGATGATATTCACCGAGCCTGGCGACGCAACCAAGATCTGC
ToMA3_A113I        TGCACTACCTGCCAGATTCCGATGATATTCACCGAGCCTGGCGACGCAACCAAGATCTGC
                   ************************************************************

ToMA3-wild-type    TATCGCGAGTCGGCCTACCTCGGCGACAAGTATCACTTCTGCAGCGACCACTGCAAGGAG
ToMA3_A113V        TATCGCGAGTCGGCCTACCTCGGCGACAAGTATCACTTCTGCAGCGACCACTGCAAGGAG
ToMA3_V106S/A113V  TATCGCGAGTCGGCCTACCTCGGCGACAAGTATCACTTCTGCAGCGACCACTGCAAGGAG
ToMA3_A113H        TATCGCGAGTCGGCCTACCTCGGCGACAAGTATCACTTCTGCAGCGACCACTGCAAGGAG
ToMA3_A113S        TATCGCGAGTCGGCCTACCTCGGCGACAAGTATCACTTCTGCAGCGACCACTGCAAGGAG
ToMA3_A113F        TATCGCGAGTCGGCCTACCTCGGCGACAAGTATCACTTCTGCAGCGACCACTGCAAGGAG
ToMA3_A113G        TATCGCGAGTCGGCCTACCTCGGCGACAAGTATCACTTCTGCAGCGACCACTGCAAGGAG
ToMA3_A113I        TATCGCGAGTCGGCCTACCTCGGCGACAAGTATCACTTCTGCAGCGACCACTGCAAGGAG
                   ************************************************************

ToMA3-wild-type    ATTTTTGACAACGAACCCGAAAAGTTCGTGCAGTCAGTCATGGCTTCCGCCGCAGCAAGTGTAT
ToMA3_A113V        ATTTTTGACAACGAACCCGAAAAGTTCGTGCAGTCAGTCATGGCTTCCGCCGCAGCAAGTGTAT
ToMA3_V106S/A113V  ATTTTTGACAACGAACCCGAAAAGTTCGTGCAGTCAGTCATGGCTTCCGCCGCAGCAAGTGTAT
ToMA3_A113H        ATTTTTGACAACGAACCCGAAAAGTTCGTGCAGTCAGTCATGGCTTCCGCCGCAGCAAGTGTAT
ToMA3_A113S        ATTTTTGACAACGAACCCGAAAAGTTCGTGCAGTCAGTCATGGCTTCCGCCGCAGCAAGTGTAT
ToMA3_A113F        ATTTTTGACAACGAACCCGAAAAGTTCGTGCAGTCAGTCATGGCTTCCGCCGCAGCAAGTGTAT
ToMA3_A113G        ATTTTTGACAACGAACCCGAAAAGTTCGTGCAGTCAGTCATGGCTTCCGCCGCAGCAAGTGTAT
ToMA3_A113I        ATTTTTGACAACGAACCCGAAAAGTTCGTGCAGTCAGTCATGGCTTCCGCCGCAGCAAGTGTAT
                   ************************************************************

ToMA3-wild-type    CAAGGAAACTGTTTCAAGCCGGATGCCGATCCGACCAAGGAGGGTTTTGATCCCTTGATG
ToMA3_A113V        CAAGGAAACTGTTTCAAGCCGGATGCCGATCCGACCAAGGAGGGTTTTGATCCCTTGATG
ToMA3_V106S/A113V  CAAGGAAACTGTTTCAAGCCGGATGCCGATCCGACCAAGGAGGGTTTTGATCCCTTGATG
ToMA3_A113H        CAAGGAAACTGTTTCAAGCCGGATGCCGATCCGACCAAGGAGGGTTTTGATCCCTTGATG
ToMA3_A113S        CAAGGAAACTGTTTCAAGCCGGATGCCGATCCGACCAAGGAGGGTTTTGATCCCTTGATG
ToMA3_A113F        CAAGGAAACTGTTTCAAGCCGGATGCCGATCCGACCAAGGAGGGTTTTGATCCCTTGATG
ToMA3_A113G        CAAGGAAACTGTTTCAAGCCGGATGCCGATCCGACCAAGGAGGGTTTTGATCCCTTGATG
ToMA3_A113I        CAAGGAAACTGTTTCAAGCCGGATGCCGATCCGACCAAGGAGGGTTTTGATCCCTTGATG
                   ************************************************************
```

(FIG. 4G)

```
ToMA3-wild-type    GCCTTGCTCTCGACTACTACAACCTGAATGTAGGCCGGACAACTTCGATTTCGAGGGATCG
ToMA3_A113V        GCCTTGCTCTCGACTACTACAACCTGAATGTAGGCCGGACAACTTCGATTTCGAGGGATCG
ToMA3_V106S/A113V  GCCTTGCTCTCGACTACTACAACCTGAATGTAGGCCGGACAACTTCGATTTCGAGGGATCG
ToMA3_A113H        GCCTTGCTCTCGACTACTACAACCTGAATGTAGGCCGGACAACTTCGATTTCGAGGGATCG
ToMA3_A113S        GCCTTGCTCTCGACTACTACAACCTGAATGTAGGCCGGACAACTTCGATTTCGAGGGATCG
ToMA3_A113F        GCCTTGCTCTCGACTACTACAACCTGAATGTAGGCCGGACAACTTCGATTTCGAGGGATCG
ToMA3_A113G        GCCTTGCTCTCGACTACTACAACCTGAATGTAGGCCGGACAACTTCGATTTCGAGGGATCG
ToMA3_A113I        GCCTTGCTCTCGACTACTACAACCTGAATGTAGGCCGGACAACTTCGATTTCGAGGGATCG
                   ************************************************************

ToMA3-wild-type    GAAGACCAAAAGAACTTTGCTGCCTGGCGTGGAGAGGTCTTGCAAGGAGAAGCCAAATGA
ToMA3_A113V        GAAGACCAAAAGAACTTTGCTGCCTGGCGTGGAGAGGTCTTGCAAGGAGAAGCCAAATGA
ToMA3_V106S/A113V  GAAGACCAAAAGAACTTTGCTGCCTGGCGTGGAGAGGTCTTGCAAGGAGAAGCCAAATGA
ToMA3_A113H        GAAGACCAAAAGAACTTTGCTGCCTGGCGTGGAGAGGTCTTGCAAGGAGAAGCCAAATGA
ToMA3_A113S        GAAGACCAAAAGAACTTTGCTGCCTGGCGTGGAGAGGTCTTGCAAGGAGAAGCCAAATGA
ToMA3_A113F        GAAGACCAAAAGAACTTTGCTGCCTGGCGTGGAGAGGTCTTGCAAGGAGAAGCCAAATGA
ToMA3_A113G        GAAGACCAAAAGAACTTTGCTGCCTGGCGTGGAGAGGTCTTGCAAGGAGAAGCCAAATGA
ToMA3_A113I        GAAGACCAAAAGAACTTTGCTGCCTGGCGTGGAGAGGTCTTGCAAGGAGAAGCCAAATGA
                   ***********************************************************
```

FIGURE 5A

| | |
|---|---|
| T4MO_G103A/A107S | ATGGCGATGCACCCACGTAAAGACTGGTATGAACTGGTATGAACTGACCAGGGCGACAAATTGGACACCT |
| T4MO_G103S | ATGGCGATGCACCCACGTAAAGACTGGTATGAACTGGTATGAACTGACCAGGGCGACAAATTGGACACCT |
| T4MO_I100A | ATGGCGATGCACCCACGTAAAGACTGGTATGAACTGGTATGAACTGACCAGGGCGACAAATTGGACACCT |
| T4MO_I100S | ATGGCGATGCACCCACGTAAAGACTGGTATGAACTGGTATGAACTGACCAGGGCGACAAATTGGACACCT |
| T4MO-wild_type | ATGGCGATGCACCCACGTAAAGACTGGTATGAACTGGTATGAACTGACCAGGGCGACAAATTGGACACCT |
| T4MO_G103S/A107G | ATGGCGATGCACCCACGTAAAGACTGGTATGAACTGGTATGAACTGACCAGGGCGACAAATTGGACACCT |
| T4MO_G103S/A107T | ATGGCGATGCACCCACGTAAAGACTGGTATGAACTGGTATGAACTGACCAGGGCGACAAATTGGACACCT |
| | ***************************************************************** |
| T4MO_G103A/A107S | AGCTATGTTACCGAAGAGCAGCTTTTCCCAGAGCGGATGTCCGGTCATATGGGTATCCCG |
| T4MO_G103S | AGCTATGTTACCGAAGAGCAGCTTTTCCCAGAGCGGATGTCCGGTCATATGGGTATCCCG |
| T4MO_I100A | AGCTATGTTACCGAAGAGCAGCTTTTCCCAGAGCGGATGTCCGGTCATATGGGTATCCCG |
| T4MO_I100S | AGCTATGTTACCGAAGAGCAGCTTTTCCCAGAGCGGATGTCCGGTCATATGGGTATCCCG |
| T4MO-wild_type | AGCTATGTTACCGAAGAGCAGCTTTTCCCAGAGCGGATGTCCGGTCATATGGGTATCCCG |
| T4MO_G103S/A107G | AGCTATGTTACCGAAGAGCAGCTTTTCCCAGAGCGGATGTCCGGTCATATGGGTATCCCG |
| T4MO_G103S/A107T | AGCTATGTTACCGAAGAGCAGCTTTTCCCAGAGCGGATGTCCGGTCATATGGGTATCCCG |
| | ***************************************************************** |
| T4MO_G103A/A107S | CTGGAAAAATGGGAAAGCTATGATGAGCCCTATAAGACATCCTATCCGGAGTACGTAAGT |
| T4MO_G103S | CTGGAAAAATGGGAAAGCTATGATGAGCCCTATAAGACATCCTATCCGGAGTACGTAAGT |
| T4MO_I100A | CTGGAAAAATGGGAAAGCTATGATGAGCCCTATAAGACATCCTATCCGGAGTACGTAAGT |
| T4MO_I100S | CTGGAAAAATGGGAAAGCTATGATGAGCCCTATAAGACATCCTATCCGGAGTACGTAAGT |
| T4MO-wild_type | CTGGAAAAATGGGAAAGCTATGATGAGCCCTATAAGACATCCTATCCGGAGTACGTAAGT |
| T4MO_G103S/A107G | CTGGAAAAATGGGAAAGCTATGATGAGCCCTATAAGACATCCTATCCGGAGTACGTAAGT |
| T4MO_G103S/A107T | CTGGAAAAATGGGAAAGCTATGATGAGCCCTATAAGACATCCTATCCGGAGTACGTAAGT |
| | ***************************************************************** |
| T4MO_G103A/A107S | ATCCAACGTGAAAAGGATGCAGGTGCTTATTCGGTGAAGGCGGCACTTGAGCGTGCAAAA |
| T4MO_G103S | ATCCAACGTGAAAAGGATGCAGGTGCTTATTCGGTGAAGGCGGCACTTGAGCGTGCAAAA |
| T4MO_I100A | ATCCAACGTGAAAAGGATGCAGGTGCTTATTCGGTGAAGGCGGCACTTGAGCGTGCAAAA |
| T4MO_I100S | ATCCAACGTGAAAAGGATGCAGGTGCTTATTCGGTGAAGGCGGCACTTGAGCGTGCAAAA |
| T4MO-wild_type | ATCCAACGTGAAAAGGATGCAGGTGCTTATTCGGTGAAGGCGGCACTTGAGCGTGCAAAA |
| T4MO_G103S/A107G | ATCCAACGTGAAAAGGATGCAGGTGCTTATTCGGTGAAGGCGGCACTTGAGCGTGCAAAA |
| T4MO_G103S/A107T | ATCCAACGTGAAAAGGATGCAGGTGCTTATTCGGTGAAGGCGGCACTTGAGCGTGCAAAA |
| | ***************************************************************** |

(FIG. 5B)

```
T4MO_G103A/A107S    ATTTATGAGAACTCTGACCCAGTTGGATCAGCAGCACTTTGAAATCCCATTACGGCGCCATC
T4MO_G103S          ATTTATGAGAACTCTGACCCAGTTGGATCAGCAGCACTTTGAAATCCCATTACGGCGCCATC
T4MO_I100A          ATTTATGAGAACTCTGACCCAGTTGGATCAGCAGCACTTTGAAATCCCATTACGGCGCCATC
T4MO_I100S          ATTTATGAGAACTCTGACCCAGTTGGATCAGCAGCACTTTGAAATCCCATTACGGCGCCTCT
T4MO-wild_type      ATTTATGAGAACTCTGACCCAGTTGGATCAGCAGCACTTTGAAATCCCATTACGGCGCCATC
T4MO_G103S/A107G    ATTTATGAGAACTCTGACCCAGTTGGATCAGCAGCACTTTGAAATCCCATTACGGCGCCATC
T4MO_G103S/A107T    ATTTATGAGAACTCTGACCCAGTTGGATCAGCAGCACTTTGAAATCCCATTACGGCGCCATC
                    ***********************************************************

T4MO_G103A/A107S    GCAGTTGCCGAATATGCATCCGTAACCGGTGAAGGTCGTATGGCCCGTTTTCAAAAGCA
T4MO_G103S          GCAGTTTCCGAATATGCAGCCGTAACCGGTGAAGGTCGTATGGCCCGTTTTCAAAAGCA
T4MO_I100A          GCAGTTGGTGAATATGCAGCCGTAACCGGTGAAGGTCGTATGGCCCGTTTTCAAAAGCA
T4MO_I100S          GCAGTTGGTGAATATGCAGCCGTAACCGGTGAAGGTCGTATGGCCCGTTTTCAAAAGCA
T4MO-wild_type      GCAGTTGGTGAATATGCAGCCGTAACCGGTGAAGGTCGTATGGCCCGTTTTCAAAAGCA
T4MO_G103S/A107G    GCAGTTTCCGAATATGCAGTGTAACCGGTGAAGGTCGTATGGCCCGTTTTCAAAAGCA
T4MO_G103S/A107T    GCAGTTTCAGAATATGCAACTGTAACCGGTGAAGGTCGTATGGCCCGTTTTCAAAAGCA
                    ******      ******       *********************************

T4MO_G103A/A107S    CCGGGAAATCGCAACATGGCTACGTTTGGCATGATGATGAACTGCGCCATGGCCAGTTA
T4MO_G103S          CCGGGAAATCGCAACATGGCTACGTTTGGCATGATGATGAACTGCGCCATGGCCAGTTA
T4MO_I100A          CCGGGAAATCGCAACATGGCTACGTTTGGCATGATGATGAACTGCGCCATGGCCAGTTA
T4MO_I100S          CCGGGAAATCGCAACATGGCTACGTTTGGCATGATGATGAACTGCGCCATGGCCAGTTA
T4MO-wild_type      CCGGGAAATCGCAACATGGCTACGTTTGGCATGATGATGAACTGCGCCATGGCCAGTTA
T4MO_G103S/A107G    CCGGGAAATCGCAACATGGCTACGTTTGGCATGATGATGAACTGCGCCATGGCCAGTTA
T4MO_G103S/A107T    CCGGGAAATCGCAACATGGCTACGTTTGGCATGATGATGAACTGCGCCATGGCCAGTTA
                    ***********************************************************

T4MO_G103A/A107S    CAGCTGTGTTTTTCCCGCATGAATACTGTAAGAAGAAGGATCGCCAGTTTGATTGGGCATGGCGG
T4MO_G103S          CAGCTGTGTTTTTCCCGCATGAATACTGTAAGAAGAAGGATCGCCAGTTTGATTGGGCATGGCGG
T4MO_I100A          CAGCTGTGTTTTTCCCGCATGAATACTGTAAGAAGAAGGATCGCCAGTTTGATTGGGCATGGCGG
T4MO_I100S          CAGCTGTGTTTTTCCCGCATGAATACTGTAAGAAGAAGGATCGCCAGTTTGATTGGGCATGGCGG
T4MO-wild_type      CAGCTGTGTTTTTCCCGCATGAATACTGTAAGAAGAAGGATCGCCAGTTTGATTGGGCATGGCGG
T4MO_G103S/A107G    CAGCTGTGTTTTTCCCGCATGAATACTGTAAGAAGAAGGATCGCCAGTTTGATTGGGCATGGCGG
T4MO_G103S/A107T    CAGCTGTGTTTTTCCCGCATGAATACTGTAAGAAGAAGGATCGCCAGTTTGATTGGGCATGGCGG
                    ***********************************************************
```

(FIG. 5C)

```
T4MO_G103A/A107S    GCCTATCACAGTAACGAATGGGCAGCCATTGCTGCAAAGCATTTCTTTGATGACATCATT
T4MO_G103S          GCCTATCACAGTAACGAATGGGCAGCCATTGCTGCAAAGCATTTCTTTGATGACATCATT
T4MO_I100A          GCCTATCACAGTAACGAATGGGCAGCCATTGCTGCAAAGCATTTCTTTGATGACATCATT
T4MO_I100S          GCCTATCACAGTAACGAATGGGCAGCCATTGCTGCAAAGCATTTCTTTGATGACATCATT
T4MO-wild_type      GCCTATCACAGTAACGAATGGGCAGCCATTGCTGCAAAGCATTTCTTTGATGACATCATT
T4MO_G103S/A107G    GCCTATCACAGTAACGAATGGGCAGCCATTGCTGCAAAGCATTTCTTTGATGACATCATT
T4MO_G103S/A107T    GCCTATCACAGTAACGAATGGGCAGCCATTGCTGCAAAGCATTTCTTTGATGACATCATT
                    ************************************************************

T4MO_G103A/A107S    ACCGGACGTGATGCGATCAGCGTTGCGATCATGTTGACGTTTTCATTCGAAACCGGCTTC
T4MO_G103S          ACCGGACGTGATGCGATCAGCGTTGCGATCATGTTGACGTTTTCATTCGAAACCGGCTTC
T4MO_I100A          ACCGGACGTGATGCGATCAGCGTTGCGATCATGTTGACGTTTTCATTCGAAACCGGCTTC
T4MO_I100S          ACCGGACGTGATGCGATCAGCGTTGCGATCATGTTGACGTTTTCATTCGAAACCGGCTTC
T4MO-wild_type      ACCGGACGTGATGCGATCAGCGTTGCGATCATGTTGACGTTTTCATTCGAAACCGGCTTC
T4MO_G103S/A107G    ACCGGACGTGATGCGATCAGCGTTGCGATCATGTTGACGTTTTCATTCGAAACCGGCTTC
T4MO_G103S/A107T    ACCGGACGTGATGCGATCAGCGTTGCGATCATGTTGACGTTTTCATTCGAAACCGGCTTC
                    ************************************************************

T4MO_G103A/A107S    ACCAACATGCAGTTTCTTGGGTTGGCGGCAGATGCCGCAGAAGCAGGTGACTACACGTTT
T4MO_G103S          ACCAACATGCAGTTTCTTGGGTTGGCGGCAGATGCCGCAGAAGCAGGTGACTACACGTTT
T4MO_I100A          ACCAACATGCAGTTTCTTGGGTTGGCGGCAGATGCCGCAGAAGCAGGTGACTACACGTTT
T4MO_I100S          ACCAACATGCAGTTTCTTGGGTTGGCGGCAGATGCCGCAGAAGCAGGTGACTACACGTTT
T4MO-wild_type      ACCAACATGCAGTTTCTTGGGTTGGCGGCAGATGCCGCAGAAGCAGGTGACTACACGTTT
T4MO_G103S/A107G    ACCAACATGCAGTTTCTTGGGTTGGCGGCAGATGCCGCAGAAGCAGGTGACTACACGTTT
T4MO_G103S/A107T    ACCAACATGCAGTTTCTTGGGTTGGCGGCAGATGCCGCAGAAGCAGGTGACTACACGTTT
                    ************************************************************

T4MO_G103A/A107S    GCAAACCTGATCTCCAGCATTCAAACCGATGAGTCGCGTCATGCACAACAGGCGGCCCC
T4MO_G103S          GCAAACCTGATCTCCAGCATTCAAACCGATGAGTCGCGTCATGCACAACAGGCGGCCCC
T4MO_I100A          GCAAACCTGATCTCCAGCATTCAAACCGATGAGTCGCGTCATGCACAACAGGCGGCCCC
T4MO_I100S          GCAAACCTGATCTCCAGCATTCAAACCGATGAGTCGCGTCATGCACAACAGGCGGCCCC
T4MO-wild_type      GCAAACCTGATCTCCAGCATTCAAACCGATGAGTCGCGTCATGCACAACAGGCGGCCCC
T4MO_G103S/A107G    GCAAACCTGATCTCCAGCATTCAAACCGATGAGTCGCGTCATGCACAACAGGCGGCCCC
T4MO_G103S/A107T    GCAAACCTGATCTCCAGCATTCAAACCGATGAGTCGCGTCATGCACAACAGGCGGCCCC
                    ***********************************************************
```

(FIG. 5D)

| | |
|---|---|
| T4MO_G103A/A107S | GCATTACAGTTGCTGATCGAAAACGAAAAAGAAGAAGAAGCCCAAAAGAAAAGTCGACATG |
| T4MO_G103S | GCATTACAGTTGCTGATCGAAAACGAAAAAGAAGAAGAAGCCCAAAAGAAAAGTCGACATG |
| T4MO_I100A | GCATTACAGTTGCTGATCGAAAACGAAAAAGAAGAAGAAGCCCAAAAGAAAAGTCGACATG |
| T4MO_I100S | GCATTACAGTTGCTGATCGAAAACGAAAAAGAAGAAGAAGCCCAAAAGAAAAGTCGACATG |
| T4MO-wild_type | GCATTACAGTTGCTGATCGAAAACGAAAAAGAAGAAGAAGCCCAAAAGAAAAGTCGACATG |
| T4MO_G103S/A107G | GCATTACAGTTGCTGATCGAAAACGAAAAAGAAGAAGAAGCCCAAAAGAAAAGTCGACATG |
| T4MO_G103S/A107T | GCATTACAGTTGCTGATCGAAAACGAAAAAGAAGAAGAAGCCCAAAAGAAAAGTCGACATG |
| | ************************************************************ |
| T4MO_G103A/A107S | GCAATTTGGCGTGCCTGGCCTGCGTCCTATTTGCGGTACTAACCGGCCGGTTATGGATTACTAC |
| T4MO_G103S | GCAATTTGGCGTGCCTGGCCTGCGTCCTATTTGCGGTACTAACCGGCCGGTTATGGATTACTAC |
| T4MO_I100A | GCAATTTGGCGTGCCTGGCCTGCGTCCTATTTGCGGTACTAACCGGCCGGTTATGGATTACTAC |
| T4MO_I100S | GCAATTTGGCGTGCCTGGCCTGCGTCCTATTTGCGGTACTAACCGGCCGGTTATGGATTACTAC |
| T4MO-wild_type | GCAATTTGGCGTGCCTGGCCTGCGTCCTATTTGCGGTACTAACCGGCCGGTTATGGATTACTAC |
| T4MO_G103S/A107G | GCAATTTGGCGTGCCTGGCCTGCGTCCTATTTGCGGTACTAACCGGCCGGTTATGGATTACTAC |
| T4MO_G103S/A107T | GCAATTTGGCGTGCCTGGCCTGCGTCCTATTTGCGGTACTAACCGGCCGGTTATGGATTACTAC |
| | ************************************************************ |
| T4MO_G103A/A107S | ACGCCGTTGGAGGACCGCAGCCAGTCATTCAAGGAGTTTATGTACGAGTGGATCATCGGA |
| T4MO_G103S | ACGCCGTTGGAGGACCGCAGCCAGTCATTCAAGGAGTTTATGTACGAGTGGATCATCGGA |
| T4MO_I100A | ACGCCGTTGGAGGACCGCAGCCAGTCATTCAAGGAGTTTATGTACGAGTGGATCATCGGA |
| T4MO_I100S | ACGCCGTTGGAGGACCGCAGCCAGTCATTCAAGGAGTTTATGTACGAGTGGATCATCGGA |
| T4MO-wild_type | ACGCCGTTGGAGGACCGCAGCCAGTCATTCAAGGAGTTTATGTACGAGTGGATCATCGGA |
| T4MO_G103S/A107G | ACGCCGTTGGAGGACCGCAGCCAGTCATTCAAGGAGTTTATGTACGAGTGGATCATCGGA |
| T4MO_G103S/A107T | ACGCCGTTGGAGGACCGCAGCCAGTCATTCAAGGAGTTTATGTACGAGTGGATCATCGGA |
| | ************************************************************ |
| T4MO_G103A/A107S | CAGTTCGAACGCTCGTTGATAGATCTGGGCTTGGACAAGCCCTGGTACTGGATCTATTC |
| T4MO_G103S | CAGTTCGAACGCTCGTTGATAGATCTGGGCTTGGACAAGCCCTGGTACTGGATCTATTC |
| T4MO_I100A | CAGTTCGAACGCTCGTTGATAGATCTGGGCTTGGACAAGCCCTGGTACTGGATCTATTC |
| T4MO_I100S | CAGTTCGAACGCTCGTTGATAGATCTGGGCTTGGACAAGCCCTGGTACTGGATCTATTC |
| T4MO-wild_type | CAGTTCGAACGCTCGTTGATAGATCTGGGCTTGGACAAGCCCTGGTACTGGATCTATTC |
| T4MO_G103S/A107G | CAGTTCGAACGCTCGTTGATAGATCTGGGCTTGGACAAGCCCTGGTACTGGATCTATTC |
| T4MO_G103S/A107T | CAGTTCGAACGCTCGTTGATAGATCTGGGCTTGGACAAGCCCTGGTACTGGATCTATTC |
| | ************************************************************ |

(FIG. 5E)

```
T4MO_G103A/A107S    CTCAAGGATATTGATGAGCTTCACCATAGTTATCACATGGGTGTTTGGTACTGGCGTACA
T4MO_G103S          CTCAAGGATATTGATGAGCTTCACCATAGTTATCACATGGGTGTTTGGTACTGGCGTACA
T4MO_I100A          CTCAAGGATATTGATGAGCTTCACCATAGTTATCACATGGGTGTTTGGTACTGGCGTACA
T4MO_I100S          CTCAAGGATATTGATGAGCTTCACCATAGTTATCACATGGGTGTTTGGTACTGGCGTACA
T4MO-wild_type      CTCAAGGATATTGATGAGCTTCACCATAGTTATCACATGGGTGTTTGGTACTGGCGTACA
T4MO_G103S/A107G    CTCAAGGATATTGATGAGCTTCACCATAGTTATCACATGGGTGTTTGGTACTGGCGTACA
T4MO_G103S/A107T    CTCAAGGATATTGATGAGCTTCACCATAGTTATCACATGGGTGTTTGGTACTGGCGTACA
                    ************************************************************

T4MO_G103A/A107S    ACCGCTTGGTGGAACCCTGCTGCCGGGTCACTCCTGAGGAGCGTGACTGGCTGGAAGAA
T4MO_G103S          ACCGCTTGGTGGAACCCTGCTGCCGGGTCACTCCTGAGGAGCGTGACTGGCTGGAAGAA
T4MO_I100A          ACCGCTTGGTGGAACCCTGCTGCCGGGTCACTCCTGAGGAGCGTGACTGGCTGGAAGAA
T4MO_I100S          ACCGCTTGGTGGAACCCTGCTGCCGGGTCACTCCTGAGGAGCGTGACTGGCTGGAAGAA
T4MO-wild_type      ACCGCTTGGTGGAACCCTGCTGCCGGGTCACTCCTGAGGAGCGTGACTGGCTGGAAGAA
T4MO_G103S/A107G    ACCGCTTGGTGGAACCCTGCTGCCGGGTCACTCCTGAGGAGCGTGACTGGCTGGAAGAA
T4MO_G103S/A107T    ACCGCTTGGTGGAACCCTGCTGCCGGGTCACTCCTGAGGAGCGTGACTGGCTGGAAGAA
                    ************************************************************

T4MO_G103A/A107S    AAGTATCCAGGATGGAATGGAATAAACGTTGGGGTCGTTGCTGGATGTGATCACCGAAAACGTT
T4MO_G103S          AAGTATCCAGGATGGAATGGAATAAACGTTGGGGTCGTTGCTGGATGTGATCACCGAAAACGTT
T4MO_I100A          AAGTATCCAGGATGGAATGGAATAAACGTTGGGGTCGTTGCTGGATGTGATCACCGAAAACGTT
T4MO_I100S          AAGTATCCAGGATGGAATGGAATAAACGTTGGGGTCGTTGCTGGATGTGATCACCGAAAACGTT
T4MO-wild_type      AAGTATCCAGGATGGAATGGAATAAACGTTGGGGTCGTTGCTGGATGTGATCACCGAAAACGTT
T4MO_G103S/A107G    AAGTATCCAGGATGGAATGGAATAAACGTTGGGGTCGTTGCTGGATGTGATCACCGAAAACGTT
T4MO_G103S/A107T    AAGTATCCAGGATGGAATGGAATAAACGTTGGGGTCGTTGCTGGATGTGATCACCGAAAACGTT
                    ************************************************************

T4MO_G103A/A107S    CTCAATGACCGTATGGATCTTGTCTCTCCAGAAACCTTGCCCAGCGTGTCAACATGAGC
T4MO_G103S          CTCAATGACCGTATGGATCTTGTCTCTCCAGAAACCTTGCCCAGCGTGTCAACATGAGC
T4MO_I100A          CTCAATGACCGTATGGATCTTGTCTCTCCAGAAACCTTGCCCAGCGTGTCAACATGAGC
T4MO_I100S          CTCAATGACCGTATGGATCTTGTCTCTCCAGAAACCTTGCCCAGCGTGTCAACATGAGC
T4MO-wild_type      CTCAATGACCGTATGGATCTTGTCTCTCCAGAAACCTTGCCCAGCGTGTCAACATGAGC
T4MO_G103S/A107G    CTCAATGACCGTATGGATCTTGTCTCTCCAGAAACCTTGCCCAGCGTGTCAACATGAGC
T4MO_G103S/A107T    CTCAATGACCGTATGGATCTTGTCTCTCCAGAAACCTTGCCCAGCGTGTCAACATGAGC
                    ************************************************************
```

(FIG. 5F)

| | |
|---|---|
| T4MO_G103A/A107S | CAGATACCGCTGGTAGTGTGTTCCTGGTGATGACTGGAATATCGAAGTTTTCAGTCTTGAG |
| T4MO_G103S | CAGATACCGCTGGTAGTGTGTTCCTGGTGATGACTGGAATATCGAAGTTTTCAGTCTTGAG |
| T4MO_I100A | CAGATACCGCTGGTAGTGTGTTCCTGGTGATGACTGGAATATCGAAGTTTTCAGTCTTGAG |
| T4MO_I100S | CAGATACCGCTGGTAGTGTGTTCCTGGTGATGACTGGAATATCGAAGTTTTCAGTCTTGAG |
| T4MO-wild_type | CAGATACCGCTGGTAGTGTGTTCCTGGTGATGACTGGAATATCGAAGTTTTCAGTCTTGAG |
| T4MO_G103S/A107G | CAGATACCGCTGGTAGTGTGTTCCTGGTGATGACTGGAATATCGAAGTTTTCAGTCTTGAG |
| T4MO_G103S/A107T | CAGATACCGCTGGTAGTGTGTTCCTGGTGATGACTGGAATATCGAAGTTTTCAGTCTTGAG |
| | ************************************************************ |
| T4MO_G103A/A107S | CACAATGGGCCGTCTCTTTATCATTTTGGCTCTCGAAGTGGATCGCTGGGTATTCCAGCAAGAT |
| T4MO_G103S | CACAATGGGCCGTCTCTTTATCATTTTGGCTCTCGAAGTGGATCGCTGGGTATTCCAGCAAGAT |
| T4MO_I100A | CACAATGGGCCGTCTCTTTATCATTTTGGCTCTCGAAGTGGATCGCTGGGTATTCCAGCAAGAT |
| T4MO_I100S | CACAATGGGCCGTCTCTTTATCATTTTGGCTCTCGAAGTGGATCGCTGGGTATTCCAGCAAGAT |
| T4MO-wild_type | CACAATGGGCCGTCTCTTTATCATTTTGGCTCTCGAAGTGGATCGCTGGGTATTCCAGCAAGAT |
| T4MO_G103S/A107G | CACAATGGGCCGTCTCTTTATCATTTTGGCTCTCGAAGTGGATCGCTGGGTATTCCAGCAAGAT |
| T4MO_G103S/A107T | CACAATGGGCCGTCTCTTTATCATTTTGGCTCTCGAAGTGGATCGCTGGGTATTCCAGCAAGAT |
| | ************************************************************ |
| T4MO_G103A/A107S | CCGGTTCAGTATCAAAATCATATGAATATCGTCGACCGCTTCCTCGCAGGTCAGATACAG |
| T4MO_G103S | CCGGTTCAGTATCAAAATCATATGAATATCGTCGACCGCTTCCTCGCAGGTCAGATACAG |
| T4MO_I100A | CCGGTTCAGTATCAAAATCATATGAATATCGTCGACCGCTTCCTCGCAGGTCAGATACAG |
| T4MO_I100S | CCGGTTCAGTATCAAAATCATATGAATATCGTCGACCGCTTCCTCGCAGGTCAGATACAG |
| T4MO-wild_type | CCGGTTCAGTATCAAAATCATATGAATATCGTCGACCGCTTCCTCGCAGGTCAGATACAG |
| T4MO_G103S/A107G | CCGGTTCAGTATCAAAATCATATGAATATCGTCGACCGCTTCCTCGCAGGTCAGATACAG |
| T4MO_G103S/A107T | CCGGTTCAGTATCAAAATCATATGAATATCGTCGACCGCTTCCTCGCAGGTCAGATACAG |
| | ************************************************************ |
| T4MO_G103A/A107S | CCGATGACTTTGGAAGGTGCCCTCAAATATATGGGCTTCCAATCTATTGAAGAGATGGGC |
| T4MO_G103S | CCGATGACTTTGGAAGGTGCCCTCAAATATATGGGCTTCCAATCTATTGAAGAGATGGGC |
| T4MO_I100A | CCGATGACTTTGGAAGGTGCCCTCAAATATATGGGCTTCCAATCTATTGAAGAGATGGGC |
| T4MO_I100S | CCGATGACTTTGGAAGGTGCCCTCAAATATATGGGCTTCCAATCTATTGAAGAGATGGGC |
| T4MO-wild_type | CCGATGACTTTGGAAGGTGCCCTCAAATATATGGGCTTCCAATCTATTGAAGAGATGGGC |
| T4MO_G103S/A107G | CCGATGACTTTGGAAGGTGCCCTCAAATATATGGGCTTCCAATCTATTGAAGAGATGGGC |
| T4MO_G103S/A107T | CCGATGACTTTGGAAGGTGCCCTCAAATATATGGGCTTCCAATCTATTGAAGAGATGGGC |
| | ************************************************************ |

(FIG. 5G)

| | |
|---|---|
| T4MO_G103A/A107S | AAAGACGCCCACGACTTTGCATGGGCTGACAAGTGCAAGCCTGCTATGAAGAAATCGGCC |
| T4MO_G103S | AAAGACGCCCACGACTTTGCATGGGCTGACAAGTGCAAGCCTGCTATGAAGAAATCGGCC |
| T4MO_I100A | AAAGACGCCCACGACTTTGCATGGGCTGACAAGTGCAAGCCTGCTATGAAGAAATCGGCC |
| T4MO_I100S | AAAGACGCCCACGACTTTGCATGGGCTGACAAGTGCAAGCCTGCTATGAAGAAATCGGCC |
| T4MO-wild_type | AAAGACGCCCACGACTTTGCATGGGCTGACAAGTGCAAGCCTGCTATGAAGAAATCGGCC |
| T4MO_G103S/A107G | AAAGACGCCCACGACTTTGCATGGGCTGACAAGTGCAAGCCTGCTATGAAGAAATCGGCC |
| T4MO_G103S/A107T | AAAGACGCCCACGACTTTGCATGGGCTGACAAGTGCAAGCCTGCTATGAAGAAATCGGCC |
| | ************************************************************ |

| | |
|---|---|
| T4MO_G103A/A107S | TGA |
| T4MO_G103S | TGA |
| T4MO_I100A | TGA |
| T4MO_I100S | TGA |
| T4MO-wild_type | TGA |
| T4MO_G103S/A107G | TGA |
| T4MO_G103S/A107T | TGA |
| | *** |

FIGURE 6A

```
T4MO-wild_type      MAMHPRKDWYELTRATNWTPSYVTEEQLFPERMSGHMGIPLEKWESYDEPYKTSYPEYVS
T4MO_I100A          MAMHPRKDWYELTRATNWTPSYVTEEQLFPERMSGHMGIPLEKWESYDEPYKTSYPEYVS
T4MO_I100S          MAMHPRKDWYELTRATNWTPSYVTEEQLFPERMSGHMGIPLEKWESYDEPYKTSYPEYVS
T4MO_G103A/A107S    MAMHPRKDWYELTRATNWTPSYVTEEQLFPERMSGHMGIPLEKWESYDEPYKTSYPEYVS
T4MO_G103S          MAMHPRKDWYELTRATNWTPSYVTEEQLFPERMSGHMGIPLEKWESYDEPYKTSYPEYVS
T4MO_G103S/A107G    MAMHPRKDWYELTRATNWTPSYVTEEQLFPERMSGHMGIPLEKWESYDEPYKTSYPEYVS
T4MO_G103S/A107T    MAMHPRKDWYELTRATNWTPSYVTEEQLFPERMSGHMGIPLEKWESYDEPYKTSYPEYVS
                    ************************************************************

T4MO-wild_type      IQREKDAGAYSVKAALERAKIYENSDPGWISTLKSHYGAIAVGEYAAVTGEGRMARFSKA
T4MO_I100A          IQREKDAGAYSVKAALERAKIYENSDPGWISTLKSHYGAAAVGEYAAVTGEGRMARFSKA
T4MO_I100S          IQREKDAGAYSVKAALERAKIYENSDPGWISTLKSHYGASAVGEYAAVTGEGRMARFSKA
T4MO_G103A/A107S    IQREKDAGAYSVKAALERAKIYENSDPGWISTLKSHYGAIAVAEYASVTGEGRMARFSKA
T4MO_G103S          IQREKDAGAYSVKAALERAKIYENSDPGWISTLKSHYGAIAVSEYAAVTGEGRMARFSKA
T4MO_G103S/A107G    IQREKDAGAYSVKAALERAKIYENSDPGWISTLKSHYGAIAVSEYAGVTGEGRMARFSKA
T4MO_G103S/A107T    IQREKDAGAYSVKAALERAKIYENSDPGWISTLKSHYGAIAVSEYATVTGEGRMARFSKA
                    ****************************************  *   ** ***********

T4MO-wild_type      PGNRNMATFGMMDELRHGQLQLFFPHEYCKKDRQFDWAWRAYHSNEWAAIAAKHFFDDII
T4MO_I100A          PGNRNMATFGMMDELRHGQLQLFFPHEYCKKDRQFDWAWRAYHSNEWAAIAAKHFFDDII
T4MO_I100S          PGNRNMATFGMMDELRHGQLQLFFPHEYCKKDRQFDWAWRAYHSNEWAAIAAKHFFDDII
T4MO_G103A/A107S    PGNRNMATFGMMDELRHGQLQLFFPHEYCKKDRQFDWAWRAYHSNEWAAIAAKHFFDDII
T4MO_G103S          PGNRNMATFGMMDELRHGQLQLFFPHEYCKKDRQFDWAWRAYHSNEWAAIAAKHFFDDII
T4MO_G103S/A107G    PGNRNMATFGMMDELRHGQLQLFFPHEYCKKDRQFDWAWRAYHSNEWAAIAAKHFFDDII
T4MO_G103S/A107T    PGNRNMATFGMMDELRHGQLQLFFPHEYCKKDRQFDWAWRAYHSNEWAAIAAKHFFDDII
                    ************************************************************

T4MO-wild_type      TGRDAISVAIMLTFSFETGFTNMQFLGLAADAAEEAGDYTFANLISSIQTDESRHAQQGGP
T4MO_I100A          TGRDAISVAIMLTFSFETGFTNMQFLGLAADAAEEAGDYTFANLISSIQTDESRHAQQGGP
T4MO_I100S          TGRDAISVAIMLTFSFETGFTNMQFLGLAADAAEEAGDYTFANLISSIQTDESRHAQQGGP
T4MO_G103A/A107S    TGRDAISVAIMLTFSFETGFTNMQFLGLAADAAEEAGDYTFANLISSIQTDESRHAQQGGP
T4MO_G103S          TGRDAISVAIMLTFSFETGFTNMQFLGLAADAAEEAGDYTFANLISSIQTDESRHAQQGGP
T4MO_G103S/A107G    TGRDAISVAIMLTFSFETGFTNMQFLGLAADAAEEAGDYTFANLISSIQTDESRHAQQGGP
T4MO_G103S/A107T    TGRDAISVAIMLTFSFETGFTNMQFLGLAADAAEEAGDYTFANLISSIQTDESRHAQQGGP
                    ************************************************************
```

(FIG. 6B)

```
T4MO-wild_type    ALQLLIENGKREEAQKKVDMAIWRAWRLFAVLTGPVMDYYTPLEDRSQSFKEFMYEWIIG
T4MO_I100A        ALQLLIENGKREEAQKKVDMAIWRAWRLFAVLTGPVMDYYTPLEDRSQSFKEFMYEWIIG
T4MO_I100S        ALQLLIENGKREEAQKKVDMAIWRAWRLFAVLTGPVMDYYTPLEDRSQSFKEFMYEWIIG
T4MO_G103A/A107S  ALQLLIENGKREEAQKKVDMAIWRAWRLFAVLTGPVMDYYTPLEDRSQSFKEFMYEWIIG
T4MO_G103S        ALQLLIENGKREEAQKKVDMAIWRAWRLFAVLTGPVMDYYTPLEDRSQSFKEFMYEWIIG
T4MO_G103S/A107G  ALQLLIENGKREEAQKKVDMAIWRAWRLFAVLTGPVMDYYTPLEDRSQSFKEFMYEWIIG
T4MO_G103S/A107T  ALQLLIENGKREEAQKKVDMAIWRAWRLFAVLTGPVMDYYTPLEDRSQSFKEFMYEWIIG
                  ************************************************************

T4MO-wild_type    QFERSLIDLGLDKPWYDLFLKDIDELHHSYHMGVWYWRTTAWWNPAAGVTPEERDWLEE
T4MO_I100A        QFERSLIDLGLDKPWYDLFLKDIDELHHSYHMGVWYWRTTAWWNPAAGVTPEERDWLEE
T4MO_I100S        QFERSLIDLGLDKPWYDLFLKDIDELHHSYHMGVWYWRTTAWWNPAAGVTPEERDWLEE
T4MO_G103A/A107S  QFERSLIDLGLDKPWYDLFLKDIDELHHSYHMGVWYWRTTAWWNPAAGVTPEERDWLEE
T4MO_G103S        QFERSLIDLGLDKPWYDLFLKDIDELHHSYHMGVWYWRTTAWWNPAAGVTPEERDWLEE
T4MO_G103S/A107G  QFERSLIDLGLDKPWYDLFLKDIDELHHSYHMGVWYWRTTAWWNPAAGVTPEERDWLEE
T4MO_G103S/A107T  QFERSLIDLGLDKPWYDLFLKDIDELHHSYHMGVWYWRTTAWWNPAAGVTPEERDWLEE
                  **********************************************************

T4MO-wild_type    KYPGWNKRWGRCWDVITENVLNDRMDLVSPETLPSVCNMSQIPLVGVPGDDWNIEVFSLE
T4MO_I100A        KYPGWNKRWGRCWDVITENVLNDRMDLVSPETLPSVCNMSQIPLVGVPGDDWNIEVFSLE
T4MO_I100S        KYPGWNKRWGRCWDVITENVLNDRMDLVSPETLPSVCNMSQIPLVGVPGDDWNIEVFSLE
T4MO_G103A/A107S  KYPGWNKRWGRCWDVITENVLNDRMDLVSPETLPSVCNMSQIPLVGVPGDDWNIEVFSLE
T4MO_G103S        KYPGWNKRWGRCWDVITENVLNDRMDLVSPETLPSVCNMSQIPLVGVPGDDWNIEVFSLE
T4MO_G103S/A107G  KYPGWNKRWGRCWDVITENVLNDRMDLVSPETLPSVCNMSQIPLVGVPGDDWNIEVFSLE
T4MO_G103S/A107T  KYPGWNKRWGRCWDVITENVLNDRMDLVSPETLPSVCNMSQIPLVGVPGDDWNIEVFSLE
                  ************************************************************

T4MO-wild_type    HNGRLYHFGSEVDRWVFQQDPVQYQNHMNIVDRFLAGQIQPMTLEGALKYMGFQSIEEMG
T4MO_I100A        HNGRLYHFGSEVDRWVFQQDPVQYQNHMNIVDRFLAGQIQPMTLEGALKYMGFQSIEEMG
T4MO_I100S        HNGRLYHFGSEVDRWVFQQDPVQYQNHMNIVDRFLAGQIQPMTLEGALKYMGFQSIEEMG
T4MO_G103A/A107S  HNGRLYHFGSEVDRWVFQQDPVQYQNHMNIVDRFLAGQIQPMTLEGALKYMGFQSIEEMG
T4MO_G103S        HNGRLYHFGSEVDRWVFQQDPVQYQNHMNIVDRFLAGQIQPMTLEGALKYMGFQSIEEMG
T4MO_G103S/A107G  HNGRLYHFGSEVDRWVFQQDPVQYQNHMNIVDRFLAGQIQPMTLEGALKYMGFQSIEEMG
T4MO_G103S/A107T  HNGRLYHFGSEVDRWVFQQDPVQYQNHMNIVDRFLAGQIQPMTLEGALKYMGFQSIEEMG
                  ************************************************************
```

(FIG. 6C)

```
T4MO-wild_type       KDAHDFAWADKCKPAMKKSA
T4MO_I100A           KDAHDFAWADKCKPAMKKSA
T4MO_I100S           KDAHDFAWADKCKPAMKKSA
T4MO_G103A/A107S     KDAHDFAWADKCKPAMKKSA
T4MO_G103S           KDAHDFAWADKCKPAMKKSA
T4MO_G103S/A107G     KDAHDFAWADKCKPAMKKSA
T4MO_G103S/A107T     KDAHDFAWADKCKPAMKKSA
                     ********************
```

Figure 7.

| Primer | Nucleotide sequence | |
|---|---|---|
| Mutagenesis | | |
| 14HCEcoRIFmut | 5'-TACGGAAATCAAGCTTTAAACCCCACAGG-3' | (SEQ ID NO.41) |
| 14MCABRear | 5'-TCCATGCTCTCACTGTTGAC-3' | (SEQ ID NO.42) |
| 14HC100Fmut | 5'-CACTTTGAAATCCATTACGGCGCCNNNGCAGTTGG-3' | (SEQ ID NO.43) |
| 14HC100Rear | 5'-GCTGCATATCACCAACTGCNNNGCCGCCGTAATGG-3' | (SEQ ID NO.44) |
| 14HCBgIIIRear | 5'-TCCAAGCCAGATCTATCAACGAGCGTTCG-3' | (SEQ ID NO.45) |
| Sequencing | | |
| 14HCEcoRIFmut | 5'-TACGGAAATCAAGCTTTAAACCCCACAGG-3' | (SEQ ID NO.46) |
| 14HO1 | 5'-CCCGCATGAATACTGAAGAAGGATCGC-3' | (SEQ ID NO.47) |
| 14HO2 | 5'-GCTCGTTGATAGATCTGGGCTTGGACAA-3' | (SEQ ID NO.48) |
| 14HO3 | 5'-AATCTATTGAAGAGATGGGCAAAGAGACGC-3' | (SEQ ID NO.49) |

Figure 8.

| Enzyme | 4-NC formation from NB[a], nmol/min·mg protein[b] | Toluene oxidation rate[c], nmol/min·mg protein[b] | Regiospecificity of toluene oxidation | | |
|---|---|---|---|---|---|
| | | | o-cresol, % | m-cresol, % | p-cresol, % |
| wild-type T4MO | 0.008 ± 0.001 | 4.4 ± 0.3 | <1 | 3 | 96 |
| NB1 (TmoA Y22M, I94 Y, 895 I, I100 S, S400 C; TmoB D79 N) | 0.0010 ± 0.0002 | 0.41 ± 0.05 | 0 | 20 | 80 |
| TmoA I100A | 0.13 ± 0.01 | 7.2 ± 1.2 | 0 | 20 | 80 |
| TmoA I100S | 0.06 ± 0.011 | 6.7 ± 1.3 | 0 | 21 | 79 |
| T4moH G103L[e] | | | 55.5 | 19.7 | 24.5 |
| wild-type T0MT[e] | 1.30 ± 0.06 | | 100 | 0 | 0 |
| TomA3 V106A[e] | 2.8 ± 0.5 | | 50 | 33 | 17 |
| TomA3 V106F[e] | 2.1 ± 0.3 | | 28 | 18 | 54 |

[a] Based on HPLC analysis over a 40 min time period. The initial NB concentration was 200 μM. Standard deviations shown (2 ≤ n ≤ 4).
[b] Based on 0.24 mg protein/mL OD.
[c] Based on GC analysis over a 20 min time period. The initial toluene concentration was 90 μM based on Henry's law constant of 0.27 (Dolfing et al 1993)(250 μM added if all the toluene in the liquid phase). Standard deviations shown (3 or 4 independent experiments).
[d] reference (Mitchell et al. 2002).
[e] reference (Rui et al. 2004).

Figure 9.

| Enzyme | NB→4ANF | | | | NB→mNF | | | | ANF→4NC | | | | mNF→4NC | | | |
|---|---|---|---|---|---|---|---|---|---|---|---|---|---|---|---|---|
| | $V_{max}$ | $K_m$ | $V_{max}/K_m$ | relative | $V_{max}$ | $K_m$ | $V_{max}/K_m$ | relative | $V_{max}$ | $K_m$ | $V_{max}/K_m$ | relative | $V_{max}$ | $K_m$ | $V_{max}/K_m$ | relative |
| wild-type | 2.04 | 122 | 0.017 | 1 | 0.18 | 155 | 0.001 | 1 | 0.17 | 793 | 0.002 | 1 | 0.75 | 103 | 0.010 | 1 |
| I100A | 1.03 | 64 | 0.016 | 0.94 | 1.25 | 58 | 0.022 | 22 | 0.69 | 20.5 | 0.034 | 17 | 3.3 | 43.5 | 0.076 | 7.6 |
| I100S | 0.71 | 172 | 0.041 | 2.4 | 0.51 | 15.5 | 0.033 | 33 | 0.63 | 14.25 | 0.044 | 22 | 2.5 | 89.3 | 0.028 | 2.8 |

Initial specific rates were determined for each reaction by monitoring the formation of the products using HPLC; substrate concentrations were 25, 50, 75, 100, 150, 200, 300 μM, and the cell OD was 2 for xNB and m-NP as substrates, and 4 for p-NP as a substrate.

*Kinetic constants were calculated from the double reciprocal Lineweaver-Burk plot.

Figure 13.

| Primers | Nucleotide sequence |
|---|---|
| Cloning | |
| T4MOEcoRIFront | 5'-TACGGAATTCAAGCTTTTAAACCCC (SEQ ID NO.50) |
| T4MOBglIIRear | 5'-TCCAAGCCCAGATCTATCAACGAG (SEQ ID NO.51) |
| T4MOG103A107Front | 5'-ATTACGGCGCCATCGCAGTTNNNG SNQNDNQNMNN GTAAC CG-3' |
| T4MOG103A107Rear | 5'-ATACGACCTTCACCGGTTACNNNT SNTNTNCNSN NAACTGCG-3' |
| T4MO100 Front | 5'-CACTTTGAAATCCCATTACGGCGC SNENNBCNGTN GG-3' |
| T4MO100Rear | 5'-GCTGCATATTCACCAACTGCNNNG SNSCNDNGNQN AN GG-3' |
| Sequencing | |
| T4MOEcoRIFront | 5'-TACGGAATTCAAGCTTTTAAACCCC (SEQ ID NO.56) |

Figure 14.

| Enzyme | Toluene oxidation rate (nmol/min·mg protein) | Regiospecificity (%) | | |
|---|---|---|---|---|
| | | p-cresol | m-cresol | o-cresol |
| wild-type T4MO | 12 ± 0.8 | 96.7 | 2 | <1 |
| I100L | 17.7 ± 0.2 | 90 | 3 | 7 |
| G103A | 20 ± 0.4 | 75 | 13 | 12 |
| G103A/A107S | 18 ± 1.6 | 71 | 17 | 12 |
| G103L[2] | - | 24.5 | 19.7 | 55.5 |
| G103S | 18 ± 1.7 | 76 | 15 | 9 |
| G103S/A107G | 15 ± 0.3 | 11 | 7 | 82 |
| G103S/A107T | 25 ± 0.4 | 100 | 0 | 0 |

[1] Initial toluene concentration was 109 μM based on a Henry's Law constant of 0.27 (9) (300 μM added if all the toluene in the liquid phase). Mean ± one standard deviation (based on at least two independent results) are shown for the rates.

[2] Purified enzyme from reference (28). This mutant was created by site-directed mutagenesis which had 64% of the activity of toluene oxidation relative to wild-type T4MO.

Figure 15.

| Enzyme | Substrate | Regiospecificity | | | Formation rate[1,2] (nmol/min·mg protein) | | | Cresol oxidation rate (nmol/min·mg protein) |
|---|---|---|---|---|---|---|---|---|
| | | 3MeC, % | MeH, % | 4MeC, % | 3MeC | MeH | 4MeC | |
| wild-type | m-cresol | 0 | 0 | 100 | 0 | 0 | 9.5 ± 1 | 10.4 ± 0.1 |
| wild-type | p-cresol | 0 | 0 | 100 | 0 | 0 | 6 ± 1.1 | 8 ± 1.6 |
| wild-type | o-cresol | 91 | 9 | 0 | 6.7 ± 2.2 | 0.5 ± 0.16 | 0 | 9 ± 2.8 |
| G103A | o-cresol | 96 | 4 | 0 | 6.2 ± 3 | 0.11 | 0 | 63 ± 3 |
| G103A/A107S | o-cresol | 98 | 2 | 0 | 13.4 ± 0.1 | 0 | 0 | 15 ± 2.1 |
| G103S | o-cresol | 20 | 80 | 0 | 0.3 ± 0.02 | 2.1 ± 0.01 | 0 | 4.1 ± 0.3 |
| G103S/A107G | o-cresol | 30 | 70 | 0 | 0.08 ± 0.03 | 0.34 ± 0.02 | 0 | 0.4 ± 0.1 |
| G103S/A107T | o-cresol | 8 | 92 | 0 | 0.16 ± 0.02 | 2.1 ± 0.7 | 0 | 2.3 ± 0.4 |

[1] Based on HPLC analysis, mean ± one standard deviation (based on at least two independent results) shown.

[2] Activity determined at saturation substrate concentration 1 mM so the formation rates represent $V_{max}$ values.

Figure 16.

| Enzyme | Regiospecificity of o-methoxyphenol oxidation | | | 3MxC formation rate[1,2] (nmol/min•mg protein) | | | MxH formation rate (nmol/min•mg protein) | o-methoxyphenol oxidation[3] (nmol/min•mg protein) |
|---|---|---|---|---|---|---|---|---|
| | 4MxR, % | 3MxC, % | MxH, % | via HPLC activity | relative activity | via colorimetric assay | | |
| wild-type | 87 | 11.3 | 1.7 | 0.21 ± 0.01 | 1 | 0.20 | 0.07 ± 0.03 | 4 ± 1.1* |
| I100L | 73 | 20 | 7 | 0.75 ± 0.2 | 3.7 | 0.85-1.31 | ~0 | 2.4 ± 0.8* |
| G103A | 41 | 52.3 | 6.7 | 1.2 ± 0.16 | 6 | 0.72-2.76 | ~0 | 2.1 ± 0.5 |
| G103A/A107S | 13 | 82.5 | 4.5 | 1.5 ± 0.2 | 7 | 1.90 | ~0 | 1.9 |
| G103S | 19 | <1 | 80 | ~0 | 0 | 0 | 0.36 ± 0.01 | 0.36 |
| G103S/A107T | 35 | 30 | 35 | ND[1] | 0 | 0 | 0.084 | ND[1] |

[1] Relative values based on HPLC analysis whereas the colorimetric assay corroborated this data.

[2] Activity determined at the saturation concentration of 1 mM so the values represent $V_{max}$.

[1] ND, not determined.

[3] The single guaiacol substrate was oxidized to 3 different products, including 4-methoxyresorcinol whose production rate was the largest component of guaiacol oxidation.

Figure 19.

| Primers | Nucleotide sequence | |
|---|---|---|
| Construction | | |
| LoMD-KpnI-KACfront | 5'-GGTGCGGTACCACCCATTAGCCG-3' | (SEQ ID NO.57) |
| LoMD-NotI-KACrear | 5'-CTCCTGCAGCGGCCGCTGTTAATGC-3' | (SEQ ID NO.58) |
| Sequencing | | |
| LoMC1 | 5'-GCCAAGCGCGCAATTAACCTC-3' | (SEQ ID NO.59) |
| LoMC2 | 5'-CCGTATGCCAATGTCAAGCGGAGC-3' | (SEQ ID NO.60) |
| LoMC3 | 5'-CGTCAGTTGCTTGATCTAGGGCTCG-3' | (SEQ ID NO.61) |
| LoMC4 | 5'-GGGTGACGACGCTCATGATTATGAG-3' | (SEQ ID NO.62) |
| LoMC5 | 5'-GGGCGTTGAAGGCGGCGATATG-3' | (SEQ ID NO.63) |
| LoMC6 | 5'-GGGCGGGGAGTGGCGATTGCG-3' | (SEQ ID NO.64) |
| LoMC7 | 5'-GCCCACTCAAACACGATGACTGG-3' | (SEQ ID NO.65) |
| LoMC8 | 5'-GGTAGTCTTGCCCAATCCGAAGG-3' | (SEQ ID NO.66) |
| LoMC9 | 5'-GCAACTCCGGCGGGTGTATCG-3' | (SEQ ID NO.67) |
| LoMC10 | 5'-CGGTCTCTGCCTACCTTCATCCG-3' | (SEQ ID NO.68) |
| Mutagenesis | | |
| I100-front | 5'-CACTATGCAACTTCACTTCGGAGCGNNNGCACTTG-3' | (SEQ ID NO.69) |
| I100-rear | 5'-GCGGCGTATCTTCAAGTGCNNNCGCTCCGAAGTG-3' | (SEQ ID NO.70) |
| Q141-front | 5'-CCGCCATGGCCAAATCNNNCTTTAC-3' | (SEQ ID NO.71) |
| Q141-rear | 5'-GGCATACGGAAAGTAAAGNNNGATTTGGCC-3' | (SEQ ID NO.72) |
| I201-front | 5'-CGCATTCGAAACAGGCTTCNNNAATATGC-3' | (SEQ ID NO.73) |
| I201-rear | 5'-CCGAGAAACTGCATATNNNGAAGCC-3' | (SEQ ID NO.74) |
| F205-front | 5'-GCTTCACCAATATGCAGNNNCTCGG-3' | (SEQ ID NO.75) |
| F205-rear | 5'-CAGCGGGCCAAACCGAGNNNCTGC-3' | (SEQ ID NO.76) |
| LoMD-SaIFmax | 5'-CCCACTCATAATCATGAGCGTCG-3' | (SEQ ID NO.77) |
| LoMD-KpnI-front | 5'-CCGGGCTCGTAGTGTGTGGAATTGTGAGCGG-3' | (SEQ ID NO.78) |
| LoMD-BgIII-rear | 5'-CAGGATCTTGAGCGACGGTCCACCTTGCGTGTGCG-3' | (SEQ ID NO.79) |

Figure 20.

| Compound | Retention time in min | $\lambda_{max}$ nm |
|---|---|---|
| toluene | 20.0[a] | 214 |
| benzene | 19.4[a] | 274 |
| benzyl alcohol | 7.5[a] | 258 |
| o-cresol | 14.2[a] | 272 |
| m-cresol | 13.6[a] | 278 |
| p-cresol | 13.5[a] | 278 |
| 3-methylcatechol | 8.7[a] | 274 |
| 4-methylcatechol | 7.6[a] | 282 |
| 2-methylresorcinol | 5.9[a] | 272 |
| 4-methylresorcinol | 6.0[a] | 280 |
| 5-methylresorcinol | 4.1[a] | 274 |
| methylhydroquinone | 5.2[a] | 290 |
| 2-hydroxybenzyl alcohol | 5.1[a] | 274 |
| 3-hydroxybenzyl alcohol | 4.3[a] | 274 |
| 4-hydroxybenzyl alcohol | 4.0[a] | 274 |
| phenol | 8.7[a] | 271 |
| catechol | 5.1[b] | 276 |
| hydroquinone | 12.8[b] | |
| | 3.7[a] | 290 |
| | 6.5[b] | |
| resorcinol | 4.3[a] | 274 |
| | 10.0[b] | |
| 1,2,3-THB | 6.0[c] | 267 |
| 1,2,4-THB | 4.6[c] | 288 |

[a] HPLC retention times and $\lambda_{max}$ for standards used for product identification via the gradient method for methylcatechols, methylresorcinols, methylhydroquinone, and hydroxybenzyl alcohols.

[b] HPLC retention times and $\lambda_{max}$ for standards used for product identification via the isocratic method (70:30) for catechol, hydroquinone, and resorcinol from phenol.

[c] HPLC retention times and $\lambda_{max}$ for standards used for product identification via the isocratic method (90-10) for 1,2,3-THB and 1,2,4-THB from catechol, hydroquinone, or resorcinol. The ratio of $H_2O$ (0.1% formic acid) increased from 70 to 90 to aid identification of the more hydrophilic THB and to distinguish them from the solvent peak in the 70:30 method.

Figure 21.

| Enzyme | Rate (nmol consumed/min·mg protein) | | | | |
|---|---|---|---|---|---|
| | phenol | o-cresol | m-cresol | p-cresol | catechol |
| wild-type | 1.8 | 1.1 | 1.0 | 1.4 | 0.75 |
| I100Q | 1.3 | 1.0 | 0.81 | 1.1 | ND* |
| F205G | 1.1 | 1.0 | 0.34 | 0.52 | ND |
| M180L/E284G | 2.8 | 2.2 | 1.5 | 2.2 | 1.1 |

*ND, not determined.

Figure 22.

| Enzyme | Oxidation rate (nmol/min/nmol P450) | Regiospecificity, % | | |
|---|---|---|---|---|
| | | o-cresol | m-cresol | p-cresol |
| wild-type | 2.63 ± 0.12 | 32 | 21 | 47 |
| L70C | 1.53 ± 0.08 | 22 | 44 | 34 |
| F87G | 1.07 ± 0.03 | 21 | 33 | 43 |
| M184L/F87G | 3.15 ± 0.02 | 32 | 26 | 42 |

Figure 26.

| Primer | Nucleotide sequence | |
|---|---|---|
| Cloning primers | | |
| 14MCEcoRIFwint | 5'-TACGGAATTCAAGCTTTTAAACCCCACAGG-3' | (SEQ ID NO.80) |
| 14MCBamHIRevr | 5'-TTCGGATCCGCTGAGAACACATTGAAACAGG-3' | (SEQ ID NO.81) |
| 13MCBamHIFwint | 5'-TGAGGGATCCCGTCAAGCAAAAACACTAC-3' | (SEQ ID NO.82) |
| 13MCXhoIRevr | 5'-AAGTTCTAGAGTCGATGCTGTGCTGTGTCC-3' | (SEQ ID NO.83) |
| Sequencing primers | | |
| 14MCEcoRIFwint | 5'-TACGGAATTCAAGCTTTTAAACCCCACAGG-3' | (SEQ ID NO.84) |
| 14MC1 | 5'-CCCGCATGAAATACTGTAAGAAGGATCGG-3' | (SEQ ID NO.85) |
| 14MC2 | 5'-GCTCGTTGATAGATCTGGGCTTGGACAA-3' | (SEQ ID NO.86) |
| 14MC3 | 5'-AATCTATTGAAGAAGAATGGGCAAAGACCGC-3' | (SEQ ID NO.87) |
| 14MC4 | 5'-TCCGATGGGTACCGAAGTC-3' | (SEQ ID NO.88) |
| 14MC5 | 5'-GGCCGAACTGATATTGACTCG-3' | (SEQ ID NO.89) |
| 14MC6 | 5'-CAATGGCCCGCTGTTATTC-3' | (SEQ ID NO.90) |
| 14MC7 | 5'-GAAGGTTGGATTGAAAAGTGG-3' | (SEQ ID NO.91) |
| 14MC8 | 5'-TGCAAACCATTATCCGACTC-3' | (SEQ ID NO.92) |
| 14MC9 | 5'-CTGATTAATGTGTCGTCGAGC-3' | (SEQ ID NO.93) |
| 13MCBamHIFwint | 5'-TGAGGGATCCCGTCAAGCAAAAAACACTAC-3' | (SEQ ID NO.94) |
| 13MCfvtA1 | 5'-ATTTCCGCACGACTATTGC-3' | (SEQ ID NO.95) |
| 13MCfvtA2 | 5'-AACGCACCTTGATCGACCTG-3' | (SEQ ID NO.96) |
| 13MCfvtA3 | 5'-GCTTCAGTACATGAACCTGGC-3' | (SEQ ID NO.97) |
| 13MCfvtB1 | 5'-TGCGTTCCAGGGAATCTGCC-3' | (SEQ ID NO.98) |
| 13MCfvtM | 5'-CGACTACGTCCGCTTCTAC-3' | (SEQ ID NO.99) |
| 13MCfvtA4 | 5'-ATCTCGAACTGCGCGGGCGTAC-3' | (SEQ ID NO.100) |
| 13MCfvtA5 | 5'-GGTGCGCGAGTTCCGGCAC-3' | (SEQ ID NO.101) |
| 13MCfvtC1 | 5'-AGTACGCGGTGCTGTATCCG-3' | (SEQ ID NO.102) |

Figure 27.

| Enzyme | Phenol formation from benzene | | Catechol formation from phenol | | 1,2,3-THB formation from catechol | | Toluene oxidation rate, nmol/min·mg protein |
|---|---|---|---|---|---|---|---|
| | Initial formation rate, nmol/min·mg protein | Maximum production, µM | Initial formation rate, nmol/min·mg protein | Maximum production, µM | Initial formation rate, nmol/min·mg protein | Maximum production, µM | |
| T4MO' | 19 ± 1.5 | 144 ± 47 | 13.6 ± 0.5 | 103 ± 10 | 2.3 ± 0.5 | 132 ± 22 | 10 ± 0.8 |
| T3MO' | 3 ± 1 | 122 ± 43 | 3.1 ± 0.5 | 119 ± 13 | 0.26 ± 0.09 | 73 ± 4 | 4 ± 0.5 |
| TOM' | 0.89 ± 0.07 | 27 ± 12 | 1.8 ± 0.5 | 140 ± 7 | 1.7 ± 0.3 | 103 ± 22 | 2.4 ± 0.3 |

' Based on HPLC analysis, the error is a standard deviation of at least two independent experiments as shown.

² Initial benzene liquid concentration of 165 µM based on a Henry's law constant of 0.22 (9) (400 µM added if all the benzene is in the liquid phase), and the total toluene concentration was 165 µM based on a Henry's law constant of 0.27 (9) (455 µM added if all the toluene is in the liquid phase).

³ Pseudomonas mendocina KR1 toluene-4-monooxygenase

⁴ Pseudomonas mendocina KR1 toluene-3-monooxygenase

Figure 30.

| Primer | Sequences | |
|---|---|---|
| M4 Front | GAAGAAGAAAC TCGGTTTAAAGNNNCGCTACGCAG | (SEQ ID NO.103) |
| M4 Rear | GCGGGTC ATCGC TGCGTAGC GNNNC TTTAAACCGA | (SEQ ID NO.104) |
| A113 Front | GTGTGACAC CGGTTGGAGTATATGNNNCACCGAGG | (SEQ ID NO.105) |
| A113 Rear | CAATGTGGGC AAAACCTCGGTGNNNCATATAC TCC | (SEQ ID NO.106) |
| V106+A113 Front | ATCC ACGGTNNNACACCGTTGGAGTATATGNNNCACCGAGG | (SEQ ID NO.107) |
| V106+A113 Rear | AACC TCGGTGNNNCATATACTCCAACGGTGNNNACCGTGG | (SEQ ID NO.108) |
| BcII Front¹ | TCGAAGAAC CGGATC GGCATGAAGTTCG | (SEQ ID NO.109) |
| SphI Rear² | GTTCTAGTCCGAGAGAGCATGCATTC | (SEQ ID NO.110) |

¹Upstream of the natural BcII restriction site in exon43.

²Underlying indicates the natural SphI restriction site in exon43.

Figure 31.

| Colony colors | Amino acid change at position V106 of Tom43 | Nucleotide change | Amino acid change at position A113 of Tom43 | Nucleotide change |
|---|---|---|---|---|
| no wt[1] | — | — | — | — |
| true blue | — | — | A113V | GTT |
| vivid blue 1 | V106S | TCC | A113V | GTT |
| vivid blue 2 | — | — | A113H | CAT |
| vivid blue 3 | V106H | CAC | A113S | TCA |
| vivid blue 4 | V106I | ATC | A113S | TCC |
| pale blue 1 | — | — | A113S | AGT |
| pale blue 2 | — | — | A113F | TTT |
| pale blue 3 | — | — | A113I | ATC |
| dirty blue[2] | V106F | TTT | — | — |
| green 1[1] | V106A | GCC | — | — |
| green 2 | V106P | CCG | — | — |
| orange 1 | — | — | A113G | GGG |
| orange 2 | V106P | CCC | A113G | GGG |
| orange 3 | V106A | GCT | A113G | GGT |
| orange 4 | V106D | GAT | A113G | GGC |
| orange 5 | V106N | AAC | A113G | GGC |
| purple | V106Q | CAA | A113G | GGC |
| white 1 | — | — | A113R | CGC |
| white 2 | V106R | CGG | A113W | TGG |
| white 3 | V106Q | CAG | A113Q | CAG |
| white 4 | — | — | Frame shift | GGCG |
| white 5 | V106H | CAC | A113 ter | TGA |

Figure 32.

| Mutations in Tom43 | Color of chloroform extract[1] | Isatin | | Indigo | | Indirubin | | Isoindigo | | Unknown colored compounds |
|---|---|---|---|---|---|---|---|---|---|---|
| | | Mµ | % | Mµ | % | Mµ | % | Mµ | % | |
| W/T (V106/A113) | Brown | 11 | 6 | 123 | 7 | — | — | 146 | 86 | — |
| A113V | Blue | 14 | 5 | 267 | 89 | 18 | 6 | — | — | — |
| V106/A113V | Purple | 313 | 52 | 136 | 23 | 152 | 25 | — | — | — |
| A113H | Purple | 335 | 58 | 125 | 22 | 118 | 20 | — | — | — |
| V106/A113H | Purple | 80 | 29 | 114 | 41 | 86 | 31 | — | — | — |
| V106/A113S | Purple | 92 | 33 | 104 | 39 | 69 | 26 | — | — | — |
| A113S | Purple | 34 | 13 | 87 | 33 | 143 | 54 | — | — | — |
| A113F | Purple | 17 | 5 | 121 | 35 | 203 | 60 | — | — | — |
| A113I | Purple | 23 | 10 | 67 | 27 | 160 | 64 | — | — | — |
| V106F | Purple | 34 | 1 | 153 | 44 | 190 | 55 | — | — | — |
| V106A | Purplish blue | 127 | 38 | 175 | 52 | 34 | 10 | — | — | — |
| V106P | Purplish blue | 71 | 21 | 241 | 73 | 21 | 6 | — | — | — |
| A113G | Yellow | — | — | — | — | — | — | — | — | + |
| V106F/A113G | Yellow | — | — | — | — | — | — | — | — | + |
| V106A/A113G | Yellow | 25 | 63 | 15 | 37 | — | — | — | — | 5 |
| V106D/A113G | Dark pink | 23 | 32 | 39 | 54 | 10 | 14 | — | — | 5 |
| V106H/A113G | Yellow | 29 | 34 | 38 | 46 | 14 | 17 | — | — | + |
| V106Q/A113G | Green | 159 | 5 | 388 | 71 | 21 | + | — | — | 3 |

[1]Chloroform extract colors do not always match those of the colonies/neofluorantly.

Figure 34.

| Compound | Retention Time (min.) | λ (nm) |
|---|---|---|
| Nitrobenzene | 16.8[a] | 264 |
| o-Nitrophenol | 15.8[a], 18.9[b], 48.4[c] | 274 |
| m-Nitrophenol | 12.9[a] | 272 |
| p-Nitrophenol | 11.5[a] | 317 |
| 3-Nitrocatechol | 8.8[a], 11.8[b], 40.5[c] | 300 |
| 4-Nitrocatechol | 7.4[a] | 348 |
| Nitrohydroquinone | 9.1[a], 14.0[b], 44.2[c] | 280 |
| 2-Nitroresorcinol | 9.4[a], 12.5[b], 37.8[c] | 312 |

[a]HPLC retention time for standards in the gradient method with the C-8 column.
[b]HPLC retention time for standards in the isocratic method (80-20) for 3-nitrocatechol, nitrohydroquinone, and 2-nitroresorcinol separation (from o-nitrophenol) by using ABZ+PLUS column.
[c]HPLC retention time for standards in the isocratic methods (95-05) for better separation of 3-nitrocatechol, and 2-nitroresorcinol (from o-nitrophenol) by using ABZ+PLUS column.

Figure 35.

| Enzyme | Method | Product from NB | | | | | | | |
|---|---|---|---|---|---|---|---|---|---|
| | | m-NP | | | p-NP | | | 4-NC | |
| | | Rate | Relative | Mol% | Rate | Relative | Mol% | Rate | Relative |
| Wild-type ToMo | - | 0.098 | 1.0 | 72 | 0.031 | 1.0 | 28 | - | |
| E214G/D312BN/M399V | shuffling | 0.59 | 6.0 | 73 | 0.19 | 6.2 | 27 | 0.074 | • |
| M180T/E284G | shuffling | 0.45 | 4.6 | 95 | 0.030 | 0.97 | 5 | 0.0070 | • |
| I100Q | sat. mut. | 0.14 | 1.5 | 61 | 0.090 | 3 | 39 | - | |
| A110T/E392D | shuffling | 0.17 | 1.7 | 78 | 0.046 | 1.5 | 22 | 0.0090 | • |
| A101T/M114T | shuffling | 0.19 | 2.0 | 84 | 0.036 | 1.2 | 16 | 0.0050 | • |

Figure 36.

| Enzyme | Method | Product | Mol % | Rate nmol/min·mg prot | Relative |
|---|---|---|---|---|---|
| Wild-type ToMO | - | *m*-NP | 72 | 0.098 | 1 |
| | | *p*-NP | 28 | 0.031 | 1 |
| I100H | sat. mut. | *p*-NP | 100 | 0.0025 | 1/12 |
| W266R | shuffling | None | - | - | - |
| F205H | sat. mut. | *m*-NP | 100 | 0.0037 | 1/26 |
| F205Y | sat. mut. | *p*-NP | 100 | 0.0023 | 1/13 |
| F205C | sat. mut. | None | - | - | - |
| T201G | sat. mut. | None | - | - | - |
| F205G | sat. mut. | *m*-NP | 65 | 0.00167 | 1/39 |
| | | *p*-NP | 35 | 0.0009 | 1/34 |
| T281A/F290S | shuffling | None | - | - | - |

Figure 37.

| Enzyme | Substrate | | | | | | | | | | | | |
|---|---|---|---|---|---|---|---|---|---|---|---|---|---|
| | o-NP | | | | m-NP | | | | p-NP | | | |
| | Product | Rate | Relative | Mol % | Product | Rate | Relative | Mol % | Product | Rate | Relative | Mol % |
| Wild-type ToMo | 3-NC | 0.11 | 1.0 | 18 | 4-NC | 0.15 | 1.0 | 100 | 4-NC | 0.0082 ± 0.0002 | 1.0 | 100 |
| | NHQ | 0.48 | 1.0 | 82 | | | | | | | | |
| E214G/D312N /M399V | 3-NC | 0.28 | 2.6 | 14 | 4-NC | 0.53 | 3.6 | 100 | 4-NC | 0.164 ± 0.002 | 20 | 100 |
| | NHQ | 1.7 | 3.6 | 86 | | | | | | | | |
| I100Q | 3-NC | 0.076 | 0.7 | 16 | 4-NC | 0.09 | 1.6 | 37 | 4-NC | 0.0137 ± 0.0001 | 1.7 | 100 |
| | NHQ | 0.41 | 0.9 | 84 | NHQ | 0.15 | . | 63 | | | | |
| M180T/E284G | 3-NC | 0.095 | 0.9 | 9 | 4-NC | 0.17 | 1.2 | 100 | 4-NC | 0.0365 ± 0.0005 | 4.5 | 100 |
| | NHQ | 1.3 | 2.7 | 91 | | | | | | | | |

Figure 38.

| Enzyme | Oxidation rate, nmol/min·mg·prot | Regiospecificity, % | | |
|---|---|---|---|---|
| | | o-cresol | m-cresol | p-cresol |
| Wild-type | 2.6 | 32 | 21 | 47 |
| I100Q | 15 | 22 | 44 | 34 |
| F205G | 11 | 24 | 33 | 43 |
| M180T/E284G | 31 | 32 | 26 | 42 |
| E214G/D312N/M399V | 23 | 35 | 22 | 43 |
| A110T/E392D | 11 | 48 | 14 | 38 |
| A101T/M114T | 0.45 | 39 | 20 | 40 |
| I100H | 0.19 | 24 | 14 | 61 |
| T201G | 0.25 | 53 | 12 | 35 |
| F205H | 0.79 | 28 | 32 | 40 |
| F205Y | 0.34 | 34 | 34 | 32 |
| F205C | 0.070 | 21 | 35 | 44 |
| T281A/F290S | - | - | - | - |
| W266R | - | - | - | - |

| Enzyme | Oxidation Rate nmol/min·mg·prot. | Regiospecificity, % | |
|---|---|---|---|
| | | 3,4-DMP | 2,3-DMP |
| Wild-type ToMo | 1.8 | 82 | 18 |
| I100Q | 1.6 | 76 | 24 |
| I100H | 0.17 | 88 | 12 |
| T201G | 0.02 | 100 | - |

Figure 39.

SEQUENCE LISTING

```
<160> NUMBER OF SEQ ID NOS: 110

<210> SEQ ID NO 1
<211> LENGTH: 1503
<212> TYPE: DNA
<213> ORGANISM: Pseudomonas mendocina
<220> FEATURE:
<221> NAME/KEY: gene
<222> LOCATION: (1)..(1503)
<223> OTHER INFORMATION: Wide type T4MO alpha subunit DNA sequence

<400> SEQUENCE: 1
atggcgatgc acccacgtaa agactggtat gaactgacca gggcgacaaa ttggacacct      60
agctatgtta ccgaagagca gcttttccca gagcggatgt ccggtcatat gggtatcccg     120
ctggaaaaat gggaaagcta tgatgagccc tataagacat cctatccgga gtacgtaagt     180
atccaacgtg aaaaggatgc aggtgcttat tcggtgaagg cggcacttga gcgtgcaaaa     240
atttatgaga actctgaccc aggttggatc agcactttga aatcccatta cggcgccatc     300
gcagttggtg aatatgcagc cgtaaccggt gaaggtcgta tggcccgttt ttcaaaagca     360
ccgggaaatc gcaacatggc tacgtttggc atgatggatg aactgcgcca tggccagtta     420
cagctgtttt tcccgcatga atactgtaag aaggatcgcc agtttgattg ggcatggcgg     480
gcctatcaca gtaacgaatg ggcagccatt gctgcaaagc atttctttga tgacatcatt     540
accggacgtg atgcgatcag cgttgcgatc atgttgacgt tttcattcga aaccggcttc     600
accaacatgc agtttcttgg gttggcggca gatgccgcag aagcaggtga ctacacgttt     660
gcaaacctga tctccagcat tcaaaccgat gagtcgcgtc atgcacaaca gggcggcccc     720
gcattacagt tgctgatcga aaacggaaaa agagaagaag cccaaaagaa agtcgacatg     780
gcaatttggc gtgcctggcg tctatttgcg gtactaaccg ggccggttat ggattactac     840
acgccgttgg aggaccgcag ccagtcattc aaggagttta tgtacgagtg gatcatcgga     900
cagttcgaac gctcgttgat agatctgggc ttggacaagc cctggtactg ggatctattc     960
ctcaaggata ttgatgagct tcaccatagt tatcacatgg gtgtttggta ctggcgtaca    1020
accgcttggt ggaaccctgc tgccggggtc actcctgagg agcgtgactg gctggaagaa    1080
aagtatccag gatggaataa acgttggggt cgttgctggg atgtgatcac cgaaaacgtt    1140
ctcaatgacc gtatggatct tgtctctcca gaaaccttgc ccagcgtgtg caacatgagc    1200
cagataccgc tggtaggtgt tcctggtgat gactggaata tcgaagtttt cagtcttgag    1260
```

```
cacaatgggc gtctttatca ttttggctct gaagtggatc gctgggtatt ccagcaagat    1320
ccggttcagt atcaaaatca tatgaatatc gtcgaccgct tcctcgcagg tcagatacag    1380
ccgatgactt tggaaggtgc cctcaaatat atgggcttcc aatctattga agagatgggc    1440
aaagacgccc acgactttgc atgggctgac aagtgcaagc ctgctatgaa gaaatcggcc    1500
tga                                                                  1503
```

<210> SEQ ID NO 2
<211> LENGTH: 500
<212> TYPE: PRT
<213> ORGANISM: Pseudomonas mendocina
<220> FEATURE:
<221> NAME/KEY: Protein
<222> LOCATION: (1)..(500)
<223> OTHER INFORMATION: wild type T4MO alpha subunit protein

<400> SEQUENCE: 2

```
Met Ala Met His Pro Arg Lys Asp Trp Tyr Glu Leu Thr Arg Ala Thr
1               5                   10                  15

Asn Trp Thr Pro Ser Tyr Val Thr Glu Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60

Lys Asp Ala Gly Ala Tyr Ser Val Lys Ala Ala Leu Glu Arg Ala Lys
65                  70                  75                  80

Ile Tyr Glu Asn Ser Asp Pro Gly Trp Ile Ser Thr Leu Lys Ser His
                85                  90                  95

Tyr Gly Ala Ile Ala Val Gly Glu Tyr Ala Ala Val Thr Gly Glu Gly
            100                 105                 110

Arg Met Ala Arg Phe Ser Lys Ala Pro Gly Asn Arg Asn Met Ala Thr
        115                 120                 125

Phe Gly Met Met Asp Glu Leu Arg His Gly Gln Leu Gln Leu Phe Phe
    130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
        195                 200                 205

Ala Ala Asp Ala Ala Glu Ala Gly Asp Tyr Thr Phe Ala Asn Leu Ile
    210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Glu Ala Gln Lys
                245                 250                 255

Lys Val Asp Met Ala Ile Trp Arg Ala Trp Arg Leu Phe Ala Val Leu
            260                 265                 270

Thr Gly Pro Val Met Asp Tyr Tyr Thr Pro Leu Glu Asp Arg Ser Gln
        275                 280                 285

Ser Phe Lys Glu Phe Met Tyr Glu Trp Ile Ile Gly Gln Phe Glu Arg
    290                 295                 300
```

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
            325                 330                 335

Tyr Trp Arg Thr Thr Ala Trp Trp Asn Pro Ala Ala Gly Val Thr Pro
        340                 345                 350

Glu Glu Arg Asp Trp Leu Glu Glu Lys Tyr Pro Gly Trp Asn Lys Arg
            355                 360                 365

Trp Gly Arg Cys Trp Asp Val Ile Thr Glu Asn Val Leu Asn Asp Arg
    370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
                405                 410                 415

Phe Ser Leu Glu His Asn Gly Arg Leu Tyr His Phe Gly Ser Glu Val
            420                 425                 430

Asp Arg Trp Val Phe Gln Gln Asp Pro Val Gln Tyr Gln Asn His Met
    435                 440                 445

Asn Ile Val Asp Arg Phe Leu Ala Gly Gln Ile Gln Pro Met Thr Leu
    450                 455                 460

Glu Gly Ala Leu Lys Tyr Met Gly Phe Gln Ser Ile Glu Glu Met Gly
465                 470                 475                 480

Lys Asp Ala His Asp Phe Ala Trp Ala Asp Lys Cys Lys Pro Ala Met
            485                 490                 495

Lys Lys Ser Ala
            500

<210> SEQ ID NO 3
<211> LENGTH: 1503
<212> TYPE: DNA
<213> ORGANISM: Pseudomonas mendocina
<220> FEATURE:
<221> NAME/KEY: codons at positions tmoA 309 and 321
<222> LOCATION: (1)..(1503)
<223> OTHER INFORMATION: T4MO G103A/A107S alpha subunit DNA sequence

<400> SEQUENCE: 3
atggcgatgc acccacgtaa agactggtat gaactgacca gggcgacaaa ttggacacct      60
agctatgtta ccgaagagca gcttttccca gagcggatgt ccggtcatat gggtatcccg     120
ctggaaaaat gggaaagcta tgatgagccc tataagacat cctatccgga gtacgtaagt     180
atccaacgtg aaaaggatgc aggtgcttat cggtgaaggc ggcacttga gcgtgcaaaa     240 atttatgaga actctgaccc aggttggatc agcactttga atcccatta cggcgccatc     300 gcagttgccg aatatgcatc cgtaaccggt gaaggtcgta tggcccgttt ttcaaaagca     360
ccgggaaatc gcaacatggc tacgtttggc atgatggatg aactgcgcca tggccagtta     420
cagctgtttt tcccgcatga atactgtaag aaggatcgcc agtttgattg gcatggcgg     480 gcctatcaca gtaacgaatg gcagccatt gctgcaaagc atttctttga tgacatcatt     540
accggacgtg atgcgatcag cgttgcgatc atgttgacgt tttcattcga accggcttc     600 accaacatgc agtttcttgg gttggcggca gatgccgcag aagcaggtga ctacacgttt     660
gcaaacctga tctccagcat tcaaaccgat gagtcgcgtc atgcacaaca gggcggcccc     720
gcattacagt tgctgatcga aaacggaaaa agaagaagaag cccaaaagaa agtcgacatg     780
gcaatttggc gtgcctggcg tctatttgcg gtactaaccg ggccggttat ggattactac     840

```
acgccgttgg aggaccgcag ccagtcattc aaggagttta tgtacgagtg gatcatcgga    900
cagttcgaac gctcgttgat agatctgggc ttggacaagc cctggtactg ggatctattc    960
ctcaaggata ttgatgagct tcaccatagt tatcacatgg gtgtttggta ctggcgtaca   1020
accgcttggt ggaaccctgc tgccggggtc actcctgagg agcgtgactg gctggaagaa   1080
aagtatccag gatggaataa cgttggggt cgttgctggg atgtgatcac cgaaaacgtt    1140
ctcaatgacc gtatggatct tgtctctcca gaaaccttgc ccagcgtgtg caacatgagc   1200
cagataccgc tggtaggtgt tcctggtgat gactggaata tcgaagtttt cagtcttgag   1260
cacaatgggc gtctttatca ttttggctct gaagtggatc gctgggtatt ccagcaagat   1320
ccggttcagt atcaaaatca tatgaatatc gtcgaccgct tcctcgcagg tcagatacag   1380
ccgatgactt tggaaggtgc cctcaaatat atgggcttcc aatctattga agagatgggc   1440
aaagacgccc acgactttgc atgggctgac aagtgcaagc tgctatgaa gaaatcggcc    1500
tga                                                                 1503
```

<210> SEQ ID NO 4
<211> LENGTH: 500
<212> TYPE: PRT
<213> ORGANISM: Pseudomonas mendocina
<220> FEATURE:
<221> NAME/KEY: T4MO G103A/A107S
<222> LOCATION: (1)..(500)
<223> OTHER INFORMATION: T4MO G103A/A107S alpha subunit protein

<400> SEQUENCE: 4

```
Met Ala Met His Pro Arg Lys Asp Trp Tyr Glu Leu Thr Arg Ala Thr
1               5                   10                  15

Asn Trp Thr Pro Ser Tyr Val Thr Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60

Lys Asp Ala Gly Ala Tyr Ser Val Lys Ala Ala Leu Glu Arg Ala Lys
65                  70                  75                  80

Ile Tyr Glu Asn Ser Asp Pro Gly Trp Ile Ser Thr Leu Lys Ser His
                85                  90                  95

Tyr Gly Ala Ile Ala Val Ala Glu Tyr Ala Ser Val Thr Gly Glu Gly
            100                 105                 110

Arg Met Ala Arg Phe Ser Lys Ala Pro Gly Asn Arg Asn Met Ala Thr
        115                 120                 125

Phe Gly Met Met Asp Glu Leu Arg His Gly Gln Leu Gln Leu Phe Phe
    130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
        195                 200                 205

Ala Ala Asp Ala Ala Glu Ala Gly Asp Tyr Thr Phe Ala Asn Leu Ile
    210                 215                 220
```

-continued

```
Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Ala Gln Lys
            245                 250                 255

Lys Val Asp Met Ala Ile Trp Arg Ala Trp Arg Leu Phe Ala Val Leu
        260                 265                 270

Thr Gly Pro Val Met Asp Tyr Tyr Thr Pro Leu Glu Asp Arg Ser Gln
    275                 280                 285

Ser Phe Lys Glu Phe Met Tyr Glu Trp Ile Ile Gly Gln Phe Glu Arg
290                 295                 300

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
                325                 330                 335

Tyr Trp Arg Thr Thr Ala Trp Trp Asn Pro Ala Ala Gly Val Thr Pro
            340                 345                 350

Glu Glu Arg Asp Trp Leu Glu Glu Lys Tyr Pro Gly Trp Asn Lys Arg
        355                 360                 365

Trp Gly Arg Cys Trp Asp Val Ile Thr Glu Asn Val Leu Asn Asp Arg
    370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
                405                 410                 415

Phe Ser Leu Glu His Asn Gly Arg Leu Tyr His Phe Gly Ser Glu Val
            420                 425                 430

Asp Arg Trp Val Phe Gln Gln Asp Pro Val Gln Tyr Gln Asn His Met
        435                 440                 445

Asn Ile Val Asp Arg Phe Leu Ala Gly Gln Ile Gln Pro Met Thr Leu
    450                 455                 460

Glu Gly Ala Leu Lys Tyr Met Gly Phe Gln Ser Ile Glu Glu Met Gly
465                 470                 475                 480

Lys Asp Ala His Asp Phe Ala Trp Ala Asp Lys Cys Lys Pro Ala Met
                485                 490                 495

Lys Lys Ser Ala
            500

<210> SEQ ID NO 5
<211> LENGTH: 1503
<212> TYPE: DNA
<213> ORGANISM: Pseudomonas mendocina
<220> FEATURE:
<221> NAME/KEY: codons at positions TmoA 309 and 321
<222> LOCATION: (1)..(1503)
<223> OTHER INFORMATION: G103S/A107G codons at positions tmoA 309 and
      321

<400> SEQUENCE: 5
atggcgatgc acccacgtaa agactggtat gaactgacca gggcgacaaa ttggacacct      60
agctatgtta ccgaagagca gcttttccca gagcggatgt ccggtcatat gggtatcccg     120
ctggaaaaat gggaaagcta tgatgagccc tataagacat cctatccgga gtacgtaagt     180
atccaacgtg aaaggatgc aggtgctat tcggtgaagg cggcacttga gcgtgcaaaa      240
atttatgaga actctgaccc aggttggatc agcactttga atcccatta cggcgccatc      300 gcagtttcgg aatatgcagg tgtaaccggt gaaggtcgta tggcccgttt ttcaaaagca    360
```

```
ccgggaaatc gcaacatggc tacgtttggc atgatggatg aactgcgcca tggccagtta    420
cagctgtttt tcccgcatga atactgtaag aaggatcgcc agtttgattg ggcatggcgg    480
gcctatcaca gtaacgaatg ggcagccatt gctgcaaagc atttctttga tgacatcatt    540
accggacgtg atgcgatcag cgttgcgatc atgttgacgt tttcattcga aaccggcttc    600
accaacatgc agtttcttgg gttggcggca gatgccgcag aagcaggtga ctacacgttt    660
gcaaacctga tctccagcat tcaaaccgat gagtcgcgtc atgcacaaca gggcggcccc    720
gcattacagt tgctgatcga aaacggaaaa agagaagaag cccaaaagaa agtcgacatg    780
gcaatttggc gtgcctggcg tctatttgcg gtactaaccg ggccggttat ggattactac    840
acgccgttgg aggaccgcag ccagtcattc aaggagttta tgtacgagtg gatcatcgga    900
cagttcgaac gctcgttgat agatctgggc ttggacaagc cctggtactg ggatctattc    960
ctcaaggata ttgatgagct tcaccatagt tatcacatgg gtgtttggta ctggcgtaca   1020
accgcttggt ggaaccctgc tgccggggtc actcctgagg agcgtgactg gctggaagaa   1080
aagtatccag gatggaataa cgttggggt cgttgctggg atgtgatcac cgaaaacgtt   1140
ctcaatgacc gtatggatct tgtctctcca gaaaccttgc ccagcgtgtg caacatgagc   1200
cagataccgc tggtaggtgt tcctggtgat gactggaata tcgaagtttt cagtcttgag   1260
cacaatgggg tcttatca ttttggctct gaagtggatc gctgggtatt ccagcaagat   1320
ccggttcagt atcaaaatca tatgaatatc gtcgaccgct tcctcgcagg tcagatacag   1380
ccgatgactt tggaaggtgc cctcaaatat atgggcttcc aatctattga agagatgggc   1440
aaagacgccc acgactttgc atgggctgac aagtgcaagc ctgctatgaa gaaatcggcc   1500
tga                                                                1503
```

<210> SEQ ID NO 6
<211> LENGTH: 500
<212> TYPE: PRT
<213> ORGANISM: Pseudomonas mendocina
<220> FEATURE:
<221> NAME/KEY: T4MO G103S/A107G
<222> LOCATION: (1)..(500)
<223> OTHER INFORMATION: T4MO G103S/A107G alpha subunit protein

<400> SEQUENCE: 6

```
Met Ala Met His Pro Arg Lys Asp Trp Tyr Glu Leu Thr Arg Ala Thr
1               5                   10                  15

Asn Trp Thr Pro Ser Tyr Val Thr Glu Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60

Lys Asp Ala Gly Ala Tyr Ser Val Lys Ala Ala Leu Glu Arg Ala Lys
65                  70                  75                  80

Ile Tyr Glu Asn Ser Asp Pro Gly Trp Ile Ser Thr Leu Lys Ser His
                85                  90                  95

Tyr Gly Ala Ile Ala Val Ser Glu Tyr Ala Gly Val Thr Gly Glu Gly
            100                 105                 110

Arg Met Ala Arg Phe Ser Lys Ala Pro Gly Asn Arg Asn Met Ala Thr
        115                 120                 125

Phe Gly Met Met Asp Glu Leu Arg His Gly Gln Leu Gln Leu Phe Phe
    130                 135                 140
```

```
Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
        195                 200                 205

Ala Ala Asp Ala Ala Glu Ala Gly Asp Tyr Thr Phe Ala Asn Leu Ile
    210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Glu Ala Gln Lys
                245                 250                 255

Lys Val Asp Met Ala Ile Trp Arg Ala Trp Arg Leu Phe Ala Val Leu
            260                 265                 270

Thr Gly Pro Val Met Asp Tyr Tyr Thr Pro Leu Glu Asp Arg Ser Gln
        275                 280                 285

Ser Phe Lys Glu Phe Met Tyr Glu Trp Ile Ile Gly Gln Phe Glu Arg
    290                 295                 300

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
                325                 330                 335

Tyr Trp Arg Thr Thr Ala Trp Asn Pro Ala Ala Gly Val Thr Pro
            340                 345                 350

Glu Glu Arg Asp Trp Leu Glu Glu Lys Tyr Pro Gly Trp Asn Lys Arg
        355                 360                 365

Trp Gly Arg Cys Trp Asp Val Ile Thr Glu Asn Val Leu Asn Asp Arg
    370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
                405                 410                 415

Phe Ser Leu Glu His Asn Gly Arg Leu Tyr His Phe Gly Ser Glu Val
            420                 425                 430

Asp Arg Trp Val Phe Gln Gln Asp Pro Val Gln Tyr Gln Asn His Met
        435                 440                 445

Asn Ile Val Asp Arg Phe Leu Ala Gly Gln Ile Gln Pro Met Thr Leu
    450                 455                 460

Glu Gly Ala Leu Lys Tyr Met Gly Phe Gln Ser Ile Glu Glu Met Gly
465                 470                 475                 480

Lys Asp Ala His Asp Phe Ala Trp Ala Asp Lys Cys Lys Pro Ala Met
                485                 490                 495

Lys Lys Ser Ala
            500

<210> SEQ ID NO 7
<211> LENGTH: 1503
<212> TYPE: DNA
<213> ORGANISM: Pseudomonas mendocina
<220> FEATURE:
<221> NAME/KEY: codons at positions tmoA 309 and 321
<222> LOCATION: (1)..(1503)
<223> OTHER INFORMATION: T4MO G103S/A107T alpha subunit DNA sequence
```

-continued

```
<400> SEQUENCE: 7
atggcgatgc acccacgtaa agactggtat gaactgacca gggcgacaaa ttggacacct    60
agctatgtta ccgaagagca gcttttccca gagcggatgt ccggtcatat gggtatcccg   120
ctggaaaaat gggaaagcta tgatgagccc tataagacat cctatccgga gtacgtaagt   180
atccaacgtg aaaaggatgc aggtgcttat tcggtgaagg cggcacttga gcgtgcaaaa   240
atttatgaga actctgaccc aggttggatc agcactttga atcccatta cggcgccatc    300 gcagtttcag aatatgcaac tgtaaccggt gaaggtcgta tggcccgttt ttcaaaagca   360
ccgggaaatc gcaacatggc tacgtttggc atgatggatg aactgcgcca tggccagtta   420
cagctgtttt tcccgcatga atactgtaag aaggatcgcc agtttgattg gcatggcgg   480 gcctatcaca gtaacgaatg gcagccatt gctgcaaagc atttctttga tgacatcatt    540
accggacgtg atgcgatcag cgttgcgatc atgttgacgt tttcattcga accggcttc    600 accaacatgc agtttcttgg gttggcggca gatgccgcag aagcaggtga ctacacgttt   660
gcaaacctga tctccagcat tcaaaccgat gagtcgcgtc atgcacaaca gggcggcccc   720
gcattacagt tgctgatcga aaacggaaaa agagaagaag cccaaaagaa agtcgacatg   780
gcaatttggc gtgcctggcg tctatttgcg gtactaaccg ggccggttat ggattactac   840
acgccgttgg aggaccgcag ccagtcattc aaggagttta tgtacgagtg gatcatcgga   900
cagttcgaac gctcgttgat agatctgggc ttggacaagc cctggtactg ggatctattc   960
ctcaaggata ttgatgagct tcaccatagt tatcacatgg gtgtttggta ctggcgtaca   1020
accgcttggt ggaaccctgc tgccggggtc actcctgagg agcgtgactg gctggaagaa   1080
aagtatccag gatggaataa acgttgggg cgttgctggg atgtgatcac cgaaaacgtt   1140
ctcaatgacc gtatggatct tgtctctcca gaaaccttgc ccagcgtgtg caacatgagc   1200
cagataccgc tggtaggtgt tcctggtgat gactggaata tcgaagttt cagtcttgag   1260 cacaatgggc gtctttatca ttttggctct gaagtggatc gctgggtatt ccagcaagat   1320
ccggttcagt atcaaaatca tatgaatatc gtcgaccgct tcctcgcagg tcagatacag   1380
ccgatgactt tggaaggtgc cctcaaatat atgggcttcc aatctattga agagatgggc   1440
aaagacgccc acgactttgc atgggctgac aagtgcaagc ctgctatgaa gaaatcggcc   1500
tga                                                                 1503

<210> SEQ ID NO 8
<211> LENGTH: 500
<212> TYPE: PRT
<213> ORGANISM: Pseudomonas mendocina
<220> FEATURE:
<221> NAME/KEY: G103S/A107T
<222> LOCATION: (1)..(500)
<223> OTHER INFORMATION: T4MO G103S/A107T residues at positions 103 and
      107

<400> SEQUENCE: 8

Met Ala Met His Pro Arg Lys Asp Trp Tyr Glu Leu Thr Arg Ala Thr
1               5                   10                  15

Asn Trp Thr Pro Ser Tyr Val Thr Glu Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60
```

-continued

```
Lys Asp Ala Gly Ala Tyr Ser Val Lys Ala Ala Leu Glu Arg Ala Lys
 65                  70                  75                  80

Ile Tyr Glu Asn Ser Asp Pro Gly Trp Ile Ser Thr Leu Lys Ser His
             85                  90                  95

Tyr Gly Ala Ile Ala Val Ser Glu Tyr Ala Thr Val Thr Gly Glu Gly
            100                 105                 110

Arg Met Ala Arg Phe Ser Lys Ala Pro Gly Asn Arg Asn Met Ala Thr
            115                 120                 125

Phe Gly Met Met Asp Glu Leu Arg His Gly Gln Leu Gln Leu Phe Phe
            130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
            165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
            195                 200                 205

Ala Ala Asp Ala Ala Glu Ala Gly Asp Tyr Thr Phe Ala Asn Leu Ile
            210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Glu Ala Gln Lys
            245                 250                 255

Lys Val Asp Met Ala Ile Trp Arg Ala Trp Arg Leu Phe Ala Val Leu
            260                 265                 270

Thr Gly Pro Val Met Asp Tyr Tyr Thr Pro Leu Glu Asp Arg Ser Gln
            275                 280                 285

Ser Phe Lys Glu Phe Met Tyr Glu Trp Ile Ile Gly Gln Phe Glu Arg
            290                 295                 300

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
            325                 330                 335

Tyr Trp Arg Thr Thr Ala Trp Trp Asn Pro Ala Ala Gly Val Thr Pro
            340                 345                 350

Glu Glu Arg Asp Trp Leu Glu Glu Lys Tyr Pro Gly Trp Asn Lys Arg
            355                 360                 365

Trp Gly Arg Cys Trp Asp Val Ile Thr Glu Asn Val Leu Asn Asp Arg
            370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
            405                 410                 415

Phe Ser Leu Glu His Asn Gly Arg Leu Tyr His Phe Gly Ser Glu Val
            420                 425                 430

Asp Arg Trp Val Phe Gln Gln Asp Pro Val Gln Tyr Gln Asn His Met
            435                 440                 445

Asn Ile Val Asp Arg Phe Leu Ala Gly Gln Ile Gln Pro Met Thr Leu
            450                 455                 460

Glu Gly Ala Leu Lys Tyr Met Gly Phe Gln Ser Ile Glu Glu Met Gly
465                 470                 475                 480

Lys Asp Ala His Asp Phe Ala Trp Ala Asp Lys Cys Lys Pro Ala Met
```

Lys Lys Ser Ala
    500

<210> SEQ ID NO 9
<211> LENGTH: 1503
<212> TYPE: DNA
<213> ORGANISM: Pseudomonas mendocina
<220> FEATURE:
<221> NAME/KEY: I100A
<222> LOCATION: (1)..(1503)
<223> OTHER INFORMATION: T4MO I100A alpha subunit DNA sequence

<400> SEQUENCE: 9

```
atggcgatgc acccacgtaa agactggtat gaactgacca gggcgacaaa ttggacacct      60
agctatgtta ccgaagagca gcttttccca gagcggatgt ccggtcatat gggtatcccg     120
ctggaaaaat gggaaagcta tgatgagccc tataagacat cctatccgga gtacgtaagt     180
atccaacgtg aaaaggatgc aggtgcttat tcggtgaagg cggcacttga gcgtgcaaaa     240
atttatgaga ctctgaccc aggttggatc agcactttga atcccatta cggcgccgcc      300
gcagttggtg aatatgcagc cgtaaccggt gaaggtcgta tggcccgttt ttcaaaagca     360
ccgggaaatc gcaacatggc tacgtttggc atgatggatg aactgcgcca tggccagtta     420
cagctgtttt tcccgcatga atactgtaag aaggatcgcc agtttgattg gcatggcgg     480
gcctatcaca gtaacgaatg gcagccatt gctgcaaagc atttctttga tgacatcatt     540
accggacgtg atgcgatcag cgttgcgatc atgttgacgt tttcattcga aaccggcttc     600
accaacatgc agtttcttgg gttggcggca gatgccgcag aagcaggtga ctacacgttt     660
gcaaacctga tctccagcat tcaaaccgat gagtcgcgtc atgcacaaca gggcggcccc     720
gcattacagt tgctgatcga aaacggaaaa agagaagaag cccaaaagaa agtcgacatg     780
gcaatttggc gtgcctggcg tctatttgcg gtactaaccg gccggttat ggattactac      840
acgccgttgg aggaccgcag ccagtcattc aaggagttta tgtacgagtg atcatcgga     900
cagttcgaac gctcgttgat agatctgggc ttggacaagc cctggtactg ggatctattc     960
ctcaaggata ttgatgagct tcaccatagt tatcacatgg gtgtttggta ctggcgtaca    1020
accgcttggt ggaaccctgc tgccggggtc actcctgagg agcgtgactg gctgaagaa     1080
aagtatccag gatggaataa cgttggggt cgttgctggg atgtgatcac cgaaaacgtt    1140
ctcaatgacc gtatggatct tgtctctcca gaaaccttgc cagcgtgtg caacatgagc     1200
cagataccgc tggtaggtgt tcctggtgat gactggaata tcgaagtttt cagtcttgag    1260
cacaatgggg tctttatca ttttggctct gaagtggatc gctgggtatt ccagcaagat     1320
ccggttcagt atcaaaatca tatgaatatc gtcgaccgct tcctcgcagg tcagatacag    1380
ccgatgactt tggaaggtgc cctcaaatat atgggcttcc aatcattga agagatgggc     1440
aaagacgccc acgactttgc atgggctgac aagtgcaagc ctgctatgaa gaaatcggcc    1500
tga                                                                  1503
```

<210> SEQ ID NO 10
<211> LENGTH: 500
<212> TYPE: PRT
<213> ORGANISM: Pseudomonas mendocina
<220> FEATURE:
<221> NAME/KEY: I100A
<222> LOCATION: (1)..(500)
<223> OTHER INFORMATION: T4MO I100A alpha subunit protein

<400> SEQUENCE: 10

```
Met Ala Met His Pro Arg Lys Asp Trp Tyr Glu Leu Thr Arg Ala Thr
1               5                   10                  15

Asn Trp Thr Pro Ser Tyr Val Thr Glu Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60

Lys Asp Ala Gly Ala Tyr Ser Val Lys Ala Ala Leu Glu Arg Ala Lys
65                  70                  75                  80

Ile Tyr Glu Asn Ser Asp Pro Gly Trp Ile Ser Thr Leu Lys Ser His
                85                  90                  95

Tyr Gly Ala Ala Ala Val Gly Glu Tyr Ala Ala Val Thr Gly Glu Gly
            100                 105                 110

Arg Met Ala Arg Phe Ser Lys Ala Pro Gly Asn Arg Asn Met Ala Thr
        115                 120                 125

Phe Gly Met Met Asp Glu Leu Arg His Gly Gln Leu Gln Leu Phe Phe
    130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
        195                 200                 205

Ala Ala Asp Ala Ala Glu Ala Gly Asp Tyr Thr Phe Ala Asn Leu Ile
    210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Glu Ala Gln Lys
                245                 250                 255

Lys Val Asp Met Ala Ile Trp Arg Ala Trp Arg Leu Phe Ala Val Leu
            260                 265                 270

Thr Gly Pro Val Met Asp Tyr Tyr Thr Pro Leu Glu Asp Arg Ser Gln
        275                 280                 285

Ser Phe Lys Glu Phe Met Tyr Gly Trp Ile Ile Gly Gln Phe Glu Arg
    290                 295                 300

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
                325                 330                 335

Tyr Trp Arg Thr Thr Ala Trp Asn Pro Ala Ala Gly Val Thr Pro
            340                 345                 350

Glu Glu Arg Asp Trp Leu Glu Glu Lys Tyr Pro Gly Trp Asn Lys Arg
        355                 360                 365

Trp Gly Arg Cys Trp Asp Val Ile Thr Glu Asn Val Leu Asn Asp Arg
    370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
                405                 410                 415
```

Phe Ser Leu Glu His Asn Gly Arg Leu Tyr His Phe Gly Ser Glu Val
          420                 425                 430

Asp Arg Trp Val Phe Gln Gln Asp Pro Val Gln Tyr Gln Asn His Met
        435                 440                 445

Asn Ile Val Asp Arg Phe Leu Ala Gly Gln Ile Gln Pro Met Thr Leu
    450                 455                 460

Glu Gly Ala Leu Lys Tyr Met Gly Phe Gln Ser Ile Glu Glu Met Gly
465                 470                 475                 480

Lys Asp Ala His Asp Phe Ala Trp Ala Asp Lys Cys Lys Pro Ala Met
            485                 490                 495

Lys Lys Ser Ala
        500

<210> SEQ ID NO 11
<211> LENGTH: 1503
<212> TYPE: DNA
<213> ORGANISM: Pseudomonas mendocina
<220> FEATURE:
<221> NAME/KEY: I100S
<222> LOCATION: (1)..(1503)
<223> OTHER INFORMATION: T4MO I100S alpha subunit DNA sequence

<400> SEQUENCE: 11

| | | | | | |
|---|---|---|---|---|---|
| atggcgatgc | acccacgtaa | agactggtat | gaactgacca | gggcgacaaa | ttggacacct | 60 |
| agctatgtta | ccgaagagca | gcttttccca | gagcggatgt | ccgtcatat | gggtatcccg | 120 |
| ctggaaaaat | gggaaagcta | tgatgagccc | tataagacat | cctatccgga | gtacgtaagt | 180 |
| atccaacgtg | aaaaggatgc | aggtgcttat | tcggtgaagg | cggcacttga | gcgtgcaaaa | 240 |
| atttatgaga | actctgaccc | aggttggatc | agcactttga | atcccatta | cggcgcctct | 300 |
| gcagttggtg | aatatgcagc | cgtaaccggt | gaaggtcgta | tggcccgttt | ttcaaaagca | 360 |
| ccgggaaatc | gcaacatggc | tacgtttggc | atgatggatg | aactgcgcca | tggccagtta | 420 |
| cagctgtttt | tcccgcatga | atactgtaag | aaggatcgcc | agtttgattg | gcatggcgg | 480 |
| gcctatcaca | gtaacgaatg | ggcagccatt | gctgcaaagc | atttctttga | tgacatcatt | 540 |
| accggacgtg | atgcgatcag | cgttgcgatc | atgttgacgt | tttcattcga | aaccggcttc | 600 |
| accaacatgc | agtttcttgg | gttggcggca | gatgccgcag | aagcaggtga | ctacacgttt | 660 |
| gcaaacctga | tctccagcat | tcaaaccgat | gagtcgcgtc | atgcacaaca | gggcggcccc | 720 |
| gcattacagt | tgctgatcga | aaacggaaaa | agagaagaag | cccaaaagaa | agtcgacatg | 780 |
| gcaatttggc | gtgcctggcg | tctatttgcg | gtactaaccg | ggccggttat | ggattactac | 840 |
| acgccgttgg | aggaccgcag | ccagtcattc | aaggagttta | tgtacgagtg | gatcatcgga | 900 |
| cagttcgaac | gctcgttgat | agatctgggc | ttggacaagc | cctggtactg | ggatctattc | 960 |
| ctcaaggata | ttgatgagct | tcaccatagt | tatcacatgg | gtgtttggta | ctggcgtaca | 1020 |
| accgcttggt | ggaaccctgc | tgccggggtc | actcctgagg | agcgtgactg | gctggaagaa | 1080 |
| aagtatccag | atggaataa | acgttggggt | cgttgctggg | atgtgatcac | cgaaaacgtt | 1140 |
| ctcaatgacc | gtatggatct | tgtctctcca | gaaaccttgc | ccagcgtgtg | caacatgagc | 1200 |
| cagatccgc | tggtaggtgt | tcctggtgat | gactggaata | tcgaagtttt | cagtcttgag | 1260 |
| cacaatgggc | gtctttatca | ttttggctct | gaagtggatc | gctgggtatt | ccagcaagat | 1320 |
| ccggttcagt | atcaaaatca | tatgaatatc | gtcgaccgct | tcctcgcagg | tcagatacag | 1380 |
| ccgatgactt | tggaaggtgc | cctcaaatat | atgggcttcc | aatctattga | agagatgggc | 1440 |

```
aaagacgccc acgactttgc atgggctgac aagtgcaagc ctgctatgaa gaaatcggcc   1500
tga                                                                 1503
```

<210> SEQ ID NO 12
<211> LENGTH: 500
<212> TYPE: PRT
<213> ORGANISM: Pseudomonas mendocina
<220> FEATURE:
<221> NAME/KEY: I100S
<222> LOCATION: (1)..(500)
<223> OTHER INFORMATION: T4MO I100S alpha subunit protein

<400> SEQUENCE: 12

```
Met Ala Met His Pro Arg Lys Asp Trp Tyr Glu Leu Thr Arg Ala Thr
1               5                   10                  15

Asn Trp Thr Pro Ser Tyr Val Thr Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60

Lys Asp Ala Gly Ala Tyr Ser Val Lys Ala Ala Leu Glu Arg Ala Lys
65                  70                  75                  80

Ile Tyr Glu Asn Ser Asp Pro Gly Trp Ile Ser Thr Leu Lys Ser His
                85                  90                  95

Tyr Gly Ala Ser Ala Val Gly Glu Tyr Ala Ala Val Thr Gly Glu Gly
            100                 105                 110

Arg Met Ala Arg Phe Ser Lys Ala Pro Gly Asn Arg Asn Met Ala Thr
        115                 120                 125

Phe Gly Met Met Asp Glu Leu Arg His Gly Gln Leu Gln Leu Phe Phe
    130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
        195                 200                 205

Ala Ala Asp Ala Ala Glu Ala Gly Asp Tyr Thr Phe Ala Asn Leu Ile
    210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Ala Gln Lys
                245                 250                 255

Lys Val Asp Met Ala Ile Trp Arg Ala Trp Arg Leu Phe Ala Val Leu
            260                 265                 270

Thr Gly Pro Val Met Asp Tyr Tyr Thr Pro Leu Glu Asp Arg Ser Gln
        275                 280                 285

Ser Phe Lys Glu Phe Met Tyr Glu Trp Ile Ile Gly Gln Phe Glu Arg
    290                 295                 300

Ser Leu Ile Asp Leu Gly Leu Asp Lys Pro Trp Tyr Trp Asp Leu Phe
305                 310                 315                 320

Leu Lys Asp Ile Asp Glu Leu His His Ser Tyr His Met Gly Val Trp
                325                 330                 335
```

| | | | | | | | | | | | | |
|---|---|---|---|---|---|---|---|---|---|---|---|---|
|Tyr|Trp|Arg|Thr|Thr|Ala|Trp|Trp|Asn|Pro|Ala|Ala|Gly|Val|Thr|Pro|
| | | |340| | | | |345| | | |350| | | |

Tyr Trp Arg Thr Thr Ala Trp Trp Asn Pro Ala Ala Gly Val Thr Pro
            340                 345                 350

Glu Glu Arg Asp Trp Leu Glu Glu Lys Tyr Pro Gly Trp Asn Lys Arg
            355                 360                 365

Trp Gly Arg Cys Trp Asp Val Ile Thr Glu Asn Val Leu Asn Asp Arg
            370                 375                 380

Met Asp Leu Val Ser Pro Glu Thr Leu Pro Ser Val Cys Asn Met Ser
385                 390                 395                 400

Gln Ile Pro Leu Val Gly Val Pro Gly Asp Asp Trp Asn Ile Glu Val
                405                 410                 415

Phe Ser Leu Glu His Asn Gly Arg Leu Tyr His Phe Gly Ser Glu Val
            420                 425                 430

Asp Arg Trp Val Phe Gln Gln Asp Pro Val Gln Tyr Gln Asn His Met
            435                 440                 445

Asn Ile Val Asp Arg Phe Leu Ala Gly Gln Ile Gln Pro Met Thr Leu
450                 455                 460

Glu Gly Ala Leu Lys Tyr Met Gly Phe Gln Ser Ile Glu Glu Met Gly
465                 470                 475                 480

Lys Asp Ala His Asp Phe Ala Trp Ala Asp Lys Cys Lys Pro Ala Met
            485                 490                 495

Lys Lys Ser Ala
            500

<210> SEQ ID NO 13
<211> LENGTH: 1503
<212> TYPE: DNA
<213> ORGANISM: Pseudomonas mendocina
<220> FEATURE:
<221> NAME/KEY: G103S
<222> LOCATION: (1)..(1503)
<223> OTHER INFORMATION: T4MO G103S alpha subunit DNA sequence

<400> SEQUENCE: 13

```
atggcgatgc acccacgtaa agactggtat gaactgacca gggcgacaaa ttggacacct      60
agctatgtta ccgaagagca gcttttccca gagcggatgt ccggtcatat gggtatcccg     120
ctggaaaaat gggaaagcta tgatgagccc ataagacat cctatccgga gtacgtaagt      180
atccaacgtg aaaaggatgc aggtgcttat tcggtgaagg cggcacttga gcgtgcaaaa     240
atttatgaga actctgaccc aggttggatc agcactttga atcccatta cggcgccatc      300
gcagtttccg aatatgcagc cgtaaccggt gaaggtcgta tggcccgttt ttcaaaagca     360
ccgggaaatc gcaacatggc tacgtttggc atgatggatg aactgcgcca tggccagtta     420
cagctgtttt tcccgcatga atactgtaag aaggatcgcc agtttgattg gcatggcgg      480
gcctatcaca gtaacgaatg gcagccatt gctgcaaagc atttctttga tgacatcatt      540
accggacgtg atgcgatcag cgttgcgatc atgttgacgt tttcattcga aaccggcttc     600
accaacatgc agtttcttgg gttggcggca gatgccgcag aagcaggtga ctacacgttt     660
gcaaacctga tctccagcat tcaaaccgat gagtcgcgtc atgcacaaca gggcggcccc     720
gcattacagt tgctgatcga aaacggaaaa agagaagaag cccaaaagaa agtcgacatg     780
gcaatttggc gtgcctggcg tctatttgcg gtactaaccg gccggttat ggattactac      840
acgccgttgg aggaccgcag ccagtcattc aaggagttta tgtacgagtg gatcatcgga     900
cagttcgaac gctcgttgat agatctgggc ttggacaagc cctggtactg ggatctattc     960
ctcaaggata ttgatgagct tcaccatagt tatcacatgg gtgtttggta ctggcgtaca    1020
```

-continued

```
accgcttggt ggaaccctgc tgccggggtc actcctgagg agcgtgactg gctggaagaa    1080
aagtatccag gatggaataa acgttggggt cgttgctggg atgtgatcac cgaaaacgtt    1140
ctcaatgacc gtatggatct tgtctctcca gaaaccttgc ccagcgtgtg caacatgagc    1200
cagataccgc tggtaggtgt tcctggtgat gactggaata tcgaagtttt cagtcttgag    1260
cacaatgggc gtctttatca ttttggctct gaagtggatc gctgggtatt ccagcaagat    1320
ccggttcagt atcaaaatca tatgaatatc gtcgaccgct ccctcgcagg tcagatacag    1380
ccgatgactt tggaaggtgc cctcaaatat atgggcttcc aatctattga agagatgggc    1440
aaagacgccc acgactttgc atgggctgac aagtgcaagc tgctatgaa gaaatcggcc    1500 tga                                                                  1503
```

<210> SEQ ID NO 14
<211> LENGTH: 500
<212> TYPE: PRT
<213> ORGANISM: Pseudomonas mendocina
<220> FEATURE:
<221> NAME/KEY: G103S
<222> LOCATION: (1)..(500)
<223> OTHER INFORMATION: T4MO G103S alpha subunit protein

<400> SEQUENCE: 14

```
Met Ala Met His Pro Arg Lys Asp Trp Tyr Glu Leu Thr Arg Ala Thr
1               5                   10                  15

Asn Trp Thr Pro Ser Tyr Val Thr Glu Glu Gln Leu Phe Pro Glu Arg
            20                  25                  30

Met Ser Gly His Met Gly Ile Pro Leu Glu Lys Trp Glu Ser Tyr Asp
        35                  40                  45

Glu Pro Tyr Lys Thr Ser Tyr Pro Glu Tyr Val Ser Ile Gln Arg Glu
    50                  55                  60

Lys Asp Ala Gly Ala Tyr Ser Val Lys Ala Ala Leu Glu Arg Ala Lys
65                  70                  75                  80

Ile Tyr Glu Asn Ser Asp Pro Gly Trp Ile Ser Thr Leu Lys Ser His
                85                  90                  95

Tyr Gly Ala Ile Ala Val Ser Glu Tyr Ala Ala Val Thr Gly Glu Gly
            100                 105                 110

Arg Met Ala Arg Phe Ser Lys Ala Pro Gly Asn Arg Asn Met Ala Thr
        115                 120                 125

Phe Gly Met Met Asp Glu Leu Arg His Gly Gln Leu Gln Leu Phe Phe
    130                 135                 140

Pro His Glu Tyr Cys Lys Lys Asp Arg Gln Phe Asp Trp Ala Trp Arg
145                 150                 155                 160

Ala Tyr His Ser Asn Glu Trp Ala Ala Ile Ala Ala Lys His Phe Phe
                165                 170                 175

Asp Asp Ile Ile Thr Gly Arg Asp Ala Ile Ser Val Ala Ile Met Leu
            180                 185                 190

Thr Phe Ser Phe Glu Thr Gly Phe Thr Asn Met Gln Phe Leu Gly Leu
        195                 200                 205

Ala Ala Asp Ala Ala Glu Ala Gly Asp Tyr Thr Phe Ala Asn Leu Ile
    210                 215                 220

Ser Ser Ile Gln Thr Asp Glu Ser Arg His Ala Gln Gln Gly Gly Pro
225                 230                 235                 240

Ala Leu Gln Leu Leu Ile Glu Asn Gly Lys Arg Glu Glu Ala Gln Lys
                245                 250                 255

Lys Val Asp Met Ala Ile Trp Arg Ala Trp Arg Leu Phe Ala Val Leu
```

```
                    260                 265                 270
Thr Gly Pro Val Met Asp Tyr Tyr Thr Pro Leu Glu Asp Arg Ser Gln
            275                 280                 285
Ser Phe Lys Glu Phe Met Tyr Glu Trp Ile Ile Gly Gln Phe Glu Arg
            290                 295                 300
Ser Leu Ile Asp Leu Gly Leu Asp Lys Pro Trp Tyr Trp Asp Leu Phe
305                 310                 315                 320
Leu Lys Asp Ile Asp Glu Leu His His Ser Tyr His Met Gly Val Trp
                325                 330                 335
Tyr Trp Arg Thr Thr Ala Trp Trp Asn Pro Ala Ala Gly Val Thr Pro
            340                 345                 350
Glu Glu Arg Asp Trp Leu Glu Glu Lys Tyr Pro Gly Trp Asn Lys Arg
            355                 360                 365
Trp Gly Arg Cys Trp Asp Val Ile Thr Glu Asn Val Leu Asn Asp Arg
            370                 375                 380
Met Asp Leu Val Ser Pro Glu Thr Leu Pro Ser Val Cys Asn Met Ser
385                 390                 395                 400
Gln Ile Pro Leu Val Gly Val Pro Gly Asp Asp Trp Asn Ile Glu Val
                405                 410                 415
Phe Ser Leu Glu His Asn Gly Arg Leu Tyr His Phe Gly Ser Glu Val
                420                 425                 430
Asp Arg Trp Val Phe Gln Asp Pro Val Gln Tyr Gln Asn His Met
            435                 440                 445
Asn Ile Val Asp Arg Phe Leu Ala Gly Gln Ile Gln Pro Met Thr Leu
            450                 455                 460
Glu Gly Ala Leu Lys Tyr Met Gly Phe Gln Ser Ile Glu Glu Met Gly
465                 470                 475                 480
Lys Asp Ala His Asp Phe Ala Trp Ala Asp Lys Cys Lys Pro Ala Met
                485                 490                 495
Lys Lys Ser Ala
            500

<210> SEQ ID NO 15
<211> LENGTH: 1497
<212> TYPE: DNA
<213> ORGANISM: Pseudomonas stutzeri
<220> FEATURE:
<221> NAME/KEY: ToMO wt
<222> LOCATION: (1)..(1497)
<223> OTHER INFORMATION: Wild type ToMO alpha subunit DNA sequence

<400> SEQUENCE: 15
atgtcaatgc taaaacgtga agattggtac gatcttacgc gtaccaccaa ctggacgcct      60
aaatatgtca ctgaaaacga actgtttccg gaggaaatga gcggagcacg tggcatttct     120
atggaagctt gggaaaaata cgatgaaccg tacaagataa cttatccgga atacgtcagt     180
attcagcgag aaaaggactc cggcgcatat tcaatcaaag cggcactgga gcgtgatggt     240
ttcgttgatc gagccgatcc aggctgggtt agcactatgc aacttcactt cggagcgatc     300
gcacttgaag aatacgccgc aagcactgct gaagcccgta tggcgcgatt cgccaaggca     360
ccgggaaacc ggaatatggc gactttcgga tgatggatg aaaaccgcca tgggcaaatc     420
caactttact ttccgtatgc caatgtcaag cggagcagga atgggattg gcgcacaaa      480 gccattcata ctaacgaatg ggccgcaatc gcggcacggt cttcttttga cgacatgat      540 atgacccgcg attccgtggc cgtctctatc atgctgacct cgcattcga aacaggcttc      600
```

```
accaatatgc agtttctcgg tttggccgct gacgctgctg aggccggtga ccataccttt    660
gccagcctga tttcaagcat acagacggac gaatcacgtc acgcacagca aggtggaccg    720
tcgctcaaga tcctggtgga gaatggtaaa aaagacgaag cacaacaaat ggtcgatgtc    780
gcaatctggc gatcttggaa gcttttctcg gtactcaccg gccccatcat ggattattac    840
acgccactgg aatcgcgtaa tcagtccttc aaggagttta tgcttgagtg gattgtggct    900
caatttgaac gtcagttgct tgatctaggg ctcgacaaac cctggtattg ggatcaattc    960
atgcaagacc tcgatgaaac acaccatggc atgcacctgg cgtgtggta ttggcgcccc   1020 acagtctggt gggatccggc agctggtgtg tctcctgaag agcgggaatg gctggaagag   1080
aaatatcccg gttggaatga tacctggggc cagtgttggg atgtcattac cgataaccta   1140
gtgaatggta aaccagagtt gactgttccg gaaaccctac ccacgatctg taacatgtgc   1200
aatctcccga ttgcccatac tccaggtaat aaatggaatg taaaggacta ccagctcgaa   1260
tatgagggac gcctttacca cttcggctct gaggccgacc gctggtgttt ccagatcgac   1320
ccggaacgtt acgaaaacca tacgaacctt gtcgaccgat tcctgaaagg tgaaattcag   1380
cctgcggatt tagcgggtgc cctaatgtac atgagtcttg agccgggcgt tatgggtgac   1440
gacgctcatg attatgagtg ggtcaaggcc taccagaaaa aaaccaacgc ggcttga      1497

<210> SEQ ID NO 16
<211> LENGTH: 498
<212> TYPE: PRT
<213> ORGANISM: Pseudomonas stutzeri
<220> FEATURE:
<221> NAME/KEY: ToMO wt
<222> LOCATION: (1)..(498)
<223> OTHER INFORMATION: Wild  type ToMO alpha subunit protein

<400> SEQUENCE: 16

Met Ser Met Leu Lys Arg Glu Asp Trp Tyr Asp Leu Thr Arg Thr Thr
1               5                  10                  15

Asn Trp Thr Pro Lys Tyr Val Thr Glu Asn Glu Leu Phe Pro Glu Glu
            20                  25                  30

Met Ser Gly Ala Arg Gly Ile Ser Met Glu Ala Trp Glu Lys Tyr Asp
        35                  40                  45

Glu Pro Tyr Lys Ile Thr Tyr Pro Glu Tyr Val Ser Ile Gln Arg Glu
    50                  55                  60

Lys Asp Ser Gly Ala Tyr Ser Ile Lys Ala Ala Leu Glu Arg Asp Gly
65                  70                  75                  80

Phe Val Asp Arg Ala Asp Pro Gly Trp Val Ser Thr Met Gln Leu His
                85                  90                  95

Phe Gly Ala Ile Ala Leu Glu Glu Tyr Ala Ala Ser Thr Ala Glu Ala
            100                 105                 110

Arg Met Ala Arg Phe Ala Lys Ala Pro Gly Asn Arg Asn Met Ala Thr
        115                 120                 125

Phe Gly Met Met Asp Glu Asn Arg His Gly Gln Ile Gln Leu Tyr Phe
    130                 135                 140

Pro Tyr Ala Asn Val Lys Arg Ser Arg Lys Trp Asp Trp Ala His Lys
145                 150                 155                 160

Ala Ile His Thr Asn Glu Trp Ala Ala Ile Ala Arg Ser Phe Phe
                165                 170                 175

Asp Asp Met Met Met Thr Arg Asp Ser Val Ala Val Ser Ile Met Leu
            180                 185                 190

Thr Phe Ala Phe Glu Thr Gly Phe Thr Asn Met Gln Phe Leu Gly Leu
```

```
                195                 200                 205
Ala Ala Asp Ala Ala Glu Ala Gly Asp His Thr Phe Ala Ser Leu Ile
        210                 215                 220

Ser Ser Ile Gln Thr Asp Glu Ser Arg His Ala Gln Gln Gly Gly Pro
225                 230                 235                 240

Ser Leu Lys Ile Leu Val Glu Asn Gly Lys Lys Asp Glu Ala Gln Gln
            245                 250                 255

Met Val Asp Val Ala Ile Trp Arg Ser Trp Lys Leu Phe Ser Val Leu
                260                 265                 270

Thr Gly Pro Ile Met Asp Tyr Tyr Thr Pro Leu Glu Ser Arg Asn Gln
            275                 280                 285

Ser Phe Lys Glu Phe Met Leu Glu Trp Ile Val Ala Gln Phe Glu Arg
290                 295                 300

Gln Leu Leu Asp Leu Gly Leu Asp Lys Pro Trp Tyr Trp Asp Gln Phe
305                 310                 315                 320

Met Gln Asp Leu Asp Glu Thr His His Gly Met His Leu Gly Val Trp
                325                 330                 335

Tyr Trp Arg Pro Thr Val Trp Asp Pro Ala Ala Gly Val Ser Pro
            340                 345                 350

Glu Glu Arg Glu Trp Leu Glu Glu Lys Tyr Pro Gly Trp Asn Asp Thr
                355                 360                 365

Trp Gly Gln Cys Trp Asp Val Ile Thr Asp Asn Leu Val Asn Gly Lys
        370                 375                 380

Pro Glu Leu Thr Val Pro Glu Thr Leu Pro Thr Ile Cys Asn Met Cys
385                 390                 395                 400

Asn Leu Pro Ile Ala His Thr Pro Gly Asn Lys Trp Asn Val Lys Asp
            405                 410                 415

Tyr Gln Leu Glu Tyr Glu Gly Arg Leu Tyr His Phe Gly Ser Glu Ala
                420                 425                 430

Asp Arg Trp Cys Phe Gln Ile Asp Pro Glu Arg Tyr Glu Asn His Thr
        435                 440                 445

Asn Leu Val Asp Arg Phe Leu Lys Gly Glu Ile Gln Pro Ala Asp Leu
450                 455                 460

Ala Gly Ala Leu Met Tyr Met Ser Leu Glu Pro Gly Val Met Gly Asp
465                 470                 475                 480

Asp Ala His Asp Tyr Glu Trp Val Lys Ala Tyr Gln Lys Lys Thr Asn
                485                 490                 495

Ala Ala

<210> SEQ ID NO 17
<211> LENGTH: 1497
<212> TYPE: DNA
<213> ORGANISM: Pseudomonas stutzeri
<220> FEATURE:
<221> NAME/KEY: E214G/D312N/M399V
<222> LOCATION: (1)..(1497)
<223> OTHER INFORMATION: ToMO E214G/D312N/M399V alpha subunit DNA
      sequence

<400> SEQUENCE: 17
atgtcaatgc taaaacgtga agattggtac gatcttacgc gtaccaccaa ctggacgcct      60
aaatatgtca ctgaaaacga actgtttccg gaggaaatga gcggagcacg tggcatttct     120
atggaagctt gggaaaaata cgatgaaccg tacaagataa cttatccgga atacgtcagt     180
attcagcgag aaaaggactc cggcgcatat tcaatcaaag cggcactgga gcgtgatggt     240
```

-continued

```
ttcgttgatc gagccgatcc aggctgggtt agcactatgc aacttcactt cggagcgatc    300
gcacttgaag aatacgccgc aagcactgct gaagcccgta tggcgcgatt cgccaaggca    360
ccgggaaacc ggaatatggc gactttcgga atgatggatg aaaaccgcca tgggcaaatc    420
caactttact ttccgtatgc caatgtcaag cggagcagga atgggattg ggcgcacaaa    480 gccattcata ctaacgaatg ggccgcaatc gcggcacggt ctttctttga cgacatgatg    540
atgacccgcg attccgtggc cgtctctatc atgctgacct tcgcattcga aacaggcttc    600
accaatatgc agtttctcgg tttggccgct gacgctgctg gggccggtga ccatacccttt    660 gccagcctga tttcaagcat acagacggac gaatcacgtc acgcacagca aggtggaccg    720
tcgctcaaga tcctggtgga gaatggtaaa aaagacgaag cacaacaaat ggtcgatgtc    780
gcaatctggc gatcttggaa gcttttctcg gtactcaccg gccccatcat ggattattac    840
acgccactgg aatcgcgtaa tcagtccttc aaggagttta tgcttgagtg gattgtggct    900
caatttgaac gtcagttgct tgatctaggg ctcaacaaac cctggtattg ggatcaattc    960
atgcaagacc tcgatgaaac acaccatggc atgcacctgg gcgtgtggta ttggcgcccc   1020
acagtctggt gggatccggc agctggtgtg tctcctgaag agcgggaatg gctggaagag   1080
aaatatcccg gttggaatga tacctggggc cagtgttggg atgtcattac cgataaccta   1140
gtgaatggta aaccagagtt gactgttccg gaaaccctac ccacgatctg taacgtgtgc   1200
aatctcccga ttgcccatac tccaggtaat aaatggaatg taaaggacta ccagctcgaa   1260
tatgagggac gcctttacca cttcggctct gaggccgacc gctggtgttt ccagatcgac   1320
ccggaacgtt acgaaaacca tacgaacctt gtcgaccgat tcctgaaagg tgaaattcag   1380
cctgcggatt tagcgggtgc cctaatgtac atgagtcttg agccgggcgt tatgggtgac   1440
gacgctcatg attatgagtg ggtcaaggcc taccagaaaa aaaccaacgc ggcttga      1497
```

<210> SEQ ID NO 18
<211> LENGTH: 498
<212> TYPE: PRT
<213> ORGANISM: Pseudomonas stutzeri
<220> FEATURE:
<221> NAME/KEY: E214G/D312N/M399V
<222> LOCATION: (1)..(498)
<223> OTHER INFORMATION: ToMO E214G/D312N/M399V alpha subunit protein

<400> SEQUENCE: 18

```
Met Ser Met Leu Lys Arg Glu Asp Trp Tyr Asp Leu Thr Arg Thr Thr
1               5                   10                  15

Asn Trp Thr Pro Lys Tyr Val Thr Glu Asn Glu Leu Phe Pro Glu Glu
            20                  25                  30

Met Ser Gly Ala Arg Gly Ile Ser Met Glu Ala Trp Glu Lys Tyr Asp
        35                  40                  45

Glu Pro Tyr Lys Ile Thr Tyr Pro Glu Tyr Val Ser Ile Gln Arg Glu
    50                  55                  60

Lys Asp Ser Gly Ala Tyr Ser Ile Lys Ala Ala Leu Glu Arg Asp Gly
65                  70                  75                  80

Phe Val Asp Arg Ala Asp Pro Gly Trp Val Ser Thr Met Gln Leu His
                85                  90                  95

Phe Gly Ala Ile Ala Leu Glu Glu Tyr Ala Ala Ser Thr Ala Glu Ala
            100                 105                 110

Arg Met Ala Arg Phe Ala Lys Ala Pro Gly Asn Arg Asn Met Ala Thr
        115                 120                 125

Phe Gly Met Met Asp Glu Asn Arg His Gly Gln Ile Gln Leu Tyr Phe
```

```
                130             135             140
Pro Tyr Ala Asn Val Lys Arg Ser Arg Lys Trp Asp Trp Ala His Lys
145                 150                 155                 160

Ala Ile His Thr Asn Glu Trp Ala Ala Ile Ala Ala Arg Ser Phe Phe
                165                 170                 175

Asp Asp Met Met Met Thr Arg Asp Ser Val Ala Val Ser Ile Met Leu
            180                 185                 190

Thr Phe Ala Phe Glu Thr Gly Phe Thr Asn Met Gln Phe Leu Gly Leu
        195                 200                 205

Ala Ala Asp Ala Ala Gly Ala Gly Asp His Thr Phe Ala Ser Leu Ile
210                 215                 220

Ser Ser Ile Gln Thr Asp Glu Ser Arg His Ala Gln Gln Gly Gly Pro
225                 230                 235                 240

Ser Leu Lys Ile Leu Val Glu Asn Gly Lys Lys Asp Glu Ala Gln Gln
                245                 250                 255

Met Val Asp Val Ala Ile Trp Arg Ser Trp Lys Leu Phe Ser Val Leu
            260                 265                 270

Thr Gly Pro Ile Met Asp Tyr Tyr Thr Pro Leu Glu Ser Arg Asn Gln
        275                 280                 285

Ser Phe Lys Glu Phe Met Leu Glu Trp Ile Val Ala Gln Phe Glu Arg
    290                 295                 300

Gln Leu Leu Asp Leu Gly Leu Asn Lys Pro Trp Tyr Trp Asp Gln Phe
305                 310                 315                 320

Met Gln Asp Leu Asp Glu Thr His His Gly Met His Leu Gly Val Trp
                325                 330                 335

Tyr Trp Arg Pro Thr Val Trp Asp Pro Ala Ala Gly Val Ser Pro
            340                 345                 350

Glu Glu Arg Glu Trp Leu Glu Glu Lys Tyr Pro Gly Trp Asn Asp Thr
        355                 360                 365

Trp Gly Gln Cys Trp Asp Val Ile Thr Asp Asn Leu Val Asn Gly Lys
    370                 375                 380

Pro Glu Leu Thr Val Pro Glu Thr Leu Pro Thr Ile Cys Asn Val Cys
385                 390                 395                 400

Asn Leu Pro Ile Ala His Thr Pro Gly Asn Lys Trp Asn Val Lys Asp
                405                 410                 415

Tyr Gln Leu Glu Tyr Glu Gly Arg Leu Tyr His Phe Gly Ser Glu Ala
            420                 425                 430

Asp Arg Trp Cys Phe Gln Ile Asp Pro Glu Arg Tyr Glu Asn His Thr
        435                 440                 445

Asn Leu Val Asp Arg Phe Leu Lys Gly Glu Ile Gln Pro Ala Asp Leu
    450                 455                 460

Ala Gly Ala Leu Met Tyr Met Ser Leu Glu Pro Gly Val Met Gly Asp
465                 470                 475                 480

Asp Ala His Asp Tyr Glu Trp Val Lys Ala Tyr Gln Lys Lys Thr Asn
                485                 490                 495

Ala Ala

<210> SEQ ID NO 19
<211> LENGTH: 1497
<212> TYPE: DNA
<213> ORGANISM: Pseudomonas stutzeri
<220> FEATURE:
<221> NAME/KEY: F205G
<222> LOCATION: (1)..(1497)
<223> OTHER INFORMATION: ToMO F205G alpha subunit DNA sequence
```

-continued

<400> SEQUENCE: 19

```
atgtcaatgc taaaacgtga agattggtac gatcttacgc gtaccaccaa ctggacgcct      60
aaatatgtca ctgaaaacga actgtttccg gaggaaatga gcggagcacg tggcatttct     120
atggaagctt gggaaaaata cgatgaaccg tacaagataa cttatccgga atacgtcagt     180
attcagcgag aaaaggactc cggcgcatat tcaatcaaag cggcactgga gcgtgatggt     240
ttcgttgatc gagccgatcc aggctgggtt agcactatgc aacttcactt cggagcgatc     300
gcacttgaag aatacgccgc aagcactgct gaagcccgta tggcgcgatt cgccaaggca     360
ccgggaaacc ggaatatggc gactttcgga atgatggatg aaaaccgcca tgggcaaatc     420
caactttact ttccgtatgc caatgtcaag cggagcagga atgggattg gcgcacaaa     480
gccattcata ctaacgaatg ggccgcaatc gcggcacggt ctttctttga cgacatgatg     540
atgacccgcg attccgtggc cgtctctatc atgctgacct tcgcattcga acaggcttc     600
accaatatgc aggggctcgg tttggccgct gacgctgctg aggccggtga ccatacccttt    660
gccagcctga tttcaagcat acagacggac gaatcacgtc acgcacagca aggtggaccg     720
tcgctcaaga tcctggtgga aatggtaaa aaagacgaag cacaacaaat ggtcgatgtc      780
gcaatctggc gatcttggaa gctttttctcg gtactcaccg gccccatcat ggattattac    840
acgccactgg aatcgcgtaa tcagtccttc aaggagttta tgcttgagtg gattgtggct    900
caatttgaac gtcagttgct tgatctaggg ctcgacaaac cctggtattg ggatcaattc    960
atgcaagacc tcgatgaaac acaccatggc atgcacctgg gcgtgtggta ttggcgcccc   1020
acagtctggt gggatccggc agctggtgtg tctcctgaag agcgggaatg gctggaagag   1080
aaatatcccg gttggaatga tacctggggc cagtgttggg atgtcattac cgataaccta   1140
gtgaatggta aaccagagtt gactgttccg gaaaccctac ccacgatctg taacatgtgc   1200
aatctcccga ttgcccatac tccaggtaat aaatggaatg taaaggacta ccagctcgaa   1260
tatgagggac gcctttacca cttcggctct gaggccgacc gctggtgttt ccagatcgac   1320
ccggaacgtt acgaaaacca tacgaacctt gtcgaccgat tcctgaaagg tgaaattcag   1380
cctgcggatt tagcgggtgc cctaatgtac atgagtcttg agccgggcgt tatgggtgac   1440
gacgctcatg attatgagtg ggtcaaggcc taccagaaaa aaaccaacgc ggcttga      1497
```

<210> SEQ ID NO 20
<211> LENGTH: 498
<212> TYPE: PRT
<213> ORGANISM: Pseudomonas stutzeri
<220> FEATURE:
<221> NAME/KEY: F205G
<222> LOCATION: (1)..(498)
<223> OTHER INFORMATION: ToMO F205G alpha subunit protein

<400> SEQUENCE: 20

```
Met Ser Met Leu Lys Arg Glu Asp Trp Tyr Asp Leu Thr Arg Thr Thr
1               5                   10                  15

Asn Trp Thr Pro Lys Tyr Val Thr Glu Asn Glu Leu Phe Pro Glu Glu
            20                  25                  30

Met Ser Gly Ala Arg Gly Ile Ser Met Glu Ala Trp Glu Lys Tyr Asp
        35                  40                  45

Glu Pro Tyr Lys Ile Thr Tyr Pro Glu Tyr Val Ser Ile Gln Arg Glu
    50                  55                  60

Lys Asp Ser Gly Ala Tyr Ser Ile Lys Ala Ala Leu Glu Arg Asp Gly
65                  70                  75                  80
```

```
Phe Val Asp Arg Ala Asp Pro Gly Trp Val Ser Thr Met Gln Leu His
                 85              90                  95
Phe Gly Ala Ile Ala Leu Glu Glu Tyr Ala Ala Ser Thr Ala Glu Ala
            100             105             110
Arg Met Ala Arg Phe Ala Lys Ala Pro Gly Asn Arg Asn Met Ala Thr
        115             120             125
Phe Gly Met Met Asp Glu Asn Arg His Gly Gln Ile Gln Leu Tyr Phe
    130             135             140
Pro Tyr Ala Asn Val Lys Arg Ser Arg Lys Trp Asp Trp Ala His Lys
145             150             155                 160
Ala Ile His Thr Asn Glu Trp Ala Ala Ile Ala Ala Arg Ser Phe Phe
            165             170             175
Asp Asp Met Met Met Thr Arg Asp Ser Val Ala Val Ser Ile Met Leu
        180             185             190
Thr Phe Ala Phe Glu Thr Gly Phe Thr Asn Met Gln Gly Leu Gly Leu
    195             200             205
Ala Ala Asp Ala Ala Glu Ala Gly Asp His Thr Phe Ala Ser Leu Ile
210             215             220
Ser Ser Ile Gln Thr Asp Glu Ser Arg His Ala Gln Gln Gly Gly Pro
225             230             235                 240
Ser Leu Lys Ile Leu Val Glu Asn Gly Lys Lys Asp Glu Ala Gln Gln
            245             250             255
Met Val Asp Val Ala Ile Trp Arg Ser Trp Lys Leu Phe Ser Val Leu
        260             265             270
Thr Gly Pro Ile Met Asp Tyr Tyr Thr Pro Leu Glu Ser Arg Asn Gln
    275             280             285
Ser Phe Lys Glu Phe Met Leu Glu Trp Ile Val Ala Gln Phe Glu Arg
    290             295             300
Gln Leu Leu Asp Leu Gly Leu Asp Lys Pro Trp Tyr Trp Asp Gln Phe
305             310             315                 320
Met Gln Asp Leu Asp Glu Thr His His Gly Met His Leu Gly Val Trp
            325             330             335
Tyr Trp Arg Pro Thr Val Trp Asp Pro Ala Ala Gly Val Ser Pro
        340             345             350
Glu Glu Arg Glu Trp Leu Glu Lys Tyr Pro Gly Trp Asn Asp Thr
    355             360             365
Trp Gly Gln Cys Trp Asp Val Ile Thr Asp Asn Leu Val Asn Gly Lys
    370             375             380
Pro Glu Leu Thr Val Pro Glu Thr Leu Pro Thr Ile Cys Asn Met Cys
385             390             395                 400
Asn Leu Pro Ile Ala His Thr Pro Gly Asn Lys Trp Asn Val Lys Asp
            405             410             415
Tyr Gln Leu Glu Tyr Glu Gly Arg Leu Tyr His Phe Gly Ser Glu Ala
        420             425             430
Asp Arg Trp Cys Phe Gln Ile Asp Pro Glu Arg Tyr Glu Asn His Thr
    435             440             445
Asn Leu Val Asp Arg Phe Leu Lys Gly Glu Ile Gln Pro Ala Asp Leu
450             455             460
Ala Gly Ala Leu Met Tyr Met Ser Leu Glu Pro Gly Val Met Gly Asp
465             470             475                 480
Asp Ala His Asp Tyr Glu Trp Val Lys Ala Tyr Gln Lys Lys Thr Asn
            485             490             495
```

Ala Ala

<210> SEQ ID NO 21
<211> LENGTH: 1497
<212> TYPE: DNA
<213> ORGANISM: Pseudomonas stutzeri
<220> FEATURE:
<221> NAME/KEY: I100Q
<222> LOCATION: (1)..(1497)
<223> OTHER INFORMATION: ToMO I100Q alpha subunit DNA sequence

<400> SEQUENCE: 21

```
atgtcaatgc taaaacgtga agattggtac gatcttacgc gtaccaccaa ctggacgcct        60
aaatatgtca ctgaaaacga actgtttccg gaggaaatga gcggagcacg tggcatttct       120
atggaagctt gggaaaaata cgatgaaccg tacaagataa cttatccgga atacgtcagt       180
attcagcgag aaaaggactc cggcgcatat tcaatcaaag cggcactgga gcgtgatggt       240
ttcgttgatc gagccgatcc aggctgggtt agcactatgc aacttcactt cggagcgcaa       300
gcacttgaag aatacgccgc aagcactgct gaagcccgta tggcgcgatt cgccaaggca       360
ccgggaaacc ggaatatggc gactttcgga atgatggatg aaaaccgcca tgggcaaatc       420
caactttact ttccgtatgc caatgtcaag cggagcagga atgggattg gcgcacaaa        480 gccattcata ctaacgaatg gccgcaatc gcggcacggt cttttctttga cgacatgatg       540 atgacccgcg attccgtggc cgtctctatc atgctgacct tcgcattcga aacaggcttc       600
accaatatgc agtttctcgg tttggccgct gacgctgctg aggccggtga ccatacctt        660 gccagcctga tttcaagcat acagacggac gaatcacgtc acgcacagca aggtggaccg       720
tcgctcaaga tcctggtgga gaatggtaaa aagacgaag cacaacaaat ggtcgatgtc        780
gcaatctggc gatcttggaa gcttttctcg gtactcaccg gccccatcat ggattattac       840
acgccactgg aatcgcgtaa tcagtcctt aaggagttta tgcttgagtg gattgtggct       900
caatttgaac gtcagttgct tgatctaggg ctcgacaaac cctggtattg ggatcaattc       960
atgcaagacc tcgatgaaac acaccatggc atgcacctgg gcgtgtggta ttggcgcccc      1020
acagtctggt gggatccggc agctggtgtg tctcctgaag agcgggaatg gctggaagag      1080
aaatatcccg gttggaatga tacctggggc cagtgttggg atgtcattac cgataaccta      1140
gtgaatggta accagagtt gactgttccg gaaaccctac ccacgatctg taacatgtgc      1200
aatctcccga ttgcccatac tccaggtaat aaatggaatg taaaggacta ccagctcgaa      1260
tatgagggac gcctttacca cttcggctct gaggccgacc gctggtgttt ccagatcgac      1320
ccggaacgtt acgaaaacca tacgaacctt gtcgaccgat tcctgaaagg tgaaattcag      1380
cctgcggatt tagcgggtgc cctaatgtac atgagtcttg agccgggcgt tatgggtgac      1440
gacgctcatg attatgagtg ggtcaaggcc taccagaaaa aaccaacgc ggcttga         1497
```

<210> SEQ ID NO 22
<211> LENGTH: 498
<212> TYPE: PRT
<213> ORGANISM: Pseudomonas stutzeri
<220> FEATURE:
<221> NAME/KEY: I100Q
<222> LOCATION: (1)..(498)
<223> OTHER INFORMATION: ToMO I100Q alpha subunit protein

<400> SEQUENCE: 22

```
Met Ser Met Leu Lys Arg Glu Asp Trp Tyr Asp Leu Thr Arg Thr Thr
1               5                   10                  15
```

```
Asn Trp Thr Pro Lys Tyr Val Thr Glu Asn Glu Leu Phe Pro Glu
            20                  25                  30
Met Ser Gly Ala Arg Gly Ile Ser Met Glu Ala Trp Glu Lys Tyr Asp
        35                  40                  45
Glu Pro Tyr Lys Ile Thr Tyr Pro Glu Tyr Val Ser Ile Gln Arg Glu
 50                  55                  60
Lys Asp Ser Gly Ala Tyr Ser Ile Lys Ala Ala Leu Glu Arg Asp Gly
 65                      70                  75                  80
Phe Val Asp Arg Ala Asp Pro Gly Trp Val Ser Thr Met Gln Leu His
                85                  90                  95
Phe Gly Ala Gln Ala Leu Glu Glu Tyr Ala Ala Ser Thr Ala Glu Ala
                100                 105                 110
Arg Met Ala Arg Phe Ala Lys Ala Pro Gly Asn Arg Asn Met Ala Thr
            115                 120                 125
Phe Gly Met Met Asp Glu Asn Arg His Gly Gln Ile Gln Leu Tyr Phe
        130                 135                 140
Pro Tyr Ala Asn Val Lys Arg Ser Arg Lys Trp Asp Trp Ala His Lys
145                 150                 155                 160
Ala Ile His Thr Asn Glu Trp Ala Ala Ile Ala Ala Arg Ser Phe Phe
                165                 170                 175
Asp Asp Met Met Met Thr Arg Asp Ser Val Ala Val Ser Ile Met Leu
            180                 185                 190
Thr Phe Ala Phe Glu Thr Gly Phe Thr Asn Met Gln Phe Leu Gly Leu
        195                 200                 205
Ala Ala Asp Ala Ala Glu Ala Gly Asp His Thr Phe Ala Ser Leu Ile
    210                 215                 220
Ser Ser Ile Gln Thr Asp Glu Ser Arg His Ala Gln Gln Gly Gly Pro
225                 230                 235                 240
Ser Leu Lys Ile Leu Val Glu Asn Gly Lys Lys Asp Glu Ala Gln Gln
                245                 250                 255
Met Val Asp Val Ala Ile Trp Arg Ser Trp Lys Leu Phe Ser Val Leu
            260                 265                 270
Thr Gly Pro Ile Met Asp Tyr Tyr Thr Pro Leu Glu Ser Arg Asn Gln
        275                 280                 285
Ser Phe Lys Glu Phe Met Leu Glu Trp Ile Val Ala Gln Phe Glu Arg
    290                 295                 300
Gln Leu Leu Asp Leu Gly Leu Asp Lys Pro Trp Tyr Trp Asp Gln Phe
305                 310                 315                 320
Met Gln Asp Leu Asp Glu Thr His His Gly Met His Leu Gly Val Trp
                325                 330                 335
Tyr Trp Arg Pro Thr Val Trp Asp Pro Ala Ala Gly Val Ser Pro
            340                 345                 350
Glu Glu Arg Glu Trp Leu Glu Glu Lys Tyr Pro Gly Trp Asn Asp Thr
        355                 360                 365
Trp Gly Gln Cys Trp Asp Val Ile Thr Asp Asn Leu Val Asn Gly Lys
    370                 375                 380
Pro Glu Leu Thr Val Pro Glu Thr Leu Pro Thr Ile Cys Asn Met Cys
385                 390                 395                 400
Asn Leu Pro Ile Ala His Thr Pro Gly Asn Lys Trp Asn Val Lys Asp
                405                 410                 415
Tyr Gln Leu Glu Tyr Glu Gly Arg Leu Tyr His Phe Gly Ser Glu Ala
            420                 425                 430
Asp Arg Trp Cys Phe Gln Ile Asp Pro Glu Arg Tyr Glu Asn His Thr
```

```
                     435                 440                 445
Asn Leu Val Asp Arg Phe Leu Lys Gly Glu Ile Gln Pro Ala Asp Leu
    450                 455                 460

Ala Gly Ala Leu Met Tyr Met Ser Leu Glu Pro Gly Val Met Gly Asp
465                 470                 475                 480

Asp Ala His Asp Tyr Glu Trp Val Lys Ala Tyr Gln Lys Lys Thr Asn
                485                 490                 495

Ala Ala

<210> SEQ ID NO 23
<211> LENGTH: 1497
<212> TYPE: DNA
<213> ORGANISM: Pseudomonas stutzeri
<220> FEATURE:
<221> NAME/KEY: M180T/E284G
<222> LOCATION: (1)..(1497)
<223> OTHER INFORMATION: ToMO M180T/E284G alpha subunit DNA sequence

<400> SEQUENCE: 23
atgtcaatgc taaaacgtga agattggtac gatcttacgc gtaccaccaa ctggacgcct      60
aaatatgtca ctgaaaacga actgtttccg gaggaaatga gcggagcacg tggcatttct     120
atggaagctt gggaaaaata cgatgaaccg tacaagataa cttatccgga atacgtcagt     180
attcagcgag aaaaggactc cggcgcatat tcaatcaaag cggcactgga gcgtgatggt     240
ttcgttgatc gagccgatcc aggctgggtt agcactatgc aacttcactt cggagcgatc     300
gcacttgaag aatacgccgc aagcactgct gaagcccgta tggcgcgatt cgccaaggca     360
ccgggaaacc ggaatatggc gactttcgga atgatggatg aaaaccgcca tgggcaaatc     420
caactttact ttccgtatgc caatgtcaag cggagcagga atgggattgg gcgcacaaa      480 gccattcata ctaacgaatg ggccgcaatc gcggcacggt ctttctttga cgacatgacg     540
atgacccgcg attccgtggc cgtctctatc atgctgacct cgcattcga aacaggcttc      600 accaatatgc agtttctcgg tttggccgct gacgctgctg aggccggtga ccataccttt     660
gccagcctga tttcaagcat acagacggac gaatcacgtc acgcacagca aggtggaccg     720
tcgctcaaga tcctggtgga gaatggtaaa aaagacgaag cacaacaaat ggtcgatgtc     780
gcaatctggc gatcttggaa gctttctcg gtactcaccg gccccatcat ggattattac      840
acgccactgg gatcgcgtaa tcagtccttc aaggagttta tgcttgagtg gattgtggct     900
caatttgaac gtcagttgct tgatctaggg ctcgacaaac cctggtattg ggatcaattc     960
atgcaagacc tcgatgaaac acaccatggc atgcacctgg gcgtgtggta ttggcgcccc    1020
acagtctggt gggatccggc agctggtgtg tctcctgaag agcgggaatg gctggaagag    1080
aaatatcccg gttggaatga tacctgggc cagtgttggg atgtcattac cgataaccta     1140
gtgaatggta aaccagagtt gactgttccg gaaaccctac ccacgatctg taacatgtgc    1200
aatctcccga ttgcccatac tccaggtaat aaatggaatg taaggactac cagctcgaa     1260 tatgagggac gcctttacca cttcggctct gaggccgacc gctggtgttt ccagatcgac    1320
ccggaacgtt acgaaaacca tacgaacctt gtcgaccgat tcctgaaagg tgaaattcag    1380
cctgcggatt tagcgggtgc cctaatgtac atgagtcttg agccgggcgt tatgggtgac    1440
gacgctcatg attatgagtg ggtcaaggcc taccagaaaa aaaccaacgc ggcttga       1497

<210> SEQ ID NO 24
<211> LENGTH: 498
<212> TYPE: PRT
```

```
<213> ORGANISM: Pseudomonas stutzeri
<220> FEATURE:
<221> NAME/KEY: M180T/E284G
<222> LOCATION: (1)..(498)
<223> OTHER INFORMATION: ToMO M180T/E284G alpha subunit DNA sequence

<400> SEQUENCE: 24
```

Met Ser Met Leu Lys Arg Glu Asp Trp Tyr Asp Leu Thr Arg Thr
1               5                   10                  15

Asn Trp Thr Pro Lys Tyr Val Thr Glu Asn Glu Leu Phe Pro Glu Glu
                20                  25                  30

Met Ser Gly Ala Arg Gly Ile Ser Met Glu Ala Trp Glu Lys Tyr Asp
            35                  40                  45

Glu Pro Tyr Lys Ile Thr Tyr Pro Glu Tyr Val Ser Ile Gln Arg Glu
    50                  55                  60

Lys Asp Ser Gly Ala Tyr Ser Ile Lys Ala Ala Leu Glu Arg Asp Gly
65              70                  75                  80

Phe Val Asp Arg Ala Asp Pro Gly Trp Val Ser Thr Met Gln Leu His
                85                  90                  95

Phe Gly Ala Ile Ala Leu Glu Glu Tyr Ala Ala Ser Thr Ala Glu Ala
            100                 105                 110

Arg Met Ala Arg Phe Ala Lys Ala Pro Gly Asn Arg Asn Met Ala Thr
    115                 120                 125

Phe Gly Met Met Asp Glu Asn Arg His Gly Gln Ile Gln Leu Tyr Phe
130                 135                 140

Pro Tyr Ala Asn Val Lys Arg Ser Arg Lys Trp Asp Trp Ala His Lys
145                 150                 155                 160

Ala Ile His Thr Asn Glu Trp Ala Ala Ile Ala Ala Arg Ser Phe Phe
                165                 170                 175

Asp Asp Met Thr Met Thr Arg Asp Ser Val Ala Val Ser Ile Met Leu
            180                 185                 190

Thr Phe Ala Phe Glu Thr Gly Phe Thr Asn Met Gln Phe Leu Gly Leu
    195                 200                 205

Ala Ala Asp Ala Ala Glu Ala Gly Asp His Thr Phe Ala Ser Leu Ile
210                 215                 220

Ser Ser Ile Gln Thr Asp Glu Ser Arg His Ala Gln Gln Gly Gly Pro
225                 230                 235                 240

Ser Leu Lys Ile Leu Val Glu Asn Gly Lys Lys Asp Glu Ala Gln Gln
                245                 250                 255

Met Val Asp Val Ala Ile Trp Arg Ser Trp Lys Leu Phe Ser Val Leu
            260                 265                 270

Thr Gly Pro Ile Met Asp Tyr Tyr Thr Pro Leu Gly Ser Arg Asn Gln
    275                 280                 285

Ser Phe Lys Glu Phe Met Leu Glu Trp Ile Val Ala Gln Phe Glu Arg
290                 295                 300

Gln Leu Leu Asp Leu Gly Leu Asp Lys Pro Trp Tyr Trp Asp Gln Phe
305                 310                 315                 320

Met Gln Asp Leu Asp Glu Thr His His Gly Met His Leu Gly Val Trp
                325                 330                 335

Tyr Trp Arg Pro Thr Val Trp Trp Asp Pro Ala Ala Gly Val Ser Pro
            340                 345                 350

Glu Glu Arg Glu Trp Leu Glu Glu Lys Tyr Pro Gly Trp Asn Asp Thr
    355                 360                 365

Trp Gly Gln Cys Trp Asp Val Ile Thr Asp Asn Leu Val Asn Gly Lys
370                 375                 380

```
Pro Glu Leu Thr Val Pro Glu Thr Leu Pro Thr Ile Cys Asn Met Cys
385                 390                 395                 400

Asn Leu Pro Ile Ala His Thr Pro Gly Asn Lys Trp Asn Val Lys Asp
                405                 410                 415

Tyr Gln Leu Glu Tyr Glu Gly Arg Leu Tyr His Phe Gly Ser Glu Ala
            420                 425                 430

Asp Arg Trp Cys Phe Gln Ile Asp Pro Glu Arg Tyr Glu Asn His Thr
        435                 440                 445

Asn Leu Val Asp Arg Phe Leu Lys Gly Glu Ile Gln Pro Ala Asp Leu
    450                 455                 460

Ala Gly Ala Leu Met Tyr Met Ser Leu Glu Pro Gly Val Met Gly Asp
465                 470                 475                 480

Asp Ala His Asp Tyr Glu Trp Val Lys Ala Tyr Gln Lys Lys Thr Asn
                485                 490                 495

Ala Ala
```

<210> SEQ ID NO 25
<211> LENGTH: 1560
<212> TYPE: DNA
<213> ORGANISM: Burkholderia cepacia
<220> FEATURE:
<221> NAME/KEY: TOM wt
<222> LOCATION: (1)..(1560)
<223> OTHER INFORMATION: Wild type TOM alpha subunit DNA sequence

<400> SEQUENCE: 25

| | |
|---|---:|
| atggacactt ctgtgcagaa gaagaaactc ggtttaaaga atcgctacgc agcgatgacc | 60 |
| cgcggtcttg gctggcagac cagctaccag ccgatggaga agtgttttcc gtacgacaag | 120 |
| tacgaaggca tcaagatcca cgattgggat aaatgggaag acccctttcg cctgaccatg | 180 |
| gacgcctact ggaaatatca gggcgagaag gaaaaaaagc tttacgccgt catcgacgct | 240 |
| ttcgcgcaga acaacgggca gttgagcatt tccgacgcgc gatatgtcaa cgcactcaag | 300 |
| gtgtttatcc agggtgtgac accgttggag tatatggcac accgaggttt tgcccacatt | 360 |
| ggtcggcatt ttacgggtga aggggcacgt gttgcttgcc agatgcagtc catcgacgag | 420 |
| ctgcgtcact tccagaccga aatgcatgct ctctcgcact acaacaagta ttttaacggt | 480 |
| ctgcacaact ccatccattg gtacgaccgg gtttggtatt tgtcggtgcc caagtcattt | 540 |
| tttgaagacg cggccaccgg tggaccgttc gagtttctta ccgcggtgag ctttcgttc | 600 |
| gaatatgtgt tgaccaacct gctgtttgtc cccttcatgt cgggtgctgc ttacaacggg | 660 |
| gacatgtcta cggtcacttt cggtttttcg gcgcaaagtg acgaatcgcg ccacatgaca | 720 |
| ctcggcatcg aatgcatcaa gttcatgcta gaacaggatc cggacaacgt gcccatcgtg | 780 |
| cagcgctgga tcgacaagtg gttctggcgc ggctatcggc tgttgagcat cgtggccatg | 840 |
| atgcaggact acatgctgcc caaccgggtg atgagctggc gcgagagctg ggagatgtac | 900 |
| gtcgagcaga acggcggcgc gctgttcaag gatcttgcgc gttatggcat ccgcaagccc | 960 |
| aagggctggg accaggcttg cgaaggcaag gaccacatca gccatcagac cttcgccgta | 1020 |
| ttctataact ataacgccgc ggcccccatc cacacctggg ttcccacaaa agaagaaatg | 1080 |
| ggatggctgt cggagaagta ccccgagacg ttcgacaagt attaccgtcc gcgttgggac | 1140 |
| tactggcgcg agcaggccgc caagggcaac cgtttctaca acaagacgct gccgatgctc | 1200 |
| tgcactacct gccagattcc gatgatattc accgagcctg cgacgcaac caagatctgc | 1260 |
| tatcgcgagt cggcctacct cggcgacaag tatcacttct gcagcgacca ctgcaaggag | 1320 |

```
atttttgaca acgaacccga aaagttcgtg cagtcatggc ttccgccgca gcaagtgtat    1380
caaggaaact gtttcaagcc ggatgccgat ccgaccaagg agggttttga tcccttgatg    1440
gccttgctcg actactacaa cctgaatgta ggccgggaca acttcgattt cgagggatcg    1500
gaagaccaaa agaactttgc tgcctggcgt ggagaggtct tgcaaggaga agccaaatga    1560
```

<210> SEQ ID NO 26
<211> LENGTH: 519
<212> TYPE: PRT
<213> ORGANISM: Burkholderia cepacia
<220> FEATURE:
<221> NAME/KEY: TOM wt
<222> LOCATION: (1)..(519)
<223> OTHER INFORMATION: Wild type TOM alpha subunit protein

<400> SEQUENCE: 26

```
Met Asp Thr Ser Val Gln Lys Lys Leu Gly Leu Lys Asn Arg Tyr
1               5                   10                  15

Ala Ala Met Thr Arg Gly Leu Gly Trp Gln Thr Ser Tyr Gln Pro Met
            20                  25                  30

Glu Lys Val Phe Pro Tyr Asp Lys Tyr Glu Gly Ile Lys Ile His Asp
        35                  40                  45

Trp Asp Lys Trp Glu Asp Pro Phe Arg Leu Thr Met Asp Ala Tyr Trp
    50                  55                  60

Lys Tyr Gln Gly Glu Lys Glu Lys Leu Tyr Ala Val Ile Asp Ala
65                  70                  75                  80

Phe Ala Gln Asn Asn Gly Gln Leu Ser Ile Ser Asp Ala Arg Tyr Val
                85                  90                  95

Asn Ala Leu Lys Val Phe Ile Gln Gly Val Thr Pro Leu Glu Tyr Met
            100                 105                 110

Ala His Arg Gly Phe Ala His Ile Gly Arg His Phe Thr Gly Glu Gly
        115                 120                 125

Ala Arg Val Ala Cys Gln Met Gln Ser Ile Asp Glu Leu Arg His Phe
    130                 135                 140

Gln Thr Glu Met His Ala Leu Ser His Tyr Asn Lys Tyr Phe Asn Gly
145                 150                 155                 160

Leu His Asn Ser Ile His Trp Tyr Asp Arg Val Trp Tyr Leu Ser Val
                165                 170                 175

Pro Lys Ser Phe Phe Glu Asp Ala Ala Thr Gly Gly Pro Phe Glu Phe
            180                 185                 190

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
    210                 215                 220

Val Thr Phe Gly Phe Ser Ala Gln Ser Asp Glu Ser Arg His Met Thr
225                 230                 235                 240

Leu Gly Ile Glu Cys Ile Lys Phe Met Leu Glu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Ser Ile Val Ala Met Met Gln Asp Tyr Met Leu Pro Asn
        275                 280                 285

Arg Val Met Ser Trp Arg Glu Ser Trp Glu Met Tyr Val Glu Gln Asn
    290                 295                 300

Gly Gly Ala Leu Phe Lys Asp Leu Ala Arg Tyr Gly Ile Arg Lys Pro
```

-continued

```
305                 310                 315                 320

Lys Gly Trp Asp Gln Ala Cys Glu Gly Lys Asp His Ile Ser His Gln
                325                 330                 335

Thr Phe Ala Val Phe Tyr Asn Tyr Asn Ala Ala Ala Pro Ile His Thr
            340                 345                 350

Trp Val Pro Thr Lys Glu Glu Met Gly Trp Leu Ser Glu Lys Tyr Pro
        355                 360                 365

Glu Thr Phe Asp Lys Tyr Tyr Arg Pro Arg Trp Asp Tyr Trp Arg Glu
    370                 375                 380

Gln Ala Ala Lys Gly Asn Arg Phe Tyr Asn Lys Thr Leu Pro Met Leu
385                 390                 395                 400

Cys Thr Thr Cys Gln Ile Pro Met Ile Phe Thr Glu Pro Gly Asp Ala
                405                 410                 415

Thr Lys Ile Cys Tyr Arg Glu Ser Ala Tyr Leu Gly Asp Lys Tyr His
            420                 425                 430

Phe Cys Ser Asp His Cys Lys Glu Ile Phe Asp Asn Glu Pro Glu Lys
        435                 440                 445

Phe Val Gln Ser Trp Leu Pro Pro Gln Gln Val Tyr Gln Gly Asn Cys
    450                 455                 460

Phe Lys Pro Asp Ala Asp Pro Thr Lys Glu Gly Phe Asp Pro Leu Met
465                 470                 475                 480

Ala Leu Leu Asp Tyr Tyr Asn Leu Asn Val Gly Arg Asp Asn Phe Asp
                485                 490                 495

Phe Glu Gly Ser Glu Asp Gln Lys Asn Phe Ala Ala Trp Arg Gly Glu
            500                 505                 510

Val Leu Gln Gly Glu Ala Lys
        515
```

<210> SEQ ID NO 27
<211> LENGTH: 1560
<212> TYPE: DNA
<213> ORGANISM: Burkholderia cepacia
<220> FEATURE:
<221> NAME/KEY: A113V
<222> LOCATION: (1)..(1560)
<223> OTHER INFORMATION: TOM alpha subunit A113V DNA sequence

<400> SEQUENCE: 27

```
atggacactt ctgtgcagaa gaagaaactc ggtttaaaga atcgctacgc agcgatgacc      60
cgcggtcttg gctggcagac cagctaccag ccgatggaga aagtgtttcc gtacgacaag     120
tacgaaggca tcaagatcca cgattgggat aaatgggaag accccttccg cctgaccatg     180
gacgcctact ggaaatatca gggcgagaag gaaaaaaagc tttacgccgt catcgacgct     240
ttcgcgcaga acaacgggca gttgagcatt tccgacgcgc gatatgtcaa cgcactcaag     300
gtgtttatcc agggtgtgac accgttggag tatatggttc accgaggttt tgcccacatt     360
ggtcggcatt ttacgggtga aggggcacgt gttgcttgcc agatgcagtc catcgacgag     420
ctgcgtcact tccagaccga aatgcatgct ctctcgcact acaacaagta ttttaacggt     480
ctgcacaact ccatccattg gtacgaccgg gtttggtatt tgtcggtgcc caagtcattt     540
tttgaagacg cggccaccgg tggaccgttc gagtttctta ccgcggtgag cttttcgttc     600
gaatatgtgt tgaccaacct gctgtttgtc cccttcatgt cgggtgctgc ttacaacggg     660
gacatgtcta cggtcacttt cggtttttcg gcgcaaagtg acgaatcgcg ccacatgaca     720
ctcggcatcg aatgcatcaa gttcatgcta gaacaggatc cggacaacgt gcccatcgtg     780
```

```
cagcgctgga tcgacaagtg gttctggcgc ggctatcggc tgttgagcat cgtggccatg    840
atgcaggact acatgctgcc caaccgggtg atgagctggc gcgagagctg ggagatgtac    900
gtcgagcaga acggcggcgc gctgttcaag gatcttgcgc gttatggcat ccgcaagccc    960
aagggctggg accaggcttg cgaaggcaag gaccacatca gccatcagac cttcgccgta   1020
ttctataact ataacgccgc ggcccccatc cacacctggg ttcccacaaa agaagaaatg   1080
ggatggctgt cggagaagta cccgagacg ttcgacaagt attaccgtcc gcgttgggac   1140
tactggcgcg agcaggccgc caagggcaac cgtttctaca acaagacgct gccgatgctc   1200
tgcactacct gccagattcc gatgatattc accgagcctg cgacgcaac caagatctgc    1260 tatcgcgagt cggcctacct cggcgacaag tatcacttct gcagcgacca ctgcaaggag   1320
atttttgaca cgaacccga aaagttcgtg cagtcatggc ttccgccgca gcaagtgtat   1380
caaggaaact gtttcaagcc ggatgccgat ccgaccaagg agggttttga tcccttgatg   1440
gccttgctcg actactacaa cctgaatgta ggccgggaca acttcgattt cgagggatcg   1500
gaagaccaaa agaactttgc tgcctggcgt ggagaggtct tgcaaggaga agccaaatga   1560

<210> SEQ ID NO 28
<211> LENGTH: 519
<212> TYPE: PRT
<213> ORGANISM: Burkholderia cepacia
<220> FEATURE:
<221> NAME/KEY: A113V
<222> LOCATION: (1)..(519)
<223> OTHER INFORMATION: TOM A113V alpha subunit protein

<400> SEQUENCE: 28

Met Asp Thr Ser Val Gln Lys Lys Leu Gly Leu Lys Asn Arg Tyr
1               5                   10                  15

Ala Ala Met Thr Arg Gly Leu Gly Trp Gln Thr Ser Tyr Gln Pro Met
            20                  25                  30

Glu Lys Val Phe Pro Tyr Asp Lys Tyr Glu Gly Ile Lys Ile His Asp
        35                  40                  45

Trp Asp Lys Trp Glu Asp Pro Phe Arg Leu Thr Met Asp Ala Tyr Trp
    50                  55                  60

Lys Tyr Gln Gly Glu Lys Glu Lys Leu Tyr Ala Val Ile Asp Ala
65                  70                  75                  80

Phe Ala Gln Asn Asn Gly Gln Leu Ser Ile Ser Asp Ala Arg Tyr Val
                85                  90                  95

Asn Ala Leu Lys Val Phe Ile Gln Gly Val Thr Pro Leu Glu Tyr Met
            100                 105                 110

Val His Arg Gly Phe Ala His Ile Gly Arg His Phe Thr Gly Glu Gly
        115                 120                 125

Ala Arg Val Ala Cys Gln Met Gln Ser Ile Asp Glu Leu Arg His Phe
    130                 135                 140

Gln Thr Glu Met His Ala Leu Ser His Tyr Asn Lys Tyr Phe Asn Gly
145                 150                 155                 160

Leu His Asn Ser Ile His Trp Tyr Asp Arg Val Trp Tyr Leu Ser Val
                165                 170                 175

Pro Lys Ser Phe Phe Glu Asp Ala Ala Thr Gly Gly Pro Glu Phe
            180                 185                 190

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
    210                 215                 220
```

| | | | | | | | | | | | | | | |
|---|---|---|---|---|---|---|---|---|---|---|---|---|---|---|
| Val | Thr | Phe | Gly | Phe | Ser | Ala | Gln | Ser | Asp | Glu | Ser | Arg | His | Met | Thr |
| 225 | | | | | 230 | | | | | 235 | | | | | 240 |

Val Thr Phe Gly Phe Ser Ala Gln Ser Asp Glu Ser Arg His Met Thr
225                 230                 235                 240

Leu Gly Ile Glu Cys Ile Lys Phe Met Leu Glu Gln Asp Pro Asp Asn
            245                 250                 255

Val Pro Ile Val Gln Arg Trp Ile Asp Lys Trp Phe Trp Arg Gly Tyr
            260                 265                 270

Arg Leu Leu Ser Ile Val Ala Met Met Gln Asp Tyr Met Leu Pro Asn
            275                 280                 285

Arg Val Met Ser Trp Arg Glu Ser Trp Glu Met Tyr Val Glu Gln Asn
            290                 295                 300

Gly Gly Ala Leu Phe Lys Asp Leu Ala Arg Tyr Gly Ile Arg Lys Pro
305                 310                 315                 320

Lys Gly Trp Asp Gln Ala Cys Glu Gly Lys Asp His Ile Ser His Gln
            325                 330                 335

Thr Phe Ala Val Phe Tyr Asn Tyr Asn Ala Ala Ala Pro Ile His Thr
            340                 345                 350

Trp Val Pro Thr Lys Glu Glu Met Gly Trp Leu Ser Glu Lys Tyr Pro
            355                 360                 365

Glu Thr Phe Asp Lys Tyr Tyr Arg Pro Arg Trp Asp Tyr Trp Arg Glu
    370                 375                 380

Gln Ala Ala Lys Gly Asn Arg Phe Tyr Asn Lys Thr Leu Pro Met Leu
385                 390                 395                 400

Cys Thr Thr Cys Gln Ile Pro Met Ile Phe Thr Glu Pro Gly Asp Ala
            405                 410                 415

Thr Lys Ile Cys Tyr Arg Glu Ser Ala Tyr Leu Gly Asp Lys Tyr His
            420                 425                 430

Phe Cys Ser Asp His Cys Lys Glu Ile Phe Asp Asn Glu Pro Glu Lys
            435                 440                 445

Phe Val Gln Ser Trp Leu Pro Pro Gln Val Tyr Gln Gly Asn Cys
            450                 455                 460

Phe Lys Pro Asp Ala Asp Pro Thr Lys Glu Gly Phe Asp Pro Leu Met
465                 470                 475                 480

Ala Leu Leu Asp Tyr Tyr Asn Leu Asn Val Gly Arg Asp Asn Phe Asp
            485                 490                 495

Phe Glu Gly Ser Glu Asp Gln Lys Asn Phe Ala Ala Trp Arg Gly Glu
                500                 505                 510

Val Leu Gln Gly Glu Ala Lys
        515

<210> SEQ ID NO 29
<211> LENGTH: 1560
<212> TYPE: DNA
<213> ORGANISM: Burkholderia cepacia
<220> FEATURE:
<221> NAME/KEY: V106S/A113V
<222> LOCATION: (1)..(1560)
<223> OTHER INFORMATION: TOM V106S/A113V alpha subunit DNA sequence

<400> SEQUENCE: 29 atggac

```
gtgtttatcc agggttccac accgttggag tatatggttc accgaggttt tgcccacatt      360
ggtcggcatt ttacgggtga aggggcacgt gttgcttgcc agatgcagtc catcgacgag      420
ctgcgtcact tccagaccga aatgcatgct ctctcgcact acaacaagta ttttaacggt      480
ctgcacaact ccatccattg gtacgaccgg gtttggtatt tgtcggtgcc aagtcattt       540 tttgaagacg cggccaccgg tggaccgttc gagtttctta ccgcggtgag cttttcgttc      600
gaatatgtgt tgaccaacct gctgtttgtc cccttcatgt cgggtgctgc ttacaacggg      660
gacatgtcta cggtcacttt cggttttccg gcgcaaagtg acgaatcgcg ccacatgaca      720
ctcggcatcg aatgcatcaa gttcatgcta gaacaggatc cggacaacgt gcccatcgtg      780
cagcgctgga tcgacaagtg gttctggcgc ggctatcggc tgttgagcat cgtggccatg      840
atgcaggact acatgctgcc aaccgggtg atgagctggc gcgagagctg ggagatgtac       900
gtcgagcaga acggcggcgc gctgttcaag gatcttgcgc gttatggcat ccgcaagccc      960
aagggctggg accaggcttg cgaaggcaag gaccacatca gccatcagac cttcgccgta     1020
ttctataact ataacgccgc ggcccccatc cacacctggg ttcccacaaa agaagaaatg     1080
ggatggctgt cggagaagta ccccgagacg ttcgacaagt attaccgtcc gcgttgggac     1140
tactggcgcg agcaggccgc caagggcaac cgtttctaca caagacgct gccgatgctc      1200 tgcactacct gccagattcc gatgatattc accgagcctg gcgacgcaac caagatctgc     1260
tatcgcgagt cggcctacct cggcgacaag tatcacttct gcagcgacca ctgcaaggag     1320
atttttgaca acgaacccga aaagttcgtg cagtcatggc ttccgccgca gcaagtgtat     1380
caaggaaact gtttcaagcc ggatgccgat ccgaccaagg agggttttga tcccttgatg     1440
gccttgctcg actactacaa cctgaatgta ggccgggaca acttcgattt cgagggatcg     1500
gaagaccaaa agaactttgc tgcctggcgt ggagaggtct tgcaaggaga agccaaatga     1560
```

<210> SEQ ID NO 30
<211> LENGTH: 519
<212> TYPE: PRT
<213> ORGANISM: Burkholderia cepacia
<220> FEATURE:
<221> NAME/KEY: V106S/A113V
<222> LOCATION: (1)..(519)
<223> OTHER INFORMATION: TOM V106S/A113V alpha subunit protein

<400> SEQUENCE: 30

```
Met Asp Thr Ser Val Gln Lys Lys Leu Gly Leu Lys Asn Arg Tyr
1               5                   10                  15

Ala Ala Met Thr Arg Gly Leu Gly Trp Gln Thr Ser Tyr Gln Pro Met
                20                  25                  30

Glu Lys Val Phe Pro Tyr Asp Lys Tyr Glu Gly Ile Lys Ile His Asp
            35                  40                  45

Trp Asp Lys Trp Glu Asp Pro Phe Arg Leu Thr Met Asp Ala Tyr Trp
        50                  55                  60

Lys Tyr Gln Gly Glu Lys Glu Lys Leu Tyr Ala Val Ile Asp Ala
65                  70                  75                  80

Phe Ala Gln Asn Asn Gly Gln Leu Ser Ile Ser Asp Ala Arg Tyr Val
                85                  90                  95

Asn Ala Leu Lys Val Phe Ile Gln Gly Ser Thr Pro Leu Glu Tyr Met
            100                 105                 110

Val His Arg Gly Phe Ala His Ile Gly Arg His Phe Thr Gly Glu Gly
        115                 120                 125
```

Ala Arg Val Ala Cys Gln Met Gln Ser Ile Asp Glu Leu Arg His Phe
        130                 135                 140

Gln Thr Glu Met His Ala Leu Ser His Tyr Asn Lys Tyr Phe Asn Gly
145                 150                 155                 160

Leu His Asn Ser Ile His Trp Tyr Asp Arg Val Trp Tyr Leu Ser Val
                165                 170                 175

Pro Lys Ser Phe Phe Glu Asp Ala Ala Thr Gly Gly Pro Phe Glu Phe
            180                 185                 190

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
210                 215                 220

Val Thr Phe Gly Phe Ser Ala Gln Ser Asp Glu Ser Arg His Met Thr
225                 230                 235                 240

Leu Gly Ile Glu Cys Ile Lys Phe Met Leu Glu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Ser Ile Val Ala Met Met Gln Asp Tyr Met Leu Pro Asn
        275                 280                 285

Arg Val Met Ser Trp Arg Glu Ser Trp Glu Met Tyr Val Glu Gln Asn
290                 295                 300

Gly Gly Ala Leu Phe Lys Asp Leu Ala Arg Tyr Gly Ile Arg Lys Pro
305                 310                 315                 320

Lys Gly Trp Asp Gln Ala Cys Glu Gly Lys Asp His Ile Ser His Gln
                325                 330                 335

Thr Phe Ala Val Phe Tyr Asn Tyr Asn Ala Ala Ala Pro Ile His Thr
            340                 345                 350

Trp Val Pro Thr Lys Glu Glu Met Gly Trp Leu Ser Glu Lys Tyr Pro
        355                 360                 365

Glu Thr Phe Asp Lys Tyr Tyr Arg Pro Arg Trp Asp Tyr Trp Arg Glu
370                 375                 380

Gln Ala Ala Lys Gly Asn Arg Phe Tyr Asn Lys Thr Leu Pro Met Leu
385                 390                 395                 400

Cys Thr Thr Cys Gln Ile Pro Met Ile Phe Thr Glu Pro Gly Asp Ala
                405                 410                 415

Thr Lys Ile Cys Tyr Arg Glu Ser Ala Tyr Leu Gly Asp Lys Tyr His
            420                 425                 430

Phe Cys Ser Asp His Cys Lys Glu Ile Phe Asp Asn Glu Pro Glu Lys
        435                 440                 445

Phe Val Gln Ser Trp Leu Pro Pro Gln Val Tyr Gln Gly Asn Cys
450                 455                 460

Phe Lys Pro Asp Ala Asp Pro Thr Lys Glu Gly Phe Asp Pro Leu Met
465                 470                 475                 480

Ala Leu Leu Asp Tyr Tyr Asn Leu Asn Val Gly Arg Asp Asn Phe Asp
                485                 490                 495

Phe Glu Gly Ser Glu Asp Gln Lys Asn Phe Ala Ala Trp Arg Gly Glu
            500                 505                 510

Val Leu Gln Gly Glu Ala Lys
        515

<210> SEQ ID NO 31
<211> LENGTH: 1560
<212> TYPE: DNA

<213> ORGANISM: Burkholderia cepacia
<220> FEATURE:
<221> NAME/KEY: A113H
<222> LOCATION: (1)..(1560)
<223> OTHER INFORMATION: TOM A113H alpha subunit DNA sequence

<400> SEQUENCE: 31

| | | |
|---|---|---|
| atggacactt ctgtgcagaa gaagaaactc ggtttaaaga atcgctacgc agcgatgacc | 60 |
| cgcggtcttg gctggcagac cagctaccag ccgatggaga aagtgtttcc gtacgacaag | 120 |
| tacgaaggca tcaagatcca cgattgggat aaatgggaag accccttccg cctgaccatg | 180 |
| gacgcctact ggaaatatca gggcgagaag gaaaaaaagc tttacgccgt catcgacgct | 240 |
| ttcgcgcaga caacgggca gttgagcatt ccgacgcgc gatatgtcaa cgcactcaag | 300 |
| gtgtttatcc agggtgtgac accgttggag tatatgcatc accgaggttt tgcccacatt | 360 |
| ggtcggcatt ttacgggtga aggggcacgt gttgcttgcc agatgcagtc catcgacgag | 420 |
| ctgcgtcact tccagaccga aatgcatgct ctctcgcact acaacaagta ttttaacggt | 480 |
| ctgcacaact ccatccattg gtacgaccgg gtttggtatt tgtcggtgcc caagtcattt | 540 |
| tttgaagacg cggccaccgg tggaccgttc gagtttctta ccgcggtgag ctttcgttc | 600 |
| gaatatgtgt tgaccaacct gctgtttgtc cccttcatgt cgggtgctgc ttacaacggg | 660 |
| gacatgtcta cggtcacttt cggttttcg gcgcaaagtg acgaatcgcg ccacatgaca | 720 |
| ctcggcatcg aatgcatcaa gttcatgcta aacaggatc cggacaacgt gcccatcgtg | 780 |
| cagcgctgga tcgacaagtg gttctggcgc ggctatcggc tgttgagcat cgtggccatg | 840 |
| atgcaggact acatgctgcc caaccgggtg atgagctggc gcgagagctg ggagatgtac | 900 |
| gtcgagcaga acggcggcgc gctgttcaag gatcttgcgc gttatggcat ccgcaagccc | 960 |
| aagggctggg accaggcttg cgaaggcaag gaccacatca gccatcagac cttcgccgta | 1020 |
| ttctataact ataacgccgc ggcccccatc cacacctggg ttcccacaaa agaagaaatg | 1080 |
| ggatggctgt cggagaagta ccccgagacg ttcgacaagt attaccgtcc gcgttgggac | 1140 |
| tactggcgcg agcaggccgc caagggcaac cgtttctaca caagacgct gccgatgctc | 1200 |
| tgcactacct gccagattcc gatgatattc accgagcctg gcgacgcaac caagatctgc | 1260 |
| tatcgcgagt cggcctacct cggcgacaag tatcacttct gcagcgacca ctgcaaggag | 1320 |
| attttttgaca cgaacccga aaagttcgtg cagtcatggc ttccgccgca gcaagtgtat | 1380 |
| caaggaaact gtttcaagcc ggatgccgat ccgaccaagg agggttttga tcccttgatg | 1440 |
| gccttgctcg actactacaa cctgaatgta ggccgggaca acttcgattt cgagggatcg | 1500 |
| gaagaccaaa agaactttgc tgcctggcgt ggagaggtct tgcaaggaga agccaaatga | 1560 |

<210> SEQ ID NO 32
<211> LENGTH: 519
<212> TYPE: PRT
<213> ORGANISM: Burkholderia cepacia
<220> FEATURE:
<221> NAME/KEY: A113H
<222> LOCATION: (1)..(519)
<223> OTHER INFORMATION: TOM A113H alpha subunit protein

<400> SEQUENCE: 32

Met Asp Thr Ser Val Gln Lys Lys Lys Leu Gly Leu Lys Asn Arg Tyr
1               5                   10                  15

Ala Ala Met Thr Arg Gly Leu Gly Trp Gln Thr Ser Tyr Gln Pro Met
            20                  25                  30

Glu Lys Val Phe Pro Tyr Asp Lys Tyr Glu Gly Ile Lys Ile His Asp

-continued

```
                35                  40                  45
Trp Asp Lys Trp Glu Asp Pro Phe Arg Leu Thr Met Asp Ala Tyr Trp
 50                  55                  60
Lys Tyr Gln Gly Glu Lys Glu Lys Lys Leu Tyr Ala Val Ile Asp Ala
 65                  70                  75                  80
Phe Ala Gln Asn Asn Gly Gln Leu Ser Ile Ser Asp Ala Arg Tyr Val
                 85                  90                  95
Asn Ala Leu Lys Val Phe Ile Gln Gly Val Thr Pro Leu Glu Tyr Met
            100                 105                 110
His His Arg Gly Phe Ala His Ile Gly Arg His Phe Thr Gly Glu Gly
        115                 120                 125
Ala Arg Val Ala Cys Gln Met Gln Ser Ile Asp Glu Leu Arg His Phe
    130                 135                 140
Gln Thr Glu Met His Ala Leu Ser His Tyr Asn Lys Tyr Phe Asn Gly
145                 150                 155                 160
Leu His Asn Ser Ile His Trp Tyr Asp Arg Val Trp Tyr Leu Ser Val
                165                 170                 175
Pro Lys Ser Phe Phe Glu Asp Ala Ala Thr Gly Gly Pro Phe Glu Phe
            180                 185                 190
Leu Thr Ala Val Ser Phe Ser Phe Glu Tyr Val Leu Thr Asn Leu Leu
        195                 200                 205
Phe Val Pro Phe Met Ser Gly Ala Ala Tyr Asn Gly Asp Met Ser Thr
    210                 215                 220
Val Thr Phe Gly Phe Ser Ala Gln Ser Asp Glu Ser Arg His Met Thr
225                 230                 235                 240
Leu Gly Ile Glu Cys Ile Lys Phe Met Leu Glu Gln Asp Pro Asp Asn
                245                 250                 255
Val Pro Ile Val Gln Arg Trp Ile Asp Lys Trp Phe Trp Arg Gly Tyr
            260                 265                 270
Arg Leu Leu Ser Ile Val Ala Met Met Gln Asp Tyr Met Leu Pro Asn
        275                 280                 285
Arg Val Met Ser Trp Arg Glu Ser Trp Glu Met Tyr Val Glu Gln Asn
    290                 295                 300
Gly Gly Ala Leu Phe Lys Asp Leu Ala Arg Tyr Gly Ile Arg Lys Pro
305                 310                 315                 320
Lys Gly Trp Asp Gln Ala Cys Glu Gly Lys Asp His Ile Ser His Gln
                325                 330                 335
Thr Phe Ala Val Phe Tyr Asn Tyr Asn Ala Ala Ala Pro Ile His Thr
            340                 345                 350
Trp Val Pro Thr Lys Glu Glu Met Gly Trp Leu Ser Glu Lys Tyr Pro
        355                 360                 365
Glu Thr Phe Asp Lys Tyr Tyr Arg Pro Arg Trp Asp Tyr Trp Arg Glu
    370                 375                 380
Gln Ala Ala Lys Gly Asn Arg Phe Tyr Asn Lys Thr Leu Pro Met Leu
385                 390                 395                 400
Cys Thr Thr Cys Gln Ile Pro Met Ile Phe Thr Glu Pro Gly Asp Ala
                405                 410                 415
Thr Lys Ile Cys Tyr Arg Glu Ser Ala Tyr Leu Gly Asp Lys Tyr His
            420                 425                 430
Phe Cys Ser Asp His Cys Lys Glu Ile Phe Asp Asn Glu Pro Glu Lys
        435                 440                 445
Phe Val Gln Ser Trp Leu Pro Pro Gln Gln Val Tyr Gln Gly Asn Cys
    450                 455                 460
```

Phe Lys Pro Asp Ala Asp Pro Thr Lys Glu Gly Phe Asp Pro Leu Met
465                 470                 475                 480

Ala Leu Leu Asp Tyr Tyr Asn Leu Asn Val Gly Arg Asp Asn Phe Asp
            485                 490                 495

Phe Glu Gly Ser Glu Asp Gln Lys Asn Phe Ala Ala Trp Arg Gly Glu
        500                 505                 510

Val Leu Gln Gly Glu Ala Lys
        515

<210> SEQ ID NO 33
<211> LENGTH: 1560
<212> TYPE: DNA
<213> ORGANISM: Burkholderia cepacia
<220> FEATURE:
<221> NAME/KEY: A113S
<222> LOCATION: (1)..(1560)
<223> OTHER INFORMATION: TOM A113S alpha subunit DNA sequence

<400> SEQUENCE: 33
atggacactt ctgtgcagaa gaagaaactc ggtttaaaga atcgctacgc agcgatgacc        60
cgcggtcttg gctggcagac cagctaccag ccgatggaga aagtgtttcc gtacgacaag       120
tacgaaggca tcaagatcca cgattgggat aaatgggaag accccttccg cctgaccatg       180
gacgcctact ggaaatatca gggcgagaag gaaaaaaagc tttacgccgt catcgacgct       240
ttcgcgcaga caacgggca gttgagcatt ccgacgcgc gatatgtcaa cgcactcaag       300
gtgtttatcc agggtgtgac accgttggag tatatgagtc accgaggttt tgcccacatt       360
ggtcggcatt ttacgggtga aggggcacgt gttgcttgcc agatgcagtc catcgacgag       420
ctgcgtcact tccagaccga aatgcatgct ctctcgcact acaacaagta ttttaacggt       480
ctgcacaact ccatccattg gtacgaccgg gtttggtatt tgtcggtgcc caagtcattt       540
tttgaagacg cggccaccgg tggaccgttc gagtttctta ccgcggtgag cttttcgttc       600
gaatatgtgt tgaccaacct gctgtttgtc cccttcatgt cgggtgctgc ttacaacggg       660
gacatgtcta cggtcacttt cggttttcg gcgcaaagtg acgaatcgcg ccacatgaca       720
ctcggcatcg aatgcatcaa gttcatgcta aacaggatc cggacaacgt gcccatcgtg       780
cagcgctgga tcgacaagtg gttctggcgc ggctatcggc tgttgagcat cgtggccatg       840
atgcaggact acatgctgcc aaccgggtg atgagctggc gcgagagctg ggagatgtac       900
gtcgagcaga acgcggcgc gctgttcaag atcttgcgc gttatggcat ccgcaagccc       960
aagggctggg accaggcttg cgaaggcaag gaccacatca gccatcagac cttcgccgta      1020
ttctataact ataacgccgc ggcccccatc cacacctggg ttcccacaaa agaagaaatg      1080
ggatggctgt cggagaagta ccccgagacg ttcgacaagt attaccgtcc gcgttgggac      1140
tactggcgcg agcaggccgc caagggcaac cgtttctaca caagacgct gccgatgctc      1200 tgcactacct gccagattcc gatgatattc accgagcctg gcgacgcaac caagatctgc      1260
tatcgcgagt cggcctacct cggcgacaag tatcacttct gcagcgacca ctgcaaggag      1320
atttttgaca acgaacccga aaagttcgtg cagtcatggc ttccgccgca gcaagtgtat      1380
caaggaaact gtttcaagcc ggatgccgat ccgaccaagg agggttttga tcccttgatg      1440
gccttgctcg actactacaa cctgaatgta ggccgggaca acttcgattt cgagggatcg      1500
gaagaccaaa agaactttgc tgcctggcgt ggagaggtct tgcaaggaga agccaaatga      1560

<210> SEQ ID NO 34

<211> LENGTH: 519
<212> TYPE: PRT
<213> ORGANISM: Burkholderia cepacia
<220> FEATURE:
<221> NAME/KEY: A113S
<222> LOCATION: (1)..(519)
<223> OTHER INFORMATION: TOM A113S alpha subunit protein

<400> SEQUENCE: 34

```
Met Asp Thr Ser Val Gln Lys Lys Leu Gly Leu Lys Asn Arg Tyr
1               5                   10                  15

Ala Ala Met Thr Arg Gly Leu Gly Trp Gln Thr Ser Tyr Gln Pro Met
                20                  25                  30

Glu

| | | | | | | | | | | | | |
|---|---|---|---|---|---|---|---|---|---|---|---|---|
|Glu|Thr|Phe|Asp|Lys|Tyr|Tyr|Arg|Pro|Arg|Trp|Asp|Tyr|Trp|Arg|Glu|
| |370| | | |375| | | |380| | | |

Glu Thr Phe Asp Lys Tyr Tyr Arg Pro Arg Trp Asp Tyr Trp Arg Glu
    370             375             380

Gln Ala Ala Lys Gly Asn Arg Phe Tyr Asn Lys Thr Leu Pro Met Leu
385             390             395             400

Cys Thr Thr Cys Gln Ile Pro Met Ile Phe Thr Glu Pro Gly Asp Ala
            405             410             415

Thr Lys Ile Cys Tyr Arg Glu Ser Ala Tyr Leu Gly Asp Lys Tyr His
        420             425             430

Phe Cys Ser Asp His Cys Lys Glu Ile Phe Asp Asn Glu Pro Glu Lys
        435             440             445

Phe Val Gln Ser Trp Leu Pro Pro Gln Gln Val Tyr Gln Gly Asn Cys
    450             455             460

Phe Lys Pro Asp Ala Asp Pro Thr Lys Glu Gly Phe Asp Pro Leu Met
465             470             475             480

Ala Leu Leu Asp Tyr Tyr Asn Leu Asn Val Gly Arg Asp Asn Phe Asp
            485             490             495

Phe Glu Gly Ser Glu Asp Gln Lys Asn Phe Ala Ala Trp Arg Gly Glu
        500             505             510

Val Leu Gln Gly Glu Ala Lys
        515

```
<210> SEQ ID NO 35
<211> LENGTH: 1560
<212> TYPE: DNA
<213> ORGANISM: Burkholderia cepacia
<220> FEATURE:
<221> NAME/KEY: A113F
<222> LOCATION: (1)..(1560)
<223> OTHER INFORMATION: TOM A113F alpha subunit DNA sequence

```
tactggcgcg agcaggccgc caagggcaac cgtttctaca acaagacgct gccgatgctc   1200
tgcactacct gccagattcc gatgatattc accgagcctg gcgacgcaac caagatctgc   1260
tatcgcgagt cggcctacct cggcgacaag tatcacttct gcagcgacca ctgcaaggag   1320 attttgaca cgaacccga aaagttcgtg cagtcatggc ttccgccgca gcaagtgtat   1380
caaggaaact gtttcaagcc ggatgccgat ccgaccaagg agggttttga tcccttgatg   1440
gccttgctcg actactacaa cctgaatgta ggccgggaca acttcgattt cgagggatcg   1500
gaagaccaaa agaactttgc tgcctggcgt ggagaggtct tgcaaggaga agccaaatga   1560
```

```
<210> SEQ ID NO 36
<211> LENGTH: 519
<212> TYPE: PRT
<213> ORGANISM: Burkholderia cepacia
<220> FEATURE:
<221> NAME/KEY: A113F
<222> LOCATION: (1)..(519)
<223> OTHER INFORMATION: TOM A113F alpha subunit protein

<400> SEQUENCE: 36
```

Met Asp Thr Ser Val Gln Lys Lys Leu Gly Leu Lys Asn Arg Tyr
1               5                   10                  15

Ala Ala Met Thr Arg Gly Leu Gly Trp Gln Thr Ser Tyr Gln Pro Met
            20                  25                  30

Glu Lys Val Phe Pro Tyr Asp Lys Tyr Glu Gly Ile Lys Ile His Asp
        35                  40                  45

Trp Asp Lys Trp Glu Asp Pro Phe Arg Leu Thr Met Asp Ala Tyr Trp
    50                  55                  60

Lys Tyr Gln Gly Glu Lys Glu Lys Lys Leu Tyr Ala Val Ile Asp Ala
65                  70                  75                  80

Phe Ala Gln Asn Asn Gly Gln Leu Ser Ile Ser Asp Ala Arg Tyr Val
                85                  90                  95

Asn Ala Leu Lys Val Phe Ile Gln Gly Val Thr Pro Leu Glu Tyr Met
            100                 105                 110

Phe His Arg Gly Phe Ala His Ile Gly Arg His Phe Thr Gly Glu Gly
        115                 120                 125

Ala Arg Val Ala Cys Gln Met Gln Ser Ile Asp Glu Leu Arg His Phe
    130                 135                 140

Gln Thr Glu Met His Ala Leu Ser His Tyr Asn Lys Tyr Phe Asn Gly
145                 150                 155                 160

Leu His Asn Ser Ile His Trp Tyr Asp Arg Val Trp Tyr Leu Ser Val
                165                 170                 175

Pro Lys Ser Phe Phe Glu Asp Ala Ala Thr Gly Gly Pro Phe Glu Phe
            180                 185                 190

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
    210                 215                 220

Val Thr Phe Gly Phe Ser Ala Gln Ser Asp Glu Ser Arg His Met Thr
225                 230                 235                 240

Leu Gly Ile Glu Cys Ile Lys Phe Met Leu Glu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Ser Ile Val Ala Met Met Gln Asp Tyr Met Leu Pro Asn

-continued

```
            275                 280                 285
Arg Val Met Ser Trp Arg Glu Ser Trp Glu Met Tyr Val Glu Gln Asn
    290                 295                 300
Gly Gly Ala Leu Phe Lys Asp Leu Ala Arg Tyr Gly Ile Arg Lys Pro
305                 310                 315                 320
Lys Gly Trp Asp Gln Ala Cys Glu Gly Lys Asp His Ile Ser His Gln
                325                 330                 335
Thr Phe Ala Val Phe Tyr Asn Tyr Asn Ala Ala Pro Ile His Thr
                340                 345                 350
Trp Val Pro Thr Lys Glu Glu Met Gly Trp Leu Ser Glu Lys Tyr Pro
            355                 360                 365
Glu Thr Phe Asp Lys Tyr Tyr Arg Pro Arg Trp Asp Tyr Trp Arg Glu
    370                 375                 380
Gln Ala Ala Lys Gly Asn Arg Phe Tyr Asn Lys Thr Leu Pro Met Leu
385                 390                 395                 400
Cys Thr Thr Cys Gln Ile Pro Met Ile Phe Thr Glu Pro Gly Asp Ala
                405                 410                 415
Thr Lys Ile Cys Tyr Arg Glu Ser Ala Tyr Leu Gly Asp Lys Tyr His
                420                 425                 430
Phe Cys Ser Asp His Cys Lys Glu Ile Phe Asp Asn Glu Pro Glu Lys
            435                 440                 445
Phe Val Gln Ser Trp Leu Pro Pro Gln Gln Val Tyr Gln Gly Asn Cys
    450                 455                 460
Phe Lys Pro Asp Ala Asp Pro Thr Lys Glu Gly Phe Asp Pro Leu Met
465                 470                 475                 480
Ala Leu Leu Asp Tyr Tyr Asn Leu Asn Val Gly Arg Asp Asn Phe Asp
                485                 490                 495
Phe Glu Gly Ser Glu Asp Gln Lys Asn Phe Ala Ala Trp Arg Gly Glu
            500                 505                 510
Val Leu Gln Gly Glu Ala Lys
        515
```

```
<210> SEQ ID NO 37
<211> LENGTH: 1560
<212> TYPE: DNA
<213> ORGANISM: Burkholderia cepacia
<220> FEATURE:
<221> NAME/KEY: A113I
<222> LOCATION: (1)..(1560)
<223> OTHER INFORMATION: TOM A113I alpha subunit DNA sequence

<400> SEQUENCE: 37
atggacactt ctgtgcagaa gaagaaactc ggtttaaaga atcgctacgc agcgatgacc        60
cgcggtcttg gctggcagac cagctaccag ccgatggaga aagtgtttcc gtacgacaag       120
tacgaaggca tcaagatcca cgattgggat aaatgggaag acccccttcc gctgaccatg       180
gacgcctact ggaaatatca gggcgagaag gaaaaaaagc tttacgccgt catcgacgct       240
ttcgcgcaga caacgggca gttgagcatt ccgacgcgc gatatgtcaa cgcactcaag       300
gtgtttatcc agggtgtgac accgttggag tatatgatcc accgaggttt tgcccacatt       360
ggtcggcatt ttacgggtga aggggcacgt gttgcttgcc agatgcagtc catcgacgag       420
ctgcgtcact tccagaccga aatgcatgct ctctcgcact acaacaagta ttttaacggt       480
ctgcacaact ccatccattg gtacgaccgg gtttggtatt tgtcggtgcc caagtcattt       540
tttgaagacg cggccaccgg tggaccgttc gagtttctta ccgcggtgag cttttcgttc       600
```

-continued

```
gaatatgtgt tgaccaacct gctgtttgtc cccttcatgt cgggtgctgc ttacaacggg    660
gacatgtcta cggtcacttt cggttttccg gcgcaaagtg acgaatcgcg ccacatgaca    720
ctcggcatcg aatgcatcaa gttcatgcta gaacaggatc cggacaacgt gcccatcgtg    780
cagcgctgga tcgacaagtg gttctggcgc ggctatcggc tgttgagcat cgtggccatg    840
atgcaggact acatgctgcc caaccgggtg atgagctggc gcgagagctg ggagatgtac    900
gtcgagcaga acggcggcgc gctgttcaag gatcttgcgc gttatggcat ccgcaagccc    960
aagggctggg accaggcttg cgaaggcaag gaccacatca gccatcagac cttcgccgta   1020
ttctataact ataacgccgc ggcccccatc cacacctggg ttcccacaaa agaagaaatg   1080
ggatggctgt cggagaagta ccccgagacg ttcgacaagt attaccgtcc gcgttgggac   1140
tactggcgcg agcaggccgc caagggcaac cgtttctaca acaagacgct gccgatgctc   1200
tgcactacct gccagattcc gatgatattc accgagcctg cgacgcaac caagatctgc   1260 tatcgcgagt cggcctacct cggcgacaag tatcacttct gcagcgacca ctgcaaggag   1320 attttgaca acgaacccga aaagttcgtg cagtcatggc ttccgccgca gcaagtgtat   1380
caaggaaact gtttcaagcc ggatgccgat ccgaccaagg agggttttga tcccttgatg   1440
gccttgctcg actactacaa cctgaatgta ggccgggaca acttcgattt cgagggatcg   1500
gaagaccaaa agaactttgc tgcctggcgt ggagaggtct tgcaaggaga agccaaatga   1560
```

```
<210> SEQ ID NO 38
<211> LENGTH: 519
<212> TYPE: PRT
<213> ORGANISM: Burkholderia cepacia
<220> FEATURE:
<221> NAME/KEY: A113I
<222> LOCATION: (1)..(519)
<223> OTHER INFORMATION: TOM A113I alpha subunit protein

<400> SEQUENCE: 38

Met Asp Thr Ser Val Gln Lys Lys Leu Gly Leu Lys Asn Arg Tyr
1               5                  10                  15

Ala Ala Met Thr Arg Gly Leu Gly Trp Gln Thr Ser Tyr Gln Pro Met
            20                  25                  30

Glu Lys Val Phe Pro Tyr Asp Lys Tyr Glu Gly Ile Lys Ile His Asp
        35                  40                  45

Trp Asp Lys Trp Glu Asp Pro Phe Arg Leu Thr Met Asp Ala Tyr Trp
    50                  55                  60

Lys Tyr Gln Gly Glu Lys Glu Lys Leu Tyr Ala Val Ile Asp Ala
65                  70                  75                  80

Phe Ala Gln Asn Asn Gly Gln Leu Ser Ile Ser Asp Ala Arg Tyr Val
                85                  90                  95

Asn Ala Leu Lys Val Phe Ile Gln Gly Val Thr Pro Leu Glu Tyr Met
            100                 105                 110

Ile His Arg Gly Phe Ala His Ile Gly Arg His Phe Thr Gly Glu Gly
        115                 120                 125

Ala Arg Val Ala Cys Gln Met Gln Ser Ile Asp Glu Leu Arg His Phe
    130                 135                 140

Gln Thr Glu Met His Ala Leu Ser His Tyr Asn Lys Tyr Phe Asn Gly
145                 150                 155                 160

Leu His Asn Ser Ile His Trp Tyr Asp Arg Val Trp Tyr Leu Ser Val
                165                 170                 175

Pro Lys Ser Phe Phe Glu Asp Ala Ala Thr Gly Gly Pro Phe Glu Phe
            180                 185                 190
```

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
210                 215                 220

Val Thr Phe Gly Phe Ser Ala Gln Ser Asp Glu Ser Arg His Met Thr
225                 230                 235                 240

Leu Gly Ile Glu Cys Ile Lys Phe Met Leu Glu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Ser Ile Val Ala Met Met Gln Asp Tyr Met Leu Pro Asn
        275                 280                 285

Arg Val Met Ser Trp Arg Glu Ser Trp Glu Met Tyr Val Glu Gln Asn
290                 295                 300

Gly Gly Ala Leu Phe Lys Asp Leu Ala Arg Tyr Gly Ile Arg Lys Pro
305                 310                 315                 320

Lys Gly Trp Asp Gln Ala Cys Glu Gly Lys Asp His Ile Ser His Gln
                325                 330                 335

Thr Phe Ala Val Phe Tyr Asn Tyr Asn Ala Ala Ala Pro Ile His Thr
            340                 345                 350

Trp Val Pro Thr Lys Glu Glu Met Gly Trp Leu Ser Glu Lys Tyr Pro
        355                 360                 365

Glu Thr Phe Asp Lys Tyr Tyr Arg Pro Arg Trp Asp Tyr Trp Arg Glu
370                 375                 380

Gln Ala Ala Lys Gly Asn Arg Phe Tyr Asn Lys Thr Leu Pro Met Leu
385                 390                 395                 400

Cys Thr Thr Cys Gln Ile Pro Met Ile Phe Thr Glu Pro Gly Asp Ala
                405                 410                 415

Thr Lys Ile Cys Tyr Arg Glu Ser Ala Tyr Leu Gly Asp Lys Tyr His
            420                 425                 430

Phe Cys Ser Asp His Cys Lys Glu Ile Phe Asp Asn Glu Pro Glu Lys
        435                 440                 445

Phe Val Gln Ser Trp Leu Pro Pro Gln Gln Val Tyr Gln Gly Asn Cys
450                 455                 460

Phe Lys Pro Asp Ala Asp Pro Thr Lys Glu Gly Phe Asp Pro Leu Met
465                 470                 475                 480

Ala Leu Leu Asp Tyr Tyr Asn Leu Asn Val Gly Arg Asp Asn Phe Asp
                485                 490                 495

Phe Glu Gly Ser Glu Asp Gln Lys Asn Phe Ala Ala Trp Arg Gly Glu
            500                 505                 510

Val Leu Gln Gly Glu Ala Lys
        515

<210> SEQ ID NO 39
<211> LENGTH: 1560
<212> TYPE: DNA
<213> ORGANISM: Burkholderia cepacia
<220> FEATURE:
<221> NAME/KEY: A113G
<222> LOCATION: (1)..(1560)
<223> OTHER INFORMATION: TOM A113G alpha subunit DNA sequence

<400> SEQUENCE: 39
atggacactt ctgtgcagaa gaagaaactc ggtttaaaga atcgctacgc agcgatgacc      60
cgcggtcttg gctggcagac cagctaccag ccgatggaga aagtgtttcc gtacgacaag     120

-continued

| | |
|---|---|
| tacgaaggca tcaagatcca cgattgggat aaatgggaag accccttccg cctgaccatg | 180 |
| gacgcctact ggaaatatca gggcgagaag gaaaaaaagc tttacgccgt catcgacgct | 240 |
| ttcgcgcaga acaacgggca gttgagcatt tccgacgcgc gatatgtcaa cgcactcaag | 300 |
| gtgtttatcc agggtgtgac accgttggag tatatggggc accgaggttt tgcccacatt | 360 |
| ggtcggcatt ttacgggtga aggggcacgt gttgcttgcc agatgcagtc catcgacgag | 420 |
| ctgcgtcact tccagaccga aatgcatgct ctctcgcact acaacaagta ttttaacggt | 480 |
| ctgcacaact ccatccattg gtacgaccgg gtttggtatt tgtcggtgcc caagtcattt | 540 |
| tttgaagacg cggccaccgg tggaccgttc gagtttctta ccgcggtgag cttttcgttc | 600 |
| gaatatgtgt tgaccaacct gctgtttgtc cccttcatgt cgggtgctgc ttacaacggg | 660 |
| gacatgtcta cggtcacttt cggttttcg gcgcaaagtg acgaatcgcg ccacatgaca | 720 |
| ctcggcatcg aatgcatcaa gttcatgcta aacaggatc cggacaacgt gcccatcgtg | 780 |
| cagcgctgga tcgacaagtg gttctggcgc ggctatcggc tgttgagcat cgtggccatg | 840 |
| atgcaggact acatgctgcc caaccgggtg atgagctggc gcgagagctg ggagatgtac | 900 |
| gtcgagcaga acggcggcgc gctgttcaag gatcttgcgc gttatggcat ccgcaagccc | 960 |
| aagggctggg accaggcttg cgaaggcaag gaccacatca gccatcagac cttcgccgta | 1020 |
| ttctataact ataacgccgc gggccccatc cacacctggg ttcccacaaa agaagaaatg | 1080 |
| ggatggctgt cggagaagta ccccgagacg ttcgacaagt attaccgtcc gcgttgggac | 1140 |
| tactggcgcg agcaggccgc caagggcaac cgtttctaca acaagacgct gccgatgctc | 1200 |
| tgcactacct gccagattcc gatgatattc accgagcctg gcgacgcaac caagatctgc | 1260 |
| tatcgcgagt cggcctacct cggcgacaag tatcacttct gcagcgacca ctgcaaggag | 1320 |
| attttgaca cgaacccga aaagttcgtg cagtcatggc ttccgccgca gcaagtgtat | 1380 |
| caaggaaact gtttcaagcc ggatgccgat ccgaccaagg agggttttga tcccttgatg | 1440 |
| gccttgctcg actactacaa cctgaatgta ggccgggaca acttcgattt cgagggatcg | 1500 |
| gaagaccaaa agaactttgc tgcctggcgt ggagaggtct tgcaaggaga agccaaatga | 1560 |

<210> SEQ ID NO 40
<211> LENGTH: 519
<212> TYPE: PRT
<213> ORGANISM: Burkholderia cepacia
<220> FEATURE:
<221> NAME/KEY: A113G
<222> LOCATION: (1)..(519)
<223> OTHER INFORMATION: TOM A113G alpha subunit protein

<400> SEQUENCE: 40

Met Asp Thr Ser Val Gln Lys Lys Lys Leu Gly Leu Lys Asn Arg Tyr
1               5                   10                  15

Ala Ala Met Thr Arg Gly Leu Gly Trp Gln Thr Ser Tyr Gln Pro Met
            20                  25                  30

Glu Lys Val Phe Pro Tyr

```
Asn Ala Leu Lys Val Phe Ile Gln Gly Val Thr Pro Leu Glu Tyr Met
                100                 105                 110

Gly His Arg Gly Phe Ala His Ile Gly Arg His Phe Thr Gly Glu Gly
            115                 120                 125

Ala Arg Val Ala Cys Gln Met Gln Ser Ile Asp Glu Leu Arg His Phe
        130                 135                 140

Gln Thr Glu Met His Ala Leu Ser His Tyr Asn Lys Tyr Phe Asn Gly
145                 150                 155                 160

Leu His Asn Ser Ile His Trp Tyr Asp Arg Val Trp Tyr Leu Ser Val
                165                 170                 175

Pro Lys Ser Phe Phe Glu Asp Ala Ala Thr Gly Gly Pro Phe Glu Phe
            180                 185                 190

Leu Thr Ala Val Ser Phe Ser Phe Glu Tyr Val Leu Thr Asn Leu Leu
        195                 200                 205

Phe Val Pro Phe Met Ser Gly Ala Ala Tyr Asn Gly Asp Met Ser Thr
    210                 215                 220

Val Thr Phe Gly Phe Ser Ala Gln Ser Asp Glu Ser Arg His Met Thr
225                 230                 235                 240

Leu Gly Ile Glu Cys Ile Lys Phe Met Leu Gln Asp Pro Asp Asn
                245                 250                 255

Val Pro Ile Val Gln Arg Trp Ile Asp Lys Trp Phe Trp Arg Gly Tyr
            260                 265                 270

Arg Leu Leu Ser Ile Val Ala Met Met Gln Asp Tyr Met Leu Pro Asn
        275                 280                 285

Arg Val Met Ser Trp Arg Glu Ser Trp Glu Met Tyr Val Glu Gln Asn
    290                 295                 300

Gly Gly Ala Leu Phe Lys Asp Leu Ala Arg Tyr Gly Ile Arg Lys Pro
305                 310                 315                 320

Lys Gly Trp Asp Gln Ala Cys Glu Gly Lys Asp His Ile Ser His Gln
                325                 330                 335

Thr Phe Ala Val Phe Tyr Asn Tyr Asn Ala Ala Ala Pro Ile His Thr
            340                 345                 350

Trp Val Pro Thr Lys Glu Glu Met Gly Trp Leu Ser Glu Lys Tyr Pro
        355                 360                 365

Glu Thr Phe Asp Lys Tyr Tyr Arg Pro Arg Trp Asp Tyr Trp Arg Glu
    370                 375                 380

Gln Ala Ala Lys Gly Asn Arg Phe Tyr Asn Lys Thr Leu Pro Met Leu
385                 390                 395                 400

Cys Thr Thr Cys Gln Ile Pro Met Ile Phe Thr Glu Pro Gly Asp Ala
                405                 410                 415

Thr Lys Ile Cys Tyr Arg Glu Ser Ala Tyr Leu Gly Asp Lys Tyr His
            420                 425                 430

Phe Cys Ser Asp His Cys Lys Glu Ile Phe Asp Asn Glu Pro Glu Lys
        435                 440                 445

Phe Val Gln Ser Trp Leu Pro Pro Gln Gln Val Tyr Gln Gly Asn Cys
    450                 455                 460

Phe Lys Pro Asp Ala Asp Pro Thr Lys Glu Gly Phe Asp Pro Leu Met
465                 470                 475                 480

Ala Leu Leu Asp Tyr Tyr Asn Leu Asn Val Gly Arg Asp Asn Phe Asp
                485                 490                 495

Phe Glu Gly Ser Glu Asp Gln Lys Asn Phe Ala Ala Trp Arg Gly Glu
            500                 505                 510

Val Leu Gln Gly Glu Ala Lys
```

515

<210> SEQ ID NO 41
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 41
tacggaattc aagcttttaa accccacagg                                    30

<210> SEQ ID NO 42
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: Synthetic oligonucleotide

<400> SEQUENCE: 42
tccatgctct tcactgttga c                                             21

<210> SEQ ID NO 43
<211> LENGTH: 36
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(36)
<223> OTHER INFORMATION: Synthetic oligonucleotide

<400> SEQUENCE: 43
cactttgaaa tcccattacg gcgccnnngc agttgg                             36

<210> SEQ ID NO 44
<211> LENGTH: 36
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(36)
<223> OTHER INFORMATION: Synthetic oligonucleotide

<400> SEQUENCE: 44
gctgcatatt caccaactgc nnnggcgccg taatgg                             36

<210> SEQ ID NO 45
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 45
tccaagccca gatctatcaa cgagcgttcg                                30

<210> SEQ ID NO 46
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 46
tacggaattc aagcttttaa accccacagg                                30

<210> SEQ ID NO 47
<211> LENGTH: 28
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic oligonucleotide

<400> SEQUENCE: 47
cccgcatgaa tactgtaaga aggatcgc                                  28

<210> SEQ ID NO 48
<211> LENGTH: 28
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic oligonucleotide

<400> SEQUENCE: 48
gctcgttgat agatctgggc ttggacaa                                  28

<210> SEQ ID NO 49
<211> LENGTH: 28
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic oligonucleotide

<400> SEQUENCE: 49
aatctattga agagatgggc aaagacgc                                  28

<210> SEQ ID NO 50
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide -continued

```
<400> SEQUENCE: 50
tacggaattc aagctttttaa accccacagg                                        30

<210> SEQ ID NO 51
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 51
tccaagccca gatctatcaa cgagcgttcg                                         30

<210> SEQ ID NO 52
<211> LENGTH: 42
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(42)
<223> OTHER INFORMATION: Synthetic oligonucleotide

<400> SEQUENCE: 52
attacggcgc catcgcagtt nnngaatatg cannngtaac cg                           42

<210> SEQ ID NO 53
<211> LENGTH: 42
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(42)
<223> OTHER INFORMATION: Synthetic oligonucleotide

<400> SEQUENCE: 53
atacgacctt caccggttac nnntgcatat tcnnnaactg cg                           42

<210> SEQ ID NO 54
<211> LENGTH: 36
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(36)
<223> OTHER INFORMATION: Synthetic oligonucleotide

<400> SEQUENCE: 54
cactttgaaa tcccattacg gcgccnnngc agttgg                                  36

<210> SEQ ID NO 55
<211> LENGTH: 36
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(36)
<223> OTHER INFORMATION: Synthetic oligonucleotide
```

<400> SEQUENCE: 55
gctgcatatt caccaactgc nnnggcgccg taatgg                              36

<210> SEQ ID NO 56
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 56
tacggaattc aagcttttaa accccacagg                                    30

<210> SEQ ID NO 57
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Synthetic oligonucleotide

<400> SEQUENCE: 57
ggtgcggtac cacccattag cg                                            22

<210> SEQ ID NO 58
<211> LENGTH: 25
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(25)
<223> OTHER INFORMATION: Synthetic oligonucleotide

<400> SEQUENCE: 58
ctcctgcagc ggccgctgtt aatgc                                         25

<210> SEQ ID NO 59
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Synthetic oligonucleotide

<400> SEQUENCE: 59
gccaagcgcg caattaaccc tc                                            22

<210> SEQ ID NO 60
<211> LENGTH: 24
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(24)

<223> OTHER INFORMATION: Synthetic oligonucleotide

<400> SEQUENCE: 60
ccgtatgcca atgtcaagcg gagc                                              24

<210> SEQ ID NO 61
<211> LENGTH: 25
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(25)
<223> OTHER INFORMATION: Synthetic oligonucleotide

<400> SEQUENCE: 61
cgtcagttgc ttgatctagg gctcg                                             25

<210> SEQ ID NO 62
<211> LENGTH: 25
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(25)
<223> OTHER INFORMATION: Synthetic oligonucleotide

<400> SEQUENCE: 62
gggtgacgac gctcatgatt atgag                                             25

<210> SEQ ID NO 63
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Synthetic oligonucleotide

<400> SEQUENCE: 63
gggcgttgaa ggcggcgata tg                                                22

<210> SEQ ID NO 64
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Synthetic oligonucleotide

<400> SEQUENCE: 64
gggcggggga tgtggcgatt gcg                                               23

<210> SEQ ID NO 65
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature

```
<222> LOCATION: (1)..(23)
<223> OTHER INFORMATION: Synthetic oligonucleotide

<400> SEQUENCE: 65
gcccactcaa acacgatgac tgg                                              23

<210> SEQ ID NO 66
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Synthetic oligonucleotide

<400> SEQUENCE: 66
ggtagtcttg cccaatccga agg                                              23

<210> SEQ ID NO 67
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Synthetic oligonucleotide

<400> SEQUENCE: 67
gcaactccgg cgggtgtggg                                                  20

<210> SEQ ID NO 68
<211> LENGTH: 22
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(22)
<223> OTHER INFORMATION: Synthetic oligonucleotide

<400> SEQUENCE: 68
cggtctcgcc taccttcatc cg                                               22

<210> SEQ ID NO 69
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: Synthetic oligonucleotide

<400> SEQUENCE: 69
cactatgcaa cttcacttcg gagcgnnngc acttg                                 35

<210> SEQ ID NO 70
<211> LENGTH: 35
<212> TYPE: DNA
<213> ORGANISM: Artificial
<220> FEATURE:
<223> OTHER INFORMATION: Synthetic oligonucleotide
<220> FEATURE:
```

```
<221> NAME/KEY: misc_feature
<222> LOCATION: (1)..(35)
<223> OTHER INFORMATION: Synthetic oligonucleotide

<400> SEQUENCE: 70
gcggcgtatt cttcaagtgc nnncgctccg aagtg                                35

<210> SEQ ID NO 71
<211> LENGTH: 25
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(25)
<223> OTHER INFORMATION: Synthetic oligonucleotide

<400> SEQUENCE: 71
ccgccatggg caaatcnnnc tttac                                           25

<210> SEQ ID NO 72
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 72
ggcatacgga aagtaaagnn ngatttgccc                                      30

<210> SEQ ID NO 73
<211> LENGTH: 29
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(29)
<223> OTHER INFORMATION: Synthetic oligonucleotide

<400> SEQUENCE: 73
cgcattcgaa acaggcttcn nnaatatgc                                       29

<210> SEQ ID NO 74
<211> LENGTH: 26
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(26)
<223> OTHER INFORMATION: Synthetic oligonucleotide

<400> SEQUENCE: 74
ccgagaaact gcatattnnn gaagcc                                          26

<210> SEQ ID NO 75
<211> LENGTH: 25
<212> TYPE: DNA
<213> ORGANISM: Artificial
<220> FEATURE:
<223> OTHER INFORMATION: Synthetic oligonucleotide
```

```
<220> FEATURE:
<221> NAME/KEY: misc_feature
<222> LOCATION: (1)..(25)
<223> OTHER INFORMATION: Synthetic oligonucleotide

<400> SEQUENCE: 75
gcttcaccaa tatgcagnnn ctcgg                                          25

<210> SEQ ID NO 76
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Synthetic oligonucleotide

<400> SEQUENCE: 76
cagcggccaa accgagnnnc tgc                                            23

<210> SEQ ID NO 77
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Synthetic oligonucleotide

<400> SEQUENCE: 77
cccactcata atcatgagcg tcg                                            23

<210> SEQ ID NO 78
<211> LENGTH: 32
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(32)
<223> OTHER INFORMATION: Synthetic oligonucleotide

<400> SEQUENCE: 78
ccggctcgta tgttgtgtgg aattgtgatc gg                                  32

<210> SEQ ID NO 79
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: Synthetic oligonucleotide

<400> SEQUENCE: 79
ccaggatctt gagcgacggt ccaccttgct gtgct                               35

<210> SEQ ID NO 80
<211> LENGTH: 30
<212> TYPE: DNA
<213> ORGANISM: Artificial
<220> FEATURE:
```

<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 80
tacggaattc aagcttttaa accccacagg                                30

<210> SEQ ID NO 81
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 81
ttcggatccg ctgagaacac attgaacagg                                30

<210> SEQ ID NO 82
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 82
tgagggatcc cgccaagcaa aaaacactac                                30

<210> SEQ ID NO 83
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 83
aagttctaga gtctatgctg tgctgtgtcc                                30

<210> SEQ ID NO 84
<211> LENGTH: 30
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(30)
<223> OTHER INFORMATION: Synthetic oligonucleotide

<400> SEQUENCE: 84
tacggaattc aagcttttaa accccacagg                                30

<210> SEQ ID NO 85
<211> LENGTH: 28
<212> TYPE: DNA
<213> ORGANISM: Artificial

-continued

```
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic oligonucleotide

<400> SEQUENCE: 85
cccgcatgaa tactgtaaga aggatcgc                                            28

<210> SEQ ID NO 86
<211> LENGTH: 28
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic oligonucleotide

<400> SEQUENCE: 86
gctcgttgat agatctgggc ttggacaa                                            28

<210> SEQ ID NO 87
<211> LENGTH: 28
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(28)
<223> OTHER INFORMATION: Synthetic oligonucleotide

<400> SEQUENCE: 87
aatctattga agagatgggc aaagacgc                                            28

<210> SEQ ID NO 88
<211> LENGTH: 18
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: Synthetic oligonucleotide

<400> SEQUENCE: 88
tccgatggta ccgaagtc                                                       18

<210> SEQ ID NO 89
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Synthetic oligonucleotide

<400> SEQUENCE: 89
ggcgaactga tattgactcg                                                     20

<210> SEQ ID NO 90
<211> LENGTH: 19
<212> TYPE: DNA
```

```
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: Synthetic oligonucleotide

<400> SEQUENCE: 90
caatggcccg ctgttattc                                              19

<210> SEQ ID NO 91
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: Synthetic oligonucleotide

<400> SEQUENCE: 91
gaaggttgga ttgaaaagtg g                                           21

<210> SEQ ID NO 92
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: Synthetic oligonucleotide

<400> SEQUENCE: 92
tgcaaaccat tatccgacct c                                           21

<210> SEQ ID NO 93
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: Synthetic oligonucleotide

<400> SEQUENCE: 93
ctgattaatg tgtcgtcgag c                                           21

<210> SEQ ID NO 94
<211> LENGTH: 30
<212> TYPE: DNA
<213> ORGANISM: Artificial
<220> FEATURE:
<223> OTHER INFORMATION: Synthetic oligonucleotide
<220> FEATURE:
```

```
<221> NAME/KEY: misc_feature
<222> LOCATION: (1)..(30)
<223> OTHER INFORMATION: Synthetic oligonucleotide

<400> SEQUENCE: 94
tgagggatcc cgccaagcaa aaaacactac                              30

<210> SEQ ID NO 95
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Synthetic oligonucleotide

<400> SEQUENCE: 95
atttcccgca cgactattgc                                         20

<210> SEQ ID NO 96
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Synthetic oligonucleotide

<400> SEQUENCE: 96
aacgcacctt gatcgacctg                                         20

<210> SEQ ID NO 97
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: Synthetic oligonucleotide

<400> SEQUENCE: 97
gcttcagtac atgaacctgg c                                       21

<210> SEQ ID NO 98
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Synthetic oligonucleotide

<400> SEQUENCE: 98
tgcgttccag ggaatctgcc                                         20

<210> SEQ ID NO 99
<211> LENGTH: 19
<212> TYPE: DNA
<213> ORGANISM: Artificial
<220> FEATURE:
<223> OTHER INFORMATION: Synthetic oligonucleotide
```

```
<220> FEATURE:
<221> NAME/KEY: misc_feature
<222> LOCATION: (1)..(19)
<223> OTHER INFORMATION: Synthetic oligonucleotide

<400> SEQUENCE: 99
cgactacgtc cgcttctac                                              19

<210> SEQ ID NO 100
<211> LENGTH: 21
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(21)
<223> OTHER INFORMATION: Synthetic oligonucleotide

<400> SEQUENCE: 100
atctcgaact gcgcggcgta c                                           21

<210> SEQ ID NO 101
<211> LENGTH: 19
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: Synthetic oligonucleotide

<400> SEQUENCE: 101
ggtgcgcgag ttccggcac                                              19

<210> SEQ ID NO 102
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Synthetic oligonucleotide

<400> SEQUENCE: 102
agtacgcgct gctgtatccg                                             20

<210> SEQ ID NO 103
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: Synthetic oligonucleotide

<400> SEQUENCE: 103
gaagaagaaa ctcggtttaa agnnncgcta cgcag                            35

<210> SEQ ID NO 104
<211> LENGTH: 34
<212> TYPE: DNA
<213> ORGANISM: Artificial
<220> FEATURE:
```

<223> OTHER INFORMATION: Synthetic oligonucleotide
<220> FEATURE:
<221> NAME/KEY: misc_feature
<222> LOCATION: (1)..(34)
<223> OTHER INFORMATION: Synthetic oligonucleotide

<400> SEQUENCE: 104
gcggtcatcg ctgcgtagcg nnnctttaaa ccga                              34

<210> SEQ ID NO 105
<211> LENGTH: 34
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(34)
<223> OTHER INFORMATION: Synthetic oligonucleotide

<400> SEQUENCE: 105
gtgtgacacc gttggagtat atgnnncacc gagg                              34

<210> SEQ ID NO 106
<211> LENGTH: 35
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(35)
<223> OTHER INFORMATION: Synthetic oligonucleotide

<400> SEQUENCE: 106
caatgtgggc aaaacctcgg tgnnncatat actcc                             35

<210> SEQ ID NO 107
<211> LENGTH: 41
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(41)
<223> OTHER INFORMATION: Synthetic oligonucleotide

<400> SEQUENCE: 107
atccagggtn nnacaccgtt ggagtatatg nnncaccgag g                      41

<210> SEQ ID NO 108
<211> LENGTH: 41
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(41)
<223> OTHER INFORMATION: Synthetic oligonucleotide

<400> SEQUENCE: 108

-continued

```
aacctcggtg nnncatatac tccaacggtg tnnnaccctg g                          41

<210> SEQ ID NO 109
<211> LENGTH: 27
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(27)
<223> OTHER INFORMATION: Synthetic oligonucleotide

<400> SEQUENCE: 109
tcgaagaccg gatcggcatg aagttcg                                         27

<210> SEQ ID NO 110
<211> LENGTH: 27
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (1)..(27)
<223> OTHER INFORMATION: Synthetic oligonucleotide

<400> SEQUENCE: 110
gttgtagtgc gagagagcgt gcatttc                                         27
```

DIRECTED EVOLUTION OF RECOMBINANT MONOOXYGENASE NUCLEIC ACIDS AND RELATED POLYPEPTIDES AND METHODS OF USE

CROSS-REFERENCE TO RELATED APPLICATIONS

Under 35 U.S.C. §119(e) this application claims the benefit of U.S. Provisional Application No. 60/577,254 filed Jun. 4, 2004, and is hereby incorporated by reference in its entirety.

FIELD OF INVENTION

The present invention relates to novel monooxygenase nucleic acids and polypeptides created using mutagenesis, DNA shuffling, or both, in a single iteration or multiple iterations, and methods for their creation and use. The monooxygenase enzymes of the present disclosure have particular utility as biocatalysts in industrial chemical redox reactions, such as the oxidation of aromatic hydrocarbons, for example, toluene, benzene, or nitrobenzene, into industrially desirable products. The systems and processes of the present invention are especially useful for the coupled synthesis and recovery of catechols, methylcatechols, resorcinols, methylresorcinols, hydroquinones, methylhydroquinones, hydroxybenzenes, cresols, nitrobenzenes, and nitrohydroxyquinones.

Sequence Listing

This application explicitly includes the nucleotide and amino acid sequences, SEQ ID NOS. 1-110 contained on the Substitute Computer Readable Format of the Sequence Listing submitted on Mar. 21, 2008 on file, "98121_00109_corrected_SeqList_ST25.txt"; created: Mar. 21, 2008; size: 149 KB; OS: Windows XP for PCs; using PatentIn 3.4 software which is submitted herewith, and hereby incorporated by reference in its entirety. The Amended Sequence Listing contains no new matter and all amendments to the Sequence Listing are supported by the specification as originally filed.

BACKGROUND ART

Di- and trihydroxy aromatics are important industrial chemicals with many applications as evidence by worldwide production of catechol, resorcinol, and hydroquinone at 110,000 tons/year. Catechol is used as an intermediate in the food, pharmaceutical, and agrochemical industries, and hydroquinone is used in photography, in cosmetics, and in both medical and industrial X-ray films. Substituted catechols, especially 3-substituted catechols, are useful precursors for making pharmaceuticals; one of these, 3-methoxycatechol is an important intermediate for the antivascular agents combretastatin A-1 and combretastatin B-1. Hydroxyquinone and its derivatives are important chemicals used mainly as photographic developers, polymerization inhibitors, rubber antioxidants, food antioxidants, synthesis intermediates, and also used in water treatment. Methoxyhydroquinone is used in the synthesis of triptycene quinones that have been shown to have anti-leukemia cell activity. Resorcinol and its derivatives are used to inhibit rust in paints, to regulate plant growth, and to act as capacitor electrolytes. Production of 4-methylresorcinol is uncommon and prices can exceed $200,000/kg (Apin Chemicals). Methylhydroquinone has been recently reported to be used in the synthesis of (±)-helibisabonol A, and puraquinonic acid which are precursors to agrochemical herbicides and antileukemia drugs, respectively. 1,2,3-Trihydroxybenzene (1,2,3-THB, pyrogallol), the first synthetic dye for hair, is primarily used as a modifier in oxidation dyes, as a pharmaceutical intermediate, and has been used as a topical antipsoriatic. Hydroxyhydroquinone (1,2,4-THB) has been used in dyes and as a corrosion inhibitor. Manufacture of these substituted dihydroxylated compounds by chemical routes is difficult due to the employment of aggressive reagents, expensive and complicated starting materials, multiple reaction steps, and low yields. Direct microbial oxidation of NB or NPs for the synthesis of NC or NHQ is attractive to reduce wastes (relative to organic-based methods) since chemical synthesis of these compounds is problematic in terms of yield and selectivity.

Nitroaromatic compounds are widely used in industry as dyes, pesticides, plasticizers, explosives, and solvents, and dihydroxy nitroaromatics are important for medicine. Nitrocatechol derivatives have been shown to be selective and potent inhibitors of catechol-o-methyltransferase, which is important in the metabolism of catechol drugs, and so nitrocatechol derivatives may be used in the treatment of Parkinson disease. Nitrocatechols have been found to be useful intermediates for the synthesis of pharmaceuticals such as Flexinoxan, an antihypertensive drug. 4-Nitrocatehcol (4-NC) and 3-NC have potential for therapeutic interest, and were recently found to be competitive inhibitors of nitric oxide synthase with potential anti-nociceptive (pain relieving) activity. 3-NC is also essential as a building block for the production of some antihypertensive pharmaceutical such as flesinoxan. Nitrohydroquinone (NHQ) has been used to synthesize dephostatin; an inhibitor of the protein tyrosine phosphatase with is a candidate therapeutic agent for diabetes mellitus and neural diseases such as Alzheimer's disease and Parkinson's disease. Industrially, 3-NC is also useful for electrolytic capacitors operating at high temperatures or used to increase the amplification factor of transistors. NHQ is mainly used as electrophotographic photoreceptor, and dyes.

As chemical synthesis of these compounds is problematic in terms of yield and selectivity, the utilization of oxygenases is advantageous. The high redox potential of oxygenases enables them to perform reactions with chemically stable substrates as well as provide a high degree of region and enantioselectivity. Transforming selectively an inexpensive and abundant chemical as nitrobenzene (NB) into a valuable feedstock for drug production, namely 4-NC, is therefore of great significance.

There have been previous reports in the literature on oxygenases capable of producing nitrocatechols. p-Nitrophenol hydroxylase of *Arthrobacter* sp. and *Bacillus sphaericus* JS905 transforms p-nitrophenol (p-NP) to 4-NC often with further removal of the nitro group to obtain 1,2,4-trihydroxybenzene (Jain et al., 1994; Kadiyala and Spain, 1998). Kieboom and co-workers screened twenty-one microorganisms for their ability to convert nitroaromatics into 3-NC. Strains containing toluene-dioxygenases from *P. putida* F1, *Nocardia* S3, *Pseudomonas* JS150, *Corynebacterium* C125, and *Zanthobacter* 124X were able to transform NB to 3-NC rapidly. They did not report a toluene monooxygenase-containing strain able to perform this reaction. Haigler and Spain reported *Pseudomonas mendocina* KR1 and *Ralstonia pickettii* PKO1 convert NB to NC; however, the enzymes responsible for the addition of the second hydroxyl group to the nitrophenols to form nitrocatechols were not identified. *Pseudomonas mendocina* KR-1 converts NB to 4-NC via m-NP (10%) and p-NP (63%), and *Pseudomonas pickettii* PKO1 converts NB to 3-NC and 4-NC via m-NP and p-NO. *Pseudomonas putida* 2NP8 grown on m-NP has been shown to degrade NB into ammonia, nitrobenzene, and hydroxylaminobenzene. O—NP is degraded by this strain with production of nitrite, and m-NP resulted in the formation of ammonia. *Pseudomonas pseudoalcoligenes* JS45 degrades NB to 2-aminomuconate, which is also an intermediate in the metabolism of tryptophan in mammals.

Twenty-one oxygenase-containing bacteria were screened for the ability to convert nitroaromatics into 3-NC. *Mycobacterium chelonae* strain NB01 was shown to degrade NB via reductive degradation mechanism, which resulted with the formation of ammonia. *Comamonas sp strain JS*765 was shown to convert NB to an unstable nitrohydrodiol that spontaneously decomposes to form catechol and nitrite via nitrobenzene 1,2-dioxygenase.

Indigo is one of the oldest dyes and is still used worldwide for textiles with 22,000 tons produced annually worth $200 million. Historically, this blue dye was obtained from various plant sources, including woad (*Isatis tinctoria*) in Europe and *Indigofera* in Asia and South America. Now production of indigo is primarily by the Adolf von Baeyer 1890 chemical synthesis which resulted in the fifth Noble Prize in chemistry. More recently, bacterial systems for commercial indigo production have been developed, which were inspired by the discovery that growth of the recombinant *Escherichia coli* strain expressing naphthalene dioxygenase from *Pseudomonas putida* PpG7 in rich medium resulted in the formation of indigo. Indigo is formed and the result of the cloned enzyme oxygenating C-3 of the indole pyrrole ring, and indole is produced from tryptophan via tryptophanase in *E. coli*. Various monooxygenases and dioxygenases have been identified that are capable of indole oxidation to form indigo, and these biological processes are inherently safer than the Adolf von Baeyer process since they do not produce such toxins as aromatic amines (bladder carcinogens), and cyanide.

Indirubin, a pink pigment, is also produced in minor amounts from plant sources. Due to the small and variable amount of indirubin, plant-derived indigo dye has a more pleasing tinge than synthetic indigo. In addition, indirubin has important and potential therapeutic applications since it is the active ingredient of a traditional Chinese medicine used to treat diseases such as chronic myelocytic leukemia (CML) and was found to be a potent inhibitor of cyclin-dependent kinases and therefore belongs to a group of promising anticancer compounds.

Some of these compounds cannot be easily synthesized chemically, and the traditional chemical processes are often lengthy and require expensive starting materials. Direct microbial synthesis of such compounds from inexpensive substrates might provide a more cost effective and more environmentally benign approach, and biocatalysis is likely to account for 30% of the chemical business by 2050. Biocatalysis has become an attractive alternative to chemical synthesis because of its high selectivity and efficiency. Since 2000, more than 400 patents on the use of microorganisms or enzymes to produce specialty chemical shave been issued. Among the various classes of enzymes, oxygenases are considered one of the most promising due to their ability to perform selective hydroxylation that are not accessible by chemical methods. One recent commercial example is the production of an intermediate for an antipolytic drug from the oxidation of 2,5-dimethylpyrazine to 5-methylpyrazine-2-carboxylic acid with whole cells of *Pseudomonas putida* ATCC 33015 expressing xylene monooxygenase. For example, it can produce relatively pure compounds compared with racemic mixtures often obtained by chemical methods. Biocatalysis also avoids tedious blocking and deblocking steps, which are common in the chemical synthesis of enantio- and regioselective compounds, and is inherently environmentally benign as the reactions are usually performed in water (avoiding harsh solvents) at room temperature and atmospheric pressure under milder conditions.

More recently, a large number of enzymes have been studied for aromatic hydroxylations such as heme P450s, flavin monooxygenases, pterin-dependent non-heme monooxygenases, non-heme mononuclear iron dioxygenases, and diiron hydroxylases. For example, Meyer et al. (2002) reported that directed evolution using error-prone PCR increased the substrate specific activity of the flavoenzyme 2-hydroxybiphenyl 3-monooxygenase 2 times towards o-methoxyphenol and 5 times towards 2-tert-butylphenol for making the corresponding 3-substituted catechols. Canada et al. (2002) used DNA shuffling to evolve toluene ortho-monooxygenase (TOM) from *Burkholderia cepacia* G4 for 1-naphthol synthesis, and one mutant (TomA3 V106A) with 6-fold increased activity was found. Furthermore, substituted catechols (e.g., 3-bromocatechol, 3-methoxycatechol, 3-iodocatechol, 3-methylcatechol) were synthesized from substituted benzenes in two steps using recombinant *E. coli* expressing both toluene dioxygenase and dihydrocatechol dehydrogenase.

Toluene 4-monooxygenase (T4MO) from *Pseudomonas mendocina* KR1 belongs to the family of diiron hydroxylases including the methane, toluene, benzene, o-xylene monooxygenases, phenol hydroxylases, and alkene epoxidases. T4MO is a soluble, non-heme, $O_2$-dependent, diiron monooxygenase, and is a four-component alkene/aromatic monooxygenase enzyme consisting of six genes designated tmoABC-DEF. The genes tmoA, tmoB, and tmoE encode the •, •, and • subunits, respectively. The hydryolase component (212-kDa with (•••)2 quaternary structure) which was recently described as responsible for the regiospecificity of the enzyme. Gene tmoF encodes a 36-kDa NADH oxidoreductase containing FAD and a [2Fe-2S] cluster. The tmoC encodes a 12.5-kDa Rieske-type [2Fe-2S] ferredoxin involved in electron transfer between the hydroxylase and reductase; tmoD gene encodes an 11.6-kDa catalytic effector protein. All four protein components from the 6 genes are required for efficient multiple catalysis and high regiospecificity. The (•••)2 hydroxylase component containing the active site for substrate binding and hydroxylation reaction (Pikus et al., 1997) was reported recently to be responsible for the monooxygenation regiospecificity of T4MO while the binding of the effector protein refined the product distribution leading to high regiospecificity. The binding effector protein has been shown to enhance the catalytic rate of the enzyme and to refine the product distribution leading to the high regiospecificity of T4MO.

T4MO is a highly regiospecific enzyme, hydroxylating nearly all monosubstituted benzenes tested including toluene, chlorobenzene, methoxybenzene, and nitrobenzene at the para position. Recent mechanistic studies reveal that active site-directed opening of an epoxide intermediate may account for this high regiospecificity. T4MO has been shown to perform single hydroxylations, transforming benzene to phenol, toluene to p-cresol and other monosubstituted benzenes to the subsequent p-hydroxylated compounds. Wood and co-workers have recently reported that T4MO expressed in *Escherichia coli* TG1 cells can perform successive hydroxylation, resulting in conversion of benzene to 1,2,3-trihydroxybenzene. Nevertheless, there is no evidence to date of T4MO being able to convert substituted benzenes (e.g., nitrobenzene) to their respective catechols (e.g., nitrocatechol). T4MO is the most efficient enzyme towards toluene oxidation among toluene monooxygenase family including TOM, toluene para-monooxygenase (formerly toluene 3-monooxygenase) of *Ralstonia picketti* PKO1, and toluene/o-xylene monooxygenase of *Pseudomonas stutzeri* OX1. T4MO has been identified to oxidize toluene to 96% p-cresol, 3% m-cresol, and less than 1% benzyl alcohol. Other enzymes, for example, ammonia monooxygenase, chloroperoxidase, cytochrome P450, methane monooxygenase, and xylene monooxygenase oxidize alkylbenzenes; however, they produce benzyl alcohols (70-100% of total products) and only negligible amounts of phenolic products. The high regiospecificity for para hydroxylation of toluene and nearly no ortho activity make T4MO a valuable and rare enzyme that is specialized for aromatic ring hydroxylation. In addition, T4MO has broad substrate specificity for mono-substituted benzenes including nitrobenzene, chlorobenzene, and methoxybenzene, which are catalyzed to single hydroxylated products in the para position.

Toluene-o-Xylene Monooxygenase (ToMO) hydroxylates toluene in the ortho, meta, and para positions as well as o-xylene in both the 3 and 4 positions, and it oxidizes many substrates including o-xylene, m-xylene, p-xylene, toluene, a benzene, ethyl-benzene, styrene, naphthalene, and trichloroethylene (TCE), and is the only known oxygenase which attacks tetrachloroethylene. The six genes coding for ToMO are touABE (three-component hydroxylase with two catalytic oxygen-bridged dinuclear centers, A2B2E2), touC (ferredoxin), touD (mediating protein), and touF (NADH-ferredoxin oxidoreductase). ToMO touA (499 amino acids has the greatest amino acid identity to the hydroxylase (TbuA1) of toluene 3-monooxygenase (T3MO) of *Pseudomonas picketti* PKO1 (68%) and the hydroxylase (TmoA) of toluene 4-monooxygenase (T4MO) of *Pseudomonas mendocina* KR1 (66.8%), but these are distinct enzymes given their different regiospecific oxidation of toluene.

The importance of position V106 as an active residue in toluene monooxygenases was reported previously by us as a result of directed evolution of toluene ortho-monooxygenase (TOM) of *Burkholderia cepacia* G4. This beneficial mutation resulted in a two-fold increase in the initial degradation rate for TCE degradation and a six-fold increase for naphthalene oxidation. This position corresponds to I100 of the alpha subunit TouA of the hydroxylase in ToMO.

The methane monooxygenase (MMO) active site residues have been identified by X-ray crystallography, and by comparison to MMO, some of these active site residues for T4MO, T3MO, and toluene 2-monooxygenase from *Pseudomonas* sp. strain JS150 have been predicted by Pikus et al. (1997); hence, several positions in the alpha subunits of aromatic monooxygenases have been studied. Position T201 of tmoA of T4MO, and positions T201, Q141, and F205 of TouA of ToMO (Vardar and Wood, 2004) have been studied via saturation mutagenesis. T4MO mutants Q141C, Q141V, I180F, and F205I of tmoA have been studied previously via site directed mutagenesis; the same residues (except M180) and positions are the same for ToMO. For T4MO TmoA mutant Q141C, oxidation of m-xylene to 3-methylbenzyl alcohol formation increased 6-fold from 2.2% to 1.7%, and for p-xylene oxidation, the product distribution completely switched to 2,5-dimethylphenol (78%) from 4-methylbenzyl alcohol (22%). T4MO tmoA mutant T201F gave a large shift in the product distribution and also formed 10-fold more benzyl alcohol from toluene. For the hydroxylation of toluene by T4MO mutant F205I of tmoA, the percentage of m-cresol formation increased 5-fold from 2.8% to 14.5%. The TouA F205G mutation in ToMO changed the hydroxylation regiospecificities of toluene, o-cresol, m-cresol, p-cresol, phenol, and resorcinol, and allowed for the novel formation of methylhydroquinone, 4-methylresorcinol, hydroquinone, resorcinol, and 1,2,3-trihydroxybenzene (Vardar and Wood, 2004). T4MO mutants from positions Q141, T201, and F205 were not studied previously for nitrobenzene oxidation with the exception of T4MO mutant T201G of TmoA that produced 7.9% o-NP whereas wild-type T4MO did not.

*Burkholderia capacia* G4 was isolated as the first pure strain that degrades trichloroethylene (TCE), and toluene ortho-monooxygensase (TOM) has been shown to oxidize mixtures of cholorinated compounds, including TCE (Shim and Wood, 2000). The subunit of TOMs are similar to the corresponding components of crystallographically-characterized soluble methane monooxygenase (sMMO) from methanotrophic bacteria, with their •-subunits sharing about 20% amino acid sequence identity. TOM is a three-component complex consisting of a 211-kDa hydroxylase (tomA1A3A4), with two binuclear iron centers in the (•••)2 quaternary structure, a 40-kDa NADH-oxidoreductase (tomA5), and a 10.4-kDa cofactor-less regulatory protein (tomA2) involved in the electron transfer between the hydroxylase and reductase. The (•••)2 component contains the active site for substrate binding and hydroxylation reaction and is capable of a peroxide-shunt mechanism like sMMO.

TOM originally was not considered as an indigo-forming strain, but our laboratory found it was responsible for color development and indole hydroxylation. During growth in complex medium, recombinant *E. coli* expressing TOM forms brown color on agar plates an in liquid culture, whereas typical indole-oxygenating enzymes in whole cells from blue colonies on agar plates and blue, water-insoluble pigments in liquid medium. In addition, one TOM variant created from DNA shuffling was identified as a potential indigo-forming enzyme; based on the color of its colonies on agar plates and in liquid culture it was termed TOM-Green with a single amino acid change of valine to alanine at position V106 of the hydroxylase a-subunit (TomA3). Thus in this variant, a single mutation was responsible of the cell color change, presumably due to the alteration in the hydroxylation of indole.

DNA shuffling is a widely used method for protein mutagenesis in which there is no need for crystal structure or any information about the structure of the protein. Using DNA shuffling, the TomA1 V106A mutation of toluene ortho-monooxygenase (TOM) of *Burkholderia cepacia* G4 was identified (corresponds to I100 of the alpha subunit TouA of the hydroxylase in ToMO) which resulted in a 2-fold increase in the initial degradation rate for TCE degradation and a 6-fold increase for naphthalene oxidation. The importance of position I100 was corroborated in saturation mutagenesis for TmoA of T4MO and TouA of ToMO (Vardar and Wood, 2004). T4MO TmoA mutant I100L was found to have a 4-fold increase in activity for 3-methoxycatechol formation from 1 mM guaiacol. In addition, T4MOTmoA mutant I100A and I100S produced 20% m-cresol and 80% p-cresol, whereas the wild-type T4MO produced 96% p-cresol. ToMO TouA variant I100Q had significantly altered hydroxylation regiospecificities for toluene, o-cresol, m-cresol, phenol, and catechol allowing for the novel formation of methylhydroquinone, hydroquinone, and 1,2,4-trihydroxybenzene (Vardar and Wood, 2004).

Despite efforts to date, a need remains for improved system(s), method(s) and/or process(es) for generating desired monooxygenase enzymes and related polypeptides.

SUMMARY OF THE INVENTION

As an alternative to chemical synthesis of important industrial intermediates that may be costly, inefficient, and involve the formation of toxic intermediates or products, the use of "evolved" or engineered enzymes or biocatalysts as described herein is highly desirable.

The term "directed evolution" is used herein to refer generally to a method of performing gene and protein engineering for generating, and selecting a nucleic acid or polypeptide based on its differential substrate regioselectivity or enantiomer specificity. In one aspect the present invention uses a combination of nucleic acid mutagenesis, DNA shuffling, or both, to generate new or improved monoxygenase genes with modified enzymatic activity.

Certain aspects of the present invention include the use of nucleic acid mutagenesis, DNA shuffling and/or both of a parental monooxygenase gene, in a single iteration or multiple iterations to "evolve" new monooxygenase genes. These evolved monooxygenase enzymes have modified physical or biochemical characteristics that make them industrially useful. In some aspects of the present invention these new and/or improved genes have surprisingly superior properties as compared to naturally occurring monooxygenase genes, for example modified substrate regioselectivity or enantiomer specificity or both. In certain aspects of the present invention the parental or wild-type monooxygenase genes are, for example, bacterially derived. However, as will be understood by one of ordinary skill, the systems, methods, processes and useful innovations described herein may be applied to any monooxygenase enzyme regardless of derivation source, e.g., whether derived from plant, animal, and/or microbial sources.

The invention is based in part upon the creation of nucleic acid sequences encoding novel and industrially useful monooxygenase polypeptides. In certain aspects, the invention relates to evolved monooxygnease genes where the parent nucleic acid is a toluene-o-xylene-monooxygenase ("ToMO"), a toluene-4-monooxygenase ("T4MO"), a toluene-ortho-monooxygenase ("TOMA3"), or a combination thereof.

In a further aspect, the invention provides an isolated monooxygenase nucleic acid molecule encoding a monooxygenase polypeptide that includes a nucleic acid sequence that has identity to the nucleic acids disclosed in SEQ ID NOS: 3, 5, 7, 9, 11, 13, 17, 19, 21, 23, 27, 29, 31, 33, 35, 37, and 39. These monooxygenase nucleic acids, and their cognate polypeptides (SEQ ID NOS: 4, 6, 8, 10, 12, 14, 18, 20, 22, 24, 28, 30, 32, 34, 36, 38, and 40) as well as derivatives, and combinations thereof, will be referred to collectively in the specification and the claims as "MOX" nucleic acid or polypeptide sequences. As one of ordinary skill in the art will recognize, the MOX nucleid acid or polypeptide sequences can be used in any of the objects, aspects, and embodiments of the present invention disclosed herein that call for the use of a monooxygenase nucleic acid or polypeptide sequence. Furthermore, the MOX nucleic acids and polypeptides referred to herein are not intended to limit the scope of the present invention, which one of ordinary skill will recognize, contemplates the use of any monooxygenase gene, homologs, analogs, fragments, mutants, and combinations thereof.

In some embodiments, the monooxygenase nucleic acid molecule, for example a MOX nucleic acid, will hybridize under stringent conditions to a nucleic acid sequence complementary to a nucleic acid molecule that includes a protein-coding sequence of a monooxygenase nucleic acid sequence. The invention also includes an isolated nucleic acid that encodes a monooxygenase polypeptide, or a fragment, homolog, analog or derivative thereof. For example, the nucleic acid can be a genomic DNA fragment or a cDNA molecule that encode a polypeptide that is at least 80% identical to a polypeptide comprising the MOX amino acid sequences (SEQ ID NOS: 2, 4, 6, 8, 10, 12, 14, 16, 18, 20, 22, 24, 26, 28, 30, 32, 34, 36, 38, and 40).

Also included in the invention is an oligonucleotide, e.g., an oligonucleotide which includes at least 6 contiguous nucleotides of a monooxygenase nucleic acid, for example a MOX nucleic acid, or a complement of said oligonucleotide. Also included in the invention are substantially purified monooxygenase polypeptides. The invention also features antibodies that immunoselectively bind to monooxygenase polypeptides, or fragments, homologs, analogs or derivatives thereof.

In a further aspect, the invention includes a method of producing a polypeptide by culturing a cell that includes a monooxygenase nucleic acid, for example a MOX nucleic acid, under conditions allowing for expression of the monooxygenase polypeptide encoded by the DNA. If desired, the monooxygenase polypeptide can then be recovered.

In another aspect, the invention includes a method of detecting the presence of a monooxygnease polypeptide, for example a MOX polypeptide, in a sample. In the method, a sample is contacted with a compound that selectively binds to the polypeptide under conditions allowing for formation of a complex between the polypeptide and the compound. The complex is detected, if present, thereby identifying the monooxygenase polypeptide within the sample.

The invention also includes methods to identify specific cell or tissue types based on their expression of a monooxygnease polypeptide, for example a MOX polypeptide. Also included in the invention is a method of detecting the presence of a monooxygnease nucleic acid molecule in a sample by contacting the sample with a monooxygnease nucleic acid probe or primer, and detecting whether the nucleic acid probe or primer bound to a monooxygenase nucleic acid molecule in the sample.

In a further aspect, the invention provides a method for modulating the activity of a monooxygenase polypeptide by contacting a cell sample that includes the monooxygnease polypeptide with a compound that binds to the monooxygnease polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

One object of the invention is to provide bacterially derived monooxygenase polynucleotides that encode enzymes with industrially useful activity. In a related aspect the present invention relates to a method of using the enzymes in the production of industrially useful chemical intermediates at the expense of added aromatic hydrocarbons. In an exemplary embodiment of the present disclosure, the enzymes are evolved from monooxygenase genes, for example toluene monooxygenases. In a major aspect the parental monooxygenases are derived from a bacterial source, for example *Pseudomonas* sp. In other exemplary embodiments, toluene monooxygenase enzymes are evolved from *Burkholderia cepacia, Pseudomonas stutzeri, Pseudomonas mendocina* or *Ralstonia pickettii* bacteria. The systems, methods and processes of the present invention may be used to obtain and/or provide enzymes with modified activity, substrate regioselectivity, enantiomer specificity, stability, robustness, or combination thereof.

Yet another object of the present invention is to provide a means for generating industrially useful chemical intermediates. In examples of the methods of preferred embodiments, the useful and advantageous generation of valuable chemical intermediates by monooxygnease enzymes are disclosed, and in certain embodiments of the present invention, the intermediates are generated by "evolved" toluene monooxygenases.

In the disclosed methods for obtaining monooxygenase genes, a plurality of forms of a selected nucleic acid for a given gene or genes are recombined. The evolved nucleic acid is derived either from one or more parental nucleic acid(s) which encode a monooxygenase enzyme, or a fragment thereof, or from a parental nucleic acid which does not encode a monooxygenase gene but which is a candidate for DNA shuffling to develop monooxygenase activity. The plurality of forms of the selected nucleic acid may differ from each other in at least one (and typically two or more) nucleotides, and upon recombination, provides a library of recombinant monooxygenase nucleic acids. The library can be an in vitro set of molecules, or present in host cells, for example bacteria, yeast, phage or the like.

The library is typically screened to identify at least one recombinant monooxygenase nucleic acid that exhibits distinct or improved enzymatic activity compared to the parental nucleic acid or nucleic acids. Many techniques for the cloning, subcloning, and transfer of recombinant nucleic acids into a plasmid vector or a host cell or both, and techniques for library screening and selection, are known in the art, and each of these formats and/or techniques is generally applicable to the present invention. For example, texts that disclose general techniques for manipulating nucleic acids of use in this invention include "Current Protocols in Molecular Biology" (Ausubel et al., eds., 1994)); Sambrook et al., "Molecular Cloning, A Laboratory Manual" (2nd ed. 1989); and Kriegler, "Gene Transfer and Expression: A Laboratory Manual" (1990), the contents and relevant teachings of which are hereby incorporated by reference.

In certain aspects of the present invention, the starting nucleic acid segments are first recombined by any of the formats referenced herein to generate a cDNA library of recombinant nucleic acids. The library can vary in size, e.g., ranging from about 10 to about $10^9$ members. In general, the initial nucleic acid segments, and the recombinant libraries of nucleic acids generated include full-length coding sequences (i.e., open reading frame (ORF), which includes the start codon, coding sequence, and stop codon), and any essential regulatory sequences, for example, a promoter and polyadenylation sequence, required for expression. However, in the event that the recombinant nucleic acid does not contain these elements, the recombinant nucleic acids in the cDNA library can be inserted into a vector that includes the missing sequences prior to screening and selection of recombinant clones.

In other aspects, the recombinant nucleic acid sequences may be combined in an in vivo format which results in a library of recombinant segments already in a cell, which are capable of expression of the enzyme with altered substrate specificity. Alternatively, the recombination may be performed in vitro, and the recombinant library is introduced into the desired cell type prior to the step of screening and selection. In some embodiments of the invention, the recombinant nucleic acid library is amplified in a first host, and is then recovered from that host and introduced to a second host for reason of expression, selection, or screening, or any other desirable parameter. The manner by which the recombinant nucleic acid is introduced into the host cell depends on the nucleic acid-uptake characteristics of the cell type (e.g., having viral receptors, being capable of conjugation, being naturally competent, and/or requiring DNA-gun or electropulse). After introduction of the library of recombinant DNA genes, the cells may be propagated to allow expression of genes to occur.

In selecting for monooxygenase activity, a candidate shuffled DNA can be tested for encoded monooxygenase activity in essentially any synthetic process. Common processes that can be used in certain embodiments for screening include screening for aromatic hydrocarbon oxidation (e.g., hydroxylation, formation of catechols, hydroquinones, resorcinol, hydroxybenzenes, cresols, indigoid compounds, nitrocatechols, nitrohydroquinones, nitro phenols, etc.), screening for epoxidation, aromatic hydroxylation, meta, ortho or para oxidation, oxidation of aryloxy phenols, conversion of aldehydes to acids, alcohols to aldehydes or ketones, dehydrogenation, decarbonylation, oxidative dehalogenation of haloaromatics and halohydrocarbons, monooxygenation, N-hydroxylation, sulfoxide formation, hydroxylation of fatty acids, hydroxylation of terpenes and/or oxygenation of sulfonylureas. Other oxidative transformations will be apparent to those of skill in the art. Similarly, instead of, or in addition to, testing for an increase in monooxygenase specific activity, it is also desirable to screen for shuffled nucleic acids which produce higher levels of monooxygenase nucleic acid or enhanced or reduced recombinant monooxygenase polypeptide expression or stability encoded by the recombinant monooxygenase nucleic acid.

Screening of a recombinant library can involve any number of methods, depending on the monooxygenase activity for which the library is selected. By way of example, the library to be screened can be present in a population of cells. The library may be selected by growing the cells in or on a medium comprising the chemical or compound to be oxidized or reduced and selecting for a detected physical difference between the oxidized or reduced form of the chemical or compound and the non-oxidized or reduced form of the chemical or compound, either in the cell, or the extracellular medium.

The present invention also relates to the iterative selection for monooxygenase nucleic acids. For example, a selected nucleic acid identified as encoding monooxygenase activity can be shuffled, either with the parental or wild-type nucleic acids, or with other nucleic acids (e.g., mutated forms of a selected nucleic acid) to produce another shuffled library (L2). The L2 library may be tested again for some monooxygenase activity, which can be the same or different relative to the monooxygenase activity previously selected. This process can be repeated as many times as desired to obtain a nucleic acid with optimized monooxygenase activity. If desired, any monooxygenase nucleic acid identified by any of the methods herein can be cloned, expressed or both.

The present invention also relates to a genome shuffling method in which a plurality of genes are shuffled in a cell (rather than specific sequences) and the resulting nucleic acids are selected for one or more monooxygenase activities. The genomic nucleic acids may be from a species or strain different from the cell in which monooxygenase activity is desired. Similarly, the shuffling reaction can be performed using genomic or cloned DNA from the same or a different species or strain. Strains or enzymes exhibiting enhanced monooxygenase activity can then be identified, and cloned.

The present invention also relates to identifying and isolating an evolved monooxygenase enzyme with modified activity after nucleic acid mutagenesis and shuffling. The modified monooxygenase activity identified may include, for example, an increased ability to chemically modify substrate, an increase in the range of monooxygenase substrates which the distinct or improved nucleic acid operates on, an increase in the chemoselectivity of a polypeptide encoded by the nucleic acid, an increase in the regioselectivity of a polypeptide encoded by the nucleic acid, an increase in the stereoselectivity or enantiomeric specificity of a polypeptide encoded by the nucleic acid, an increased expression level of a polypeptide encoded by the nucleic acid, a decrease in susceptibility of a polypeptide encoded by the nucleic acid to protease cleavage, a decrease in susceptibility of a polypeptide encoded by the nucleic acid to high or low pH levels, a decrease in susceptibility of the protein encoded by the nucleic acid to high or low temperatures, a decrease in peroxide-mediated enzyme inactivation, a decrease in toxicity to a host cell of a polypeptide encoded by the selected nucleic acid, the ability to use low-cost starting materials, and a reduction in the sensitivity of the polypeptide and/or an organism expressing the polypeptide to inactivation by organic solvents and the feedstocks for and products of the enzymatic oxidations.

The present invention also relates to the selection of nucleic acids to be mutated and shuffled. Selected nucleic acids to be used may be synthetic or cloned nucleic acids from a variety of enzymes, including toluene monooxygenases, P450 monooxygenases, heme-dependent peroxidases, iron sulfur monooxygenases, quinone-dependent monooxygenases, and the like. In typical example of the method of the current invention, the nucleic acids are cloned into expression vectors, which are specially modified to achieve protein expression under proper conditions.

In another aspect, the current invention includes the production of libraries containing mutated and shuffled nucleic acids for use in the methods described above, and the nucleic acids identified therein. Similarly, a mixture containing at least two homologous deoxyribonucleic acids, each of which is derived from a nucleic acid encoding a polypeptide or fragment thereof is provided. These polypeptides can be, for example, toluene monooxygenases, P450 monooxygenases, heme-dependent peroxidases, iron sulfur monooxygenases, quinone-dependent monooxygenases, and the like.

Additional advantageous features and functionalities associated with the systems, methods and processes of the present invention will be apparent from the detailed description which follows. The publications and other materials used herein to illuminate the background of the invention, and in particular cases, to provide additional details respecting the practice, are incorporated by reference, and for convenience are referenced in the following text by author and date and are listed alphabetically by author in the appended bibliography.

BRIEF DESCRIPTION OF THE FIGURES

FIG. 1. Nucleic acid sequence alignment of TouA subunits from wild-type toluene-o-monooxygenase (ToMO), and variants, which produce useful chemical compounds are given by way of example, and are included as preferred embodiments of the present invention.

FIG. 2. Polypeptide sequence alignment of TouA subunits from wild-type toluene-o-monooxygenase (ToMO), and variants, which produce useful chemical compounds are given by way of example, and are included as preferred embodiments of the present invention.

FIG. 3. Polypeptide sequence alignment of TOM variants, which produce useful chemical compounds are given by way of example, and are included as preferred embodiments of the present invention.

FIG. 4. Nucleic acid sequence alignment of TOM variants, which produce useful chemical compounds are given by way of example, and are included as preferred embodiments of the present invention.

FIG. 5. Nucleic acid sequence alignment of TmoA subunits from wild-type toluene 4-monooxygenase (T4MO), and variants, which produce useful chemical compounds are given by way of example, and are included as preferred embodiments of the present invention.

FIG. 6. Polypeptide sequence alignment of TmoA subunits from wild-type toluene 4-monooxygenase (T4MO), and variants, which produce useful chemical compounds are given by way of example, and are included as preferred embodiments of the present invention.

FIGURES FROM EXAMPLES OF THE PREFERRED EMBODIMENTS

FIG. 7. Primers used for mutagenesis (error-prone PCR of TmoA and saturation mutagenesis of TmoA I100) and sequencing of the tmo locus in pBS(Kan)T4MO. Restriction enzyme sites indicated in the primer name are underlined.

FIG. 8. 4-NC formation rates from NB, toluene oxidation rates, and toluene product distribution by TG1 cells expressing wild-type T4MO, TmoA variants, and TOM, and by purified T4MO isoform G103L. Position TomA3 V106 of TOM is analogous to TmoA I100 of T4MO.

FIG. 9. Apparent V (nmol/min.mg protein) and K (•M) values for T4MO and its TmoA variants towards NB and nitrophenols[a,b].

Figure 10:
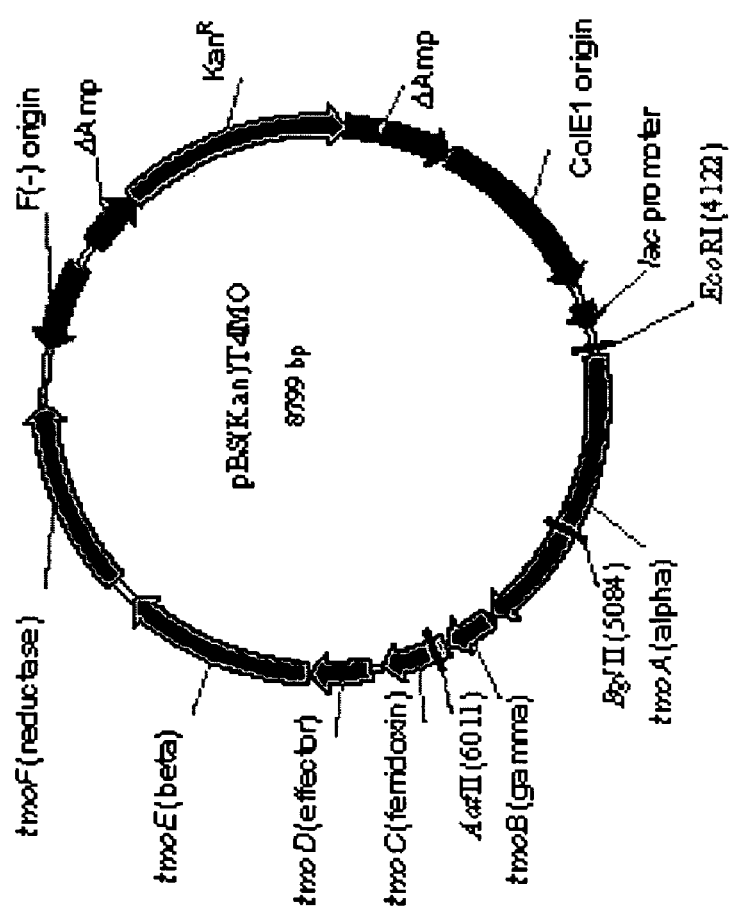

FIG. 10. Vector pBS(Kan)T4MO for constitutive expression of wild-type T4MO and mutants. KanR is the kanamycin resistance gene. The six genes coding for T4MO are tmoABE (hydroxylase A2B2E2), tmoC (ferredoxin), tmoD (effector protein), and tmoF (NADH-ferredoxin oxidoreductase).

Figure 11:
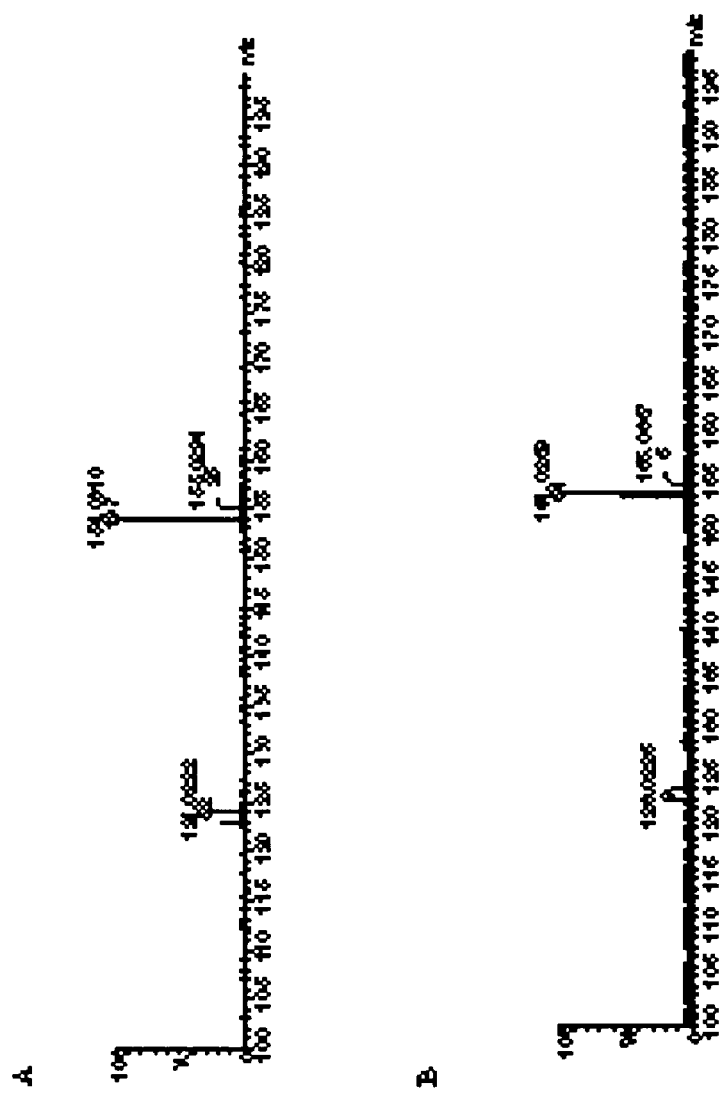

FIG. 11. LC-MS analysis of 4-NC produced from NB oxidation by TG1 expressing TmoA I100A. 4-NC standard (A) and 4-NC produced by E. coli expressing TmoA I100A (B).

Figure 12:
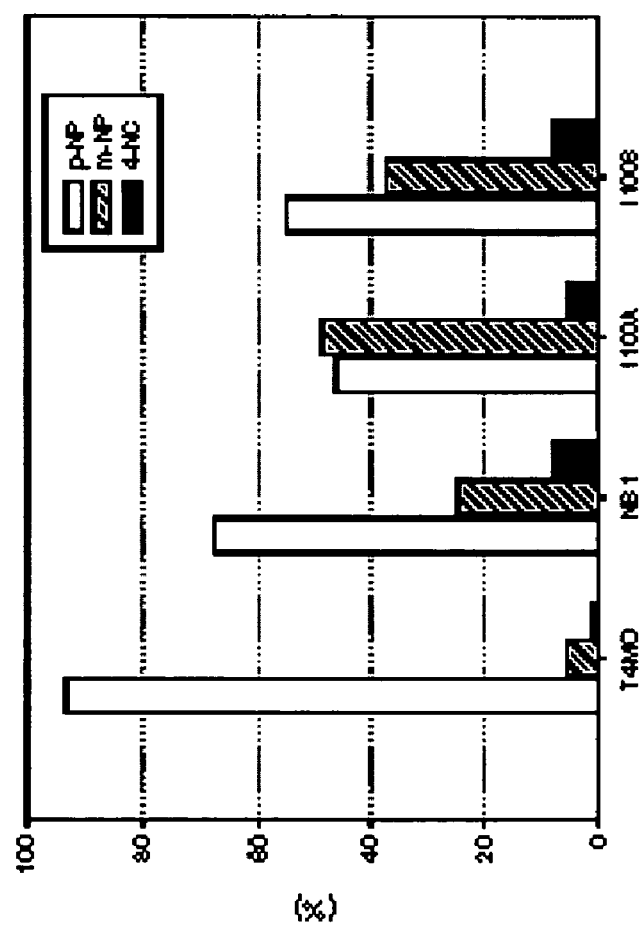

FIG. 12. Product distribution observed during oxidation of NB by TG1 cells expressing wild-type T4MO and mutants I100A, I100S, and NB1 (TmoA Y22N, I84Y, S95T, I100S, S400C; TmoB D79N). Initial NB concentration was 200 µM, and the contact period was 15 min. Results represent an average of two independent experiments FIG. 13. Primers used for saturation mutagenesis at positions I100, G103, and A107 of the alpha subunit of the T4MO hydroxylase (TmoA) and for sequencing T4MO tmoA. Restriction enzyme sites (indicated in the primer names) are underlined.

FIG. 14. Toluene oxidation rates and regiospecificity by TG1 expressing wild-type T4MO and saturation mutagenesis TmoA variants1.

FIG. 15. Cresol hydroxylation and dihydroxylated product synthesis (3-methylcatechol (3MeC), 4-methylcatechol (4MeC), and methylhydroquinone (MeH)) by E. coli TG1 expressing wild-type T4MO and saturation mutagenesis TmoA variants.

FIG. 16. 3-Methoxycatechol (3MxC), methoxyhydroquinone (MxH), and 4-methoxyresorcinol (4MxR) synthesis from o-methoxyphenol by E. coli TG1 expressing wild-type T4MO and saturation mutagenesis TmoA variants.

Figure 17:
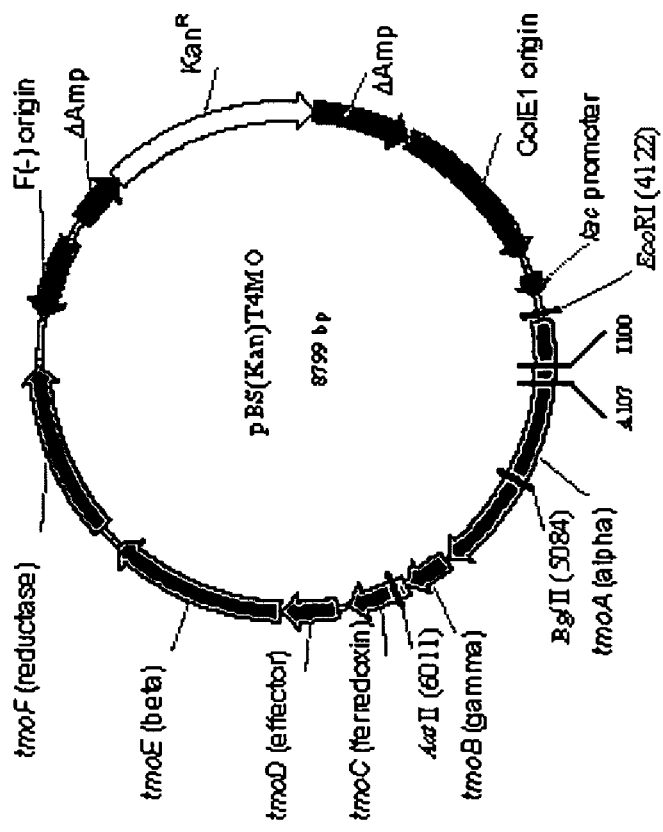

FIG. 17. Plasmid pBS(Kan)T4MO for constitutive expression of wild-type T4MO and mutants. KanR is the kanamycin resistance gene, and the relevant restriction enzyme sites EcoRI and BglII are indicated.

Figure 18:
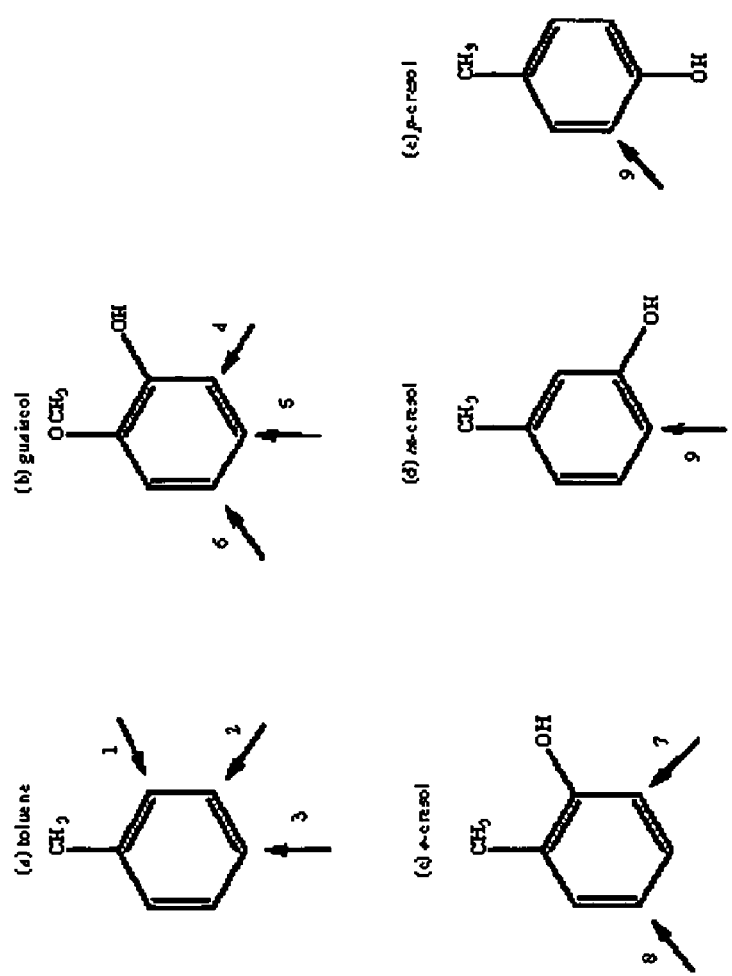

FIG. 18. Position of hydroxylation of toluene, cresols, and o-methoxyphenol by wild-type T4MO and the TmoA variants. The thick arrow indicates the site of hydroxylation. 1, o-cresol; 2, m-cresol; 3, p-cresol; 4,3-methoxycatechol; 5, 4-methoxyresorcinol; 6, methoxyhydroquinone; 7,3-methylcatechol; 8, methylhydroquinone; 9,4-methylcatechol.

FIG. 19. Primers used for constructing pBS(Kan)ToMO, for sequencing the ToMO touABCDEF locus of *P. stutzeri* OX1 in pBS(Kan)ToMO and pBZ1260, and for mutagenizing the ToMO touA locus via DNA shuffling and saturation mutagenesis at positions I100, Q141, T201, and F205.

FIG. 20. Retention times and maximum wavelengths (•max) of substrates and products used in HPLC analysis FIG. 21. Substrate utilization rates by TG1/pBS(Kan)ToMO expressing wild-type ToMO and TouA variants I100Q, F205G, and M180T/E284G.

FIG. 22. Toluene oxidation rates and regiospecificity by TG1/pBS(Kan)ToMO expressing wild-type ToMO and TouA variants I100Q, F205G, and M180T/E284G via GC. Initial toluene concentration was 91 µM based on Henry's law (250 µM if all the volatile organic was in the liquid phase).

Figure 23:
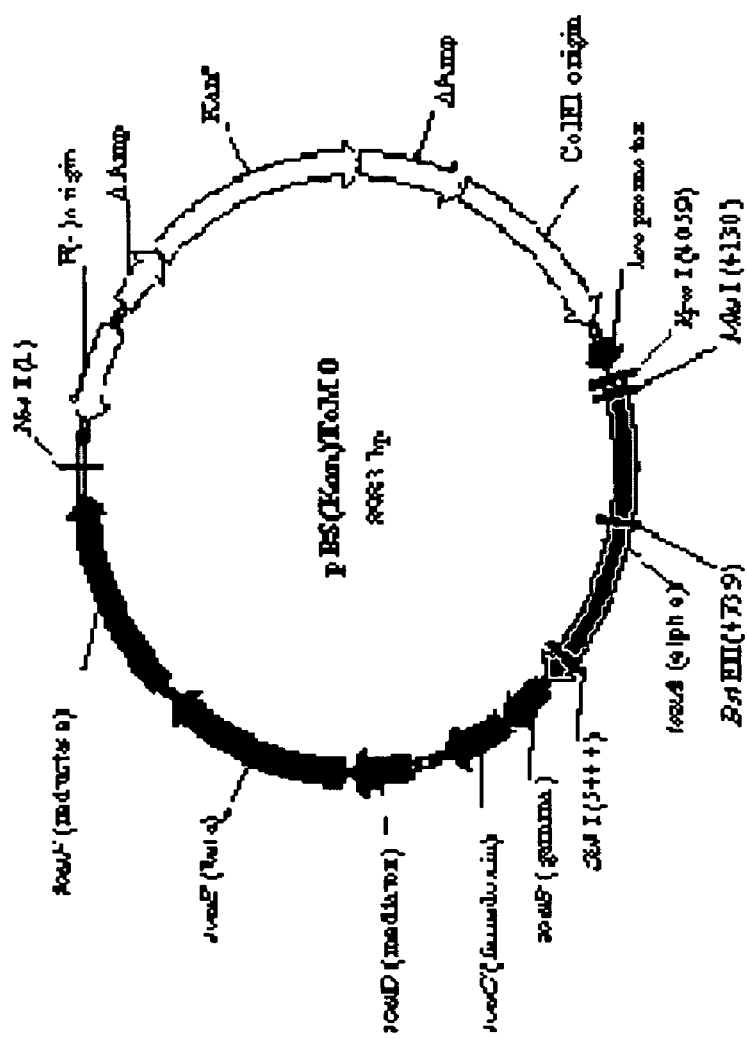

FIG. 23. Vector pBS(Kan)ToMO for constitutive expression of wild-type ToMO and mutants. KanR is the kanamycin resistance gene. The six genes coding for ToMO are touABE (three-component hydroxylase, A2B2E2), touC (ferredoxin), touD (mediating protein) and touF (NADH-ferredoxin oxidoreductase).

Figure 24:
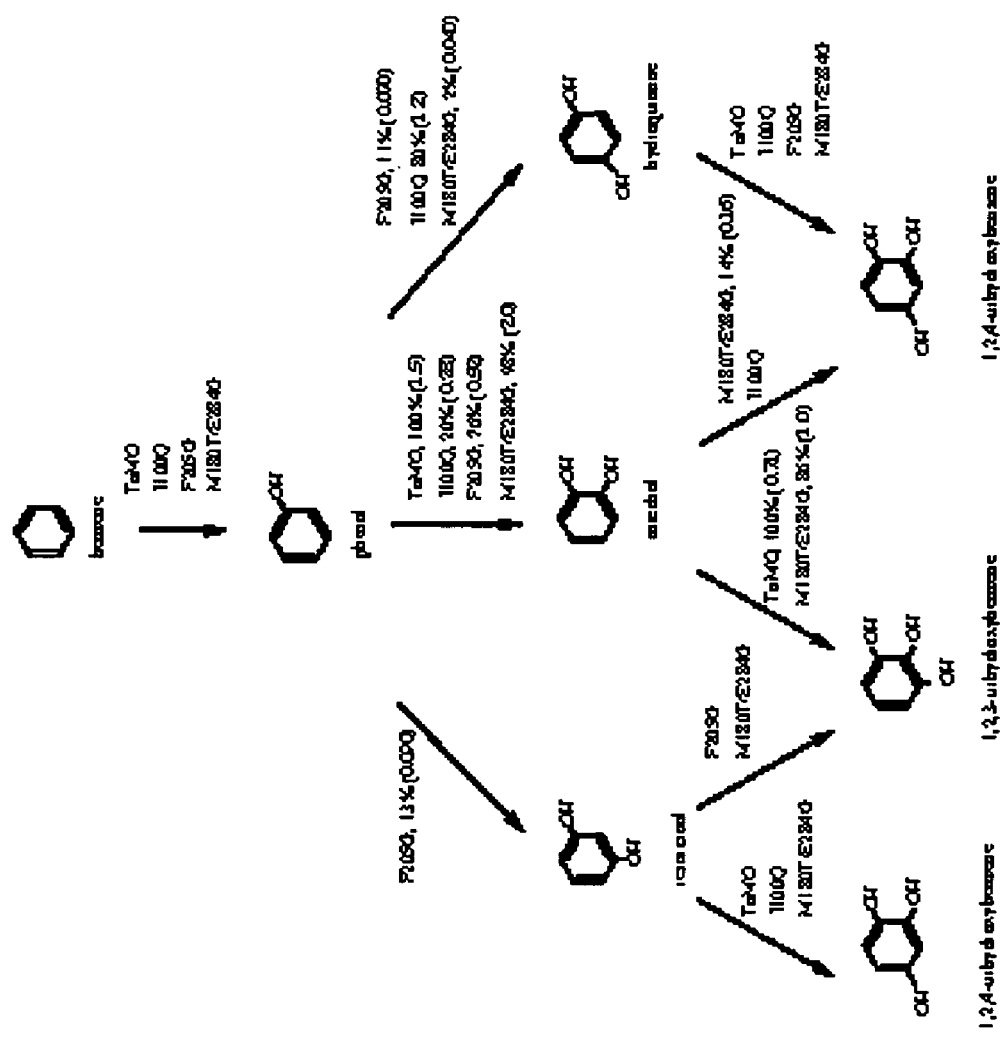

FIG. 24. Pathways for the oxidation of benzene (0.8 mM) to phenol, phenol (0.8 mM) to dihydroxy-benzenes, and dihydroxy-benzenes (0.8 mM) to trihydroxybenzenes by *E. coli* TG1/pBS(Kan)ToMO expressing wild-type ToMO and TouA variants I100Q, F205G, and M180T/E284G. Molar product percentages are shown followed by bold numbers in parenthesis, ( ), which indicate the product formation rates in nmol/min.mg protein.

Figure 25:
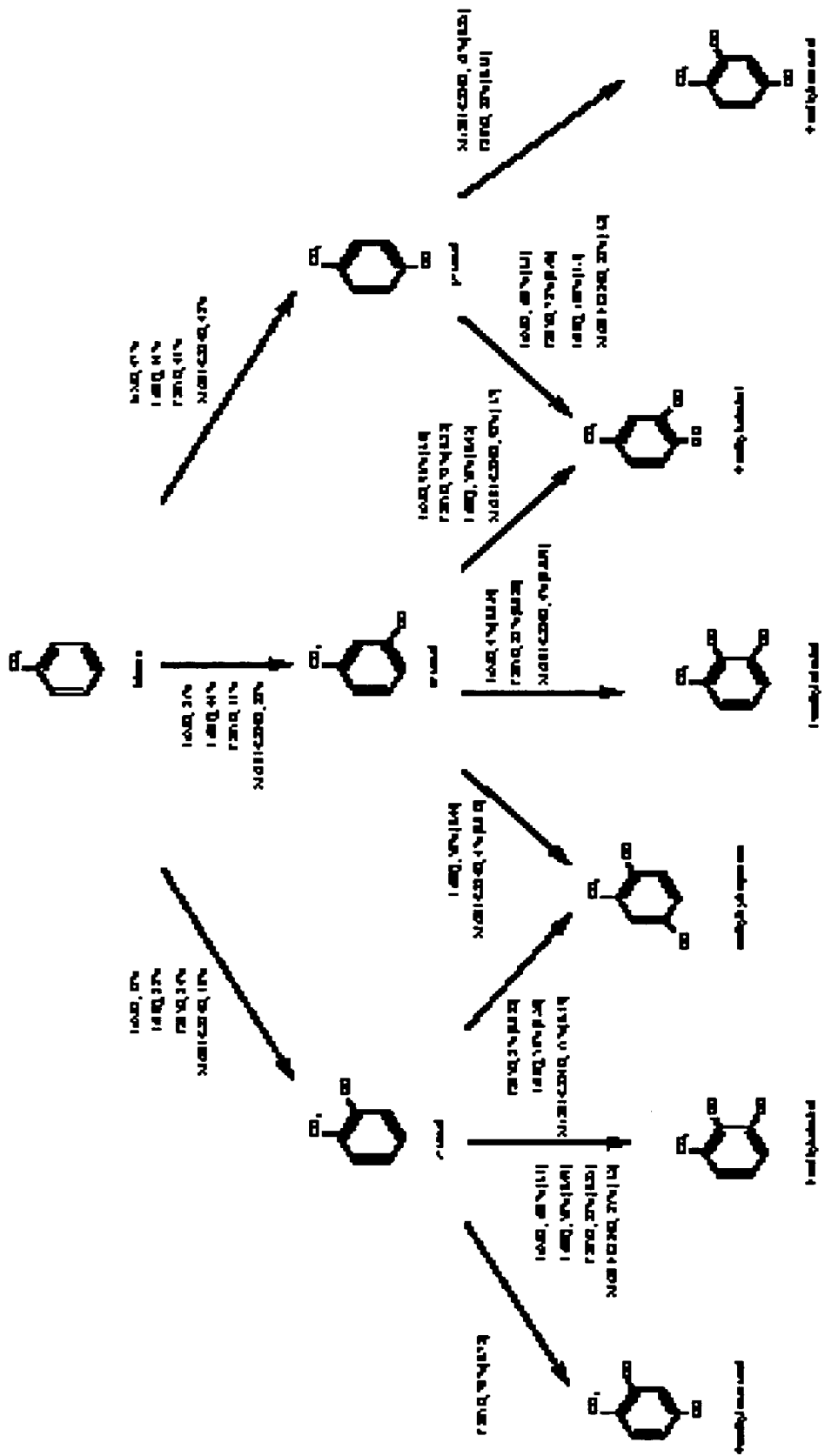

FIG. 25. Pathways for the oxidation of toluene (0.8 mM) to o-cresol, m-cresol, and p-cresol, and oxidation of o-cresol (0.8 mM), m-cresol (0.8 mM), and p-cresol (0.8 mM) to methylcatechols, methyl-resorcinols, and methylhydroquinone by *E. coli* TG1/pBS(Kan)ToMO expressing wild-type ToMO and TouA variants I100Q, F205G, and M180T/E284G. Bold numbers in parenthesis, ( ), indicate the product formation rates in nmol/min.mg protein. Molar product percentages are shown before the rate values.

FIG. 26. Primers used for cloning and sequencing of the T4MO tmoABCDEF locus of *P. mendocina* KR1 and the T3MO tbuA1UBVA2C locus of *R. pickettii* PKO1.

FIG. 27. Synthesis1 of phenol from benzene, catechol from phenol, and 1,2,3-THB from catechol by *E. coli* TG1 cells expressing wild-type T4MO, T3MO, and TOM. Initial concentration of substrates was 165 µM2.

Figure 28:
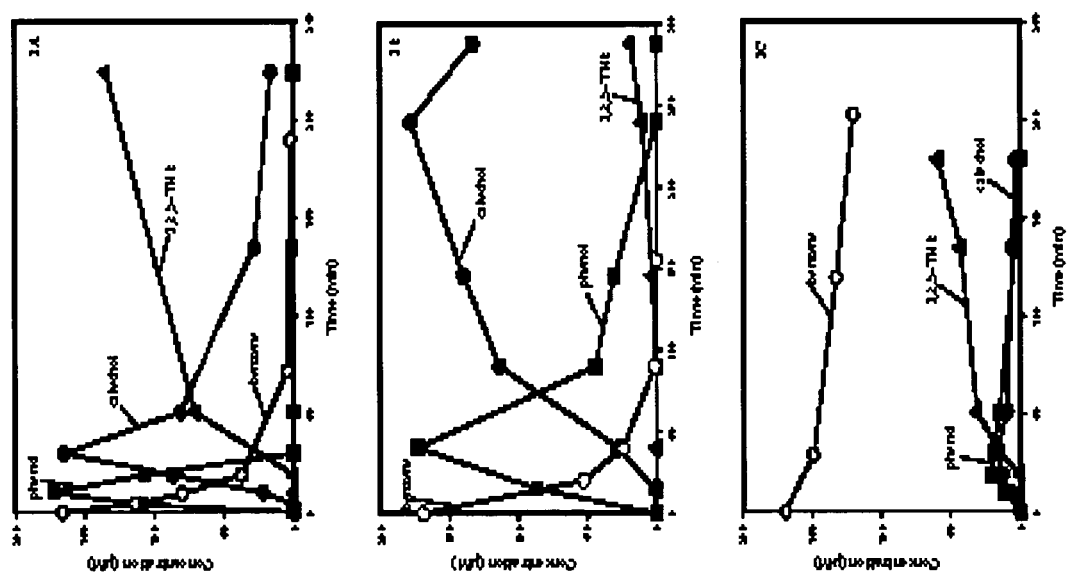

FIG. 28. Time course of hydroxylated product formation from benzene using HPLC and liquid benzene disappearance using GC by exponentially-growing TG1(T4MO) (1A), TG1(T3MO) (1B), and TG1(TOM) (1C). Symbols: •, benzene; •, phenol; •, catechol; •, 1,2,3-THB. The initial liquid benzene concentration was 165 •M (400 •M benzene was added if all in the liquid phase). Representative figures of at least two independent results are shown.

Figure 29:
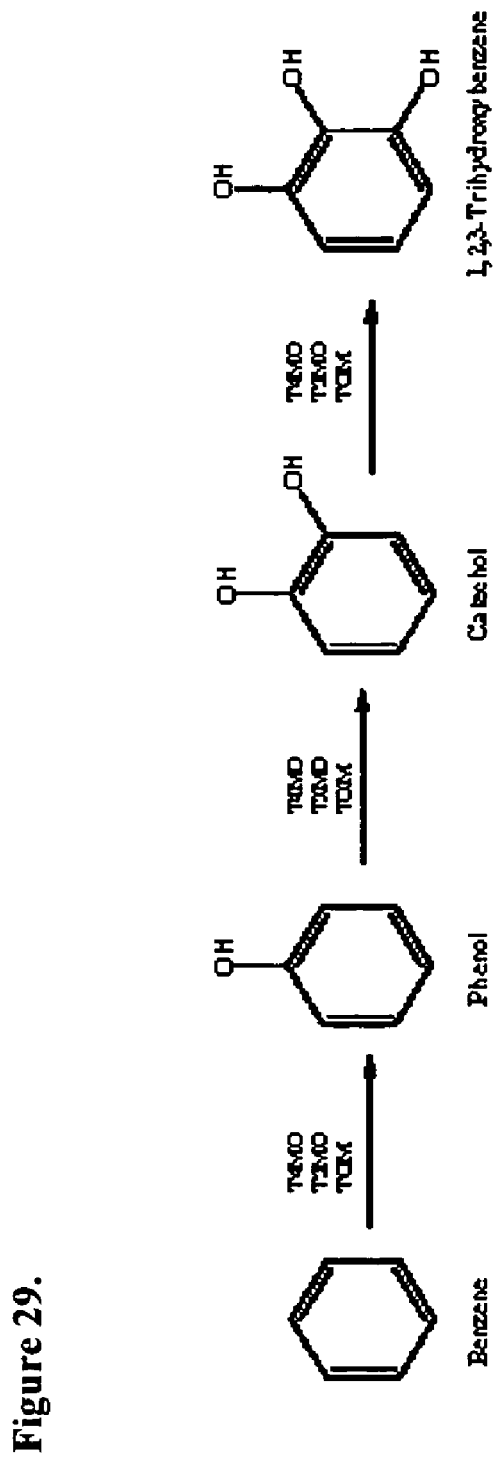

FIG. 29. Pathway for benzene oxidation by TG1(T4MO), TG1(T3MO), and TG1(TOM).

FIG. 30. Oligonucleotide primers used for saturation mutagenesis at positions N14, A113, and simultaneous V106/A113 of the TOM hydroxylase •-subunit, TomA3.

FIG. 31. Sequence changes of TOM variants with different colony colors based on visual screening. Dashes indicate no sequence change.

FIG. 32. Hydroxylation of indole by TOM variants. Dashes indicate that product not detected.

Figure 33:
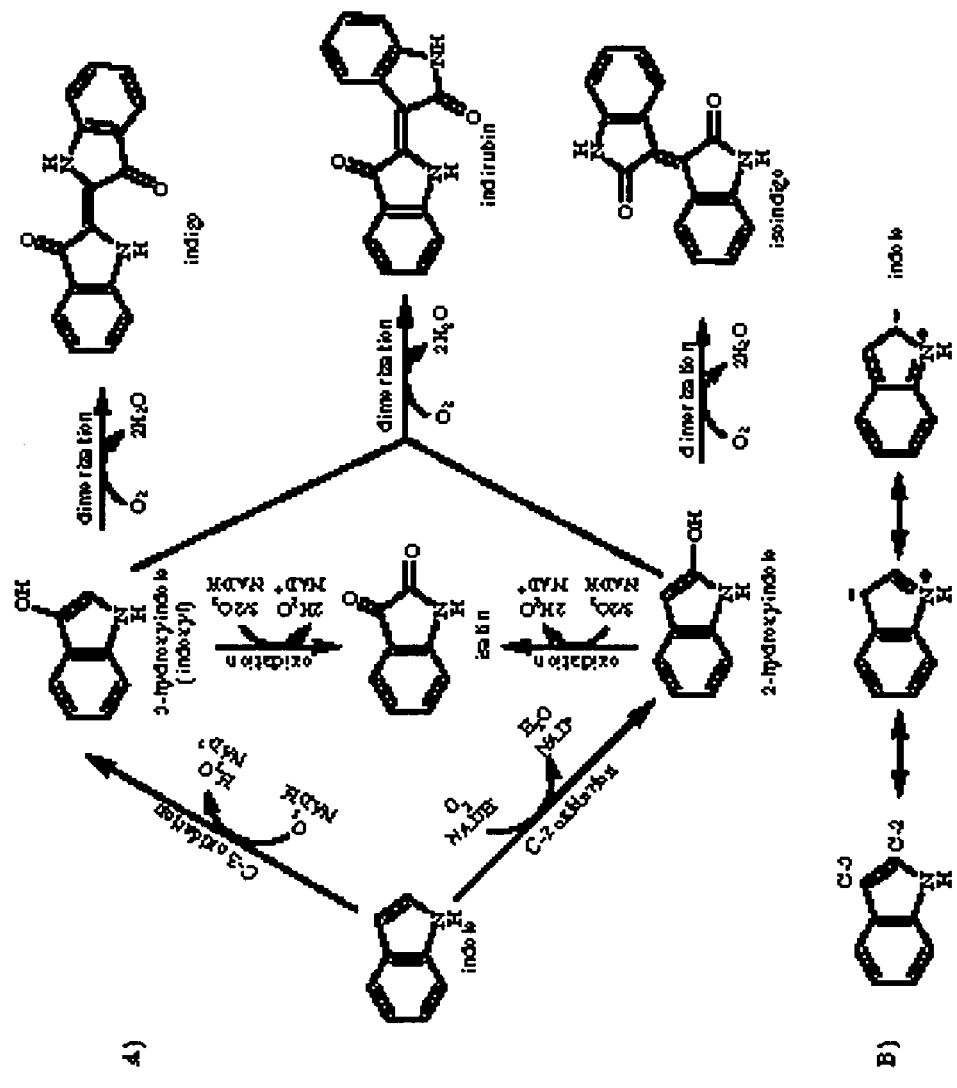

FIG. 33. Proposed pathway for converting indole to indigoid compounds (adapted from (13, 24) (A) and resonance structure of indole (50) (B).

FIG. 34. Retention times and maximum wavelengths ($•_{max}$) of substrates and products used in the HPLC analysis.

FIG. 35. Enhanced rate and altered regiospecific oxidation of NB (200 µM) by high-activity mutants of TG1/pBS(Kan)ToMO.

FIG. 36. Altered regiospecific oxidation of NB (200 µM) by low-activity mutants of TG1/pBS(Kan)ToMO.

FIG. 37. Enhanced rate and altered regiospecific oxidation of o-NP, m-NP, and p-NP by TG1/pBS(Kan)ToMO expressing wild-type ToMO and TouA variants E214G/D312N/M399V, M180T/E284G, and I100Q.

FIG. 38. Toluene oxidation rate and regiospecificity by TG1/pBS(Kan)ToMO expressing wild-type ToMO and TouA variants via GC. Initial toluene concentration was 91 µM based on Henry's law (250 µM if all the volatile organic was in the liquid phase).

FIG. 39. o-Xylene oxidation rate and regiospecificity by TG1/pBS(Kan)ToMO expressing wild-type ToMO and TouA variants I100Q, I100H, and T201G via GC. Initial o-ylene concentration was 106 µM based on Henry's law (250 µM if all the volatile organic was in the liquid phase).

DETAILED DESCRIPTION OF THE INVENTION AND THE PREFERRED EMBODIMENTS

This application claims the benefit of U.S. Provisional Application No. 60/577,254 filed Jun. 4, 2004, and is hereby incorporated by reference in its entirety.

Definitions

Unless clearly indicated to the contrary, the following definitions supplement definitions of terms known in the art.

The term "nucleic acid" refers to deoxyribonucleotides, deoxyribonucleic acids, ribonucleotides, and ribonucleic acids, and polymeric forms thereof, and includes either single- or double-stranded forms. Also, unless expressly limited, the term "nucleic acid" includes known analogues of natural nucleotides that have similar binding properties as the reference nucleic acid. In addition, a particular nucleotide or nucleic acid sequence includes conservative variations (e.g. degenerate codon substitutions; see below), complementary sequences, and the sequence explicitly indicated. A degenerate codon substitution is one in which the third position of one or more selected codons is substituted with any nucleotide which results in the same amino acid. The term nucleic acid is generic to the terms "gene," "DNA," "cDNA," "oligonucleotide," "RNA," "mRNA," "nucleotide," "polynucleotide," and the like.

"Nucleic acid template," or "parental nucleic acid" refers to a nucleic acid that has served as a template for a subsequent step or process. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

The term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

A "recombinant" nucleic acid is any nucleic acid produced by an in vitro or artifical (meaning not naturally occurring) process or by recombination of two or more nucleic acids. The recombinant MOX nucleic acids and polypeptides referred to herein are not intended to limit the scope of the present invention, which one of ordinary skill will recognize, contemplates the use of any monooxygenase gene, homologs, analogs, fragments, mutants, and combinations thereof.

The term "host cell" includes a cell might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or cells that contain a nucleic acid endogenous to the cell that has been artificially modified without removing the nucleic acid from the cell.

Nucleic acid modifications include those obtained by gene replacement, site-specific mutation, shuffling, endonuclease digestion, PCR, subcloning, and related techniques.

A "plurality of forms" of a selected nucleic acid is used to refer to a plurality of nucleic acids derived from the same parental nucleic acid, or a plurality of homologs of the nucleic acid. The homologs can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence.

If the homology between two nucleic acids is not expressly described, homology can be inferred by a nucleic acid comparison between two or more sequences. If the sequences demonstrate some degree of sequence similarity it is concluded that they share a common ancestor. The degree of similarity will vary and important factors include for example, the degree of overall similarity, the degree of similarity within specific regions of the coding sequence, the similarity of noncoding sequence, and the activity of the polypeptide. For purposes of the present invention, genes are homologous if the sequences are sufficiently similar to allow recombination.

The terms "degree of similarity" or "identity," in the context of two or more nucleic acid or polypeptide sequences, refer to two or more sequences or subsequences that are the same or homologous and have a specified percentage of amino acid residues or nucleotides that are the same, when compared and aligned for maximum correspondence, as measured using one of the sequence comparison algorithms such as Basic Local Alignment Search Tool (i.e. BLAST®), ClustalW, or other algorithms available to persons of skill or by visual inspection.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Other determinations of homology include hybridization of nucleic acids under stringent conditions. The phrase "hybridizing," refers to the binding, duplexing, or hybridizing of a molecule only to a particular nucleotide sequence under stringent conditions, including when that sequence is present in a complex mixture (e.g., total cellular) DNA or RNA.

"Conservative mutations" of a nucleic acid sequence refers to those nucleotides that encode identical or essentially identical amino acid sequences, or where the nucleotide does not encode an amino acid sequence, to essentially identical sequences. This is based on the fact that the genetic code is "degenerate," that is to say a number of distinct nucleic acids encode for the same amino acid. For instance, the codons GTT, GTA, GTC, and GTG all encode the amino acid valine. Thus, at every position where a valine is specified by a codon, the codon can be altered to any of the corresponding codons described without altering the encoded polypeptide. Such nucleic acid variations are "silent mutations," which are one species of "conservative mutation." Unless otherwise described every nucleotide sequence described herein which encodes an amino acid also includes every possible silent variation. One of ordinary skill will recognize that each codon in a nucleic acid (except AUG, which is ordinarily the only codon for methionine) can be modified to yield a functionally identical molecule by standard techniques. Accordingly, in each instance where mutagenesis is used each "silent mutation" of a nucleic acid, which encodes an amino acid, is implicitly included.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

A "subsequence" refers to a sequence of nucleic acids or amino acids that comprise a part of a longer sequence of nucleic acids or amino acids (e.g., polypeptide) respectively.

A nucleic acid "operon" includes a gene that is situated in a functional relationship with other nucleic acid sequences, for example, a promoter, an enhancer, termination signals, or another gene if it increases the transcription of the coding sequence.

"Regioselectivity" is used herein to refer to the ability to discriminate between different positions of the monooxygenase target or between two or more potential sites of action in the monooxygenase target.

"Stereoselectivity" is used herein to refer to the ability to discriminate between enantiomeric sites in the monooxygenase target.

The term "halogen" is used herein to refer to fluorine, bromine, chlorine and iodine atoms.

The term "hydroxy" is used herein to refer to an —OH moiety.

The term "amino" is used to describe primary amines, R—$NH_2$, wherein R is alkyl.

INTRODUCTION

This present invention relates to the generation of monooxygenases for use in the production of chemicals of industrial interest using any of a variety of shuffling techniques. In one embodiment, the monooxygenases are bacterially derived. In any of the preferred embodiments the bacterial source of the parental monooxygenase can be for example, *Pseudomonas* sp., for example *P. stutzeri* or *P. mendocina*; *Burkholderia* sp., for example *B. cepacia*; or *Ralstonia pickettii*.

Furthermore, in any of the preferred embodiments, the parental monooxygenase can be, for example, a toluene monooxygnease, such as for example, a toluene-o-xylene monooxygenase, a toluene-4-monooxygenase, a toluene-ortho-monooxygenase, a P450 monooxygnease, a heme-dependent peroxidase, an iron sulfur monooxygenase, a quinone-dependent monooxygenase, and the like. In one aspect of an exemplary embodiment, the current invention includes the use of mutagenesis or nucleic acid shuffling or both, to alter or evolve the physical properties of a monooxygenase enzyme, for example, the forward rate kinetics, substrate specificity, regioselectivity, stereoselectivity, or substrate affinity. Another embodiment of the present invention includes mutagenesis, DNA shuffling, or both to decrease susceptibility of monooxygenases to reversible inhibitors and inactivation by solvents, starting materials and reaction products, and intermediates generated during the catalytic cycle. In exemplary embodiments of the present invention the monooxygenase of the invention is a nucleic acid selected from the group consisting of SEQ ID NOS: 3, 5, 7, 9, 11, 13, 17, 19, 21, 23, 27, 29, 31, 33, 35, 37, 39, or a polypeptide selected from the group consisting of 4, 6, 8, 10, 12, 14, 18, 20, 22, 24, 28, 30, 32, 34, 36, 38, 40 as well as derivatives, homologs, analogs, and fragments thereof. The recombinant MOX nucleic acids and polypeptides referred to herein are not intended to limit the scope of the present invention, which one of ordinary skill will recognize, contemplates the use of any monooxygenase gene, homologs, analogs, fragments, mutants, and combinations thereof.

While a substantial portion of the discussion below applies explicitly to toluene monooxygenases, this is meant to be by way of example and illustration only. The systems, methods, processes, improvements and alterations described with reference to toluene monooxygenases are representative of techniques and chemistries that could be applied to other materials, e.g., other members of the monooxygenase family, for example, structurally and functionally related monooxygenases (FIGS. 1-6), as will be readily apparent to persons skilled in the art. FIGS. 1-6 are provided by way of example only and show the nucleic acid, and polypeptide sequence alignments of several monooxygenases, which are included in the present invention. The recombinant form of the naturally occurring monooxygenases as well as the novel recombinant variant forms are hereby encompassed as compositions in the present invention, aspects of a preferred embodiment or both. Another preferred embodiment includes a method of using the recombinant form of a naturally occurring version of a monooxygenase, or a recombinant variant form for the production of useful chemical compounds.

In one aspect, the present invention provides a method for obtaining a nucleic acid that encodes a polypeptide possessing improved or evolved monooxygenase activity. In one embodiment, the improved monooxygenase polypeptide has at least one property improved over a naturally occurring, wild-type, monooxygenase polypeptide. The method of this exemplary aspect includes the steps of: creating a library of recombinant polynucleotides or nucleic acids that encode recombinant monooxygenase polypeptides; and screening the library to identify a recombinant polynucleotide that encodes a recombinant monooxygenase polypeptide that has at least one property improved or altered over the naturally occurring, wild-type, polypeptide.

In a preferred embodiment, the nucleic acid libraries of the invention are constructed by a method that includes mutating one or more nucleotides in the gene sequence, or shuffling a plurality of parental polynucleotides or both to produce one or more recombinant monooxygenase polynucleotides encoding the polypeptides with the altered or improved properties. In another preferred embodiment, the polynucleotides are homologous.

In another embodiment, at least one of the parental or wild-type polynucleotides is selected from a group of nucleic acid molecules that encode a toluene monooxygenase activity. In another aspect of the preferred embodiment, at least one nucleic acid molecule encoding a toluene monooxygenase activity is selected along with at least another polynucleic acid that does not encode a monooxygenase activity. In another aspect of this embodiment, the present invention includes a nucleic acid sequence that will hybridize under stringent conditions to a nucleic acid sequence complementary to a nucleic acid molecule that includes a protein-coding sequence of a monooxygnease nucleic acid sequence. In an exemplary embodiment, the monooxygenase nucleic acid may be selected from the group consisting of SEQ ID NOS: 3, 5, 7, 9, 11, 13, 17, 18, 21, 23, 27, 29, 31, 33, 35, 37, and 39. Other embodiments of the present invention include an isolated nucleic acid or polypeptide that encodes a monooxygenase enzyme. In yet another of the preferred embodiments, the invention includes a nucleic acid with at least 80% identity to a nucleic acid selected from the group consisting of SEQ ID NOS: 3, 5, 7, 9, 11, 13, 17, 18, 21, 23, 27, 29, 31, 33, 35, 37, and 39. In still another embodiment, the invention includes a monooxygenase polypeptide sequence with at least 80% identity to a polypeptide selected from the group consisting of SEQ ID NOS: 4, 6, 8, 10, 12, 14, 18, 20, 22, 24, 28, 30, 32, 34, 36, 38, and 40.

In another embodiment, the system, method and process of the present disclosure provides for advantages over previous methods for the optimization of monooxygenase activity. For example, mutagenesis of selected regions or amino acids of the gene combined with the use of DNA shuffling can result in optimization of a particular property, even in the absence of a detailed understanding of the mechanism by which the particular property is mediated. In addition, entirely new properties can be obtained upon shuffling of DNAs, i.e., shuffled DNAs can encode polypeptides or RNAs with properties entirely absent in the parental polypeptides or RNAs by the DNAs that are shuffled.

The physical properties or characteristics of a monooxygenase enzyme that can be acquired, altered, improved or modified vary widely. For example, for monooxygenase genes, properties that one can acquire, alter, improve or modify include, but are not limited to, the range of monooxygenases activity; the potency against an enzymatic substrate; the regioselectivity of action against an enzymatic substrate; the chemoselectivity of action against an enzymatic substrate; the stereoselectivity of action against an enzymatic substrate; the level of expression of the monooxygenase gene; the tolerance of the protein encoded by the monooxygenase gene to protease degradation (or other natural protein or RNA degradative processes); sensitivity of enzymatic activity to physical parameters like high or low pH, heat, cold, ionic conditions; toxicity to the host cell; and resistance of the polypeptide and/or the organism expressing the polypeptide to organic solvents, reaction feedstocks, intermediates, and products. The monooxygenase gene used for modification may vary depending on the application, as do the properties sought to be acquired, altered, improved, or modified. In a preferred embodiment the candidate genes for modification using the methods described herein include genes which encode monooxygenase enzymes. In another preferred embodiment the monooxygenase genes selected include those whose substrates include aromatic hydrocarbons.

The method of a preferred embodiment of the present disclosure includes the use of at least two variants of a monooxygenase gene. The two forms may include a single variance but preferably contain at least two differences but share significant amino acid structure, domain structure or sequence homology. The two variants may be homologs from the same organism, related organisms or strains, or completely different organisms. Also, the variants may contain naturally occurring sequence differences or may be engineered to contain the sequence variations using, for example, one or more steps of site-directed mutagenesis, saturation mutagenesis, error-prone PCR, DNA shuffling, transformation of nucleic acid into a strain of bacteria impaired in mismatch repair or any combination thereof, or any like method which will be recognized by one of ordinary skill in the pertinent part.

In performing the method of an embodiment of the present invention, at least two forms of a monooxygenase encoding nucleic acid, or fragment thereof are combined to create a library of recombinant monooxygenase genes. In an exemplary embodiment, the method includes screening the resulting recombinant monooxygenase nucleic acids for those demonstrating altered, acquired, improved or modified enzymatic activity compared to the parental monooxygenase activity, and may also include cloning of the desired recombinant monooxygenase nucleic acid.

On occasion, improvements in monooxygenase activity may be observed after one round of recombination. However, the method of the invention also includes iterative rounds of mutagenesis, DNA shuffling, or both, with the same or different monooxygenase variants, in accord with the methods described herein, in order to achieve further improvements in a desired property or to bring about novel properties. Iterative rounds of mutagenesis, DNA shuffling, or both, include repeated cycles of recombination, screening, cloning or any combination thereof, to generate greater molecular diversity (i.e., directed evolution), and to result in useful or desirable monooxygenase activity.

The screening or selection method of the invention generally depends on what property or characteristic is to be altered, acquired, improved or modified. Typically, it is unnecessary to understand the structural or molecular basis for the altered activity of a recombinant nucleic acid relative to the parental nucleic acids.

Depending on the particular screening protocol used for a desired property, initial round(s) of screening can sometimes be performed using bacterial cells due to high transfection efficiencies and ease of culture. In a related embodiment, the present invention includes a host cell containing an evolved monooxygenase nucleic acid, alone or contained within a plasmid or viral vector. The host cell may be, for example, eukaryotic or prokaryotic. In a further embodiment, the invention relates to the detection of expression of a monooxygenase nucleic acid or polypeptide by a host cell. In a preferred embodiment, the invention relates to the detection of the expression of a nucleic acid or polypeptide selected from the group consisting of SEQ ID NOS: 1-40. The detection may be performed, for example, by contacting a sample with a monooxygenase probe, for example a nucleic acid probe, a small molecule, or protein, for example an antibody, and detecting whether the probe bound to a complementary molecule in the sample.

In a preferred embodiment, the invention provides an iterative method for generating a nucleic acid that encodes a specific monooxygenase activity. In this exemplary method, the parental nucleic acids are shuffled and the method further optionally includes one or more of: (a) recombining nucleic acids from at least two enzymes that display monooxygenase activity to create a library of monooxygenase nucleic acids; (b) transforming the recombinant monooxygenase genes into a competent cell; (c) screening the cells; (d) isolating the desired monooxygenase nucleic acid for further cycles of recombination with another monooxygenase nucleic acid; and (e) repeating (a) through (c) until the further recombined cells have acquired a desired monooxygenase activity. The method of this invention may also involve the construction of recombinant nucleic acids, plasmid vectors, or both, and the expression of genes in transformed host cells. The molecular cloning techniques required to achieve these goals are well known in the art.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS 1N MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47; Sakamoto, et al., Laboratory evolution of toluene dioxygenase to accept 4-picoline as a substrate. *Appl. Environ. Microbiol.* 67:3882-3887 (2001); Lueng, et al., A method for random mutagenesis of a defined DNA segment using a modified polymerase chain reaction. *Technique: J Methods Cell Molec Biol* 1(1):11-15 (1989).

Essentially any monooxygenase property can be selected in using the systems, methods and processes of the present invention. A preferred target property is the activity of the polypeptide towards a particular class of substrates. In a preferred embodiment, the monooxygenase property of interest is its ability to effect aromatic hydroxylation, for example, hydroxylation of benzenes, nitrobenzenes, toluenes, indoles, and phenols.

In another aspect, the invention provides a nucleic acid shuffling mixture comprising: at least two homologous monooxygenase nucleic acids or fragments thereof. In a preferred embodiment of such system, method or process, the at least two homologous monooxygenase nucleic acids or fragments are present in vitro or within a cell.

Exemplary methods of the present invention include performing sequence mutagenesis, recombination for example DNA shuffling, or both, and screening or selection to "evolve" individual genes, multigene clusters, operons, or genomes. In gene shuffling, a single sequence is mutated or otherwise altered and then recombined. Reiterative cycles of recombination and screening/selection can be performed to further evolve the nucleic acids of interest. Shuffling allows the recombination of large numbers of mutations in a minimum number of selection cycles. Therefore, the technique of directed evolution (steps of mutagenesis, shuffling or both in a single or multiple iterations) provides a rapid way of determining ways in which an enzyme's activity may be affected.

These techniques can be supplemented in some cases where structural and/or functional information is known or can be inferred.

The typical shuffling procedure starts with at least two nucleic acids that show substantial sequence similarity to each other, but differ at certain other positions. The difference can be any type of mutation, for example, substitutions, insertions and deletions. For recombination to generate increased diversity relative to the starting materials, the starting materials must differ from each other in at least two nucleotide positions. The starting DNA segments can be natural variants of each other, for example, allelic or species variants. The segments can also be from nonallelic genes showing some degree of structural and usually functional relatedness (e.g., different genes within a superfamily, such as the toluene monooxygenase superfamily). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example, one segment can be a subsequence of another. The segments can be present as part of larger molecules, such as vectors, or can be in isolated form.

The starting DNA segments are recombined by any of the sequence recombination formats provided herein to generate a diverse library of recombinant DNA segments. Such library can vary widely in size, e.g., from having fewer than 10 to more than $10^{12}$ or more members. In some embodiments, the starting segments and the recombinant libraries generated will include full-length coding sequences and any essential regulatory sequences, such as a promoter and polyadenylation sequences, required for expression. In other embodiments, the recombinant DNA segments in the library can be inserted into a common vector providing sequences necessary for expression before performing screening and selection.

Use of Restriction Enzyme Sites to Recombine Mutations

In some situations it is advantageous to use restriction enzyme sites in nucleic acids to direct the recombination of mutations in a nucleic acid sequence of interest. These techniques are particularly preferred in the evolution of fragments that cannot readily be shuffled by existing methods due to the presence of repeated DNA or other problematic primary sequence motifs. These situations also include recombination formats in which it is preferred to retain certain sequences unmutated. The use of restriction enzyme sites is also preferred for shuffling large fragments (typically greater than 10 kb), such as gene clusters that cannot be readily shuffled and "PCR-amplified" because of their size. Preferably, the restriction endonucleases generate nonpalindromic sticky end overhangs that allow for efficient ordered reassembly with DNA ligase. Typically, restriction enzyme (or endonuclease) sites are identified by conventional restriction enzyme mapping techniques, by analysis of sequence information for that gene, or by introduction of desired restriction sites into a nucleic acid sequence by synthesis (i.e. by incorporation of silent mutations).

The nucleic acid molecules to be digested can be from replicated DNA, such as a plasmid preparation, or from PCR amplified nucleic acid fragments that contain the restriction enzyme recognition sites of interest. In the typical situation two homologous genes are digested with at least one restriction endonuclease, and the fragments are the rejoined by using a DNA ligase enzyme to restore the full length gene having shuffled regions. The number of regions to be shuffled will vary and depend also on the number of restriction enzymes used and the number of individual restriction recognition sites for each enzyme. The shuffled molecules can be introduced into cells as described and screened or selected for a desired property as described herein. Nucleic acid can then be isolated from pools (libraries), or clones having desired properties and subjected to the same procedure until a desired degree of improvement is obtained.

In some embodiments, at least one DNA substrate molecule or fragment thereof is isolated and subjected to mutagenesis. In some embodiments, the pool or library of religated restriction fragments are subjected to mutagenesis before the digestion-ligation process is repeated. "Mutagenesis" as used herein includes such techniques known in the art as PCR mutagenesis, oligonucleotide-directed mutagenesis, site-directed mutagenesis, random mutagenesis, error-prone PCR mutagenesis, etc., and reiterative sequence recombination by any of the techniques described herein.

Reassembly PCR

A further technique for recombining mutations in a nucleic acid sequence utilizes "reassembly PCR." This method can be used to assemble multiple segments that have been separately evolved into a full length nucleic acid template such as a gene. This technique is performed when a pool of advantageous mutants is known from previous work or has been identified by screening mutants that may have been created by any mutagenesis technique known in the art, such as PCR mutagenesis, cassette mutagenesis, doped oligo mutagenesis, chemical mutagenesis, or propagation of the DNA template in vivo in mutator strains. Boundaries defining segments of a nucleic acid sequence of interest preferably lie in intergenic regions, introns, or areas of a gene not likely to have mutations of interest. Preferably, oligonucleotide primers (oligos) are synthesized for PCR amplification of segments of the nucleic acid sequence of interest, such that the sequences of the oligonucleotides overlap the junctions of two segments. Each of the segments is amplified with a set of such primers. The PCR products are then "reassembled" according to assembly protocols such as those discussed herein to assemble randomly fragmented genes. In brief, in an assembly protocol the PCR products are first purified away from the primers, by, for example, gel electrophoresis or size exclusion chromatography. Purified products are mixed together and subjected to a desired number of cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes. In some embodiments, the resulting reassembled genes are subjected to mutagenesis before the process is repeated.

In a further embodiment, the PCR primers for amplification of segments of the nucleic acid sequence of interest are used to introduce variation into the gene of interest as follows. Mutations at sites of interest in a nucleic acid sequence are identified by screening or selection, by sequencing homologues of the nucleic acid sequence, and so on. Oligonucleotide PCR primers are then synthesized which encode wild type or mutant information at sites of interest. These primers are then used in PCR mutagenesis to generate libraries of full length genes encoding permutations of wild type and mutant information at the designated positions. This technique is typically advantageous in cases where the screening or selection process is expensive, cumbersome, or impractical relative to the cost of sequencing the genes of mutants of interest and synthesizing mutagenic oligonucleotides.

Site Directed Mutagenesis (SDM) with Oligonucleotides Encoding Homologue Mutations Followed by Shuffling In some embodiments of the invention, sequence information from one or more substrate sequences is added to a given "parental" sequence of interest, with subsequent recombination between rounds of screening or selection. Typically, this is done with site-directed mutagenesis performed by techniques well known in the art (e.g., Berger, Ausubel and Sambrook, supra.) with one substrate as template and oligonucleotides encoding single or multiple mutations from other substrate sequences, e.g. homologous genes. After screening or selection for an improved phenotype of interest, the selected recombinant(s) can be further evolved using PCR techniques described herein. After screening or selection, site-directed mutagenesis can be done again with another collection of oligonucleotides encoding homologue mutations, and the above process repeated until the desired properties are obtained.

When the difference between two homologues is one or more single point mutations in a codon, degenerate oligonucleotides can be used that encode the sequences in both homologues. One oligonucleotide can include many such degenerate codons and still allow one to exhaustively search all permutations over that block of sequence.

When the homologue sequence space is very large, it can be advantageous to restrict the search to certain variants. Thus, for example, computer modeling tools can be used to model each homologue mutation onto the target protein and discard any mutations that are predicted to grossly disrupt structure and function.

In Vitro DNA Shuffling

In one exemplary embodiment for shuffling DNA sequences in vitro, the parental nucleic acids available for recombination are a pool of related sequences, e.g., different variant forms, homologs from different individuals, strains, species or related sequences from the same organism, as allelic variations or any combination thereof. The sequences can be DNA or RNA and can be of various lengths depending on the size of the gene or DNA fragment to be recombined or reassembled.

The process of denaturation, renaturation and incubation in the presence of polymerase of overlapping fragments to generate a collection of polynucleotides containing different permutations of fragments is sometimes referred to as shuffling of the nucleic acid in vitro. This cycle is repeated for a desired number of times. The resulting nucleic acids are a family of double-stranded polynucleotides. The population represents variants of the starting substrates showing substantial sequence identity thereto but also diverging at several positions. The population has many more members than the starting substrates. The population of fragments resulting from shuffling is used to transform host cells, optionally after cloning into a vector.

In an exemplary embodiment utilizing in vitro shuffling, subsequences of recombination substrates can be generated by amplifying the full-length sequences under conditions which produce a substantial fraction, typically at least ten percent (10%) or more, of incompletely extended amplification products. Another embodiment uses random primers to prime the entire template DNA to generate less than full length amplification products. The amplification products, including the incompletely extended amplification products are denatured and subjected to at least one additional cycle of reannealing and amplification. This variation, in which at least one cycle of reannealing and amplification provides a substantial fraction of incompletely extended products, is termed "stuttering." In the subsequent amplification round, the partially extended (less than full length) products reanneal to and prime extension on different sequence-related template species. In another embodiment, the conversion of substrates to fragments can be effected by partial PCR amplification of substrates.

In another embodiment, a mixture of fragments is spiked with one or more oligonucleotides. The oligonucleotides can be designed to include precharacterized mutations of a wild type sequence, or sites of natural variations between individuals or species. The oligonucleotides also include sufficient sequence or structural homology flanking such mutations or variations to allow annealing with the wild type fragments. Annealing temperatures can be adjusted depending on the length of homology.

In a further embodiment, recombination occurs in at least one cycle by template switching, such as when a DNA fragment derived from one template primes on the homologous position of a related but different template. Template switching can be induced by addition of recA, and increased by increasing the DNA template concentration.

In some exemplary embodiments of the invention, shuffled nucleic acids obtained by use of the reiterative recombination methods of the invention, are put into a cell and/or organism for screening. Shuffled monooxygenase genes can be introduced into, for example, bacterial cells, yeast cells, fungal cells vertebrate cells, invertebrate cells or plant cells for initial screening. E. coli is an example of a suitable bacterial cell into which one can insert and express shuffled monooxygenase genes which provide for convenient shuttling to other cell types. The shuffled genes can be introduced into bacterial, fungal or yeast cells either by integration into the chromosomal DNA or as plasmids.

Family Shuffling Monooxygenases

To illustrate the family shuffling approach to improving toluene monooxygenase enzymes, one or more of the members of this superfamily is selected, aligned with similar homologous sequences, and shuffled against these homologous sequences. The screening is done in a bacterial system. DNA from clones with improved activity can be shuffled together in subsequent rounds of DNA shuffling and screened for further improvement.

Codon Modification Shuffling

Codon modification procedures can be used to modify any nucleic acid described herein, e.g., prior to performing DNA shuffling, or codon modification approaches can be used in conjunction with oligonucleotide shuffling procedures as described.

In these methods, a first nucleic acid sequence encoding a first polypeptide sequence is selected. A plurality of codon altered nucleic acid sequences, each of which encode the first polypeptide, or a modified or related polypeptide, is then selected (e.g., a library of codon altered nucleic acids can be selected in a biological assay which recognizes library components or activities), and the plurality of codon-altered nucleic acid sequences is recombined to produce a target codon altered nucleic acid encoding a second protein. The target codon altered nucleic acid is then screened for a detectable functional or structural property, optionally including comparison to the properties of the first polypeptide and/or related polypeptides. The goal of such screening is to identify a polypeptide that has a structural or functional property equivalent or superior to the first polypeptide or related polypeptide. A nucleic acid encoding such a polypeptide can be used in essentially any procedure desired, including introducing the target codon altered nucleic acid into a cell, vector, virus, attenuated virus (e.g., as a component of a vaccine or immunogenic composition), transgenic organism, or the like.

Oligonucleotide and In Silico Shuffling Formats

In addition to the formats for shuffling noted above, at least two additional related formats are useful in the practice of the present invention. The first, referred to as "in silico" shuffling utilizes computer algorithms to perform "virtual" shuffling using genetic operators in a computer. As applied to the present invention, gene sequence strings are recombined in a computer system and desirable products are made, e.g., by reassembly PCR of synthetic oligonucleotides. In brief, genetic operators (algorithms which represent given genetic events such as point mutations, recombination of two strands of homologous nucleic acids, etc.) are used to model recombinational or mutational events which can occur in one or more nucleic acid, e.g., by aligning nucleic acid sequence strings (using standard alignment software, or by manual inspection and alignment) and predicting recombinational outcomes. The predicted recombinational outcomes are used to produce corresponding molecules, e.g., by oligonucleotide synthesis and reassembly PCR.

Another useful technique is known as "oligonucleotide mediated shuffling" in which oligonucleotides corresponding to a family of related homologous nucleic acids (e.g., as applied to the present invention, interspecific or allelic variants of a dioxygenase nucleic acid) are recombined to produce selectable nucleic acids. The technique can be used to recombine homologous or even non-homologous nucleic acid sequences.

One advantage of the oligonucleotide-mediated recombination is the ability to recombine homologous nucleic acids with low sequence similarity, or even non-homologous nucleic acids. In these low-homology oligonucleotide shuffling methods, one or more set of fragmented nucleic acids are recombined, e.g., with a with a set of crossover family diversity oligonucleotides. Each of these crossover oligonucleotides have a plurality of sequence diversity domains corresponding to a plurality of sequence diversity domains from homologous or non-homologous nucleic acids with low sequence similarity. The fragmented oligonucleotides, which are derived by comparison to one or more homologous or non-homologous nucleic acids, can hybridize to one or more region of the crossover oligos, facilitating recombination.

When recombining homologous nucleic acids, a group of overlapping family gene shuffling oligonucleotides (which are derived by comparison of homologous nucleic acids and synthesis of oligonucleotide fragments) are hybridized and extended (e.g., by PCR), providing a population of recombined nucleic acids, which can be selected for a desired trait or property. Typically, the set of overlapping family shuffling gene oligonucleotides include multiple oligonucleotide member types which have consensus region subsequences derived from multiple homologous target nucleic acids.

Typically, family gene shuffling oligonucleotide are provided by aligning homologous nucleic acid sequences to select conserved regions of sequence identity and regions of sequence diversity. A plurality of family gene shuffling oligonucleotides are synthesized (serially or in parallel) which correspond to at least one region of sequence diversity.

Sets of fragments, or subsets of fragments used in oligonucleotide shuffling approaches can be provided by cleaving one or more homologous nucleic acids (e.g., with a DNase), or, more commonly, by synthesizing a set of oligonucleotides corresponding to a plurality of regions of at least one nucleic acid (typically oligonucleotides corresponding to a full-length nucleic acid are provided as members of a set of nucleic acid fragments). In the shuffling procedures herein, these cleavage fragments (e.g., fragments of monooxygenases) can be used in conjunction with family gene shuffling oligonucleotides, e.g., in one or more recombination reaction to produce recombinant monooxygenase nucleic acids.

Chimeric Shuffling Templates

Nucleic acids encoding chimeric polypeptide can be used as substrates for shuffling in any of the above-described shuffling techniques. Nucleic acids encoding chimeras prepared by methods known to those in the art are encompassed herein. Thus, in another embodiment, the invention provides a chimeric monooxygenase polynucleotide shuffling template. Preferred templates are derived from the toluene monooxygenase superfamily.

In another aspect, the invention provides a method of obtaining a polynucleotide that encodes a recombinant toluene monooxygenase polypeptide comprising a backbone domain and an active site domain. The method involves: (a) recombining at least first and second forms of a nucleic acid that encodes a toluene monooxygenase active site domain, wherein the first and second forms differ from each other in two or more nucleotides to produce a library of recombinant active site domain encoding polynucleotides; and (b) linking the recombinant active site domain-encoding polynucleotide to a backbone-encoding polynucleotide so that the active site-encoding domain and the backbone-encoding domain are in-frame.

In yet another aspect, the invention provides a method for obtaining a polynucleotide that encodes a recombinant toluene monooxygenase polypeptide comprising a backbone domain and an active site domain. The exemplary method involves: (a) recombining at least first and second forms of a nucleic acid that encodes a toluene monooxygenase backbone domain, wherein the first and second forms differ from each other in two or more nucleotides to produce a library of recombinant backbone domain encoding polynucleotides; and (b) linking the recombinant backbone domain-encoding polynucleotide to a active site-encoding polynucleotide so that the backbone-encoding domain and the active site-encoding domain are in-frame.

In a still further aspect, the invention provides a method of obtaining a polynucleotide that encodes a recombinant toluene monooxygenase polypeptide comprising a backbone domain and an active site domain. The exemplary method involves: (a) recombining at least first and second forms of a nucleic acid that encodes a toluene monooxygenase active site domain, wherein the first and second forms differ from each other in two or more nucleotides to produce a library of recombinant active site domain encoding polynucleotides; (b) recombining at least first and second forms of a nucleic acid that encodes a toluene monooxygenase backbone domain, wherein the first and second forms differ from each other in two or more nucleotides to produce a library of recombinant backbone domain encoding polynucleotides; and (c) linking the recombinant active site domain-encoding polynucleotide to the recombinant backbone-encoding polynucleotide so that the recombinant active site-encoding domain and the recombinant backbone-encoding domain are in-frame.

Chimeric monooxygenases having optimized activities towards any of the substrates described herein can be obtained. The creation of an improved nucleic acid with one activity may start from a previously improved chimeric nucleic acid encoding a different activity. This iterative effect leads to rapid improvement of the monooxygenase nucleic acid for any and all of the desired properties. This process also allows for improvements in stability, expression level or both of polypeptides with monooxygenase activity. Another advantage of this process is the ability to create improved nucleic acids for a particular activity without isolation of the nucleic acid encoding that activity.

In a preferred embodiment, the present invention provides monooxygenase nucleic acids and fragments thereof produced according to these disclosed methods, and also provides for organisms that express the nucleic acids produced by the exemplary methods of the invention. The organisms of the invention can thus express one or more of the wild-type or improved monooxygenase polypeptides.

Also provided by the present invention are methods of synthesizing a desired useful chemical compound. This method includes contacting an appropriate chemical substrate with a polypeptide of the invention. In one preferred embodiment a chemical substrate is contacted with an organism of the present invention which expresses one or more monooxygenase nucleic acids of the invention.

Another exemplary embodiment of the present invention includes a method for rapid screening, detection, and selection of recombinants using for example a matrix for growing cells containing the recombinant polynucleic acids. In one aspect of this embodiment, the matrix contains components which limit, prevent, or promote growth or detection or cells expressing the recombinant nucleic acids. Another aspect of this embodiment is a method for subsequent analysis of the production of chemical intermediates by monooxygenase enzymes. For example, in one aspect of this embodiment, high performance liquid chromatography (HPLC), gas chromatography (GC), UV/vis spectroscopy, IR spectroscopy or mass spectrometry (MS) or any combination thereof, can be used to monitor the presence and rate of formation of products of monooxygenase oxidation. The consumption of molecular oxygen by the monooxygenase can be measured using an oxygen sensing system, such as an electrode. In a high-throughput modality, the method of choice is high-throughput MS, or MS with an electron spray-based detection method. Knowledge of the various methods, and configurations of use for HPLC, GC, or MS is common to one of ordinary skill.

Gene shuffling offers a means of generating new monooxygenase polypeptides with altered selectivity, activity or stability. Whereas certain chemical intermediates are costly to produce in industrial chemistry, biological systems offer the potential to generate low-cost, high-volume commodity chemicals.

A number of analytical techniques are useful in practicing the present invention. These analytical techniques are used to measure the extent of conversion of a particular substrate to product, and the chemoselectivity, regioselectivity, enantiomeric selectivity or any combination thereof of a particular reaction catalyzed by a polypeptide of the invention. These techniques are also used to determine the effect of nucleic acid shuffling experiments on the efficiency and selectivity of the polypeptides produced following the shuffling. The analytical techniques discussed are given by way of example, and are broadly applicable to other aspects of the invention, and the utility of the methods are not limited to the techniques disclosed herein.

Although it will be apparent to those of skill in the art that many screening methods can be used in conjunction with the present invention, the invention provides a screening process comprising: (a) introducing a library of recombinant monooxygenase nucleic acids or fragments thereof into a population of test organisms such that the recombinant nucleic acids are expressed; (b) disposing the organisms in a medium which comprises at least one chemical substrate; (c) screening for those organisms that exhibiting a modified or altered property compared to organisms without the recombinant monooxygenase nucleic acid or fragments thereof, and (d) selecting for the organisms which display the modified or altered property.

In another embodiment, the present invention includes a method for selecting for recombinant monooxygenase nucleic acids that confer resistance to an organism to concentrations of organic solvents. This is accomplished by transforming a library of recombinant monooxygenase nucleic acids into a population of organisms and subjecting the organisms to growth on a medium containing a particular concentration of hydrophobic compounds of interest, for example aromatic hydrocarbons, for example, benzene, toluene, phenol, cresol, catechols, resorcinols, and the like. In one aspect of this embodiment, the method includes a screening strategy to identify the recombinant nucleic acids conferring resistance to the compound by calorimetric assay, creation of radiolabeled by product, or other means that will be known to those of ordinary skill in the art. In yet another embodiment, to create further improvement in solvent resistance the recombinant nucleic acid can be subjected to a series of iterative cycles of mutagenesis, DNA shuffling, or both.

General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984).

In another embodiment of the method of the present invention, the recombinant polypeptides can be immobilized on a matrix or membrane, or contained in a cell extract or lysate, or organisms expressing the recombinant polypeptides can be immobilized or in the form of a suspension. Methods of immobilizing polypeptides and cells are well known in the art and include such techniques as attachment to affinity columns, polyacrylamide gel electrophoresis, and protein affinity membranes. In a presently preferred embodiment, the polypeptide and/or cell is immobilized onto nylon membrane as described in Vardar and Wood (2004).

Cell suspensions may be prepared by culturing the organisms in a volume of suitable sterile nutrient broth, or on a solid or semi-solid matrix at a suitable temperature, and pH (preferably from about 10° C. to about 40° C.; and at a pH of about 2 to about 10). The organisms are typically grown to a particular optical density (indicating log-phase growth), harvested by centrifugation, and either resuspended in a smaller volume or cellular lysate is prepared by disrupting the cells. Methods to break up cells include, for example, mechanical disruption, physical disruption, chemical disruption, and enzymatic disruption, and include ultrasonic treatments, French press, nitrogen gas, homogenizer, grindings with quartz sand, autolysis, heating, osmotic shock, alkali treatment, detergents, or repeated freezing and thawing. For measuring the production of useful chemical intermediates the chemical substrate is added to the cell suspension, or cellular lysate and the oxidation reaction according to the invention is carried out under the conditions described below.

In addition to the methods discussed above, the present invention provides a range of methods for preparing useful organic compounds by the oxidation and further elaboration of appropriate precursors. Among the methods provided by the present invention are, for example, the oxidation of aromatic hydrocarbon compounds.

The reaction types and sequences set forth below are illustrative of the scope of the invention. The monooxygenases of the invention are capable of oxidizing any organic substrate comprising an oxidizable moiety. Additional reaction sequences utilizing the polypeptides of the invention will be apparent to those of skill in the art.

In yet another preferred embodiment, the invention provides a method for altering or controlling the regiospecificity of the oxidation reaction. An exemplary method includes contacting the chemical precursor with a microorganism comprising an improved polypeptide having a monooxygenase activity. The polypeptide can be a naturally occurring polypeptide, or it can be improved using the method of the invention.

Also disclosed according to the present invention is a kit or system utilizing any one of the selection strategies, materials, components, methods or substrates hereinbefore described. Exemplary kits according to the present disclosure will optionally additionally include instructions for performing methods or assays, packaging materials, one or more containers which contain assay, device or system components, or the like.

In an additional aspect, the present invention provides kits embodying the methods and apparatus herein. Kits of the invention optionally include one or more of the following: (1) a shuffled component as described herein; (2) instructions for practicing the methods described herein, and/or for operating the selection procedure herein; (3) one or more monooxygenase assay component; (4) a container for holding monooxygenase nucleic acids or polypeptides, other nucleic acids, transgenic plants, animals, cells, or the like and, (5) packaging materials.

In another preferred embodiment, the kit provides a library of improved toluene monooxygenases, that have been produced by shuffling for improved stability, ease of handling, etc. In a further embodiment, the present invention provides for the use of any component or kit herein, for the practice of any method or assay herein, and/or for the use of any apparatus or kit to practice any assay or method herein.

In yet another embodiment, the kit of the invention includes one or more improved monooxygenase polypeptides of the invention. In a preferred embodiment, the kit includes a library of improved monooxygenase polypeptides.

It is understood that the examples and embodiments described herein are for illustrative purposes only and that various modifications or changes in light thereof will be suggested to persons skilled in the art and are included within the spirit and purview of this application and are considered within the scope of the appended claims. All publications, patents, and patent applications cited herein are hereby incorporated by reference in their entirety for all purposes.

EXAMPLES OF PREFERRED EMBODIMENTS

Examples of the reactions of altered monooxygenases are summarized in the following examples of the preferred embodiments of the present invention. As will be understood by one of ordinary skill in the art the techniques described and hereby incorporated into the present invention are generally applicable and may be varied in any number of ways without departing from the general scope of the invention. Also, the following detailed examples are given by way of example of the preferred embodiments, and are in no way considered to be limiting to the invention.

Example #1

Directed Evolution of Toluene-4-Monooxygenase of *Pseudomonas mendocina* KR1 for the Production of 4-Nitrocatechol from Nitrobenzene Detailed Methods.

Chemicals. NB was purchased from Fisher Scientific Co. (Fairlawn, N.J.) and 4-NC, p-cresol, and o-, m-, and p-nitrophenol were obtained from Acros Organics (Morris Plains, N.J.). o-Cresol and m-cresol were obtained from Aldrich Chemical Co. (Milwaukee, Wis.). All materials used were of the highest purity available and were used without further purification.

Bacterial strains and growth conditions. *Escherichia coli* strain TG1 (supE hsd.5 thi .(lac-proAB) F.[traD36 proAB+ lacI q lacZ.M15]) (Sambrook et al. 1989) was utilized as the host for gene cloning and 15 expression. TG1 was routinely cultivated at 37° C. in Luria-Bertani (LB) medium (Sambrook et al. 1989) with kanamycin (100 •g/mL) added to maintain the vector pBS(Kan)T4MO (Tao et al. 2004) which expresses the tmoABCDEF genes from a constitutive lac promoter and which avoids feeder colonies due to the kanamycin resistance marker (FIG. 10). Expression of wild-type T4MO from pBS(Kan)T4MO within *E. coli* strains produced blue-colored cells on agar plates and in broth cultures. The blue color is indicative of indigo, formed by oxidation of indole from tryptophan (Eaton and Chapman 1995).

Protein analysis and plasmid manipulation. The Total Protein Kit (Sigma Chemical Co.) was used to determine the total cellular protein of *E. coli* TG1 pBS(Kan)T4MO (henceforth TG1(T4MO)) for calculation of whole-cell specific activities. Cellular protein samples of cell grown with and without 1 mM isopropyl •-D-thiogalactopyranoside were analyzed on standard 12% Laemmli discontinuous sodium dodecyl sulfate (SDS)-polyacrylamide gels (Sambrook et al. 1989). Plasmid DNA was isolated using a Midi or Mini Kit (Qiagen, Inc., Chatsworth, Calif.), and DNA fragments were isolated from agarose gels using the GeneClean III Kit (Bio 101, Vista, Calif.). *E. coli* strains were transformed by electroporation using a Bio-Rad GenePulser/Pulse Controller (Hercules, Calif.) at 15 kV/cm, 25 µF, and 200•.

Random mutagenesis. The tmoAB genes, • and • hydroxylase subunits, respectively, and 20% of tmoC 5 gene (1936 bp) in pBS(Kan)T4MO were amplified using error-prone PCR (ep-PCR) (Leung et al. 1989). A 100 •L reaction contained 10 mM Tris-HCl (pH 8.3), 50 mM KCl, 0.001% gelatin, 6 mM MgCl2, 0.35 mM MnCl2, 1 M Betaine, 80 ng of template DNA, 0.2 mM dATP and dGTP, 1 mM dCTP and dTTP, 5U Taq DNA polymerase (Promega, Madison, Wis.), and 30 pmole of each primer (T4MOEcoRIFront and T4MOABrear, FIG. 7). The T4MOEcoRIFront primer contains an EcoRI restriction site located upstream of the tmoA gene (FIG. 10), and T4MOABrear is downstream of the naturally-occurring AatII site within the tmoC gene. A PCR program of 30 cycles of 94° C. for 1 min, 52° C. for 1 min, and 72° C. for 2.5 min, with a final extension of 72° C. for 7 min, was used in a Perkin Elmer PCR system 2400 (Perkin Elmer, Norwalk, Conn.). The resulting randomized PCR product was cloned into pBS (Kan)T4MO after double digestion with AatII and EcoRI (New England Biolabs, Beverly, Mass.), replacing the corresponding fragment in the original plasmid. The resulting plasmid library was transformed into *E. coli* TG1 competent cells via electroporation.

Saturation mutagenesis. A gene library encoding all possible amino acids at position 100 of T4MO tmoA in pBS(Kan)T4MO was constructed by replacing the target codon with NNN via overlap-extension polymerase chain reaction (PCR) (Sakamoto et al. 2001). Two primers, T4MO100Front and T4MO100Rear (FIG. 7) were designed to randomize position 100 of TmoA. Two additional primers for cloning were T4MOEcoRIFront and T4MOBglIIRear (FIG. 7) which encode the EcoRI and BglII restriction enzyme sites; the BglII site occurs naturally downstream from TmoA position 100 and the EcoRI site is upstream of tmoA in the multiple cloning site (FIG. 10). Pfu DNA polymerase (Stratagene, La Jolla, Calif.) was used in the PCR to minimize random point mutations, and pBS(Kan)T4MO was used as the template. The first 366 nucleotide degenerate fragment was amplified by PCR using primers T4MOEcoRIFront and T4MO100Rear, and the second degenerate fragment of 663 nucleotides was amplified by PCR using primers T4MO100Front and T4MOBglIIRear. After purifying from agarose gels, the two fragments were combined at a 1:1 ratio as templates to obtain the full-length degenerate PCR product (981 bp) using T4MOEcoRIFront and T4MOBglIIRear as primers. A PCR program of 30 cycles of 94° C. for 1 min, 55° C. for 1 min, and 72° C. for 2 min, with a final extension of 72° C. for 7 min was used. The resulting PCR product containing randomized nucleotides at TmoA position 100 was cloned into pBS(Kan)T4MO after double digestion with EcoRI and BglII, replacing the corresponding fragment in the original plasmid. The resulting plasmid library was transformed into E. coli TG1 competent cells via electroporation.

Screening method. High-activity mutants were screened based on the instability of the T4MO reaction products. At neutral pH, the catechol derivatives formed from NB autoxidize to quinones and semiquinones which readily polymerize and form a red or brown color (Meyer et al. 2002). To enable screening of several substrates after transformation, E. coli TG1 colonies were transferred using sterile toothpicks to 3-4 agar plates containing LB medium supplemented with 100 •g/mL kanamycin and 1% w/v glucose. Each plate contained 50 transformants, a negative control (E. coli TG1 pBS (Kan)) and the wild-type enzyme TG1(T4MO). Following overnight incubation at 37° C., the colonies were transferred to LB plates containing 100 •g/mL kanamycin and 1 mM of the desired substrate (the substrate was added to the LB medium from a 500 mM stock solution in ethanol) using a nylon membrane (0.45 micron, Fisher Scientific co., Fairlawn, N.J.) which lifted the colonies from the glucose plate and then transferred them to the substrate plate with the cells facing away from the agar. The substrate plates were then incubated at room temperature for 18-48 hours. A red or brown halo was formed around transformants producing catechol derivatives from the incorporated substrate. The positive red colonies were re-screened using more cell mass to verify the results.

Enzymatic activity. Experiments were conducted using exponential-phase cultures obtained by diluting overnight cells to an optical density at 600 nm (OD) of 0.1 to 0.2 and growing to an OD of 1.2. The exponentially-growing cells were centrifuged at 13,000×g for 8 min at 25° C. in a Beckman J2-HS centrifuge (Palo Alto, Calif.). The collected cells were washed once in Tris-nitrite buffer (50 mM, pH 7) to remove residual broth and then resuspended in the same buffer. Two mL of concentrated cell suspensions (OD of 2-5) were contacted with substrate concentrations of 25-300 •M (from a 50 mM stock solution in ethanol) in 15-mL serum vials sealed with a Teflon-coated septum and aluminum crimp seal. The specific initial reaction rate was constant over this range of cell biomass. The negative controls used in these experiments contained the same monooxygenase without substrates (plus solvent) as well as TG1pBS(Kan) with substrates (no monooxygenase control). The inverted vials were shaken at room temperature at 300 rpm on an IKA-Vibrax-VXR shaker (Cincinnati, Ohio) for 2.5-30 min, then one mL of the cell suspension was removed and centrifuged in a 16M Labnet Spectrafuge (Edison, N.J.) for 1-2 min. The supernatant was filtered and analyzed by high-pressure liquid chromatography (HPLC). For toluene oxidation, the cells were prepared in the same way, but phosphate buffer (50 mM, pH 7) was used for washing and resuspending the cells. The serum vials containing exponentially-grown cells at a final OD of 5-10 were sealed and then 250 •M toluene was added with a syringe, calculated as if all the toluene is in the liquid phase (actual initial liquid concentration was 90 •M based on Henry's law (Dolfing et al. 1993)). The reaction was stopped by adding 1 mL of 500 •M hexadecane in ethyl acetate to the vial with a syringe, and the vial was vortexed thoroughly to ensure full extraction of the toluene. The organic phase was separated from the aqueous phase by centrifugation, and 2-3 •L were injected to the gas chromatograph (GC) column. At least two independent experiments were performed to characterize each strain with each substrate described in this paper.

Analytical methods. Oxidation of NB and nitrophenols was measured using reverse-phase HPLC. Filtered samples were injected into a Zorbax SB-C8 column (Agilent Technologies, 5 µm, 4.6×250 mm) with a Waters Corporation (Milford, Mass.) solvent delivery system coupled to a photodiode array detector (Waters 996). The gradient elution was performed with $H_2O$ (0.1% formic acid) and acetonitrile (70:30 0-8 min, 40:60 15 min, 70:30 20 min) as the mobile phase at a flow rate of 1 mL/min. Compounds were identified by comparison of retention times and UV-visible spectra to those of authentic standards as well as by co-elution with standards. The identity of 4-nitrocatechol was confirmed by reverse-phase liquid chromatography-mass spectrometry (LC-MS) using a Hewlett-Packard (Palo Alto, Calif.) 1090 series II Liquid Chromatograph with a diode array detector coupled to a Micromass Q-TOF2 (Beverly, Mass.) mass spectrometer. Separation was achieved using a Zorbax SB-C18 column (3 µm, 2.1×150 mm) with a mobile phase consisting of $H_2O$ (0.1% formic acid) and acetonitrile and a gradient elution at 0.3 mL/min starting from 100% $H_2O$ (0.1% formic acid) to 0% in 12 minutes, with a 3 minute hold at the final composition. The Q-TOF2 was operated in negative ion electrospray mode with 3.0 kV applied to the inlet capillary and 75V applied to the extraction cone. Toluene oxidation by TG1 (T4MO) variants was measured by GC using a Hewlett-Packard 6890N gas chromatograph equipped with an EC-WAX capillary column (30 m×0.25 mm, 0.25 •m thickness; Alltech Associates, Inc., Deerfield, Ill.) and a flame ionization detector. The injector and detector were maintained at 250° C. and 275° C. respectively, and a split ratio of 3:1 was used. The He carrier gas flow rate was maintained at 0.8 mL/min. The temperature program was 80° C. for 5 min; 80° C.-205° C. at a rate of 5° C./min, 205° C.-280° C. at 15° C./min, and 280° C. for 5 min. Under these conditions, the retention times for toluene, o-, p-, and m-cresols were 4.2, 27.5, 29.2, 29.4 min, respectively. Hexadecane was used as an internal standard. Retention times were determined by comparisons to neat standards as well as by co-elution with standards.

DNA sequencing. A dideoxy chain termination technique (Sanger et al. 1977) with the ABI. Prism BigDye Terminator Cycle Sequencing Ready Reaction Kit (PerkinElmer, Wellesley, Mass.) and PE Biosystems ABI. 373 DNA sequencer (PerkinElmer, Wellesley, Mass.) was used to determine the nucleotide sequence of TG1(T4MO) mutants. Four primers were generated from the wild-type T4MO sequence (GenBank M65106 (Yen et al. 1991) and M95045 (Yen and Karl 1992)) for sequencing a total of 2 kb including the tmoAB genes and 20% of tmoC gene: T4MOEcoRIFront, T4MO-1, T4MO-2, and T4MO-3 (FIG. 7). For determining the sequence of the saturation mutagenesis mutants, only the T4MOEcoRIFront primer was used. Sequence data generated were analyzed using the Vector NTI software (InfoxMax, Inc., Bethesda, Md.).

Homology structure modeling of TmoA. Residues TmoA 44-240 of the wild-type T4MO •-subunit were modeled into the known three-dimensional structure of soluble methane monooxygenase (sMMO) hydroxylase from *Methylococcus Capsulatus* (Bath) (Rosenzweig et al. 1997) (PDB accession code 1MTY) using SWISS-MODEL Server (Guex and Peitsch 1997; Peitsch 1993; Schwede et al. 2003). The molecular visualization program, Swiss-PdbViewer, was utilized to visualize and manipulate the molecular model, including performing amino acid substitutions isosterically at TmoA I100 based on residue interactions, steric hindrance, and energy minimization.

Results

Toluene Degradation.

Mutant E4 showed relatively weak red color on NB plates and therefore was not further characterized. TG1(T4MO) and its mutants NB1, TmoA I100A, and TmoA I100S were evaluated for their ability to degrade toluene, the natural substrate of this enzyme. Toluene transformation was performed using whole cell catalysis with about 90 •M of substrate. The two single-mutation variants degrade toluene faster than wild-type T4MO by about 50-65%, whereas the epPCR mutant, NB1, is about 8-fold slower (FIG. 8). The mutants have an altered regiospecificity and produce higher concentrations of m-cresol than TG1(T4MO); all three mutants show a similar product distribution (FIG. 8).

4-NC Product Distribution from NB and Kinetic Constants.

Product formation from NB was measured using reverse phase HPLC. For 4-NC formation from TG1 expressing TmoA I100A, the identity of 4-NC was also confirmed by LC-MS by comparison of its mass spectrum with that of an authentic standard (FIG. 11). Whole cell biotransformations were carried out with Tris-nitrite buffer (instead of phosphate buffer) to suppress the reduction of NB to aniline by the host cells, aerobically-grown *E. coli* TG1; in this way, NB was only oxidized by the plasmid-encoding monooxygenases and rates were measured accurately. This change in buffer did not influence the activity of T4MO but reduced the transformation of NB to aniline by TG1 pBS(Kan) to negligible amounts. To evaluate the product distribution from NB oxidation and to discern the pathway by which 4-NC is produced, whole-cell transformations were performed with about 200 •M NB. Following 15 min of incubation, the reaction was stopped by harvesting the cells and the reaction medium was analyzed and quantified (FIG. 12). T4MO is considered to be a very regiospecific monooxygenase producing primarily p-hydroxylated products (Mitchell et al. 2002; Pikus et al. 1997), and our results with TG1 cells expressing T4MO confirm these findings; however, the three mutants (NB1, I100A, I100S) exhibited lower regiospecificity and produced larger fractions of m-NP and 4-NC (FIG. 12). I100A and I100S produced nearly equal amounts of p-NP and m-NP indicating a drastic change in regiospecificity, much more pronounced than the changes observed for toluene product distribution. The formation rates of 4-NC from about 200 •M NB by TG1 expressing wild-type T4MO and the mutants are shown in FIG. 8. 3-NC was not observed when NB was the substrate. TG1 pBS(Kan) cells did not oxidize NB, indicating that the NB oxidation was due to the expression of T4MO. The kinetic constants (apparent $V_{max}$ and $K_m$) for formation of the nitrophenols from NB, as well as the formation of 4-NC from the intermediate nitrophenols, were measured (FIG. 9). NB1 (the mutant containing 6 amino acid changes) had decreased activity for all of the reactions investigated (at a substrate concentration of about 200 •M) and therefore its kinetic constants were not measured. TG1 cells expressing the mutant enzymes followed saturation kinetics with all substrates tested (as did wild-type T4MO), and no inhibition was seen by NB or the nitrophenols at concentrations of about 200-400 •M (slight inhibition was seen for concentrations greater than about 500 •M). Both I100A and I100S showed lower $V_{max}$ values for the transformation of NB to p-NP, although variant I100S had a much lower $K_m$ value than wild-type leading to a two-fold increase in the $V_{max}/K_m$ ratio. In contrast, both mutants had increased $V_{max}$ as well as decreased $K_m$ values in the NB transformation to m-NP, resulting in $V_{max}/K_m$ ratios of about 22-33 times higher (FIG. 9). It is also evident from the data that the formation of 4-NC from m-NP is much faster than from p-NP for all the enzymes including wild-type T4MO. Therefore, I100A has about 16-fold greater 4-NC production compared to the wild-type T4MO (at saturating substrate levels of about 200 •M) since more NB is converted to m-NP, which is then rapidly oxidized to 4-NC. To verify that the increase in activity of mutants I100A and I100S derives from the amino acid substitutions rather than expression level changes, SDS-PAGE was used to visualize two of the six subunits: TmoA (55 kDa) and a combined band from TmoE (35 kDa) and TmoF (36 kDa); mutant and wild-type bands had similar intensities. Furthermore, the ribosome-binding site of the tmoA gene in I100A and I100S was unaltered during the mutagenesis as confirmed from DNA sequencing. As the cell growth and the biotransformation conditions were identical for the wild-type and mutants, the changes in activity appear to arise from the mutations at TmoA I100 and not from different expression levels.

TmoA Structural Modeling.

To gain insights on the role of I100 in the T4MO active site cavity, a three-dimensional model was constructed based on the known crystal structure of hydroxylase MmoX of (sMMO) (Rosenzweig et al. 1997). Despite the rather low homology between the two enzymes (about 27% identity), the correct fold was generated as judged by the positions of the diiron coordinating residues in T4MO (E104, E134, H137, E197, E231, and H234) compared to sMMO: the distance between the respective C• of the iron binding residues was less than about 0.1 Å for all six residues. The structural alignment of the template and model also showed conserved spatial configurations. Although there are limitations to homology modeling, especially in cases of low identity between the enzyme and the template (Guex and Peitsch 1997; Schwede et al. 2003), the role of I100 as a part of the hydrophobic cavity around the diiron center is clear. The distances between the Ile side chain and the amino acids in the opposing •helix (F205, Q204, L208) are shown in yellow and highlight the possible function of I100 as a gate restricting the size and conformation of the substrates entering the active site. The size of the channel is increased significantly for mutants I100A and I100S and may provide an explanation for the altered activity and specificity of the mutants.

Conclusions.

After discovering that toluene 4-monooxygenase (T4MO) of *Pseudomonas mendocina* KR1 oxidizes nitrobenzene to 4-nitrocatechol, this reaction was improved using directed evolution and saturation mutagenesis. Screening a random mutagenesis library generated by error-prone PCR of tmoAB using *Escherichia coli* TG1/pBSKanT4MO on agar plates containing nitrobenzene led to the discovery of nitrocatechol-producing mutants. One mutant, NB1, contained six amino acid substitutions (TmoA Y22N, I84Y, S95T, I100S, S400C; TmoB D79N). It was believed that position I100 of the • subunit of the hydroxylase (TmoA) is the most significant for the change in substrate reactivity due to previous results in our lab with a similar enzyme, toluene ortho-monooxygenase of *Burkholderia cepacia* G4. Saturation mutagenesis at this position resulted in the generation of two more nitrocatechol mutants, I100A and I100S; the rate of 4-nitrocatechol formation by I100A was more than 16 times higher than that of wild-type T4MO at about 200 μM nitrobenzene (about 0.13±0.01 vs. about 0.008±0.001 nmol/min.mg protein). HPLC and mass spectrometry analysis revealed that variants NB1, I100A, and I100S produce 4-nitrocatechol via m-nitrophenol, while the wild-type produces primarily p-nitrophenol and negligible amounts of nitrocatechol. Relative to wild-type T4MO, whole cells expressing variant I100A convert nitrobenzene into m-nitrophenol with a $V_{max}$ of about 1.25 vs. about 0.18 nmol/min.mg protein and convert m-nitrophenol into nitrocatechol with a $V_{max}$ of about 3.3 vs. about 0.75 nmol/min.mg protein. Hence the regiospecificity of nitrobenzene oxidation was changed by the random mutagenesis, and this led to a significant increase in 4-nitrocatechol production. The regiospecificity of toluene oxidation was also altered, and all of the mutants produced about 20% m-cresol and about 80% p-cresol, whereas the wild-type produces about 96% p-cresol. Interestingly, the rate of toluene oxidation (the natural substrate of the enzyme) by I100A was also higher by about 65% (about 7.2±1.2 vs. about 4.4±0.3 nmol/min.mg protein). Homology-based modeling of TmoA suggests reducing the size of the side chain of I100 leads to an increase in the width of the active site channel which facilitates access of substrates and promotes more flexible orientations.

Example #2

Directed Evolution of Toluene 4-Monooxygenase by Active Site Engineering for the Synthesis of 3-Methoxycatechol, Methoxyhydroquinone, and Methylhydroquinone Detailed Methods Chemicals. o-Methoxyphenol (guaiacol, 98%), 3-methoxycatechol, and p-cresol (99+%) were obtained from Acros Organics (Morris Plains, N.J.). o-Cresol (99+%), m-cresol (97%), methoxyhydroquinone, 4-methoxyresorcinol, 3-methylcatechol, 4-methylcatechol, methylhydroquinone, and 2-methoxyresorcinol were obtained from Sigma-Aldrich Co. (Milwaukee, Wis.). All materials used were of the highest purity available and were used without further purification.

Bacterial strains, plasmids, and growth conditions. Plasmid pBS(Kan)T4MO (FIG. 17) which constitutively expresses T4MO tmoABCDEF was constructed as described previously. In pBS(Kan)T4MO, the lac promoter yields constitutive expression of T4MO due to the high copy number of the plasmid and lack of the lacI repressor. Kanamycin resistance was added to pBS(Kan)T4MO to reduce plasmid segregational instability. *Escherichia coli* TG1 (supE hsd.5 thi (lac-proAB) F' [traD36 proAB+lacIq lacZ.M15]) expressing wild-type and mutant T4MO from plasmid pBS(Kan)T4MO was used as the whole-cell biocatalyst. Cells were routinely cultivated at 37° C. with shaking at 250 rpm on a C25 incubator shaker (New Brunswick Scientific Co., Edison, N.J.) in Luria-Bertani (LB) medium supplemented with kanamycin at 100 μg/mL. Exponential-phase cultures were used in all experiments by inoculating from single colonies and growing to an optical density at 600 nm (OD) of 1.5. Cells were centrifuged at 13000×g 20 for 5 min at 25° C. in a Beckman J2-HS centrifuge (Palo Alto, Calif.). The collected cells were resuspended in 50 mM Tris-HCl buffer (pH 7.4) or in 50 mM Tris-HCl buffer (pH 7.4).

Molecular techniques and protein analysis. Plasmid DNA was isolated using a Midi or Mini Kit (Qiagen, Inc., Chatsworth, Calif.), and DNA fragments were isolated from agarose gels using the GeneClean® III, DNA purification Kit (Bio 101, Vista, Calif.). *E. coli* strains were electroporated using a Bio-Rad 25 GenePulser/Pulse Controller (Hercules, Calif.) at 15 kV/cm, 25 μF, and 200 •. The total protein concentration of TG1/pBS(Kan)T4MO was determined as 0.24 mg protein/mL.OD using the Total Protein Kit (Sigma Chemical Co., St. Louis, Mo.). Cellular protein samples were analyzed on sodium dodecyl sulfate-polyacrylamide gels (SDS-PAGE) (12% polyacrylamide) followed by staining with coomassie brilliant blue.

Saturation mutagenesis. Saturation mutagenesis was performed using the procedure of Sakamoto et al. with random DNA mutations introduced at the desired positions during PCR. The 100-μL PCR mixture contained 30 ng of template DNA, 30 pmole of each primer, 20 nmole of each dNTP, and 5 U of Pfu DNA polymerase. A PCR program of 30 cycles was performed with 1 min at 94° C., 1 min at 55° C., and 2.5 min at 72° C. (with a final extension of 7 min at 72° C.). Two primers, T4MOG103A107Front and T4MOG103A107Rear (FIG. 13) were designed to randomize simultaneously both positions 103 and 107 of TmoA, the alpha subunit of T4MO hydroxylase. Two additional primers for cloning were T4MOEcoRIFront and T4MOBglIIRear (FIG. 13) which generate the unique restriction sites EcoRI and BglII which are indicated in the primer names and are also underlined; the BglII site occurs naturally downstream of TmoA 103 and 107, and the EcoRI site is upstream of tmoA in the multiple cloning site (FIG. 17). A two-step saturation mutagenesis was performed to generate the mutations at the desired positions, and pBS(Kan)T4MO (FIG. 17) was used as template for the initial PCR. A 386 nucleotide degenerate product was amplified by PCR using primers T4MOEcoRIFront and T4MOG103A107Rear, and a 648 nucleotide degenerate product of tmoA was amplified by PCR using primers T4MOG103A107Front and T4MO BglIIRear. After purifying with the Wizard PCR Purification Kit (Promega, Madison, Wis.), the two initial PCR products (50 ng each) were combined and used as the template in the second PCR using T4MOEcoRIFront and T4MOBglIIRear to obtain the full-length, degenerate, 981-nucleotide fragment. This product, containing randomized positions at 103 and 107, was cloned back into pBS(Kan)T4MO after double digestion with EcoRI and BglII. Similarly, to generate mutations at the TmoA I100 position, a 366 nucleotide degenerate product was amplified by PCR using primers T4MOEcoRIFront and T4MO100Rear (FIG. 13), and a 663 nucleotide degenerate product of tmoA was amplified by PCR using primers T4MO100Front (FIG. 13) and T4MOBglIIRear. After purifying with the Wizard PCR Purification Kit, the two initial PCR products (50 ng each) were combined and used as the template in the second PCR using T4MOEcoRIFront and T4MOBglIIRear to obtain the full-length, degenerate, 981-nucleotide fragment, which was cloned back into pBS(Kan)T4MO after double digestion with EcoRI and BglII.

Colony screening. Saturation mutagenesis mutant libraries of E. coli TG1/pBS(Kan)T4MO were screened on agar plates containing o-methoxyphenol or o-cresol using a modification of a procedure which is based on the enzymatic production of catechols that, upon secretion, autooxidize to red-brown metabolites. Along with the negative control E. coli TG1/pBS(Kan) and TG1/pBS(Kan)T4MO, around 50 T4MO transformants were transferred by sterile toothpicks to a single LB plate containing 10 μg/mL kanamycin and 1% glucose for overnight incubation (the glucose serves to prevent enzyme production from pBS(Kan)T4MO and to reduce plasmid segregational instability during growth). The colonies were transferred with a nylon membrane (Osmonics Inc., Minnetonka, Minn.) to a LB plate containing 100 μg/mL kanamycin and 1 mM of o-methoxyphenol or o-cresol. Plates were periodically inspected over a 12-24 h incubation period at room temperature. Those that developed a different color around the cell mass or more intense color than wild-type T4MO were chosen for another round of screening. If positive mutants were detected, the plasmids were isolated and sequenced.

Enzymatic activity. Oxidations of o-methoxyphenol, o-, m-, and p-cresol by the wild-type T4MO and the mutants identified from saturation mutagenesis were examined for regiospecificity and product formation rates. One mL of concentrated exponential cell suspensions (OD 10) in Tris-HCl buffer was contacted with 1 mM substrates (dissolved in 99.5% ethanol) in 15-mL serum vials sealed with a Teflon-coated septum and aluminum crimp seal. The negative controls used in these experiments contained the same monooxygenase without substrate (plus solvent) as well as TG1/pBS(Kan) with substrates (no monooxygenase control). The inverted vials were shaken at 37° C. at 300 rpm on an IKA-Vibrax-VXR shaker (Cincinnati, Ohio) for 10-240 min, and the cell suspension was removed and centrifuged in a 16M Labnet Spectrafuge (Edison, N.J.) for 2 min. The supernatant was analyzed by using the catechol spectrophotometric method developed previously for the 3-methoxycatechol concentration determination from o-methoxyphenol and by high performance liquid chromatography (HPLC) for the identification and quantification of all products for all the substrates tested. For toluene oxidation activity, two mL of concentrated cell suspensions (OD 5-8) in Tris-HNO3 buffer were sealed in a 15-mL serum vial, and 300 •M toluene was added to the vials with a syringe, calculated as if all the substrate is in the liquid phase (actual initial liquid concentration was 109 •M based on Henry's Law constant of 0.27. The inverted vials were shaken at room temperature at 300 rpm. The reaction was stopped by adding 2 mL of 500 •M hexadecane (the internal standard) in ethyl acetate to the vial with a syringe, and the vial was vortexed thoroughly to ensure full extraction of the toluene. The organic phase was separated from the aqueous phase by centrifugation, and 2-3 •L were injected to the gas chromatograph (GC) column. Activity data reported in this paper are in the form of the mean±one standard deviation (based on at least two independent results).

Analytical methods. Reverse-phase HPLC was conducted to determine the product formation rates and the regiospecificity from o-methoxyphenol, o-, m-, and p-cresol oxidations. Supernatants (20 μL) were injected by an autosampler (Waters 717 plus) and analyzed using a Zorbax SB-C8 column (Agilent 15 Technologies, 5 μm, 4.6×250 mm) with a Waters Corporation (Milford, Mass.) solvent delivery system coupled to a photodiode array detector (Waters 996). For o-methoxyphenol as the substrate, an isocratic elution was performed with $H_2O$ (0.1% formic acid) and acetonitrile (70:30) as the mobile phase at a flow rate of 1 mL/min except for G103S for which a gradient elution (85:15 0-8 min, 65:35 13 min, 85:15 18 min) was used for better separation of the methoxyhydroquinone and 4-methoxyresorcinol products. For the cresol substrates, a gradient elution was used with $H_2O$ (0.1% formic acid) and acetonitrile (70:30 0-8 min, 40:60 15 min, 70:30 20 min) as the mobile phase. The identity of all products produced by the enzymes was determined by comparing both retention times and UV-visible spectra to those of authentic standards and was corroborated by coeluting with the standards. Toluene concentrations were measured by GC using a Hewlett-Packard 6890N GC equipped with an EC-WAX column (30 m×0.25 mm, 0.25 μm thickness; Alltech Associates, Inc., Deerfield, Ill.) and a flame ionization detector. The injector and detector were maintained at 250° C. and 275° C. respectively, and a split ratio of 3:1 was used. The He carrier gas flow rate was maintained at 0.8 mL/min. The temperature program was 80° C. for 5 min; 80° C.-205° C. at a rate of 5° C./min, 205° C.-280° C. at 15° C./min, and 280° C. for 5 min. Under these conditions, toluene, o-, p-, and m-cresols eluted at 4.2, 27.4, 29.1, and 29.3 min, respectively, while the internal standard hexadecane eluted at 17.8 min. Retention times were determined by comparisons to neat standards.

DNA sequencing. A dideoxy chain termination technique with the ABI. Prism BigDye Terminator Cycle Sequencing Ready Reaction Kit (PerkinElmer, Wellesley, Mass.) and PE Biosystems ABI. 373 DNA sequencer (PerkinElmer, Wellesley, Mass.) was used to determine the nucleotide sequence in the subcloned region for the T4MO enzyme variants using T4MOEcoRIFront as the sequencing primer. Sequence data generated were analyzed using the Vector NTI software (InfoxMax, Inc., Bethesda, Md.).

TmoA modeling. Amino acids 44-243 of the T4MO alpha-subunit TmoA (500 aa) were modeled into the known three-dimensional structure of the Methylococcus capsulatus (Bath) soluble methane monooxygenase (sMMO) hydroxylase •-subunit MmoX (PDB accession code 1MTY) using SWISS-MODEL Server. The molecular visualization program, Swiss-PdbViewer, was utilized to visualize and manipulate the molecular model, including performing amino acid substitutions isosterically at TmoA I100, G103, and A107 based on residue interactions, steric hindrance, and energy minimization.

Results

Oxidation of toluene, o-Cresol, m-Cresol, and p-Cresol by Wild-Type T4MO.

A whole-cell system was used to oxidize toluene and alternative substrates due to the multiple components of T4MO (hydroxylase, reductase, mediating protein, and ferredoxin) (FIG. 17) and its dependence on the cofactor NADH. Recombinant whole-cell TG1/pBS(Kan)T4MO oxidized toluene to about 96% p-cresol, about 3% m-cresol, and less than about 1% o-cresol (FIG. 14) giving nearly an identical product distribution to that of the purified T4MO (about 96.0% p-cresol, about 0.4% o-cresol, about 2.8% m-cresol, and about 8% benzyl alcohol) (Pikus et al., 2000). The negative control E. coli TG1/pBS(Kan) did not produce any product from the substrates tested (o-methoxyphenol and the cresols) or degrade any catechol in the time scale of these experiments; hence, the products were formed due to hydroxylation by the cloned T4MO. Based on the recent discovery that T4MO successively hydroxylates benzene to phenol, catechol, and 1,2,3-trihydroxybenzene (Tao et al., 2004), wild-type T4MO was investigated for its activity with cresols and found to hydroxylate them to methylcatechols, further indicating that T4MO can hydroxylate phenols (FIG. 15). Kinetic analysis of o-, m-, and p-cresol oxidation at seven different concentrations of about 0.025, 0.05, 0.125, 0.25, 0.5, 0.8, and 1.0 mM by wild-type T4MO showed this enzyme follows typical saturation kinetics with these three cresol substrates; the apparent Vmax and Km were about 8.5 nmol/min.mg protein and about 0.11 mM for 3-methylcatechol formation from o-cresol, about 7.0 nmol/min.mg protein and about 0.14 mM for 4-methylcatechol formation from m-cresol, and about 7.0 nmol/min.mg protein and about 0.16 mM for 4-methylcatechol formation from p-cresol. These Vmax values were consistent with the initial formation rates at 1 mM (FIG. 15), thus the specific rates at about 1 mM shown in FIG. 15 represent Vmax values. Determining at the saturation concentration of about 1 mM (no inhibition effect), substrate (cresol) oxidation rates and dihydroxylated product formation rates compared well and are shown in FIG. 15. All three cresol isomers were utilized and transformed by T4MO to corresponding catechols at significant levels and the oxidation rates of the different cresol isomers are similar and were comparable to the oxidation rate of the physiological substrate, toluene (apparent Vmax of toluene oxidation for wild-type T4MO was about 15.1±0.8 nmol/min.mg protein (Fishman and Wood, 2004)); hence, the rates of methylcatechol formation are significant. HPLC analysis determined TG1 expressing wild-type T4MO oxidizes o-methoxyphenol to 4-methoxyresorcinol (about 87%), 3-methoxycatechol (about 11.3%), and methoxyhydroquinone (about 1.7%); oxidizes o-cresol to 3-methylcatechol (about 91%) and methylhydroquinone (about 9%); as well as oxidizes m-cresol and p-cresol to 4-methylcatechol (about 100%) (FIGS. 14, 15, and 18).

Oxidation of Toluene by the Saturation Mutagenesis Variants.

Six saturation mutagenesis TmoA mutants (I100L, G103A, G103S, G103A/A107S, G103S/A107G, G103S/A107T) were characterized both for their initial specific activity and for their mono-hydroxylation regiospecificity on the natural substrate toluene (FIG. 14). These mutants have an initial specific activity for toluene oxidation comparable to that of wild-type T4MO (about 13%-166% of wild-type T4MO activity) demonstrating that each is an effective catalyst of aromatic hydroxylation. T4MO site-directed mutant TmoA G103L was reported previously to produce about 55.5% o-cresol from toluene oxidation (Mitchell et al., 2002). Here, regiospecific oxidation of toluene was observed with these TmoA saturation mutagenesis mutants that were identified through the nylon membrane assay; in particular, G103S/A107G and G103S/A107T produced about 82% o-cresol and about 100% p-cresol, respectively, therefore, these mutations serve to completely change the nature of toluene oxidation by T4MO converting it to T2MO and an even better T4MO. Moreover, toluene oxidation by the other saturation mutagenesis mutants (I100 L, G103A, G103S, and G103A/A107S) resulted in elevated yields of ortho- and meta-mono-hydroxylation products relative to wild-type T4MO.

Oxidation of o-Methoxyphenol by the Saturation Mutagenesis Variants.

The best mutants identified from o-methoxyphenol oxidation by the nylon membrane assay and colorimetric assay, T4MO TmoA I100 L, G103A, G103A/A107S, and G103S, were further examined by HPLC and found to make different regioselective products from o-methoxyphenol (FIG. 16 and FIG. 18); HPLC also was used to corroborate the initial 3-methoxycatechol formation rates determined by the colorimetric assay and to confirm the possible product identification based on the nylon membrane assay and catechol colorimetric assay. G103A synthesized 3-methoxycatechol 6 times faster than wild-type T4MO (FIG. 16) and had an increased regiospecificity for 3-methoxycatechol formation (about 52.3%). Notably, G103A/A107S produced primarily 3-methoxycatechol whose synthesis rate was more than about 7 times faster than that of wild-type (FIG. 16). The additional mutation A107S makes this enzyme yield about 30% more 3-methoxycatechol than that of G103A mutant; G103A/A107S produced about 82.5% 3-methoxycatechol after the accumulation of these two beneficial mutations. I100L was found to have nearly unchanged regiospecificity for o-methoxyphenol oxidation and produced predominantly 4-methoxyresorcinol (about 73%). The second major product, 3-methoxycatechol was made at a rate nearly 4 times faster than wild-type T4MO. The specific activities for 3-methoxycatechol formation by HPLC analysis corroborated those of the colorimetric assay (FIG. 16). In contrast, two mutants, G103S and G103S/A107T, produced methoxyhydroquinone as a major product (about 80% and about 35% respectively) from o-methoxyphenol whereas wild-type T4MO produced methoxyhydroquinone only in trace amounts (FIG. 16). Since methoxyhydroquinone auto-oxidizes easily in aqueous solutions, care was taken for analyzing this compound. HPLC confirmed the initial product identification for these two mutants via the nylon membrane and catechol colorimetric assay. G103S synthesized methoxyhydroquinone at a 5-fold faster rate and with an about 47-fold increase in the percentage of methoxyhydroquinone formation relative to wild-type T4MO (FIG. 16); however, the o-methoxyphenol oxidation rate decreased about 10-fold relative to wild-type T4MO. G103S/A107T produced methoxyhydroquinone at the same rate as the wild-type while changing its regiospecificity. To confirm that the activity of the mutants were not improved because of some artifact of growth or change in expression, growth rates, toluene oxidation, and total cellular protein profiles via SDS-PAGE were measured. Using SDS-PAGE, the expression levels of these mutants were compared with wild-type T4MO and found to remain approximately constant except for T4MO G103S/A107G which had about 5-fold reduced expression levels compared to wild-type T4MO; two T4MO subunit polypeptides TmoA (55 KDa) and TmoE (36 kDa) were seen on the gel for both the mutant and wild-type enzymes. Variant I100L grew nearly at the same rate as the wild-type (about 1.34±0.01/h vs. about 1.14±0.03/h in LB kanamycin medium). Among the six mutants (T4MO TmoA I100 L, G103A, G103A/A107S, G103S, G103S/A107T, and G103S/A107G), the toluene oxidation rates varied from about 13% to about 166% of wild-type T4MO activity (FIG. 14), indicating that the six mutants were active with toluene as a substrate even though the mutations created regiospecific changes in toluene oxidation (FIG. 14). These results also show that the changes in enzyme activity with the saturation mutants are not due to differences in protein expression; for example, if the increases in the activity for 3-methoxycatechol and methoxyhydroquinone synthesis seen with G103A/A107S were due to expression differences, toluene oxidation and o-methoxyphenol oxidation would have been enhanced proportionally; instead, this variant had about 1.5-fold increase in toluene oxidation but about 2-fold decrease in o-methoxyphenol oxidation. Similarly, G103S had about 10-fold less activity for o-methoxyphenol oxidation but about 1.5-fold increase in toluene oxidation relative to wild-type T4MO. In contrast, G103S/A107G had about 13% of wild-type toluene oxidation activity and about 4% of wild-type o-cresol oxidation activity (below), which is probably due to its about 5-fold reduced protein expression.

Oxidation of o-Cresol by the Saturation Mutagenesis Variants.

T4MO TmoA variants G103S/A107G and G103S that were identified using the o-cresol nylon membrane screen, as well as G103A, G103A/A107S, and G103S/A107T that were identified using the o-methoxyphenol nylon membrane screen, were characterized by HPLC at about 1 mM saturation o-cresol concentration for product formation rates and regiospecificity. These variants demonstrated comparable o-cresol oxidation rates to the wild-type T4MO while the product distributions were changed substantially (FIG. 15). Mutants G103S, G103S/A107G, and G103S/A107T oxidized o-cresol to about 70-92% methylhydroquinone, which is about 8-10 times higher as a methylhydroquinone percentage than wild-type T4MO (FIG. 15). In addition, the methylhydroquinone formation rates by mutants G103S and G103S/A107T were more than about 4 times higher than wild-type T4MO (about 2.1±0.1 and about 2.1±0.7 nmol/min.mg protein vs. about 0.5±0.15 nmol/min.mg 10 protein). On the other hand, G103A and G103A/A107S produced 3-methylcatechol from o-cresol at a percentage of about 96% and about 98%, respectively, while about 91% 3-methylcatechol was observed with the wild-type T4MO. The specific formation rates of 3-methylcatechol by G103A and G103A/A107S were about 92% and about 216% of that of wild-type T4MO, respectively (FIG. 15). As with wild-type T4MO, substrate (o-cresol) depletion rates agreed well with the measured product formation rates.

TmoA Structure Homology Modeling.

To access the effects of amino acid substitutions at positions I100, G103, and A107 on the T4MO catalytic properties, an approximate three-dimensional model was constructed based on the known crystal structure of hydroxylase MmoX of sMMO (Rosenzweig et al., 1997). sMMO consists of a (•••)2 hydroxylase, a reductase, a coupling protein, and an open reading frame (OrfY), and each • subunit of hydroxylase contains one dinuclear iron center (Coufal et al., 2000). At the dinuclear iron center, oxygen is activated, and substrate hydroxylation coupled to NADH oxidation occurs (Kopp et al., 2002). Though TmoA and MmoX (the large subunit of T4MO and sMMO, respectively) have only about 27% identity and there are limitations to homology modeling with low identity (Guex et al., 2002), the correct fold was generated as judged by the positions of the diiron coordinating residues in T4MO (E104, E134, H137, E197, E231, and H234) compared to sMMO (Rosenzweig et al., 1193, and 1997): the root mean square deviation between the respective C. of the six coordinates of TmoA model and template sMMO model was about 0.07 Å. The structural alignment of the template and model also showed conserved spatial configurations. The model helped to visualize the locations of the mutations and the side chains of G103S, A107S, A107G, and A107T. The TmoA model showed that all three mutated residues I100, G103, and A107 lie in a very closed region of the same •-helix (helix B) of the four-helix bundle of TmoA (since all 3 are separated by 4 aa, they appear on the roughly the same side of the helix). A107 is one constituent of this hydrophobic pocket and G103 is located to the right side of the Fe-coordinating residue E104.

Conclusions.

Wild-type toluene 4-monooxygenase (T4MO) of *Pseudomonas mendocina* KR1 oxidizes toluene to p-cresol (about 96%) and oxidizes benzene sequentially to phenol, to catechol, and to 1,2,3-trihydroxybenzene. T4MO was discovered here to oxidize o-cresol to 3-methylcatechol (about 91%) and methylhydroquinone (about 9%), to oxidize m-cresol and p-cresol to 4-methylcatechol (about 100%), as well as to oxidize o-methoxyphenol to 4-methoxyresorcinol (about 87%), 3-methoxycatechol (about 11.3%), and methoxyhydroquinone (about 1.7%). A saturation kinetics study of o-, m-, and p-cresol oxidation of T4MO demonstrated cresol oxidation rates of about 8±1.6 to about 10.4±0.1 nmol/min.mg protein that are comparable to toluene oxidation rates (about 15.1±0.8 nmol/min.mg protein). After discovering these new reactions, the substrate specificity and regiospecificity of T4MO were investigated using saturation mutagenesis at positions I100, G103, and A107 of the alpha subunit of the hydroxylase (TmoA) using o-cresol and o-methoxyphenol as model substrates. When expressed in *Escherichia coli*, variant G103A/A107S produced 3-methylcatechol (about 98%) from o-cresol about two-fold faster and produced 3-methoxycatechol (about 82.5%) from about 1 mM o-methoxyphenol about 7 times faster than wild-type T4MO (about 1.5±0.2 vs. about 0.2±0.1 nmol/min.mg protein). G103S/A107T produced methylhydroquinone (about 92%) from o-cresol about 4-fold faster than wild-type T4MO. Variant G103S produced methoxyhydroquinone from o-methoxyphenol 47-fold higher than the wild type enzyme (about 80% vs. about 1.7%) and produced methylhydroquinone (about 80%) from o-cresol. Hence the regiospecific oxidation of o-methoxyphenol and o-cresol was changed for significant synthesis of 3-methoxycatechol, methoxyhydroquinone, 3-methylcatechol, and methylhydroquinone. The enzyme variants also demonstrated altered mono-hydroxylation regiospecificity for toluene; for example, G103S/A107G formed about 82% o-cresol, so saturation mutagenesis converted T4MO into an ortho-hydroxylating enzyme. Furthermore, G103S/A107T formed about 100% p-cresol from toluene; hence, a better p-hydroxylating enzyme than wild-type T4MO was formed. Structure homology modeling suggests that hydrogen bonding interactions of the hydroxyl groups of S103, S107, and T 107 influence the regiospecificity of the oxygenase reaction.

Example #3

Protein Engineering of Toluene-o-Xylene Monooxygenase from *Pseudomonas stutzeri* OX1 for Synthesizing 4-Methylresorcinol, Methylhydroquinone, and Pyrogallol Detailed Methods Bacterial strains, growth conditions, and SDS-PAGE. *Escherichia coli* strain TG1 was used as the host with pBS (Kan)ToMO and its variants. Cells were initially streaked from −80° C. glycerol stocks on Luria-Bertani (LB) agar plates containing 100 •g/mL kanamycin and incubated at 37° C. After growth on LB agar plates, cells were cultured from a fresh single colony in LB medium supplemented with 100 •g/mL kanamycin at 37° C. with shaking at 250 rpm (New Brunswick Scientific Co., Edison, N.J.). The relative expression of the touA loci from *E. coli* TG1/pBS(Kan) ToMO was evaluated using sodium dodecyl sulfate-polyacrylamide gel electrophoresis (SDS-PAGE) with a 12% Tris-HCl gel both with and without 1 mM isopropyl-•-D-thiogalactopyranoside (IPTG, Fisher Scientific. Co., Fairlawn, N.J.).

Chemicals. Benzene, toluene, phenol, p-cresol, catechol, 3-methylcatechol, 4-methylcatechol, and methylhydroquinone were purchased from Fisher Scientific Co.; resorcinol, 1,2,3-THB, 1,2,4-THB, o-cresol, and m-cresol were purchased from Sigma Chemical CO. (St. Louis, Mo.); hydroquinone, benzyl alcohol, 2-hydroxybenzyl alcohol, 3-hydroxybenzyl alcohol, 4-hydroxybenzyl alcohol, 2-methylresorcinol, and 5-methylresorcinol were obtained from Acros Organics (Morris Plains, N.J.), and 4-methylresorcinol was obtained from Apin Chemicals (Abingdon, United Kingdom).

Construction of pBS(Kan)ToMO. To create pBS(Kan)ToMO for constitutive expression of ToMO, the touABCDEF locus was PCR amplified from plasmid pBZ1260 with a mixture of Taq and Pfu polymerase (1:1) and primers ToMO-KpnI-KACFront (primers shown in FIG. 19) which generates an unique KpnI site upstream of the touA start codon and ToMO-NotI-KACRear which generates an unique NotI site downstream of the touF stop codon (FIG. 23). The PCR product was then cloned into the multiple cloning site in pBS(Kan) after double digestion with KpnI and NotI to create pBS(Kan) ToMO (8983 bp). Colonies expressing active ToMO are distinguished based on their dark blue color on LB plates.

Saturation mutagenesis and DNA shuffling of ToMO. Saturation mutagenesis at positions I100, Q141, T201, and F205 of the alpha subunit (touA) of ToMO (499 amino acids) was performed as described previously, and FIG. 19 shows the primers used for cloning. To substitute other amino acids at position I100 of TouA, primers I100-front and I100-rear with NNN at the position encoding I100 were used, and ToMO-KpnI-front and ToMO-BstEII-rear are upstream and downstream of the unique KpnI and BstEII restriction sites (FIG. 23) (BstEII occurs naturally in touA and KpnI occurs in the multiple cloning site). Pfu polymerase (Stratagene, La Jolla, Calif.) was used in the PCR to minimize random point mutations, and pBS(Kan)ToMO was used as the template (FIG. 23). A 364 bp DNA fragment was amplified using primers ToMO-KpnI-front and I100-rear, and a 385 bp DNA fragment was amplified using primers I100-front and ToMO-BstEII-rear. After purifying from agarose gels, the two fragments were combined at a 1:1 ratio as templates with the ToMO-KpnI-front and ToMO-BstEII-rear primers to obtain the full-length, 701 bp product that introduces random mutations at position I100 of TouA and has two unique restriction enzyme sites. A PCR program of 30 cycles of 94° C. for 45 s, 55° C. for 45 s, and 72° C. for 2.15 min, with a final extension of 72° C. for 7 min was used. The resulting PCR product was cloned into pBS(Kan)ToMO after double digestion with KpnI and BstEII, replacing the corresponding fragment in the original plasmid. The resulting plasmid library was electroporated into *E. coli* TG1 competent cells using a Bio-Rad GenePulser/Pulse Controller (Hercules, Calif.) at 15 kV/cm, 25•F., and 200•. Similarly, to substitute other amino acids at position Q141 of TouA, a 594 bp DNA fragment was amplified using primers ToMO-KpnI-front and Q141-rear (FIG. 19), and a 332 bp DNA fragment was amplified using primers Q141-front and ToMO-BstEII-rear (FIG. 19). The two fragments were combined at a 1:1 ratio as templates to obtain the full-length, product (890 bp) with the ToMO-KpnI-front and ToMO-BstEII-rear primers which was cloned using KpnI and BstEII (FIG. 23). To substitute other amino acids at position T201 of TouA, a 773 bp DNA fragment was amplified using primers ToMO-KpnI-front and T201-rear (FIG. 19), and an 881 bp DNA fragment was amplified using primers T201-front and ToMO-SalI-rear (FIG. 19). The two fragments were combined at a 1:1 ratio as templates to obtain the full-length, product (1615 bp) with the ToMO-KpnI-front and ToMO-SalI-rear primers which was cloned using MluI and SalI (FIG. 23). To substitute other amino acids on position F205 of TouA, a 784 bp DNA fragment was amplified using primers ToMO-KpnI-front and F205-rear (FIG. 19), and a 867 bp DNA fragment was amplified using primers F205-front and ToMO-SalI-rear (FIG. 19). The two fragments were combined at a 1:1 ratio as templates to obtain the full-length, product (1615 bp) with the ToMO-KpnI-front and ToMO-SalI-rear primers which was cloned using MluI and SalI (FIG. 23). 10 DNA shuffling of 90% of touA of ToMO was performed as described previously for TOM. ToMO-KpnI-front and ToMO-SalI-rear (FIG. 19) were designed to be 50-100 bp upstream and downstream of the natural restriction sites MluI and SalI respectively used for cloning; these two sites lie within the coding region of touA so that the promoter and the ribosome binding site regions were not shuffled. The shuffled product was then cloned into plasmid pBS(Kan)ToMO, replacing the 1314 bp region between the natural MluI and SalI sites of the wild-type ToMO with shuffled DNA (90% of touA) (FIG. 23). Amplifications were carried out in the GeneAmp PCR System 2400 (Perkin Elmer, Norwalk, Conn.). Plasmid Midi Kit and QIAquick Gel Extraction Kit (Qiagen, Inc., Chatsworth, Calif.) were used to isolate plasmids and DNA fragments from agarose gels, respectively. A Bio-Rad GenePulser/Pulse Controller (Hercules, Calif.) was used for electroporation (15 kV/cm, 25 •F., and 200•).

Colony screening. The plate assay used is a variation of the method described previously by Meyer et al. The mutant libraries were first streaked from transformant plates to LB (100 •g/mL kanamycin) agar plates containing 1% (w/v) glucose to turn off the tou operon to increase stability. The glucose-grown colonies were then transferred to fresh LB (100 •g/mL kanamycin) plates containing 1 mM substrate (toluene or benzene) with a nylon membrane. After incubating for 24 hours at room temperature in a chamber, the colonies were checked visually to search for those that developed a dark brown-red color around the cell mass indicating the formation of derivatives of hydroquinone, resorcinol, or catechol from toluene or benzene. The control expressing wild-type ToMO remained yellow to light red on toluene or benzene agar plates (indicates the formation of catechol derivatives only). The negative control expressing no monooxygenase, TG1/pBS(Kan), remained colorless on toluene or benzene. At least three replicates were checked before proceeding with HPLC analysis.

Product identification and rates of formation. The possible mutants initially identified by screening via the agar plate assay were further examined by reverse-phase HPLC. Experiments were conducted with exponentially-grown cells with an optical density at 600 nm (OD) of 1.0. The cells were washed once at 6,000 g for 5 min at 25° C. (JA-17 rotor in a J2 series centrifuge, Beckman, Palo Alto, Calif.) and resuspended with 1 volume 50 mM Tris-HNO3 buffer, pH 7.0, to an OD of 5-10. Cell suspensions (2.5 mL) were sealed with a Teflon-coated septum and aluminum seal in 15 mL glass vials, and the substrates, benzene, phenol, toluene, o-cresol, m-cresol, p-cresol, catechol, hydroquinone, and resorcinol were added from ethanol stock solutions at 0.8 mM. After contacting at room temperature at 250 rpm in an IKA Laboratories (Cincinnati, Ohio) KS250 benchtop shaker for 15 to 240 min, 1 mL of the cell suspension was centrifuged at 13,000 g for 2-3 min, the supernatants (500 µL) were filtered with a 1 mL syringe (Becton Dickinson) coupled to a nylon membrane filter unit (Millex-HN, 0.45 •m, 4 mm). Via HPLC, the dihydroxy and trihydroxy derivatives of benzene and toluene were analyzed immediately, and the derivatives of monohydroxy benzene or toluene were either kept at −20° C. (not more than 24 hrs) or analyzed immediately. A Zorbax SB-C8 column (Agilent Technologies, 5 •m, 4.6×250 mm) was used with a Waters Corporation (Milford, Mass.) solvent delivery system coupled to a photodiode array detector (Waters 996). To detect the methyl-substituted catechols, methyl-substituted resorcinols, and methylhydroquinone, and to determine their formation rates, a gradient elution was performed with $H_2O$ (0.1% formic acid) and acetonitrile (70:30 0-8 min, 40:60 15 min, 70:30 20 min) as the mobile phases at a flow rate of 1 mL/min. To detect and determine the formation rates of catechol, resorcinol, and hydroquinone, an isocratic mobile phase of $H_2O$ (0.1% formic acid)-acetonitrile (70:30) was used. To detect the THBs from catechol, resorcinol, and hydroquinone, an isocratic mobile phase of $H_2O$ (0.1% formic acid)-acetonitrile (90:10) was used. To confirm product identifications, the retention times and UV-visible spectra of the standard chemicals were compared with those of the enzyme-derived samples (FIG. 20), and the enzyme products were co-eluted with authentic standards. At least two independent cultures were analyzed for each substrate and strain tested, and at least five injections were made for each substrate. Initial product formation rates at 0.8 mM were determined by sampling at 15 minute intervals for 2 hrs and were quantified in nmol/(min.mg protein) by converting product peak areas to concentrations using standard curves prepared at the specific absorbance wavelength (FIG. 20) for each product formed. Protein content was 0.22 mg protein/(mL 1 OD) for recombinant E. coli TG1 as determined using the Protein Assay Kit (Sigma Diagnostics Inc., St. Louis, Mo.). The whole-cell catalytic parameters $V_{max}$ and $K_m$ were determined for catechol formation from phenol (at 25, 50, 100, 200, and 400 •M) for wild-type ToMO and variant M180T/E284G as well as for 4-methylcatechol formation from p-cresol (at 25, 50, 100, 200, and 400 •M) for wild-type ToMO and variant I100Q. The experiments involved HPLC measurements of the initial rates of catechol formation from 25, 50, 100, 200, 400 •M phenol.

Toluene oxidation and regiospecificity. To determine the toluene oxidation products, experiments were conducted with exponentially-grown cells with an OD of 1.0. The cells were washed once at 6,000 g for 5 min at 25° C. (JA-17 rotor in a J2 series centrifuge, Beckman, Palo Alto, Calif.), resuspended with 1 volume 50 mM Tris-HNO3, pH 7.0 to an OD of 10, and contacted with 91 µM toluene (based on Henry's law) at room temperature and harvested every 5 minutes. Hexadecane (0.5 mM) was used as an internal standard for calculations (17.8 min retention time) and added prior to extraction. An ethyl acetate-hexadecane (0.5 mM) was used to extract the toluene by adding 1 mL to the 2 mL cell suspension. The suspension was centrifuged for 1-2 min, and the ethyl acetate phase (upper phase) analyzed with GC using a Hewlett-Packard 6890N gas chromatograph (Wilmington, Del.) equipped with an EC-WAX capillary column (30 m×0.25 mm, 0.25 µm thickness; Alltech Associates, Inc., Deerfield, Ill.) and a flame ionization detector. The injector and detector were maintained at 250° C. and 275° C., respectively, and a split ratio of 3:1 was used. The He carrier flow rate was maintained at 0.8 mL/min. The temperature program was 80° C. for 5 min, 80° C.-205° C. at a rate of 5° C./min, 205° C.-280° C. at a rate of 15° C./min, and 280° C. for 5 min. Under these conditions, p- and m-cresol may be separated, and the retention times for toluene, o-, p-, and m-cresol were 4.2, 27.6, 29.3, and 29.5 min, respectively. The experiments were performed at least two times for each strain tested. The molar amount of toluene degraded and o-, m-, and p-cresol formed was calculated by making a calibration curve, and the retention times were compared with the standards.

DNA sequencing. A dideoxy chain termination technique with the ABI. Prism BigDye Terminator Cycle Sequencing Ready Reaction Kit (PerkinElmer, Wellesley, Mass.) and PE Biosystems ABI. 373 DNA sequencer (PerkinElmer, Wellesley, Mass.) was used to determine the ToMO nucleotide sequence. Ten primers (FIG. 19) of 20 to 25 nucleotides in length were generated from the wild-type ToMO sequence (GenBank AJ005663) for sequencing the ToMO touABC-DEF locus in one direction for pBS(Kan)ToMO (FIG. 23) and pBZ1260. Sequence data generated were analyzed using the Vector NTI 15 software (InfoxMax, Inc., Bethesda, Md.).

Modeling of ToMO TouA. Part of the wild-type ToMO TouA alpha-subunit (amino acid residues P65-E284) was modeled using SWISS-MODEL Server and was based on the sMMO MmoX alpha-subunit (polymer chain D) from *M. capsulatus* (Bath). The I100Q, F205G, and M180T mutations were modeled from the generated wild-type TouA ToMO model using the Swiss-Pdb Viewer program (DeepView). The program Swiss-Pdb Viewer performed the amino acid substitutions isosterically for the ToMO TouA based on residue interactions, steric hindrance, and energy minimization.

Results

Oxidation of Benzene by Wild-Type Monooxygenase and Variants.

The pathways for the oxidation of benzene to phenol, dihydroxybenzene derivatives, and trihydroxybenzene derivatives by monooxygenase enzymes according to the method of the invention is shown in FIG. 24.

For both wild-type ToMO and the TouA variants, there was a good agreement between the disappearance rates of all substrates (phenol, o-cresol, m-cresol, p-cresol and catechol) and the overall product appearance rates (THB, catechol, hydroquinone, resorcinol, 3-methylcatechol, 4-methylcatechol, methylhydroquinone, and 4-methylresorcinol) (FIG. 21). For example, with wild-type ToMO, the formation rate of 1,2,3-THB (about 0.71 nmol/min.mg protein) and the disappearance rate of catechol (about 0.75 nmol/min.mg protein) were consistent.

In one aspect of this embodiment is a method for mutating the alpha subunit of ToMO, TouA, resulting in the hydroxylation of benzene to hydroquinone, catechol, and 1,2,4-THB, whereas wild-type ToMO performs the second hydroxylation only at position 2 and forms catechol. In another aspect of this embodiment includes the method for production of 1,2,4-THB from hydroquinone and resorcinol by wild-type ToMO, and a ToMO variant, for example I100Q.

Another aspect of this embodiment includes a method of using a TouA variant to hydroxylate benzene for form phenol, resorcinol, and hydroquinone different from wild type ToMO. For example, TouA variant F205G hydroxylates phenol at positions 2, 3, and 4, and forms significant resorcinol (about 13%), along with catechol (about 76%) and hydroquinone (about 11%) whereas wild-type ToMO forms only catechol. Included in this aspect is a method for using a ToMO variant for the production of 1,2,3-THB from resorcinol, and 1,2,4-THB from hydroquinone.

Another aspect of this embodiment includes a method for evolving a monooxygenase nucleic acid encoding a monooxygenase or a fragment thereof to modify the production of useful chemical intermediates. In one example of this aspect TouA variant M180T/E284G is used to produce thirty-three percent more catechol from benzene than wild-type ToMO. Another example of this aspect includes a method of using the TouA variant M180T/E284G to produce 1,2,4-THB from hydroquinone, and 1,2,3-THB and 1,2,4-THB from catechol or resorcinol at greater rates than wild-type ToMO. Another example of this aspect includes a method for the formation of 3-methylcatechol, and 4-methylcatechol with variant M180T/E284G at faster rates than wild-type ToMO (FIG. 25).

Oxidation of Toluene by Wild-Type ToMO and TouA Variants.

Toluene oxidation was also evaluated as a substrate with these enzyme variants to see whether the addition of methyl groups to the benzene ring would affect the regiospecificity and to determine if the oxidation rate of this natural substrate has been altered significantly. FIG. 22 summarizes the products obtained from whole cell oxidation of toluene with wild-type ToMO and TouA variants I100Q, F205G, and M180T/E284G. It was previously shown that wild-type ToMO hydroxylates toluene to o-cresol, m-cresol, and p-cresol and 3- and 4-methylcatechol (Bertoni et al., 1996) and the same results were obtained here except that slight 3-methylcatechol formation (about 4%) from m-cresol was found in addition to 4-methylcatechol (about 96%) (FIG. 25). To determine the toluene activity and regiospecificity, GC was used rather than HPLC since m- and p-cresol were not separated under the HPLC conditions. The wild-type product distribution agrees well with that reported previously by Bertoni et al. (1996). Both the TouA I100Q and F205G mutations caused a shift in product distribution for the first hydroxylation of toluene and resulted in elevated m-cresol formation at the expense of o-cresol (FIG. 22). M180T/E284G gave no substantial shift in the product distribution for the first hydroxylation (about 32% o-cresol, 26% m-cresol, and 42% p-cresol). The oxidation rates of toluene are also shown in FIG. 22; M180T/E284G oxidized toluene (about 91 •M according to Henry's law) slightly faster than wild-type (about 20%). Variants I100Q and F205G had a different regiospecificity for the second hydroxylation of toluene. FIG. 25 shows the oxidation of o-cresol with wild-type ToMO and with TouA variants I100Q, F205G, and M180T/E284G. Wild-type ToMO forms only 3-methylcatechol; however, variant I100Q forms methylhydroquinone (about 50%) and 3-methylcatechol (about 50%). Unlike wild-type ToMO, F205G forms 4-methylresorcinol (about 70%), 3-methylcatechol (about 22%), and methylhydroquinone (about 8%) from o-cresol. Variant M180T/E284G forms 3-methylcatechol (about 85%) at slightly elevated rates compared with the wild-type isoform along with methylhydroquinone (about 15%). FIG. 25 shows the pathways for the oxidation of m-cresol. Wild-type ToMO forms 4-methylcatechol (about 96%) and 3-methylcatechol (about 4%). Unlike wild-type ToMO, variant I100Q forms methylhydroquinone (about 50%) and 4-methylcatechol (about 50%). Like wild-type ToMO, F205G forms 4-methylcatechol (about 78%) and 3-methylcatechol (about 22%); however, F205G forms 3-methylcatechol about 2.4-fold faster from about 0.8 mM m-cresol. Unlike wild-type ToMO and variants I100Q and F205G, variant M180T/E284G forms 4-methylcatechol (about 92%, about 1.7-fold faster than wild-type), 3-methylcatechol (about 4%), and methylhydroquinone (about 4%). FIG. 25 shows the pathways for the oxidation of p-cresol by ToMO and the variants. ToMO and variant I100Q form only 4-methylcatechol with comparable rates; however, variants F205G and M180T/E284G form both 4-methylcatechol (about 78% and about 88%, respectively), and 4-methylresorcinol (about 22% and about 12%, respectively). To characterize the p-cresol to 4-methylcatechol reaction more fully (FIG. 25), apparent $V_{max}$ for the whole cells was found to be about 3.3 nmol/min.mg protein for I100Q and about 2.7 nmol/min.mg protein for wild-type. Apparent $K_m$ was about 111 •M for I100Q and about 58 •M for wild-type; hence, $V_{max}/K_m$ was reduced about 63% for I100Q. All the methyl-substituted catechol, methylhydroquinone, and methyl-substituted resorcinol samples were relatively unstable due to non-enzymatic reactions since standards contacted with Tris-$HNO_3$ buffer (no cells) overnight formed unknown compounds (as observed by HPLC). However, this did not affect the results here because the analyses were done in the first four hours.

Enzyme Expression Level.

Both TouA variants I100Q and F205G are expression down mutants as evidenced by SDS-PAGE; a single nucleotide change in one codon led to a less elevated protein expression level (about 1.5-2 fold). Hence, the enzymes are even more active than the rates of FIGS. 24 and 25 indicate. Similar changes in expression levels due to mutation have been seen with naphthalene dioxygenase and para-nitrobenzyl esterase (Moore and Arnold, 1996; Sakamoto et al., 2001). The variation in the protein expression level could be due to the modification of the primary amino acid sequence which leads to an increase in protein lability or the single nucleotide change may lead to increased lability of the transcript (the ribosome binding site and promoter are unaltered). The expression level of variant M180T/E284G remains approximately the same as that of wile-type ToMO.

ToMO TouA Modeling.

The approximate three-dimensional coordinates for the TouA four-helix bundle anchoring the active site were based on the crystal structure of sMMO. The accuracy of the wild-type ToMO TouA alpha-subunit model was judged by the conservation of the spatial positions of the diiron coordinating residues in ToMO (E104, E134, H137, E197, E231, and H234) compared to those of sMMO (E114, E144, H147, E209, E243, and H246 (Rosenzweig et al., 1997)). Although there are limitations to homology modeling (Guex et al., 1997; Schwede et al., 2003) (only about 30% sequence identity here for the modeled part), the model did help to visualize the positions of the side chains for the variants I100Q, M180T, and F205G. The E284G amino acid substitution in variant M180T/E284G is not near the active site (not shown). If one considers the proximal location of these mutations to the active site, it appears the I100Q, M180T, and F205G mutations might lead to variations in the active site shape as the volume occupied by the side chains are altered. The substantial change in the regiospecific oxidation of phenol, o-cresol, m-cresol, p-cresol, catechol, and resorcinol by variants I100Q, M180T/E284G, and F205G suggests these substrates dock in the active site in an altered manner when these residues are changed.

Conclusion.

Toluene-o-xylene monooxygenase (ToMO) from *Pseudomonas stutzeri* OX1 oxidizes toluene to 3- and 4-methylcatechol as well as oxidizes benzene to form phenol; ToMO was found here to also form catechol and 1,2,3-trihydroxybenzene (1,2,3-THB) from phenol. To synthesize novel dihydroxy and trihydroxy derivatives of benzene and toluene, DNA shuffling of the alpha hydroxylase fragment of ToMO (TouA) and saturation mutagenesis of the TouA active site residues I100, Q141, T201, and F205 were used to generate random mutants. The mutants were initially identified by screening via a rapid agar plate assay and then were further examined by high performance liquid chromatography (HPLC) and gas chromatography (GC). Several regiospecific mutants with high rates of activity were identified; for example, *Escherichia coli* TG1/pBS(Kan)ToMO expressing TouA saturation mutagenesis variant F205G formed 4-methylresorcinol (about 0.78 nmol/min.mg protein), 3-methylcatechol (about 0.25 nmol/min.mg protein), and methylhydroquinone (about 0.088 nmol/min.mg protein) from o-cresol whereas wild-type ToMO formed only 3-methylcatechol (about 1.1 nmol/min.mg protein). From o-cresol, saturation mutagenesis mutant I100Q and DNA shuffling mutant M180T/E284G formed methylhydroquinone (about 0.50 and about 0.19 nmol/min.mg protein, respectively) and 3-methylcatechol (about 0.49 and about 1.5 nmol/min.mg protein, respectively). F205G formed catechol (about 0.52 nmol/min.mg protein), resorcinol (about 0.090 nmol/min.mg protein), and hydroquinone (about 0.070 nmol/min.mg protein) from phenol whereas wild-type ToMO formed only catechol (about 1.5 nmol/min.mg protein). Both I100Q and M180T/E284G formed hydroquinone (about 1.2 and about 0.040 nmol/min.mg protein, respectively) and catechol (about 0.28 and about 2.0 nmol/min.mg protein, respectively) from phenol. Dihydroxybenzenes were further oxidized to trihydroxybenzenes with different regiospecificities; for example, I100Q formed 1,2,4-THB from catechol whereas wild-type ToMO formed 1,2,3-THB (pyrogallol). Regiospecific oxidation of the natural substrate toluene was also checked, for example, I100Q forms about 22%, about 44%, and about 34% of o-, m-, and p-cresol, respectively, whereas wild-type ToMO forms about 32%, about 21%, and about 47% of o-, m-, and p-cresol, respectively.

Example #4

Oxidation of Benzene to Phenol, Catechol, and 1,2,3-Trihydroxybenzene by Toluene 4-Monooxygenase of *Pseudomonas mendocina* KR1 and Toluene 3-Monooxygenase of *Ralstonia pickettii* PKO1

Detailed Methods

Chemicals. Benzene (99%), phenol (99%), and catechol (99+%) were obtained from Fisher Scientific Co. (Fairlawn, N.J.). Hydroquinone (99%) was obtained from Acros Organics (Morris Plains, N.J.). Resorcinol (98%), 1,2,4-trihydroxybenzene (1,2,4-THB) (99%), and 1,2,3-THB (98%) were obtained from Sigma Chemical Co. (St. Louis, Mo.). All materials used were of the highest purity available and were used without further purification.

Bacterial strains and growth conditions. *Escherichia coli* TG1 (supE hsd.5 thi .(lac-proAB) F' [traD36 proAB+lacIq lacZ.M15]) with the plasmid constructs was routinely cultivated at 37° C. with shaking at 250 rpm on a C25 incubator shaker (New Brunswick Scientific Co., Edison, N.J.) in Luria-Bertani (LB) medium supplemented with kanamycin at 100 µg/mL to maintain the plasmids. All experiments were conducted by diluting overnight cells to an optical density at 600 nm (OD) of 0.1 to 0.2 and growing to an OD of 1.2. The exponentially-grown cells were centrifuged at 13,000 g for 5 min at 25° C. in a Beckman J2-HS centrifuge (Palo Alto, Calif.) and resuspended in Tris-HNO$_3$ buffer (50 mM, pH 7.0) or potassium phosphate buffer (50 mM, pH 7.0).

Protein analysis and molecular techniques. The Total Protein Kit (Sigma Chemical Co.) was used to determine the total cellular protein of *E. coli* TG1 pBS(Kan)T4MO (henceforth TG1(T4MO)) and *E. coli* 10 TG1 pBS(Kan)T3MO (henceforth TG1(T3MO)) for calculating whole-cell specific activities. The total protein concentration of *E. coli* TG1 pBS(Kan) TOM (henceforth TG1(TOM)) was determined previously. Plasmid DNA was isolated using a Midi or Mini Kit (Qiagen, Inc., Chatsworth, Calif.), and DNA fragments were isolated from agarose gels using the GeneClean III Kit (Bio 101, Vista, Calif.). *E. coli* strains were electroporated using a Bio-Rad GenePulser/Pulse Controller (Hercules, Calif.) at 15 kV/cm, 25 µF, and 200•.

Construction of expression vectors. To stably and constitutively express the toluene monooxygenase genes from the same promoter, the expression vectors pBS(Kan)T4MO, pBS(Kan)T3MO, and pBS(Kan)TOM were constructed. The construction of pBS(Kan) and pBS(Kan)TOM were described previously; note that our wild-type TOM (AF349675) used here has one amino acid (D14N in tomA3) different from the TOM sequence in GenBank (AF319657), but this mutation has no effect on activity. To create pBS(Kan) T4MO, a 4.7-kbp DNA fragment including the tmoABCDEF genes was PCR amplified from plasmid pMY486 with a mixture of Taq and Pfu polymerases (1:1) and primers T4MOEcoRIFront (FIG. 26) and T4MOBamHIRear (FIG. 26) and cloned into the multiple cloning site in pBS(Kan) after double digestion with EcoRI and BamHI. To create pBS(Kan)T3MO, a 4.6-kbp DNA fragment including the tbuA1UBVA2C genes was PCR amplified from plasmid pRO1996 (5, 22) with a mixture of Taq and Pfu polymerases (1:1) and primers T3MOBamHIFront (FIG. 26) and T3MOXbaIRear (FIG. 26). The PCR product was cloned into the multiple cloning site in pBS(Kan) after double digestion with BamHI and XbaI. In pBS(Kan)T4MO, pBS(Kan) T3MO, or pBS(Kan)TOM, the lac promoter yields constitutive expression of T4MO, T3MO, or TOM due to the high copy number of the plasmid and lack of the lacIrepressor. Expression of wild-type T4MO from pBS(Kan)T4MO and T3MO from pBS(Kan)T3MO within *E. coli* strains produced blue-colored cells on agar plates and in broth cultures, but expression of wild-type TOM from pBS(Kan)TOM within *E. coli* strains produced the normal brown-colored cells on agar plates and in broth cultures.

Enzymatic activity. Successive hydroxylation activity of TG1 (T4MO), TG1(T3MO), and TG1(TOM) was determined by a colorimetric assay and HPLC. Two mL of concentrated cell suspensions (OD 2-10) in Tris-HNO$_3$ buffer were contacted with 165 µM substrate (benzene, phenol, or catechol dissolved in 99.5% ethanol; for benzene, 400 µM added if all in aqueous phase based on a Henry's law constant of 0.22) in 15-mL serum vials sealed with a Teflon-coated septum and aluminum crimp seal. The negative controls used in these experiments contained the same monooxygenase without substrates (plus solvent) as well as TG1/pBS(Kan) with substrates (no monooxygenase control). The inverted vials were shaken at room temperature at 300 rpm on an IKA-Vibrax- VXR shaker (Cincinnati, Ohio) for 4 min-4 h, then one mL of the cell suspension was removed and centrifuged in a 16M Labnet Spectrafuge (Edison, N.J.) for 1-2 min. The supernatant was analyzed by the colorimetric assay for catechol and by HPLC for the identification and quantification of all intermediates. For benzene and toluene oxidation activity, 2 mL of concentrated cell suspensions in Tris-HNO$_3$ buffer or in phosphate buffer were sealed in 15-mL serum vials, and 400 μM benzene or 455 μM toluene was added to the vials with a syringe, calculated as if all the substrate is in the liquid phase (actual initial liquid concentration was 165 μM based on Henry's law). The inverted vials were shaken at room temperature at 300 rpm. The reaction was stopped by injecting 2 mL ethyl acetate containing 500 mM hexadecane (the internal standard) to the vial, and the vial was vortexed thoroughly to ensure full extraction of the toluene. The organic phase was separated from the aqueous phase by centrifugation, and 2-3 μL were injected to the gas chromatograph (GC) column. Activity data reported in this paper are in the form of the mean one standard deviation (based on at least two independent results).

Catechol colorimetric assay. The catechol generated by whole cells from the biotransformation of benzene, or remaining after the catechol oxidation experiments, was measured spectrophotometrically by modifying the procedure of Fujita for 1.5 mL microcentrifuge tubes; this assay measures catechol based on the color reaction of catechol, iron (III), and phenylfluorone (a xanthene dye), and phenol does not interfere with this assay while 1,2,3-THB interferes slightly (yields 5% of the catechol signal). The catechol concentration was measured by adding 300 μL of 0.1 M sodium carbonate-0.1 M sodium hydrogen carbonate buffer, 100 μL of 5% polyoxyethelene monolauryl ether (Acros Organics), 60 μL of 1 mM iron (III) ammonium sulfate, 60 μL of 1 mM phenylfluorone (Acros Organics) in methanol, and 380 μL of sterile water to the 100 μL of supernatant for a 1.0 mL final volume in a 1.5 mL microcentrifuge tube. After 1 min, the absorbance of the color complex [catechol-FeIII-phenylfluorone] was measured at 630 nm using a Shimadzu UVmini-1240 Spectrophotometer (Kyoto, Japan). The molar amount of catechols was calculated by comparison to a catechol standard curve (molar extinction coefficient measured as 22,600 M-1 cm-1). The minimum detectable catechol concentration with this method was 10 μM.

Analytical methods. Reverse-phase HPLC was conducted to analyze TG1(T4MO), TG1(T3MO), and TG1(TOM) samples for the conversion of benzene to phenol, phenol to catechol, and catechol to 1,2,3-THB (FIG. 29). Filtered samples were injected into a Zorbax SB-C8 column (Agilent Technologies, 5 μm, 4.6×250 mm) with a Waters Corporation (Milford, Mass.) solvent delivery system coupled to a photodiode array detector (Waters 996). The gradient elution was performed with H$_2$O (0.1% formic acid) and acetonitrile (70:30 0-8 min, 40:60 15 min, 70:30 20 min) as the mobile phase at a flow rate of 1 mL/min. Under these conditions, the retention times for phenol, catechol, resorcinol, and hydroquinone standards were 9.6, 5.9, 5.0, and 4.3 min, respectively, and the absorbance maxima were 269, 276, 274, and 291 nm, respectively. For detection of 1,2,3-THB, an isocratic mobile phase of H$_2$O (0.1% formic acid)-acetonitrile (90:10) was used, and under these conditions, the retention times for catechol, 1,2,3-THB, and 1,2,4-THB were 12.6, 6.0, and 4.5 min, respectively, and the absorbance maxima were 276, 265, and 290 nm, respectively. Compounds were identified by comparison of retention times and UV-visible spectra to those of authentic standards as well as by co-elution with the standards. The identity of catechol and 1,2,3-THB were confirmed by reverse-phase liquid chromatography-mass spectrometer (LC-MS) using a Hewlett-Packard (Palo Alto, Calif.) 1090 series II Liquid Chromatograph with a diode array detector coupled to a Micromass Q-TOF2 (Beverly, Mass.) mass spectrometer. Separation of catechol from benzene and phenol was achieved using a Zorbax SB-C18 column (3 μm, 2.1×150 mm) with a mobile phase consisting of H$_2$O (0.1% formic acid) and acetonitrile and a gradient elution at 0.3 mL/min starting from 100% H$_2$O (0.1% formic acid) to 0% in 12 minutes, with a 3 minute hold at the final composition. Separation of 1,2,3-THB from catechol was achieved using a mobile phase comprising of 90% H$_2$O (0.1% formic acid) and 10% acetonitrile. The Q-TOF2 was operated in negative ion electrospray mode with 3.0 kV applied to the inlet capillary and 75V applied to the extraction cone. Benzene and toluene concentrations were measured by GC using a Hewlett-Packard 6890N GC equipped with an EC-WAX column (30 m×0.25 mm, 0.25 μm thickness; Alltech Associates, Inc., Deerfield, Ill.) and a flame ionization detector. The injector and detector were maintained at 250° C. and 275° C., respectively. The detection of benzene was achieved with a split ratio of 1:1 and helium as carrier gas at a constant flow rate of 1.0 mL/min. The temperature program was 50° C. for 6 min followed by 50° C.-250° C. at a rate of 20° C./min. Under these conditions, benzene eluted at 5.1 min, while the internal standard hexadecane eluted at 13.8 min. Separation of toluene oxidation products was achieved with a split ratio of 3:1 and helium as carrier gas at a constant flow rate of 0.8 mL/min. The temperature program for toluene oxidation was 80° C. for 5 min, 80° C.-205° C. at a rate of 5° C./min, 205° C.-280° C. at 15° C./min, and 280° C. for 5 min. Under these conditions, toluene, o-, p-, and m-cresols eluted at 4.2, 27.6, 29.3, and 29.5 min, respectively, while the internal standard hexadecane eluted at 17.8 min.

DNA sequencing. A dideoxy chain termination technique with the ABI Prism BigDye Terminator Cycle Sequencing Ready Reaction Kit (PerkinElmer, Wellesley, Mass.) and PE Biosystems ABI. 373 DNA sequencer (PerkinElmer, Wellesley, Mass.) was used to determine the T4MO and T3MO nucleotide sequence. Ten primers (FIG. 26) of 19 to 32 bp in length were generated from the wild-type T4MO sequence (GenBank M65106 and M95045) for sequencing T4MO tmoABCDEF in one direction, and 9 primers (FIG. 26) of 19-29 bp were designed based on the wild-type T3MO sequence (GenBank U04052) for sequencing T3MO tbuA1UBVA2C. Sequence data generated were analyzed using the Vector NTI software (InfoxMax, Inc., Bethesda, Md.).

Results

Benzene Oxidation Intermediates.

By analyzing benzene oxidation via a colorimetric assay, it was discovered that catechol was formed from benzene by TG1(T4MO) and TG1(T3MO) (results not shown). To corroborate these results, supernatants of TG1(T4MO), TG1(T3MO), or TG1(TOM) exponentially-grown cultures (on LB-kanamycin and reacted with about 165 μM benzene) were analyzed directly by reverse-phase HPLC, and two reaction products for both TG1(T4MO) and TG1(T3MO) were detected from benzene that co-eluted with authentic phenol and catechol standards and had the same UV-visible spectra. Phenol is known to be the intermediate of benzene oxidation by T4MO (Pikus et al., 1997) and T3MO (Olsen et al., 1994), thus no further work was performed to confirm the phenol product. LC-MS analysis further confirmed the identity of catechol by comparison of its mass spectrum with that of authentic catechol (major fragment ions at about m/z 109 (M-1)). It was observed from both HPLC and the colorimetric assay that the catechol concentration as a result of benzene oxidation decreased after reaching a maximum for TG1 (T4MO), TG1(T3MO), and TG1(TOM) (results similar to those of FIG. 28), which suggested catechol intermediates preceded a third oxidation product from benzene. HPLC identified 1,2,3-THB was produced from catechol by TG1 (T4MO), TG1(T3MO), and TG1(TOM); note it was clear that the product was not 1,2,4-THB based on its different retention time and UV-visible spectrum. LC-MS also confirmed the identity of that peak, which gave the same mass spectrum as that of authentic 1,2,3-THB (major fragment ion at about m/z 125 (M-1)).

Time Course of Benzene Oxidation.

Successive hydroxylation activity of TG1(T4MO), TG1 (T3MO), and TG1(TOM) was determined by GC analysis of benzene disappearance and by HPLC analysis of the hydroxylated products formed from about 165 µM benzene after a contact period of about 4 min-4 h (FIG. 28). The HPLC catechol concentrations were also corroborated by analogous, independent experiments using the colorimetric assay. The time course of benzene oxidation by TG1 (T4MO) (FIG. 28A) showed that along with the decrease of benzene, the three intermediates (phenol, catechol, and 1,2,3-THB) formed sequentially. Phenol concentrations transiently accumulated then rapidly subsided as catechol was produced, followed the synthesis of 1,2,3-THB which was relatively slow (FIG. 28A). As shown in FIG. 28B, TG1(T3MO) demonstrated a similar pattern of product formation, but showed relatively slower formation rates. TG1 expressing TOM, which is known to perform double hydroxylations of toluene to 3-methylcatechol (Newman et al., 1995), accumulated low concentrations of phenol and catechol but relatively high concentrations of 1,2,3-THB (FIG. 28C). The negative control TG1 pBS(Kan) lacking a monooxygenase did not produce any product under these conditions (data not shown); therefore, phenol, catechol, and 1,2,3-THB produced from benzene were from the expression of the cloned T4MO enzyme of *P. mendocina* KR1, the cloned T3MO enzyme of *R. pickettii*, and the cloned TOM enzyme of *B. cepacia* G4.

Phenol, Catechol, and 1,2,3-THB Formation Rates.

Analysis by both HPLC (FIG. 28) and by the colorimetric assay (results not shown) revealed benzene is converted to phenol, catechol, and subsequently to 1,2,3-THB. To quantify the rates of transformation, the initial reaction rates of benzene to phenol, phenol to catechol, and catechol to 1,2,3-THB at an initial concentration of about 165 µM for all substrates were investigated by TG1(T4MO), TG1(T3MO), and TG1 (TOM) using HPLC (FIG. 27). All the synthesis rates were corroborated by the corresponding substrate consumption rates; for example, the benzene disappearance rates for TG1 (T4MO) and TG1(T3MO) found by independent experiments using GC, about 19±1 and about 2.9±0.3 nmol/min.mg protein, respectively, were consistent with the phenol formation rates obtained by HPLC, about 19±1.6 and about 3±1 nmol/min.mg protein, respectively (FIG. 27). In addition, the rates of catechol formation from phenol (FIG. 27) were corroborated by independent HPLC experiments in which the rates of synthesis of catechol from benzene were measured (initial formation rate of catechol from benzene was measured to be about 5.3±0.2, about 1.3±0.7, and about 0.9±0.2 nmol/min.mg protein, respectively, for TG1(T4MO), TG1 (T3MO), and TG1(TOM)). Note that the catechol formation rates from benzene were two times slower than those from phenol because conversion of benzene to catechol was a two-step reaction requiring adequate concentrations of the phenol intermediate to accumulate before significant catechol was formed. Of the strains tested, the initial rates of phenol formation from benzene, catechol formation from phenol, and 1,2,3-THB formation from catechol were greatest in TG1 (T4MO) (FIG. 27). In the series of reactions (from benzene to 1,2,3-THB), both T4MO and T3MO showed comparable phenol and catechol formation rates; however, for 1,2,3-THB formation, TG1(T4MO) and TG1(T3MO) oxidized catechol 5-12 times slower. TG1(TOM) showed comparable rates of reaction for all three substrates (FIG. 27); hence, no large amounts of phenol or catechol accumulated as with TG1 (T4MO) and TG1(T3MO) (FIG. 28). Rates of phenol, catechol, and 1,2,3-THB synthesis were sustainable as shown in FIG. 28, and for TG1(T4MO) the yields were comparable to the initial benzene concentration (FIG. 27). Catechol in the presence of live, negative control cells TG1 pBS(Kan) or in Tris-HNO$_3$ buffer (pH 7.0) without cells was stable during the time scale of these experiments (up to 4 h). 1,2,3-THB was found unstable in the buffer system and turned brown rapidly (about 100% degraded after about 2 h); however, 1,2,3-THB in the presence of live TG1 pBS(Kan) cells was relatively stable with substantially no degradation during the first 30 min and about 15-60% of 1,2,3-THB was degraded after about 1-4 h. Hence, the time points for the initial rate data (FIG. 27) were taken in less than about 30 min for 1,2,3-THB and less than about one hour for catechol to minimize abiotic degradation and to accurately measure the oxidation rates.

Toluene Oxidation.

To compare the newly-discovered catechol and 1,2,3-THB formation rates to the rate of oxidation of the natural substrate, toluene, cells were contacted with about 165 •M toluene (initial concentration based on Henry's law) and the initial rate of toluene disappearance was monitored using GC (FIG. 27). These toluene oxidation rates (about 2.4-10 nmol/min.mg protein) are similar to the formation rates of phenol, catechol, and 1,2,3-THB (with the exception of 1,2,3-THB synthesis from T3MO); hence, the newly-discovered catechol and 1,2,3-THB activities of these enzymes are significant (FIG. 27).

Conclusions.

Aromatic hydroxylations are important bacterial metabolic processes but difficult using traditional chemical synthesis, so to convert the priority pollutant benzene into industrially-relevant intermediates using a biological catalyst, benzene oxidation was investigated. It was discovered that toluene 4-monooxygenase (T4MO) of *Pseudomonas mendocina* KR1, toluene 3-monooxygenase (T3MO) of *Ralstonia pickettii* PKO1, and toluene ortho-monooxygenase (TOM) of *Burkholderia cepacia* G4 convert benzene to phenol, catechol, and 1,2,3-trihydroxybenzene by successive hydroxylations. At a concentration of about 165 µM, under control of a constitutive lac promoter, *E. coli* TG1 pBS(Kan) T4MO expressing T4MO formed phenol from benzene at about 19±1.6 nmol/min.mg protein, catechol from phenol at about 13.6±0.3 nmol/min.mg protein, and 1,2,3-trihydroxybenzene from catechol at about 2.5±0.5 nmol/min.mg protein. The catechol and 1,2,3-trihydroxybenzene products were identified by both high pressure liquid chromatography (HPLC) and mass spectrometry. Using analogous plasmid constructs, *E. coli* TG1 pBS(Kan)T3MO expressing T3MO formed phenol, catechol, 1,2,3-trihydroxybenzene at a rate of about 3±1, about 3.1±0.3, and about 0.26±0.09 nmol/min.mg protein, respectively, and *E. coli* TG1 pBS(Kan)TOM expressing TOM formed 1,2,3-trihydroxybenzene at a rate of about 1.7±0.3 nmol/min.mg protein (phenol and catechol formation rates were about 0.89±0.07 and about 1.5±0.3 nmol/min.mg protein, respectively). Hence, the rates of synthesis of catechol by both T3MO and T4MO and the 1,2,3-trihydroxybenzene formation rate by TOM were found to be comparable to the rates of oxidation of the natural substrate toluene for these enzymes (about 10.0±0.8, about 4.0±0.6, and about 2.4±0.3 nmol/min.mg protein for T4MO, T3MO, and TOM, respectively, at about 165 µM toluene).

Example #5

Altering Toluene ortho-Monooxygenase of Burkholderia cepacia G4 for Regiospecific Hydroxylation of Indole to Form Indigoid Compounds Detailed Methods Chemicals and synthesis of isoindigo. Indigo, indirubin, isatin, 4-hydroxyindole, 5-hydroxyindole, and oxindole (FIG. 33A) were purchased from Fisher Scientific Company (Pittsburgh, Pa.). 6-Hydroxyindole was obtained from Matrix Scientific (Columbia, S.C.). All materials used were of the highest purity available and were used without further purification. Lacking a commercial source, isoindigo (FIG. 33A) was prepared as described previously by reacting isatin (FIG. 33A, 19 mmol) with oxindole (FIG. 33A, 14 mmol) under acidic conditions in a mixture of 30 mL glacial acetic acid and 0.5 mL concentrated hydrochloric acid with stirring at 95° C. for 3 hrs. The resulting dark brown precipitate was filtered and washed with methanol and diethyl ether. The final pigment was identified both by its UV-visible absorbance spectrum and by mass spectroscopy using a Hewlett-Packard (Palo Alto, Calif.) 1090 series II Liquid Chromatograph with a diode array detector coupled to a Micromass Q-TOF2 (Beverly, 15 MA) mass spectrometer. The major ion of m/z 263.1 (MH+) matched the molecular weight of 262, and the UV-visible spectrum also matched the published data for isoindigo.

Bacterial strains and growth conditions. Escherichia coli strain TG1 (supE hsd.5 thi .(lac-proAB) F.[traD36 proAB+ lacIq lacZ.M15]) (42) was utilized as the host for gene cloning and expression. TG1 was routinely cultivated at 37° C. in Luria-Bertani (LB) medium with kanamycin (100 •g/mL) added to maintain the plasmid pBS(Kan)TOM which expresses tomA012345 from a constitutive lac promoter.

DNA shuffling of TOM. DNA shuffling was performed as reported to generate TOM-Green which was an adaptation of the methods of Stemmer and Zhao and Arnold. A 3.5-kb fragment was subjected to DNA shuffling; this fragment was flanked by the naturally-occurring AvrII and PpuMI restriction sites which were used to clone the shuffled fragment in pBS(Kan)TOM. Effectively shuffled were all of tomA2A3A3, 57% of tomA1, and 56% of tomA5. Cells were screened based on colony color (e.g., blue, green) on LB kanamycin plates.

Site-directed saturation mutagenesis. Saturation mutagenesis was performed at sites N14 and A113 as well as simultaneously at sites V106 and A113 of TOM-Green TomA3 (GeneBank accession no. AF349675). By replacing the target codon with NNN via overlap-extension polymerase chain reaction (PCR), all 64 codons were created at the corresponding positions. The primers used in this study are listed in FIG. 30. Degenerate primers, N14 Front and N14 Rear, were designed to randomize position N14 in the nucleotide sequence; A113 Front and A113 Rear, were designed to randomize position A113; and V106+A113 Front and V106+A113 Rear were used to randomize positions V106 and A113 at the same time. The two additional primers for cloning were BclI Front and SphI Rear, where the two restriction enzyme sites, BclI and SphI, occur naturally in TomA3 upstream and downstream, respectively from position N14 and A113. For saturation mutagenesis of TomA3 A113, plasmid pBS(Kan) TOM was used as the template, and Pfu DNA polymerase (Stratagene Corp., La Jolla, Calif.) was used in the PCR to minimize random point mutations. A 499 bp DNA degenerate fragment was amplified using primers BclI Front and A113 Rear, 15 and a 152 bp DNA degenerate fragment was amplified using SphI Rear and A113 Front. After purifying from agarose gels, the two PCR fragments were combined at a 1:1 ratio as templates to obtain the full-length PCR product with the BclI Front and SphI Rear primers. A PCR program of 30 cycles of 94° C. for 45 s, 55° C. for 45 s, and 72° C. for 1.5 min, with a final extension of 72° C. for 10 min was used. The resulting randomized PCR products (603 bp) were cloned into pBS(Kan)TOM after double digestion with BclI and SphI and replaced the corresponding fragment in the original plasmid. The resulting plasmid library was electroporated into E. coli TG1 competent cells using a Bio-Rad GenePulser/ Pulse Controller (Bio-Rad Laboratories, Hercules, Calif.) at 15 kV/cm, 25 •F, and 200. An analogous procedure was used for saturation mutagenesis at N14 (PCR products of 201 bp, 449 bp, and 603 bp) as well as for simultaneous saturation mutagenesis for V106/A113 (PCR products of 486 bp, 160 bp, and 603 bp). Cells were screened based on colony color (e.g., blue, green, yellow) on LB kanamycin plates.

DNA sequencing. A dye terminator cycle sequencing protocol based on the dideoxy method developed by Sanger et al. was used to sequence the sub-cloned region (603 bp) in the TOM color variants using the BclI Front and SphI Rear primers and the ABI. Prism BigDye Terminator Cycle Sequencing Ready Reaction Kit (Perkin-Elmer, Wellesley, Mass.). A PE Biosystems ABI. 373 DNA sequencer (Perkin-Elmer, Wellesley, Mass.) was used for analyzing the fluorescently-labeled DNA fragments by gel electrophoresis. Sequence data were analyzed using the Vector NTI Suite sequencing alignment editor (InforMax Inc. Frederick, Md.).

Isolation and characterization of indigoid compounds. To identify the colored compounds formed during cell growth in complex medium, TG1 expressing TOM variants were grown in 50 mL of LB medium inoculated from fresh, single colonies. After overnight (13-14 hrs) incubation at 37° C., the entire culture was extracted once with an equal volume of chloroform since colored compounds may be associated with the cell material. For wild-type TOM, the cell culture was started from a fresh pre-culture (OD 1.2, 0.4% inoculum), and after 3 hrs incubation at 37° C., isopropyl-•-D-thiogalactopyranoside (IPTG) (0.4 mM) was added for additional TOM expression for 15-16 hrs. The chloroform layer was separated from the aqueous layer by centrifugation and dried with anhydrous sodium sulfate. Chloroform-extracted products were concentrated to 4 mL and qualitatively analyzed by thin-layer chromatography (TLC) on activated silica gel plates (Selecto Scientific, Suwanee, Ga.), which were developed with toluene-acetone (4:1). To confirm that indole is the precursor of the indigoid compounds, exponentially-growing TG1 expressing wild-type TOM, TOM-Green (V106A), or TOM A113G was harvested at OD 1.2 (note color does not develop until OD approximately 2 so these cultures were uncolored) was washed and resuspended in Tris.HCl buffer to an OD of 2.5 and incubated with 0.5 mM indole for 3 hrs, then the whole cells were extracted once with an equal volume of chloroform (TG1/pBS(Kan) was the negative control). The chloroform layer was again dried with anhydrous sodium sulfate after centrifugation separation from the aqueous phase. To investigate whether the unknown colored compounds produced by TomA3 A113G in TG1 were from hydroxylation of the indole benzene ring, exponentially-grown cultures of TG1 expressing A113G (OD 1.2) were washed and resuspended in 40 mL of Tris.HCl buffer at an OD of 2.5 and incubated with 0.5 mM 4-, 5-, and 6-hydroxy-indole for specific times (3.5 hrs for 5-hydroxyindole and 20 hrs for 4-hydroxyindole and 6-hydroxyindole) and extracted once with an equal volume of chloroform. As controls, TG1 expressing wild-type TOM, TG1/pBS(Kan), and Tris.HCl buffer were also incubated with the 3 substrates. The chloroform layer was further separated and concentrated the same way as above for high performance HPLC analysis. Quantitative analysis and separation of the pigments and intermediates were conducted using an HPLC system from Waters Corp. (Milford, Mass.), including 515 HPLC pumps, a 996 photodiode array detector, and Millenium32 Chromatography Manager Software. Analysis was done with a Zorbax C8 (4.6×250 mm, 5 •m) reverse-phase column from Agilent Technologies (Palo Alto, Calif.) with a flow rate of 1.0 mL/min using gradients composed of 0.1% formic acid in $H_2O$ (HPLC grade) and acetonitrile: 15 min from 0 to 60% acetonitrile; 22 min hold at 60% acetonitrile; 32 min from 60 to 0% acetonitrile. UV/visible spectra were acquired online using a diode array detector (scanning from 200 to 700 nm) to characterize and quantify the indole oxidation and dimmer-ization products. Products were identified by comparing the retention times and UV-visible spectra with authentic standards, and were confirmed by co-eluting with the standards. The indigoid compounds formed by wild-type TOM were analyzed by LC-MS using a Hewlett-Packard (Palo Alto, Calif.) 1090 series II Liquid Chromatograph coupled to a Micromass Q-TOF2 (Beverly, Mass.) mass spectrometer.

Homology structure modeling. Part of the amino acid sequence of TOM α-subunit (residues 95-250 of TomA3) was modeled into the known three-dimensional structure of the homologue sMMO hydroxylase (PDB accession code 1 MTY) from *Methylococcus capsulatus* (Bath) using SWISS-MODEL Server. The approximate three-dimensional coordinates for the atoms of the TOM model were obtained, and a molecular visualization program, Swiss-PdbViewer, was utilized to visualize and manipulate the model, including performing amino acid substitutions isosterically at A 113/V106 based on residue interactions, steric hindrance, and energy minimization.

Results

Identification of Indigoid Compounds from the Tom Variants.

Extraction and HPLC analysis identified the major compounds produced by TG1 expressing TOM color variants. The concentration of each compound was determined by making calibration curves under the same HPLC conditions. The concentration of the colored compounds produced by each TOM variant are listed in FIG. 32 (the color of the chloroform extract from the broth sometimes is a slightly different color than that of the colonies and LB broth). In addition, when the cells expressing TOM variants were incubated with indole, the same indigoid compounds were obtained as cells growing in complex medium. The compounds were identified by HPLC (not shown), and the results are exemplified by TOM-Green (V106A) which produced isatin, indigo, and indirubin as the majo colored compounds after incubation with indole, the same as the products generated from LB medium (FIG. 32). No colored products were produced in the absence of indole. These results indicate that the colored compounds originate from indole. Further, the monooxygenase is responsible for color formation since no colored compounds were produced from indole by the negative control TG1/pBS(Kan) (which lacks the monooxygenase). The qualitative analysis of colored compound by TLC (data not shown) also corroborated our HPLC results. The indole hydroxylation patterns of the mutants vary and may be categorized into several groups. Wild-type TOM expressed in TG1 is unique in its brown color seen both on LB agar plates and in LB liquid medium, and in its ability to produce isoindigo as the primary product (about 146 •M) as well as indigo (about 12.5 •M) and isatin (about 11 •M) which were not found with other variants. L C-MS analysis corroborated that isoindigo is the primary indigoid compound formed by wild-type TOM since the major peak has the predominant ion of about m/z 263.1 (MH+) that appears with the retention time of isoindigo. TG1 expressing mutant TomA3 A113V hydroxylated indole mainly into indigo (about 90%), and indirubin only accounts for a very minor part (about 5%). Mutants V106S/A113V and A113H produced isatin as the major compound (>50%), while indigo and indirubin ranked as minor products with similar amounts. This product distribution may contribute to their vivid blue color on agar plates. Mutants V106H/A113S and V106I/A113S may also fall into this category based on cell color and indigoid compounds produced. Another category includes the mutants A113S, A113F, and A113I, which share the common features that they appeared as pale-blue colonies on agar plates (chloroform extract was purple) and produced indirubin as the major products (about 60%). They also produced about 30% indigo and about 10% isatin. V106F is unique in that it was blue on agar plates but brown in liquid cultures. Although it did not produce any special compounds, it was characterized by its exceptionally low production of isatin (about 1%), which together with about 44% indigo and about 55% indirubin, may contribute to its cell color. Both mutants V106A and V106P were green on agar plates, and their cell color stems from that the mixture of indigo (about 52% and about 73%, respectively) and isatin (about 38% and about 21%, respectively) are formed. The TOM A113G variants are also interesting. Together with the V106-substitution variants, they add a great variety to the color development from indole oxidation. TOM A113G does not produce isatin, indirubin, or isoindigo, which means that it was not capable of indole C-3 or C-2 hydroxylation. Instead, it produces colored compounds with absorbance within the visible spectrum around 400 nm which contribute to its orange-colored colony and yellow chloroform extracts. These compounds appear to be the result of hydroxylation of the indole benzene ring (rather than the pyrrole ring) and subsequent dimerization since two of the four unknown colored compounds (FIG. 32) that were produced by TG1 expressing A113G were found when these cells were incubated with 4-hydroxyindole (4-hydroxyindole itself is not colored). These compounds were not found with TG1 expressing wild-type TOM with 4-hydroxyindole, in the absence of monooxygenase with 4-hydroxyindole, nor in the absence of 4-hydroxyindole. The other two unknown colored compounds may be derived from 7-hydroxyindole as A113G in TG1 incubated with 5- or 6-hydroxyindole did not yield any of the unknown compounds. Substitution at position V106 of TomA3 (V106A, V106D, and V106N) in addition to the A113G mutation restores the ability of the enzyme to produce isatin, indigo, and indirubin in addition to the original unique colored compounds associated with TOM A113G. This is shown by V106Q/A113G variant which actually produced the highest amount of indigo (about 388 •M) in vivo. Although indole C-3 hydroxylation was not restored in the V106P/A113G variant, it was able to produce more colored compounds than A113G. Whereas whole cells expressing wild-type TOM primarily produce isoindigo, by altering the residues at V106 and A113, primarily indirubin can be made by A113S, A113F, and A113I, primarily indigo can be made by A113V, and primarily isatin can be made by V106S/A113 and A113H.

Structural Modeling.

An approximate three-dimensional structure of part of the TOM •-subunit (residues 95-250 of TomA3) was created using the crystal structure of sMMO from *Methylococcus capsulatus* as the template (Rosenzweig et al., 1997). The quality of the model was deemed to be good as judged by the conservation of positions of the diiron coordinating residues in TOM (E110, E140, H143, E201, E235, and H238) compared to sMMO (the average distance of the C• carbons of the model to sMMO for the metal binding residues is about 0.07 Å). Although there are limitations to homology modeling (Guex et al., 1999) and no absolute statement can be made due to the low homology between TOM and sMMO (about 30% identity in the modeled part), the model did help to visualize the active site of TOM. TOM contains two Glu-Glu-His segments (Glu110-Glu140-His143 and Glu201-Glu235-His238) serving as ligands to the diiron center located in a four-helix bundle which are also conserved in sMMO (Rosenzweig et al., 1993, and 1997). At the dinuclear iron center, oxygen is activated, and substrate hydroxylation coupled to NADH oxidation occurs (Kopp and Lippard, 2002). Both TomA3 residues V106 and A113 are constituents of the hydrophobic pocket adjacent to the binuclear iron cluster and located in the same •-helix of the four-helix bundle of TomA3. Both of the sites are in the vicinity of the diiron center, but notably, A113 is located closer to the diiron center than V106: about 6.88 Å versus about 8.35 Å to the canonical FeA site (the iron that coordinated by E110, E140, and H143 in TOM), and about 6.96 versus about 10.41 Å to the FeB site (the iron that coordinated by E201, E235, and H238).

Conclusions.

Previously random mutagenesis produced a mutant of toluene ortho-monooxygenase (TOM) of *Burkholderia cepacia* G4 containing the VI 06A substitution in the hydroxylase •-subunit (TomA3) that changed the color of the cell suspension from wild-type brown to green in rich medium (*J. Bacteriol.* 184:344, 2002). Here, DNA shuffling was used to isolate a random TOM mutant that turned blue due to mutation TomA3 A113V. To better understand the TOM reaction mechanism, we have studied the specificity of indole hydroxylation using a spectrum of colored TOM mutants expressed in *Escherichia coli* TG1 and formed as a result of separate and simultaneous site-directed saturation mutagenesis at TomA3 positions A113 and V106. Colonies expressing these altered enzymes range in color from blue through green and purple to orange, and enzyme products were identified using HPLC and LC-MS. Enzymes were identified that produce primarily isoindigo (wild-type TOM), indigo (A113V), indirubin (A113I), and isatin (A113H and V106A/A113G). Cells expressing wild-type TOM oxidize indole via C-2 hydroxylation with the formation of isoindigo in addition to C-3 hydroxylation leading to indigo; variant TOM A113G is unable to form indigo, indirubin, or isoindigo, but produces unknown yellow compounds from indole hydroxylation presumably at the indole benzene ring. Mutations at V106 in addition to A113G restored C-3 indole oxidation so along with C-2 indole oxidation, isatin, indigo, and indirubin were formed in TG1. Other TomA3 V106/A113 mutants with hydrophobic, polar, or charged amino acids in place of the Val and/or Ala residues hydroxylated indole at the C-3 and C-2 positions forming isatin, indigo, and indirubin in a variety of distributions. A structural model was built for TOM based on the soluble methane monooxygenase X-ray structure and possible reasons for the alteration in the regiospecificity of indole hydroxylation and variation in products distribution are proposed.

Example #6

Protein Engineering of Toluene-o-Xylene Monooxygenase from *Pseudomonas stutzeri* OX1 for Oxidizing Nitrobenzene to 3-Nitrocatechol, 4-Nitrocatechol, and Nitrohydroquinone Detailed Methods Bacterial strains, growth conditions, and SDS-PAGE. *Escherichia coli* strain TG1 (supE hsd.5 thi .(lac-proAB) F.[traD36 proAB+ lacIq lacZ.M15]) was utilized as the host with pBS(KAN)ToMO and its variants which express the touABCDEF genes form a constitutive lac promoter. Cells were initially streaked from −80° C. glycerol stocks on Luria-Bertani (LB) agar plates (Sambrook et al., 1989) containing 100 ug/ml kanamycin and incubated at 37° C. with shaking at 250 rpm (New Brunswick Scientific Co., Edison, N.J.). The relative expression of the touA loci from *E. coli* TG1/pBS (Kan)ToMO was evaluated using sodium dodecyl sulfate-polyacrylamide gel electrophoresis (SDS-PAGE) (Sambrook et al., 1989) with a 12% Tris-HCl gel both with and without 1 mM isopropyl-β-D-thiogalactopyranoside (IPTG, Fisher Scientific, Co., Fairlawn, N.J.).

Chemicals. NB, toluene, o-xylene, and p-cresol were purchased from Fisher Scientific Co. (Fairlawn, N.J.); o-cresol and m-cresol were purchased from Sigma Chemical Co. (St. Louis, Mo.); 4-NC, 2-nitroresorcinol (2-NR), o-NP, M-NP, and p-NP were obtained form Acros Organics (Morris Plains, N.J.); 2—NHQ was obtained from Frinton Labs (Vineland, N.J.), and 3-NC was obtained from Vitas-M (Moscow, Russia). All materials used were of the highest purity available and were used without further purification.

Saturation Mutagenesis and DNA Shuffling of ToMO. Saturation mutagenesis at positions I100, Q141, T201, and F205 of the alpha subunit (touA) of ToMO and DNA shuffling of 90% of touA of ToMO was performed as described previously (Vardar and Wood, 2004).

Colony screening for NB and p-NP. A nylon membrane plate assay was used as described previously (Vardar and Wood, 2004). The mutant libraries were first streaked from transformant plates to LB (100 ug/mL kanamycin) agar plates containing 1% (w/V) glucose. The glucose grown colonies were then transferred to fresh LB (100 ug/mL kanamycin) plates containing 1 mM substrate (NB or p-NP) with a nylon membrane. After incubating for 24 hours at room temperature in a chamber, the colonies were checked visually to search for those that developed a red color around the call mass, indicating the formation of NCs or NHQ from NB or p-NP. The control expressing wild-type ToMO remained yellow on NB (indicates the formation of NPs only) and very light red on p-NP agar plates (indicates the formation of small amounts of 4-NC). The negative control expressing no monooxygenase, TG1/pBS(Kan), remained colorless on NB and p-NP. At least three replicates were checked before proceeding with HPLC analysis.

Product identification and rates of formation. The possible mutants initially identified by screening via the agar plate assay were further examined by reverse-phase HPLC. Experiments were conducted with exponentially-grown cells harvested at an optical density at 600 nm (OD) of 1.0. Centrifuged cells [6,000 g for 5 min at 25 C (JA-17 rotor in a J2 series centrifuge, Beckman, Palo Alto, Calif.)] were washed once with 1 volume 50 mM Tris-$HNO_3$ buffer, pH 7.0 and resuspended to an OD of 5-10. Cell suspensions (2.5 mL) were sealed with a Teflon-coated septum and aluminum seal in 15 mL glass vials, and the substrates, NB at 200 uM and o-NP, m-NP, and p-NP at 500 uM were added from ethanol stock solutions. After contacting at room temperature, 1 mL of the cell suspension was centrifuged for 2-3 min, the supernatants (500 uL) were filtered with a 1 mL syringe (Becton Dickinson) coupled to a nylon membrane filter unit (Millex-HN, 0.45 um, 4 mm), and the samples were analyzed with HPLC. A Zorbax SB-C8 column (Agilent Technologies, 5 um, 4.6×250 mm) was used with a Waters Corporation (Milford, Mass.) solvent delivery system coupled to a photodiode array detector (Waters 996) and injected by an autosampler (Waters 717 plus). To detect an determine the formation rates of nitro-substituted catechols, nitro-substituted resorcinols, and nitro-substituted hydroquinone, a gradient elution was performed with $H_2O$ (0.1% formic acid) and acetonitrile (70: 30 0-8 min, 40:60 15 min, 70:30 20 min) as the mobile phases at a flow rate of 1 mL/min. A supelcosil ABZ+PLUS column (Supelco TEchologies, 3 um, 15 cm×4.6 mm) was used to separate 3-NC, NHQ, and 2-NR from o-NP. To detect and determine the formation rates of NHQ and 3-NC from o-NP, a gradient elution was performed with H2O (0.1% formic acid) and acetonitrile (80:20, 0-20 min) as the mobile phases at a flow rate of 1 mL/min. A gradient elution was performed with $H_2O$ (0.1% formic acid) and acetonitrile (95:05, 0-60 min) for a better separation of 2-NR and 3-NC from o-NP (FIG. 34), and the enzyme products were co-eluted with authentic standards. At least two independent cultures were analyzed for each substrate and strain tested, and at least five injections were made for each substrate, The molar amounts of products formed was calculated using calibration curves for each product. Initial product formation rates were determined by sampling at 15 minute intervals for 2 hrs and were quantified in nmol/(min.mg protein) by converting product peak areas to concentration using standard curves prepared at the specific absorbance wavelength (FIG. 34) for each product formed. Protein content was 0.22 mg protein/(mL 1 OD) for recombinant *E. coli* TG1 as determined using the Protein Assay Kit (Sigma Diagnostics Inc., St. Louis, Mo.). To determine the toluene oxidation rates and regiospecificities, gas chromatography experiments were performed as described previously (Vardar and Wood, 2004). To determine o-xylene oxidation rates and regiospecificities, the same conditions were used as for toluene (Vardar and Wood, 2004); the retention times for o-xylene, 2,3-dimethylphenol (2,3-DMP), and 3,4-DMP were 6.5, 30.3, and 31.7 min, respectively.

DNA sequencing. A dideoxy chain termination technique (Sanger et al., 1977) with the ABI™ Prism BigDye Terminator Cycle Sequencing Ready Reaction Kit (PerkinElmer, Wellesley, Mass.) and PE Biosystems ABI™ 373 DNA sequencer (PerkinElmer, Wellesley, Mass.) was used to determine the ToMO nucleotide sequences.

Modeling of ToMO TouA. Part of the wild-type ToMO TouA alpha-subunit (amino acid residues W44-N380) was modeled using SWISS-MODEL Server (Peitsch, 1995; Guex and Peitsch, 1997; Schwede et al., 2003) and was based on the sMMO MmoX alpha-subunit (polymer chain D) from M. capsulatus (Bath) (Rosenzweig et al., 1997). The E214G and D312N mutations were modeled from the generated wild-type TouA ToMO model using the Swiss-Pdb Viewer program (DEEPVIEW) (Pietsch, 1995; Guex and Peitsch, 1997; Schwede et al., 2003). The program Swiss-Pdb Viewer performed the amino acid substitutions isosterically for the ToMO TouA based on residue interaction s, steric hindrance, and energy minimization.

Results

Oxidation of NB by wild-type ToMO and high-activity mutants. The pathways for the oxidation of NB to NPs, NC, and NHQ with wild-type ToMO and high activity TouA variants (I100Q, M180T/E284G, and E214G/D312N/M399V) are shown in FIGS. 35, and 37. There is no previous report about the hydroxylation of NB or NPs by ToMO. Here, it was discovered that *E. coli* TG1/pBS(Kan)ToMO expressing wild-type ToMO performs two different hydroxylations and forms m-NP (about 72%) and p-NP (about 28%) with an initial rate of about 0.098 and about 0.031 nmol/min.mg protein from 200 μM NB (FIG. 35). Interestingly, ToMO does not form o-NP from NB. No 4-NC peak was observed from about 200 μM NB with TG1 expressing wild-type ToMO. Here, it was also discovered that ToMO hydroxylates m-NP and p-NP and forms 4-NC (about 0.15 and about 0.0082 nmol/min.mg protein, respectively). Also, from about 500 μM o-NP, ToMO forms 3-NC (about 18%) and NHQ (about 82%) with an initial rate of about 0.11 and about 0.48 nmol/min.mg protein, respectively. The negative control, TG1 expressing pBS(Kan), did not form NPs or NCs; therefore, ToMO is responsible for the formation of NP, NC, and NHQ. All the substrate (NB, o-NP, m-NP, and p-NP) disappearance rates were similar with the overall product (m-NP, p-NP, 4-NC, 3-NC, and NHQ) appearance rates with wild-type ToMO and the TouA mutants. For example, there was a good agreement between the formation rate of m-NP and p-NP from NB and the disappearance rate of NB with wild-type ToMO (about 0.15 nmol NB react/min.mg protein vs. about 0.13 nmol m-NP formed and p-NP formed/min.mg protein). TouA DNA shuffling mutant E214G/D312N/M399V hydroxylates NB at elevated rates compared with the wild-type ToMO. Mutant E214G/D312N/M399V performs the hydroxylation both at positions 3 and 4 and forms m-NP (about 73%) (about 6-fold faster than wild-type ToMO) and p-NP (about 27%) (about 6.2-fold faster than wild-type ToMO) from NB (FIG. 35). Mutant E214G/D312N/M399V forms 4-NC from about 200 μM NB, whereas wild-type ToMO does not. Mutant E214G/D312N/M399V hydroxylates NB with higher rates compared to wild-type ToMO, but gives no substantial shift in the product distribution (about 73% m-NP and about 27% p-NP with mutant E214G/D312N/M399V vs. about 72% m-NP and about 28% p-NP with wild-type ToMO, FIG. 35). TouA DNA shuffling mutant M180T/E284G hydroxylates NB and forms m-NP and p-NP with substantially different regiospecificities (about 95% m-NP and about 5% p-NP for mutant M180T/E284G vs. about 72% m-NP and about 28% p-NP for wild-type ToMO) and at elevated rates compare to wild-type ToMO (mutant M180T/E284G forms m-NP about 4.6-fold faster than wild-type ToMO, FIG. 35). Different from wild-type ToMO, mutant M180T/E284G forms 4-NC from about 200 μM nitrobenzene. TouA saturation mutagenesis mutant I100Q also hydroxylates NB and forms m-NP and p-NP like wild-type ToMO does but it does so with a different regiospecificity and with elevated rates (FIG. 35). Mutant I100Q forms m-NP about 1.5-fold faster than wild-type ToMO and p-NP about 3-fold faster than wild-type ToMO from NB (FIG. 36).

The I100Q mutation caused a shift in product distribution for the hydroxylation of NB with about 61% m-NP and about 44% p-NP formed, whereas wild-type ToMO made about 72% m-NP and about 28% p-NP (FIG. 35). TouA DNA shuffling mutant A110T/E392D forms m-NP (about 78%) (about 1.7-fold faster than wild-type ToMO) and p-NP (about 22%) (about 1.5-fold faster than wild-type ToMO) from NB (FIG. 35). Different from wild-type ToMO, mutant A110T/E392D forms 4-NC from about 200 µM NB. No substantial shift in the product distribution for the hydroxylation of NB was observed with this mutant (FIG. 35). TouA DNA shuffling mutant A101T/M114T hydroxylates NB and forms m-NP and p-NP like wild-type ToMO does but with a different regiospecificity (FIG. 35). Mutant A101T/M114T oxidized NB to form more m-NP (about 84%) and less p-NP (about 16%) than wild-type ToMO. Mutant A101T/M114T forms m-NP about 2-fold faster than wild-type ToMO. Different from wild-type ToMO, mutant A101T/M114T forms 4-NC from about 200 µM NB. Substrate inhibition was observed with NB with all strains. For example, mutant I100Q forms m-NP and p-NP with an initial rate of about 0.37 and about 0.24 nmol/min.mg protein, respectively at about 100 µM NB, but these rates are reduced by about 62% and about 63%, respectively at about 200 µM NB, and about 80% and about 75%, at about 800 µM NB. Similar behavior was observed when NPs were used as substrates.

Oxidation of NB by low activity mutants of ToMO. The oxidation of NB with wild-type ToMO and low activity TouA variants are shown in FIG. 36; the rate of NP formation is decreased about 12 to about 9-fold compared to that by the wild-type ToMO but there were interesting changes in oxidation regiospecificity. TouA saturation mutagenesis mutants I100H and F205Y oxidize about 200 µM NB to form only p-NP (about 100%) unlike wild-type ToMO (about 72% m-NP and about 28% p-NP) but with lower rates (FIG. 36). A substantial shift for the hydroxylation of NB is also observed with TouA saturation mutagenesis mutant F205H which oxidizes NB to form only m-NP (about 100%) unlike wild-type ToMO (FIG. 36). TouA saturation mutagenesis mutant F205G hydroxylates NB and forms m-NP (about 65%) and p-NP (about 35%) similar to wild-type ToMO but with lower rates (FIG. 36). No products with about 200 µM NB are observed with TouA DNA shuffling mutants W266R and T281A/F290S and for TouA saturation mutagenesis mutants F205C and T201G.

Oxidation of NPs by wild-type ToMO and TouA mutants. FIG. 37 summarizes the products obtained from whole cell oxidation of o-NP, m-NP, and p-NP with wild-type ToMO and TouA mutants I100Q, M180T/E284G, and E214G/D312N/M399V. For o-NP, all mutants produce mixtures of NHQ and 3-NC, but with different rates. Wild-type ToMO forms NHQ (about 82%) and 3-NC (about 18%) from o-NP; however, mutant E214G/D312N/M399V forms NHQ (about 86%) about 3.6-fold faster and 3-NC (about 14%) about 2.6-fold faster than wild-type ToMO. Mutant M180T/E284G gives a regiospecific change by forming more NHQ (about 91%) and less 3-NC (about 9%) from o-NP; this mutant forms NHQ about 2.7-fold faster than wild-type ToMO. Mutant I100Q forms NHQ (about 84%) and 3-NC (about 16%) from o-NP like wild-type ToMO. For m-NP, mutant I100Q has a different regiospecificity for the hydroxylation of m-NP. Wild-type ToMO forms only 4-NC (about 100%) from m-NP; however, mutant I100Q forms NHQ (about 63%) and 4-NC (about 37%). Like wild-type ToMO, mutant E214G/D312N/M399V forms 4-NC (about 100%) but it does so at an elevated rate (about 3.6 fold faster than wild-type ToMO). Mutant M180T/ E284G also forms 4-NC about 1.2 fold faster than wild-type ToMO from m-NP. The data presented in FIG. 37 also show the biochemical pathways for the oxidation of p-NP. Wild-type ToMO forms 4-NC from p-NP. Like wild-type ToMO, TouA mutants I100Q, M180T/E284G, and E214G/D312N/M399V form 4-NC from p-NP, but with higher initial formation rates (about 20, about 4.5, and about 1.7 fold, respectively). The activity of NP oxidation with TouA mutants A110T/E392D and A101T/M114T (high-activity NB mutants) did not increase, and the oxidation regiospecificity was unchanged (data not shown).

Oxidation of toluene and o-xylene by wild-type ToMO and TouA mutants. Oxidation rates and regiospecificity for the natural substrate toluene by wild-type ToMO and mutants I100Q, F205G, and M180T/E284G were reported previously by us (Vardar and Wood, 2004). The I100Q mutation caused a shift in product distribution for the first hydroxylation of toluene and made about 22% o-cresol, about 44% m-cresol, and about 34% p-cresol whereas wild-type ToMO made about 2% o-cresol, about 21% m-cresol, and about 47% p-cresol which agreed with Bertoni et al. (1996). Mutant M180T/E284G gave no substantial shift in the product distribution for the first hydroxylation but the rate of toluene oxidation increased slightly (about 1.2 fold) (Vardar and Wood, 2004). Here, the toluene activity of mutants E214G/D312N/M399V, A110T/E392D, A101T/M114T, I100H, T201G, F205H, F205Y, T281A/F290S, and W266R are reported (FIG. 38). Mutant E214G/D312N/M399V gave no substantial shift in the product distribution (about 35% o-cresol, about 22% m-cresol, and about 43% p-cresol) and oxidized toluene (about 91 µM according to Henry's law) with an initial rate slightly lower than wild-type ToMO. The I100H and T201G mutations caused a shift in product distribution for the first hydroxylation of toluene (about 60% p-cresol formed for I100H and about 53% o-cresol for T201G) and reduced the rate of toluene oxidation compare to wild-type ToMO. The regiospecificity of toluene is slightly changed with mutants A110T/E392D, A101T/M114T, F205H, and F205Y (FIG. 38). No products are observed with TouA mutants W266R, T281A/F290S from about 90 µM toluene. The oxidation rates and regiospecificity for the second natural substrate, o-xylene, by wild-type ToMO and mutants I100Q, I100H, and T201G were also measured (FIG. 39). Wild-type ToMO oxidizes o-xylene (about 106 µM according to Henry's law) with an initial rate of about 1.78 nmol/min.mg protein and makes about 82% 3,4-dimethylphenol (DMP) and about 18% 2,3-DMP which agreed with the results Bertoni et. al. (1996). The best regiospecific mutants of toluene (mutants I100H, I100Q, and T201G) gave a slight shift in the product distribution for the hydroxylation of o-xylene (FIG. 39). For example, mutant I100Q makes about 76% of 3,4-DMP and about 24% of 2,3-DMP, whereas wild-type ToMO makes about 82% of 3,4-DMP and about 18% of 2,3-DMP from o-xylene.

Enzyme Expression level. The expression level of TouA variant E214G/D312N/M399V remained approximately the same as that of wild-type ToMO. The expression levels of TouA variants I100Q, F205G, and M180T/E284G were reported previously (Vardar and Wood, 2004) both TouA variants I100Q and F205G are expression down mutants as evidenced by SDS-PAGE with a single nucleotide change in one codon leading to less-elevated protein expression (about 1.5-2 fold). The expression level of variant M180T/E284G remained approximately the same as that of wild-type ToMO. Hence, the increase in the activity of mutants E214G/D312N/M399B and M180T/E284G derives from the amino acid substitutions rather than protein expression level changes; for TouA mutants I100Q and F205G, the activity might be about 2-fold more than it is reported.

ToMO TouA modeling. Although there are limitations to homology modeling (Guex et al., 1999; Schwede et al., 2003), the model did help to visualize the positions of the side chains for the variant E214G/D312N/M399V. The substantial increase in the oxidation rate of nitroaromatics by variant E214G/D312N/M399V suggests these substrates dock in the active site in an altered manner when these residues are altered; however, the advantage of directed evolution is that mutations like these may be identified even though their impact is through subtle, longer range interactions (Joo et al., 1999). The accuracy of the wild-type ToMO TouA alpha-subunit model was judged by the conservation of the spatial positions of the diiron-coordinating residues in ToMO (E104, E134, H137, E197, E231, and H234) compared to those of sMMO (E114, E144, H147, E209, E243, and H246 (Rosenzweig et al., 1997)). The average distance between the C• carbons of the target ToMO model relative to the sMMO template for the metal binding residues was about 0.075 Å. To allow for a better fit between the template and target sequence, different portions of the target DNA were modeled, and W44-N380 of TouA (337 amino acid) resulted with the highest amino acid identity (about 27.4%). When 304 residues (out of 337) of sMMO and ToMO alpha subunit were superimposed upon each other, the root-mean-square between pairs of C• atoms were found to be about 0.07 Å. Since proteins which have about 50% amino acid sequence identity deviate by about 1 Å and since identical proteins solved by NMR can deviate by more than about 1 Å (Guex et al., 1999), the ToMO TouA model generated by SWISS-MODEL should be reliable.

Conclusions.

Toluene-o-xylene monooxygenase (ToMO) from *Pseudomonas stutzeri* OX1 was found to oxidize nitrobenzene (NB) to form m-nitrophenol (m-NP, about 72%) and p-NP (about 28%) with an initial rate of about 0.098 and about 0.031 nmol/min.mg protein, respectively. A novel method of 4-nitrocatechol (4-NC) from m-NP and p-NP by wild-type ToMO is disclosed with an initial rate of about 0.15 and about 0.0082 nmol/min.mg protein, respectively, and 3-NC (about 18%) and nitrohydroquinone (NHQ, about 82%) from o-NP with an initial rate of about 0.11 and about 0.48 nmol/min.mg protein, respectively.

To increase the oxidation rate of nitro aromatics the active site residues I100, Q141, T201, and F205 of the alpha hydroxylase fragment of ToMO (TouA), DNA shuffling and saturation mutagenesis were used to generate random mutants. The mutants were initially identified by screening via a rapid agar plate assay and then were further examined by high performance liquid chromatography (HPLC) and gas chromatography (GC). Several mutants with higher rates of activities and with different regiospecificities were identified; for example, *Escherichia coli* TG1 cells expressing either TouA shuffling mutant E214G/D312N/M399V or M180T/E284G produced 4-NC about 20 and about 4.5 times faster than wild-type ToMO (about 0.16 and about 0.037 nmol/min.mg protein) from p-NP, respectively. From about 200 µM NB, shuffling variants E214G/D312N/M399V, M180T/E284G, A110T/E392D, and A101T/M114T produced 4-NC whereas wild-type ToMO did not. From m-NP, TouA saturation mutagenesis variant I100Q produced 4-NC (about 37%) and NHQ (about 63%) whereas wild-type ToMO produced only 4-NC (about 100%). Regiospecific oxidation of the natural substrate toluene as well as o-xylene was altered for saturation mutants I100H and T201G; for example, I100H forms about 24%, about 14%, and about 61% of o-, m-, and p-cresol, respectively, T201G forms about 53%, about 12%, and about 35% of o-, m-, and p-cresol, respectively, whereas wild-type ToMO forms about 32%, about 21%, and about 47% of o-, m-, and p-cresol, respectively.

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein.

APPENDIX

References

Adachi, J., Y. Mori, S. M. Takigami, J. Fujino, H. Kitagawa, C. A. Miller III, T. Kato, K. Saeki, and T. Matsuda. 2001. Indirubin and Indigo Are Potent Aryl Hydrocarbon Receptor Ligands Present in Human Urine. J. Biol. Chem. 276: 31475-31478.

Ahamad, P. Y. A., A. A. M. Kunhi, and S. Divakar. 2001. New metabolic pathway for o-cresol degradation by *Pseudomonas* sp. CP4 as evidenced by H NMR spectroscopic studies. World J. Microbiol. Biotechnol. 17:371-377.

Azerad, R. 2001. Chemical Biotechnology Better Enzyme for Green Chemistry. Curr. Opin. Biotechnol. 12:533-534.

Berry, A., T. C. Dodge, M. Pepsin, and W. Weyler. 2002. Application of metabolic engineering to improve both the production and use of biotech indigo. J. Ind. Microbiol. Biotechnol. 28:127

Bertoni, G., F. Bolognese, E. Galli, and P. Barbieri. 1996. Cloning of the genes for and characterization of the early stages of toluene and o-xylene catabolism in *Pseudomonas stutzeri* OX1. Appl. Environ. Microbiol. 62:3704-3711.

Bertoni, G., M. Martino, E. Galli, and P. Barbieri. 1998. Analysis of the gene cluster encoding toluene/o-xylene monooxygenase from *Pseudomonas stutzeri* OX1. Appl. Environ. Microbiol. 64:3626-3632.

Bhushan, B., S. K. Samanta, and R. K. Jain. 2000. Indigo production by naphthalene-degrading bacteria. Lett. Appl. Microbiol. 31:5-9.

Bialy, H. 1997. Biotechnology, bioremediation, and blue genes. Nat. Biotechnol. 15:110.

Brannigan, J. A., and A. J. Wilkinson. 2002. Timeline: Protein engineering 20 years on. Nat. Rev. Mol. Cell. Biol. 3:964-970.

Buolamwini, J. K. 2000. Cell Cycle Molecular Targets in Novel Anticancer Drug Discovery. Curr. Pharm. Des. 6:379-392.

Burdi, D., B. E. Sturgeon, W. H. Tong, J. Stubbe, and B. M. Hoffman. 1996. Rapid Freeze-Quench ENDOR of the Radical X Intermediate of *Escherichia coli* Ribonucleotide Reductase Using O2, H2O, and 2H2O. J. Am. Chem. Soc. 118:281-282.

Burton, S. G., A. Boshoff, W. Edwards, and P. D. Rose. 1998. Biotransformation of phenols using immobilised polyphenol oxidase. Journal of Molecular Catalysis B: Enzymatic 5:411-416.

Byrne, A. M., J. J. Kukor, and R. H. Olsen. 1995. Sequence analysis of the gene cluster encoding toluene-3-monooxygenase from *Pseudomonas pickettii* PKO1. Gene 154:65-70.

Byrne, A. M., and R. H. Olsen. 1996. Cascade regulation of the toluene-3-Monooxygenase operon (tbuA1UBVA2C) of *Burkholderia pickettii* PKO1: role of the tbuA1 promoter (PtbuA1) in the expression of its cognate activator, TbuT. J. Bacteriol. 178:6327-6337.

Cafaro, V., R. Scognamiglio, A. Viggiani, V. Izzo, I. Passaro, E. Notomista, F. D. Piaz, A. Amoresano, A. Casbarra, P. Pucci, and A. D. Donato. 2002. Expression and purification of the recombinant subunits of toluene/o-xylene monooxygenase and reconstitution of the active complex. Eur. J. Biochem. 269:5689-5699.

Canada, K. A., S. Iwashita, H. Shim, and T. K. Wood. 2002. Directed evolution of toluene ortho-monooxygenase for enhanced 1-naphthol synthesis and chlorinated ethene degradation. J. Bacteriol. 184:344-349.

Cardy, D. L. N., V. Laidler, G. P. C. Salmond, and J. C. Murrell. 1991. The methane monooxygenase gene cluster of *Methylosinus trichosporium*: cloning and sequencing of the mmoCGene. Arch. Microbiol. 156:477-483.

Chauhan, S., P. Barbieri, and T. K. Wood. 1998. Oxidation of Trichloroethylene, 1,1-Dichloroethylene, and Chloroform by Toluene/o-Xylene Monooxygenase from *Pseudomonas stutzeri* OX1. Appl. Environ. Microbiol. 64:3023-3024.

Damani, L. A., and P. A. Crooks. 1982. Oxidative Metabolism of Heterocyclic Ring Systems. In W. B. Jakoby, J. R. Bend, and J. Caldwell (ed.), Metabolic Basis of Detoxication. Academic Press Inc., New York, N.Y.

Dolfing, J., A. J. v. d. Wijngaard, and D. B. Janssen. 1993. Microbiological aspects of the removal of chlorinated hydrocarbons from air. Biodegradation 4:261-282.

Draths, K. M., and J. W. Frost. 1991. Conversion of D-glucose into catechol: the not-so-common pathway of aromatic biosynthesis. J. Am. Chem. Soc. 113:9361-9363.

Draths, K. M., and J. W. Frost. 1995. Environmentally compatible synthesis of catechol from D-glucose. J. Am. Chem. Soc. 117:2395-2400.

Dressler, H. 1994. Resorcinol, Its Uses and Derivatives. 1st ed., Plenum Press, New York.

Eaton, R. W., and P. J. Chapman. 1995. Formation of Indigo and Related Compounds from Indolecarboxylic Acids by Aromatic Acid-Degrading Bacteria: Chromogenic Reactions for Cloning Genes Encoding Dioxygenases That Act on Aromatic Acids. J. Bacteriol. 177:6983-6988.

Ensley, B. D., B. J. Ratzkin, T. D. Osslund, and M. J. Simon. 1983. Expression of Naphthalene Oxidation Genes in *Escherichia coli* Results in the Biosynthesis of Indigo. Science 222: 167-169.

Elango, N., R. Radhakrishnan, W. A. Froland, B. J. Wallar, C. A. Earhart, J. D. Lipscomb, and D. H. Ohlendorf. 1997. Crystal Structure of the Hydroxylase Component of Methane Monooxygenase from *Methylosinus trichosporium* OB3b. Protein Sci. 6:556-568.

Frost, J. W., and J. Lievense. 1994. Prospects for biocatalytic synthesis of aromatics in the 21st century. New J. Chem. 18:341-348.

Fujita, Y., I. Mori, K. Fujita, S. Kitano, and T. Tanaka. 1985. A color reaction of 1,2-diphenols based on colored complex formation with phenylfluorone and iron (III) and its application to the assay of catecholamines in pharmaceutical preparations. Chem. Pharm. Bull. 33:5385-5392.

Gibson, T. J. 1984. Studies on the Epstein-Barr virus genome. Ph.D. thesis. Cambridge University, Cambridge, England.

Gillner, M., G. S. Moore, H. Cederberg, and K. Gustafsson. 1994. Hydroquinone, Environmental Health Criteria 157. International Programme on Chemical Safety, Geneva.

Glover, V., J. M. Halket, P. J. Watkins, A. Clow, B. L. Goodwin, and M. Sandler. 1988. Isatin: Identity with the Purified Endogenous Monoamine Oxidase Inhibitor Tribulin. J. Neurochem. 51:656-659.

Guex, N., A. Diemand, and M. C. Peitsch. 1999. Protein modeling for all. Trends Biotechnol. 24:364-367.

Guex, N., and M. C. Peitsch. 1997. SWISS-MODEL and the Swiss-PdbViewer: An environment for comparative protein modelling. Electrophoresis 18:2714-2723.

Hisaindee, S., and D. L. J. Clive. 2001. A synthesis of puraquinonic acid. Tetrahedron Lett. 42:2253-2255.

Hoessel, R., S. Leclerc, J. A. Endicott, M. E. M. Noble, A. Lawrie, P. Tunnah, M. Leost, E. Damiens, D. Marie, D. Marko, E. Niederberger, W. Tang, G. Eisenbrand, and L. Meijer. 1999. Indirubin, the active constituent of a Chinese antileukaemia medicine, inhibits cyclin-dependent kinases. Nat. Cell Biol. 1:60-67.

Howe-Grant, M. (ed.). 1991. Kirk-Othmer encyclopedia of chemical technology, fourth ed, vol. 13. Wiley-Interscience Publishers, New York.

Kopp, D. A., and S. J. Lippard. 2002. Soluble methane monooxygenase: activation of dioxygen and methane. Curr. Opin. Chem. Biol. 6:568-576.

Johnson, G. R., and R. H. Olsen. 1997. Multiple pathways for toluene degradation in *Burkholderia* sp. strain JS150. Appl. Environ. Microbiol. 63:4047-4052.

Leahy, J. G., P. J. Batchelor, and S. M. Morcomb. 2003. Evolution of the soluble diiron monooxygenases. FEMS Microbiol. Rev. 27:449-479. 23.

Luu, P. P., C. W. Yung, A. K. Sun, and T. K. Wood. 1995. Monitoring trichloroethylene mineralization by *Pseudomonas cepacia* G4 PR1. Appl. Microbiol. Biotechnol. 44:259-264.

Kadiyala, V., and J. C. Spain. 1998. A two-component monooxygenase catalyzes both the hydroxylation of p-nitrophenol and the oxidative release of nitrite from 4-nitrocatechol in *Bacillus sphaericus* JS905. Appl. Environ. Microbiol. 64:2479-2484.

Korte, J. E., I. Hertz-Picciotto, M. R. Schulz, L. M. Ball, and E. J. Duell. 2000. The contribution of benzene to smoking-induced leukemia. Environmental Health Perspectives 108:333-339.

Krolikowska, A., W. Bokszczanin, A. Kozlowski, and T. Dzikowicz. April 1991. Mixtures of dihydroxybenzene derivatives and alkylphenols as rust inhibitors for paints. Polland patent 153,464.

Macias, F. A., D. Marin, D. Chinchilla, and J. M. G. Molinillo. 2002. First total synthesis of (+/-)-helibisabonol A. Tetrahedron Lett. 43:6417-6420.

Masunaga, S., Y. Urushigawa, and Y. Yonezawa. 1986. Biodegradation pathway of o-cresol by heterogeneous culture. Phenol acclimated activated sludge. Water Res. 20:477-484.

Masunaga, S., Y. Urushigawa, and Y. Yonezawa. 1983. Microbial Transformation of o-cresol to dihydroxytoluenes by phenol acclimated activated sludge. Chemosphere 12: 1075-1082.

Maugard, T., E. Enaud, P. Choisy, and M. D. Legoy. 2001. Identification of an indigo precursor from leaves of *Isatis tinctoria* (Woad). Phytochemistry 58:897-904.

Maugard, T., E. Enaud, A. de La Sayette, P. Choisy, and M. D. Legoy. 2002. Beta-Glucosidase-Catalyzed Hydrolysis of Indican from Leaves of *Polygonum tinctorium*. Biotechnol. Prog. 18:1104-1108.

Mermod, N., S. Harayama, and K. N. Timmis. 1986. New Route to Bacterial Production of Indigo. Bio/Technol. 4:321-324.

Meyer, A., A. Schmid, M. Held, A. H. Westphal, M. Röthlisberger, H. E. Kohler, W. J. H. v. Berkel, and B. Witholt. 2002. Changing the Substrate Reactivity of 2-Hydroxybiphenyl 3-Monooxygenase from *Pseudomonas azelaica* HBP1 by Directed Evolution. J. Biol. Chem. 277:5575-5582.

Mitchell, K. H., J. M. Studts, and B. G. Fox. 2002. Combined participation of hydroxylase active site residues and effector protein binding in a para to ortho modulation of toluene 4-monooxygenase regiospecificity. Biochem. 41:3176-3188.

Murdock, D., B. D. Ensley, C. Serdar, and M. Thalen. 1993. Construction of Metabolic Operons Catalyzing the De Novo Biosynthesis of Indigo in *Escherichia coli*. Bio/Technol. 11:381-386.

Miyazaki, K., and F. H. Arnold. 1999. Exploring Nonnatural Evolutionary Pathways by Saturation Mutagenesis Rapid Improvement of Protein Function. J. Mol. Evol. 49:716-720.

Moore, J. C., and F. H. Arnold. 1996. Directed Evolution of a para-Nitrobenzyl esterase for aqueous-organic solvents. Nat. Biotechnol. 14:458-467.

Nelson, M. J. K., S. O. Montgomery, W. R. Mahaffey, and P. H. Pritchard. 1987. Biodegradation of Trichloroethylene and Involvement of an Aromatic Biodegradative Pathway. Appl. Environ. Microbiol. 53:949-954.

Nelson, M. J. K., S. O. Montgomery, E. J. O'Neill, and P. H. Pritchard. 1986. Aerobic Metabolism of Trichloroethylene by a Bacterial Isolate. Appl. Environ. Microbiol. 52:383-384.

Newman, L. M., and L. P. Wackett. 1995. Purification and Characterization of Toluene 2-Monooxygenase from *Burkholderia cepacia* G4. Biochem. 34:14066-14076.

Nordlund, I., J. Powlowski, and V. Shingler. 1990. Complete Nucleotide Sequence and Polypeptide Analysis of Multicomponent Phenol Hydroxylase from *Pseudomonas* sp. strain $CF_{600}$. J. Bacteriol. 172:6826-6833.

O'Connor, K. E., and S. Hartmans. 1998. Indigo Formation by Aromatic Hydrocarbon-Degrading Bacteria. Biotechnology Letters 20:219-223.

O'Connor, K. E., A. D. Dobson, and S. Hartmans. 1997. Indigo Formation by Microorganisms Expressing Styrene Monooxygenase Activity. Appl. Environ. Microbiol. 63:4287-4291.

Oppenheim, S. F., J. M. Studts, B. G. Fox, and J. S. Dordick. 2001. Aromatic hydroxylation catalyzed by toluene 4-monooxygenase in organic solvent/aqueous buffer mixtures. Applied Biochemistry & Biotechnology 90:187-197.

Othmer, K. 1991. Kirk-Othmer encyclopedia of chemical technology. 4th ed., Wiley-Interscience Publishers, New York.

Othmer, K. 1991. Kirk-Othmer encyclopedia of chemical technology. 4th ed., Wiley-Interscience Publishers, New York.

Peitsch, M. C. 1995. Protein modeling by E-mail. Bio/Technology 13:658-660.

Pikus, J. D., K. H. Mitchell, J. M. Studts, K. McClay, R. J. Steffan, and B. G. Fox. 2000. Threonine 201 in the Diiron Enzyme Toluene 4-Monooxygenase Is Not Required for Catalysis. Biochemistry 39:791-799.

Pikus, J. D., J. M. Studts, K. McClay, R. J. Steffan, and B. G. Fox. 1997. Changes in the regiospecificity of aromatic hydroxylation produced by active site engineering in the diiron enzyme toluene 4-monooxygenase. Biochemistry 36:9283-9289.

Robinson, G. K., G. M. Stephens, H. Dalton, and P. J. Geary. 1992. The production of catechols from benzene and toluene by *Pseudomonas putida* in glucose fed-batch culture. Biocatalysis 6:81-100.

Rosenzweig, A. C., H. Brandstetter, D. A. Whittington, P. Nordlund, S. J. Lippard, and C. A. Frederick. 1997. Crystal structures of the methane monooxygenase hydroxylase from *Methylococcus capsulatus* (Bath): Implications for substrate gating and component interactions. Proteins: Struct. Funct. Genet. 29:141-152.

Rosenzweig, A. C., P. Nordlund, P. M. Takahara, C. A. Frederick, and S. J. Lippard. 1995. Geometry of the Soluble Methane Monooxygenase Catalytic Diiron Center in Two Oxidation States. Chem. Biol. 2:409-418.

Rui, L., Y. M. Kwon, A. Fishman, K. F. Reardon, and T. K. Wood. 2004. Saturation Mutagenesis of Toluene ortho-Monooxygenase from *Burkholderia cepacia* G4 for Enhanced 1-Naphthol Synthesis and Chloroform Degradation. Appl. Environ. Microbiol., 70:3246-3252.

Ryoo, D., H. Shim, K. Canada, P. Barbieri, and T. K. Wood. 2000. Aerobic Degradation of Tetrachloroethylene by Toluene-o-Xylene Monooxygenase of *Pseudomonas stutzeri* OX1. Nat. Biotechnol. 18:775-778.

Sakamoto, T., J. M. Joern, A. Arisawa, and F. H. Arnold. 2001. Laboratory Evolution of Toluene Dioxygenase To Accept 4-Picoline as a Substrate. Appl. Environ. Microbiol. 67:3882-3887.

Sambrook, J., E. F. Fritsch, and T. Maniatis. 1989. Molecular cloning, a laboratory manual. 2nd ed., Cold Spring Harbor Laboratory Press, Cold Spring Harbor, N.Y.

Sanger, F., S, Nicklen, and A. R. Coulson. 1977. DNA sequencing with chain-terminating inhibitors. Proc. Natl. Acad. Sci. U.S.A 74:5463-5467.

Schwede, T., J. Kopp, N. Guex, and M. C. Peitsch. 2003. SWISS-MODEL: an automated protein homology-modeling server. Nucleic Acids Res. 31:3381-3385.

Shields, M. S., S. O. Montgomery, P. J. Chapman, S. M. Cuskey, and P. H. Pritchard. 1989. Novel Pathway of Toluene Catabolism in the Trichloroethylene-Degrading Bacterium G4. Appl. Environ. Microbiol. 55:1624-1629.

Shim, H., and T. K. Wood. 2000. Aerobic Degradation of Mixtures of Chlorinated Aliphatics by Cloned Toluene-o-Xylene Monooxygenase and Toluene o-Monooxygenase in Resting Cells. Biotechnol. Bioeng. 70:693-698.

Stainthorpe, A. C., V. Lees, G. P. C. Salmond, H. Dalton, and J. C. Murrell. 1990. The methane monooxygenase gene cluster of *Methylococcus capsulatus* (Bath). Gene 91:27-34.

Stemmer, W. P. C. 1994. DNA Shuffling by Random Fragmentation and Reassembly: In vitro Recombination for Molecular Evolution. Proc. Natl. Acad. Sci. USA 91:10747-10751.

Studts, J. M., K. H. Mitchell, J. D. Pikus, K. McClay, R. J. Steffan, and B. G. Fox. 2000. Optimized expression and purification of toluene 4-monooxygenase hydroxylase. Protein Expression and Purification 20:58-65.

Sundberg, R. J. 1970. The Chemistry of Indoles. Academic Press Inc., New York, N.Y.

Sundberg, R. J. 1996. Indoles. Academic Press Inc., San Diego, Calif.

Tao, Y., A. Fishman, W. E. Bentley, and T. K. Wood. 2004. Oxidation of Benzene to Phenol, Catechol, and 1,2,3-Trihydroxybenzene by Toluene 4-Monooxygenase of *Pseudomonas mendocina* KR1 and Toluene 3-Monooxygenase of *Ralstonia pickettii* PKO1. Appl. Environ. Microbiol, 70:3814-3820.

Tice, R. 1998. Review of Toxicological Literature, Pyrogallol 87-66-1. National Toxicology Program, North Carolina.

van Beilen, J. B., W. A. Duetz, S. A., and B. Witholt. 2003. Practical issues in the application of oxygenases. Trends Biotechnol. 21:170-177.

Vardar, G., and T. K. Wood. 2004. Protein Engineering of Toluene-o-Xylene Monooxygenase from *Pseudomonas stutzeri* OX1 for Synthesizing 4-Methylresorcinol, Methylhydroquinone, and Pyrogallol, Appl. Environ. Microbiol., 70:3253-3262.

Yonezawa, T. March 2003. Capacitor electrolytes containing dihydroxytoluenes for low specific resistance. Japan patent 2,003,068,585.

Wallar, B. J., and J. D. Lipscomb. 1996. Dioxygen Activation by Enzymes Containing Binuclear Non-heme Iron Clusters. Chem. Rev. 96:2625-2657.

Wick, C. B. 1995. Genencor International Takes A Green Route to Blue Dye. Genet. Eng. News 15:22.

Whited, G. M., and D. T. Gibson. 1991. Separation and partial characterization of the enzymes of the toluene-4-monooxygenase catabolic pathway in *Pseudomonas mendocina* KR1. J. Bacteriol. 173:3017-3020.

Yen, K.•M., M. R. Karl, L. M. Blatt, M. J. Simon, R. B. Winter, P. R. Fausset, H. S. Lu, A. A. Harcourt, and K. K. Chen. 1991. Cloning and Characterization of a *Pseudomonas mendocina* KR1Gene Cluster Encoding Toluene-4-Monooxygenase. J. Bacteriol. 173:5315-5327.

Zhao, H., and F. H. Arnold. 1997. Optimization of DNA shuffling for high fidelity recombination. Nucleic Acids Res. 25:1307-1308.

The invention claimed is:

1. An isolated nucleic acid molecule comprising a MOX nucleic acid sequence that encodes a recombinant MOX polypeptide whose enzymatic substrate includes an aromatic hydrocarbon, wherein the MOX nucleic acid that encodes the recombinant MOX polypeptide is derived from one or more parental nucleic acids encoding a toluene-o-xylene monooxygenase (ToMO) polypeptide and wherein the MOX nucleic acid is selected from the group consisting of SEQ ID NOs: 17, 19, 21, 23, and combinations thereof.

2. The isolated nucleic acid molecule of claim 1, wherein the MOX nucleic acid encodes a recombinant MOX polypeptide selected from the group consisting of SEQ ID NOs. 18, 20, 22, and 24.

3. A vector comprising the nucleic acid molecule of claim 1.

4. The vector of claim 3, further comprising a promoter operably-linked to said nucleic acid molecule.

5. A host cell comprising the vector of claim 3.

6. The host cell of claim 5, wherein the cell is cultured in the presence of an aromatic hydrocarbon chemical compound.

7. The host cell of claim 6, wherein the aromatic hydrocarbon chemical compound is a substituted aryl, wherein the substituted aryl comprises at least one side group selected from —$CH_3$; —$OCH_3$; —OH; —COOH; —NOOH; a C1-C9 alkyl or alkenyl; a phenyl; a benzyl; a heterocyclic alkane or alkene; or a combination thereof.

8. The host cell of claim 7, wherein the aromatic hydrocarbon compound is chosen from the group consisting of benzene, dihydroxybenzene, trihydroxybenzene, nitrobenzene, toluene, cresol, nitrocresol, phenol, nitrophenol, catechol, methylcatechol, nitrocatechol, hydroquinone, methylhydroquinone, resorcinol, and methylresorcinol.

9. The host cell of claim 8, wherein the aromatic hydrocarbon compound is toluene.

10. The host cell of claim 8, wherein the aromatic hydrocarbon compound is phenol.

11. The host cell of claim 8, wherein the aromatic hydrocarbon compound is catechol.

12. The host cell of claim 8, wherein the aromatic hydrocarbon compound is benzene.

13. The host cell of claim 8, wherein the aromatic hydrocarbon compound is resorcinol.

14. The host cell of claim 8, wherein the aromatic hydrocarbon compound is nitrobenzene.

15. A library of recombinant nucleic acids comprising at least one recombinant monooxygenase nucleic acid selected from the group consisting of SEQ ID NOs: 17, 19, 21, and 23.

16. A recombinant monooxygenase polypeptide selected from the group consisting of SEQ ID NOs: 18, 20, 22, and 24.

17. A kit comprising at least one of a MOX nucleic acid, a vector containing a MOX nucleic acid, a cell containing a MOX nucleic acid or a combination thereof, disposed in at least one container suitable for storage and transport, and instructions for use, wherein the MOX nucleic acid is a member selected from the group consisting of SEQ ID NOs: 17, 19, 21, 23, and combinations thereof.

18. A method for producing useful chemical compounds by comprising the steps of:
 (a) providing at least one recombinant monooxygenase nucleic acid selected from the group consisting of SEQ ID NOs: 17, 19, 21, and 23;
 (b) transferring said recombinant monooxygenase nucleic acid into a nucleic acid expression vector;
 (c) introducing said nucleic acid expression vector containing the recombinant monooxygenase nucleic acid into an organism suitable for expression of the monooxygenase polypeptide; and
 (d) screening the organism expressing the recombinant monooxygenase polypeptide for the ability to oxidize a chemical substrate by allowing the organism to grow in a suitable medium in the presence of an aromatic hydrocarbon chemical compound;

(e) selecting an organism expressing said recombinant monooxygenase polypeptide based on an altered property; and (f) growing the selected organism expressing the recombinant monooxygenase polypeptide in a larger volume for the production of a chemical product of aromatic hydrocarbon oxidation, wherein the chemical product of aromatic hydrocarbon oxidation may be collected, purified or concentrated or any combination thereof.

19. A method for determining the presence or amount of a MOX nucleic acid or polypeptide molecule in a sample, the method comprising:

(a) providing the sample;

(b) contacting the sample with a probe that specifically binds to at least one MOX nucleic acid selected from the group consisting of SEQ ID NOs: 17, 19, 21, and 23 or at least one MOX polypeptide molecule selected from the group consisting of SEQ ID NOs: 18, 20, 22, and 24; and (c) determining the presence or amount of the probe bound to said MOX nucleic acid or MOX polypeptide molecule, thereby determining the presence, amount or both of the MOX nucleic acid or MOX polypeptide molecule in said sample.

20. The method of claim 19, wherein the presence or amount of the MOX nucleic acid or MOX polypeptide molecule is a marker for cell or tissue type.

* * * * *